(12) United States Patent
Beaton et al.

(10) Patent No.: US 9,150,651 B2
(45) Date of Patent: Oct. 6, 2015

(54) SINGLE VARIABLE DOMAIN IMMUNOGLOBULINS THAT BIND TGF-BETA RECEPTOR II

(75) Inventors: Andrew Beaton, Stevenage (GB);
Caroline Dimech, Stevenage (GB);
Peter Franz Ertl, Stevenage (GB);
Susannah Karen Ford, Stevenage (GB);
Ruth Mcadam, Stevenage (GB)

(73) Assignee: Glaxo Group Limited (GB)

( * ) Notice: Subject to any disclaimer, the term of this patent is extended or adjusted under 35 U.S.C. 154(b) by 0 days.

(21) Appl. No.: 13/978,228

(22) PCT Filed: Jan. 4, 2012

(86) PCT No.: PCT/EP2012/050061
§ 371 (c)(1),
(2), (4) Date: Jul. 3, 2013

(87) PCT Pub. No.: WO2012/093125
PCT Pub. Date: Jul. 12, 2012

(65) Prior Publication Data
US 2013/0302335 A1     Nov. 14, 2013

Related U.S. Application Data

(60) Provisional application No. 61/430,235, filed on Jan. 6, 2011.

(51) Int. Cl.
*C07K 16/28*     (2006.01)

(52) U.S. Cl.
CPC .......... *C07K 16/2863* (2013.01); *C07K 2317/21* (2013.01); *C07K 2317/565* (2013.01); *C07K 2317/567* (2013.01); *C07K 2317/569* (2013.01); *C07K 2317/76* (2013.01); *C07K 2317/92* (2013.01); *C07K 2317/94* (2013.01)

(58) Field of Classification Search
None
See application file for complete search history.

(56) References Cited

FOREIGN PATENT DOCUMENTS

| EP | 1 245 676 A1 | 10/2002 |
|---|---|---|
| WO | WO 2011/012609 A2 | 2/2011 |
| WO | WO 2010/053814 A1 | 5/2014 |

OTHER PUBLICATIONS

Rudikoff S. et al. Proc. Natl. Acad. Sci. USA, 79:1979-1983, 1982.*
Colman, PM. Research in Immunology, Elsevier, NY, 145(1):33-36, 1994.*
Chen, W., et al., Journal of Molecular Biology, vol. 382, No. 3, Oct. 10, 2008, pp. 779-789.
Demarest, Stephen J., et al., Current Opinion in Drug Discovery and Development, vol. 11, No. 5, Sep. 1, 2008, pp. 675-687.
Saerens, Dirk, et al., Current Opinion in Pharmacology, vol. 8, No. 5, Oct. 1, 2008, pp. 600-608.
Wesolowski, Janusz, et al., Medical Microbiology and Immunology, vol. 198, No. 3, Jun. 16, 2009, pp. 157-174.

* cited by examiner

*Primary Examiner* — Robert Landsman
(74) *Attorney, Agent, or Firm* — William T. Han; Jason C. Fedon

(57) ABSTRACT

The disclosure provides an anti-TGFbetaRII immunoglobulin single variable domain. Suitably, an anti-TGFbetaRII immunoglobulin single variable domain in accordance with the disclosure is one having an amino acid sequence as set forth in any one of SEQ ID NO:1-28 having up to 5 amino acid substitutions, deletions or additions. The disclosure further provides a polypeptide and pharmaceutical composition for treating a disease associated with TGFbeta signalling and suitably a disease selected from the group of: tissue fibrosis, such as pulmonary fibrosis, including idiopathic pulmonary fibrosis; liver fibrosis, including cirrhosis and chronic hepatitis; rheumatoid arthritis; ocular disorders; fibrosis of the skin, including keloid of skin; Dupuytren's Contracture; kidney fibrosis such as nephritis and nephrosclerosis; wound healing; scarring reduction; and a vascular condition, such as restenosis.

8 Claims, No Drawings

ID NO:4) and DOM-23h-439 (SEQ ID NO:10) as
SINGLE VARIABLE DOMAIN IMMUNOGLOBULINS THAT BIND TGF-BETA RECEPTOR II This application is a 371 of International Application No. PCT/EP2012/050061, filed 4 Jan. 2012, which claims the benefit of U.S. Provisional Application No. 61/430,235, filed 4 Jan. 2011, both of which are herein incorporated by reference in their entireties.

BACKGROUND

Transforming Growth Factor-β (TFGbeta; TGFβ (TGF-β) is a signaling molecule that mediates signal transduction into cells through binding to a TGFbeta receptor (TGFbetaR; TGFβR (TGF-βR)). TGFbeta signaling activity regulates cell differentiation and growth, the nature of its effect, i.e. as cell growth-promoter, growth-suppressor or inducer of other cell functions, being dependent on cell type (see Roberts, et al., The transforming growth factor-betas, Peptide Growth Factors and Their Receptors, Part I, ed. by Sporn, M. B. & Roberts, A. B., Springer-Verlag, Berlin, 1990, p. 419-472).

TGFbeta is produced by a wide variety of cell types, and its cognate receptors are expressed in a wide variety of organs and cells (see Shi and Massague, Cell, Volume 113, Issue 6, 13 Jun. 2003, Pages 685-700; Biol. Signals., Vol. 5, p. 232, 1996 and Pulmonary Fibrosis, Vol. 80 of Lung Biology in Health and Disease Series, ed. by Phan, et al., p. 627, Dekker, New York, 1995). TGFbeta receptors have been identified to fall into three types: TGFbetaRI (TGFβRI) (TGFbeta type I receptor (Franzen et al., Cell, Vol. 75, No. 4, p. 681, 1993; GenBank Accession No: L11695)); TGFbetaRII (TGFβRII) (TGFbeta type II receptor (Herbert et al., Cell, Vol. 68, No. 4, p. 775, 1992; GenBank Accession No: M85079)) and TGF-betaRIII (TGFbeta type III receptor (Lopez-Casillas, Cell, Vol. 67, No. 4, p. 785, 1991; GenBank Accession No: L07594)). TGFbetaRI and TGFbetaRII have been shown to be essential for the signal transduction of TGF-beta (Laiho et al., J. Biol. Chem., Vol. 265, p. 18518, 1990 and Laiho et al., J. Biol. Chem., Vol. 266, p. 9108, 1991), while TGFbetaRIII is not thought to be essential.

TGFbeta signaling is mediated through its binding to both TGFbetaRI and RII. When the ligand binds to the extracellular ligand binding domain, the two receptors are brought together, allowing RII to phosphorylate RI and begin the signaling cascade through the phosphorylation of Smad proteins (see Shi and Massague as referred to above).

Three isoforms of TGFbeta have been identified in mammals: TGFbeta1, TGFbeta2, and TGFbeta3. Each isoform is multifunctional and acts in self-regulatory feedback mechanisms to control bioavailability for developmental processes and to maintain tissue homeostasis (as reviewed in ten Dijke and Arthur, Nature Reviews, Molecular Cell Biology, Vol. 8, November 2007, p. 857-869). Levels of TFGbeta are controlled by regulation through TGFbeta expression as well as through binding to proteoglycan, i.e., the extracellular matrix (ECM).

Dysregulated TGFbeta signaling, such as excess TGFbeta signaling and high levels of bioavailable TGFbeta, is implicated in a number of pathologies, including fibroses of various tissues, such as pulmonary fibrosis and cirrhosis, chronic hepatitis, rheumatoid arthritis, ocular disorders, vascular restenosis, keloid of skin, and the onset of nephrosclerosis.

Accordingly, there is a need to provide compounds that block or disrupt TGFbeta signaling in a specific manner, such as through binding to the TGFbeta receptor II. Such compounds can be used in therapeutics.

SUMMARY

The disclosure relates to an anti-TGFbetaRII immunoglobulin single variable domain. Suitably, an anti-TGFbetaRII immunoglobulin single variable domain in accordance with the disclosure is one which binds to TGFbetaRII with an equilibrium dissociation constant (KD) in the range of 10 pM to 50 nM, optionally 10 pM to 10 nM, optionally 100 pM to 10 nM. In one embodiment, the anti-TGFbetaRII immunoglobulin single variable domain is one which binds TGFbetaRII with high affinity (high potency) and has an equilibrium dissociation constant of 10 pM to 500 pM. In one embodiment, the anti-TGFbetaRII immunoglobulin single variable domain is one which binds TGFbetaRII with an affinity (KD) of approximately 100 pM. In one embodiment, the anti-TGFbetaRII immunoglobulin single variable domain is one which binds TGFbetaRII with an affinity (KD) of less than 100 pM. In another embodiment, the anti-TGFbetaRII immunoglobulin single variable domain is one which binds TGFbetaRII with moderate affinity (low potency) and has an equilibrium dissociation constant of 500 pM to 50 nM, preferably 500 pM to 10 nM. In another aspect, the disclosure provides an isolated polypeptide comprising an anti-TGFbetaRII immunoglobulin single variable domain. Suitably, the isolated polypeptide binds to human TGFbetaRII. In another embodiment, the isolated polypeptide also binds to TGFbetaRII derived from a different species such as mouse, dog or monkeys, such as cynomolgus monkeys (cyno). Suitably, the isolated polypeptide binds to both mouse and human TGFbetaRII. Such cross reactivity between TGFbetaRII from humans and other species allows the same antibody construct to be used in an animal disease model, as well as in humans.

In an aspect of the disclosure there is provided an anti-TGFbetaRII immunoglobulin single variable domain having an amino acid sequence as set forth in any one of SEQ ID NO:1-38, 204, 206, 208, 214, 234, 236, 238, 240, 263, 265, 267, 269, 271, 273, 275, 277, 279, 281, 283, 285 and 287, and having up to 5 amino acid alterations, wherein each amino acid alteration is an amino acid substitution, deletion or addition i.e. up to 5 amino acid substitutions, deletions or additions, in any combination. In a particular embodiment the amino acid substitutions are conservative substitutions.

In an embodiment, the anti-TGFbetaRII immunoglobulin single variable domain has the amino acid sequence as set forth in SEQ ID NO: 234 or 279 and having up to 5 amino acid alterations, wherein each amino acid alteration is a an amino acid substitution, deletion or addition. In a particular embodiment, the amino acid alteration(s) are not within CDR3, more specifically not within CDR3 and CDR1, or CDR3 and CDR2, more specifically not within any of the CDRs. In an embodiment, the anti-TGFbetaRII immunoglobulin single variable domain consists of any one of the following sequences: SEQ ID NO:1-38, 204, 206, 208, 214, 234, 236, 238, 240, 263, 265, 267, 269, 271, 273, 275, 277, 279, 281, 283, 285 and 287. In an embodiment the anti-TGFbetaRII immunoglobulin single variable domain consists of an amino acid sequence of SEQ ID NO: 234 or 236.

It is not intended to cover any specific anti-TGFbetaRII immunoglobulin single variable domain sequence disclosed in WO 2011012609. For the avoidance of doubt each and every sequence disclosed in WO 2011012609 may be disclaimed from the present invention. In particular DOM23h-271 (SEQ ID NO:4) and DOM-23h-439 (SEQ ID NO:10) as disclosed in WO 2011012609 may be disclaimed. An anti- TGFbetaRII immunoglobulin single variable domain consisting of the amino acid sequence as set forth in SEQ ID NO: 199 or 201 herein may be disclaimed.

An anti-TGFbetaRII immunoglobulin single variable domain according to the invention may comprise one or more (e.g. 1, 2, 3, 4, or 5) C-terminal alanine residues. Alternatively, an anti-TGFbetaRII immunoglobulin single variable domain may comprise a C-terminal peptide of up to 5 amino acids in length. In an embodiment, the C-terminal peptide comprises 1, 2, 3, 4, or 5 amino acids.

A person skilled in the art is able to deduce from a given single variable domain sequence, e.g. one having a sequence as set out in any one of SEQ ID NO:1-38, 204, 206, 208, 214, 234, 236, 238, 240, 263, 265, 267, 269, 271, 273, 275, 277, 279, 281, 283, 285 and 287 which CDR sequences are contained within them using the various methods outlined herein e.g. CDR sequences as defined by reference to Kabat (1987), Chothia (1989), AbM or contact methods, or a combination of these methods. Suitably, CDR sequences are determined using the method of Kabat described herein. In one embodiment, the CDR sequences of each sequence are those set out in tables 1, 2, 9, and 13.

In an aspect of the invention an anti-TGFbetaRII immunoglobulin single variable domain of the disclosure has 90% or greater than 90% sequence identity to an amino acid sequence selected from the group consisting of SEQ ID NO:1-28.

In an aspect of the invention an anti-TGFbetaRII immunoglobulin single variable domain of the disclosure has an amino acid sequence selected from the group consisting of SEQ ID NO:1-28 with 25 or fewer amino acid changes. In a particular embodiment an anti-TGFbetaRII immunoglobulin single variable domain of the disclosure has an amino acid sequence selected from the group consisting of SEQ ID NO:1-28 with 20 or fewer, 15 or fewer, 10 or fewer, 9 or fewer, 8 or fewer, 7 or fewer, 6 or fewer, or 5 or fewer amino acid changes.

In an aspect of the disclosure there is provided an isolated polypeptide comprising an anti-TGFbetaRII immunoglobulin single variable domain of the disclosure, in particular an anti-TGFbetaRII immunoglobulin single variable domain identical to an amino acid sequence selected from the group consisting of SEQ ID NO:1-38, 204, 206, 208, 214, 234, 236, 238, 240, 263, 265, 267, 269, 271, 273, 275, 277, 279, 281, 283, 285 and 287 wherein said isolated polypeptide binds to TGFbetaRII.

In an aspect of the disclosure there is provided an isolated polypeptide encoded by a nucleotide sequence that is at least 80% identical to at least one nucleic acid sequence selected from the group of: SEQ ID NOS:39-66, wherein said isolated polypeptide binds to TGFbetaRII.

An anti-TGFbetaRII immunoglobulin single variable domain or a polypeptide in accordance with any aspect of the disclosure may comprise any of the following amino acids: R at position 39, I at position 48, D at position 53, N at position 61, R at position 61, K at position 61, R at position 64, F at position 64, D at position 64, E at position 64, Y at position 64, H at position 102, or S at position 103 of the immunoglobulin single variable domain, said position being according to the kabat numbering convention. In one embodiment, the immunoglobulin single variable domain or polypeptide comprises a combination of these amino acids. In another embodiment, the immunoglobulin single variable domain or polypeptide comprises amino acid N at 61 and R at 64. In another embodiment, the immunoglobulin single variable domain or polypeptide comprises amino acid R or K at position 61. In an embodiment, the anti-TGFbetaRII immunoglobulin single variable domain comprises an I at position 48 in addition to any one of the aforementioned residues at position 61 and/or 64. In these embodiments, the amino acid numbering is that of the immunoglobulin single variable domain, as exemplified, for example, by those sequences given in SEQ ID NOs:1-38, 204, 206, 208, 214, 234, 236, 238, 240, 263, 265, 267, 269, 271, 273, 275, 277, 279, 281, 283, 285 and 287.

An anti-TGFbetaRII immunoglobulin single variable domain or a polypeptide in accordance with any aspect of the disclosure may comprise one of the following amino acid combinations selected from the group: N at position 61 and R at position 64; R at position 61 and E at position 64; R at position 61 and M at position 64; R at position 61 and F at position 64; R at position 61 and Y at position 64; and R at position 61 and D at position 64 of the immunoglobulin single variable domain. In an embodiment, the anti-TGFbetaRII immunoglobulin single variable domain comprises an I at position 48 in addition to any one of the aforementioned combination of residues at positions 61 and 64.

In another aspect, there is provided a ligand or binding moiety that has binding specificity for TGFbetaRII and inhibits the binding of an anti-TGFbetaRII immunoglobulin single variable domain comprising an amino acid sequence selected from the group of SEQ ID NOs:1-28 to TGFbetaRII.

In a further aspect of the disclosure, there is provided a fusion protein comprising an immunoglobulin single variable domain, polypeptide or ligand in accordance with any aspect of the disclosure.

In one embodiment, the immunoglobulin single variable domain, polypeptide, ligand or fusion protein in accordance with the disclosure is one which neutralises TGFbeta activity. Suitably, the immunoglobulin single variable domain or polypeptide in accordance with the disclosure inhibits binding of TGFbeta to TGFbetaRII. In another embodiment, the immunoglobulin single variable domain or polypeptide in accordance with the disclosure inhibits TGFbeta signalling activity through TGFbetaRII. In another embodiment, the immunoglobulin single variable domain or polypeptide in accordance with the disclosure suppresses TGFbeta activity, in particular, TGFbeta cell growth activity and/or fibrogenic activity. Suitably, TGFbetaRII is human TGFbetaRII.

In one embodiment, the immunoglobulin single variable domain, polypeptide, ligand or fusion protein in accordance with the disclosure is devoid of TGFbetaRII agonist activity at 15 micromolar (μM).

In another aspect, there is provided an immunoglobulin single variable domain, polypeptide, ligand or fusion protein in accordance with any aspect of the disclosure further comprising a half-life extending moiety. Suitably, the half-life extending moiety is a polyethylene glycol moiety, serum albumin or a fragment thereof, transferrin receptor or a transferrin-binding portion thereof, or an antibody or antibody fragment comprising a binding site for a polypeptide that enhances half-life in vivo. In one embodiment, the half-life extending moiety is an antibody or antibody fragment comprising a binding site for serum albumin or neonatal Fc receptor. In another embodiment, the half-life extending moiety is a dAb, antibody or antibody fragment.

In another aspect, the disclosure provides an isolated or recombinant nucleic acid encoding a polypeptide comprising an anti-TGFbetaRII immunoglobulin single variable domain, polypeptide, ligand or fusion protein in accordance with any aspect of the disclosure.

In one embodiment, the isolated or recombinant nucleic acid molecule comprises or consists of a nucleic acid molecule selected from the group of any of the nucleic acid molecules having the sequences set out in SEQ ID NOS:39-

76, 203, 205, 207, 212, 233, 235, 237, 239, 262, 264, 266, 268, 270, 272, 274, 276, 278, 280, 282, 284, 286.

In one aspect, the disclosure provides an isolated or recombinant nucleic acid, wherein the nucleic acid comprises a nucleotide sequence that is at least 80% identical to the nucleotide sequence of any of the nucleic acid molecules having the sequences set out in SEQ ID NOS:39-66, and wherein the nucleic acid encodes a polypeptide comprising an immunoglobulin single variable domain that specifically binds to TGFbetaRII.

In another aspect, there is provided a vector comprising a nucleic acid in accordance with the disclosure.

In a further aspect, there is provided a host cell comprising a nucleic acid or a vector in accordance with the disclosure. In yet another aspect of the disclosure there is provided a method of producing a polypeptide comprising an anti-TGFbetaRII immunoglobulin single variable domain or a polypeptide or ligand or a fusion protein in accordance with the disclosure, the method comprising maintaining a host cell in accordance with the disclosure under conditions suitable for expression of said nucleic acid or vector, whereby a polypeptide comprising an immunoglobulin single variable domain, polypeptide or ligand or fusion protein is produced. Optionally, the method further comprises the step of isolating the polypeptide and optionally producing a variant, e.g., a mutated variant, having an improved affinity (Kd); or EC50 for TGFbeta neutralization in a standard assay than the isolated polypeptide. Suitable assays for TGFbeta activity, such as a cell sensor assay, are described herein, for example, in the Examples section.

In one aspect of the disclosure, the anti-TGFbetaRII immunoglobulin single variable domain, polypeptide or ligand or fusion protein in accordance with the disclosure is for use as a medicament. Accordingly, there is provided a composition comprising anti-TGFbetaRII immunoglobulin single variable domain, polypeptide or ligand or fusion protein in accordance with the disclosure for use as a medicament.

In one aspect of the disclosure, there is provided a use of an anti-TGFbetaRII immunoglobulin single variable domain, polypeptide or ligand or fusion protein in accordance with the disclosure for the manufacture of a medicament, particularly for use in treating disease associated with TGFbeta signalling.

Suitably, the anti-TGFbetaRII immunoglobulin single variable domain, polypeptide or ligand or fusion protein or composition in accordance with the disclosure is for treatment of a disease associated with TGFbeta signaling. Suitably, the disease is a tissue fibrosis, such as pulmonary fibrosis including idiopathic pulmonary fibrosis; liver fibrosis, including cirrhosis and chronic hepatitis; rheumatoid arthritis; ocular disorders; or fibrosis of the skin including keloid of skin; Dupuytren's Contracture; and kidney fibrosis such as nephritis and nephrosclerosis; or a vascular condition such as restenosis. Other diseases associated with TGFbeta signaling include vascular diseases such as hypertension, pre-eclampsia, hereditary haemorrhagic telangtiectasia type I (HHT1), HHT2, pulmonary arterial hypertension, aortic aneurysms, Marfan syndrome, familial aneurysm disorder, Loeys-Dietz syndrome, arterial tortuosity syndrome (ATS). Other diseases associated with TGFbeta signaling include diseases of the musculoskeletal system, such as Duchenne's muscular dystrophy and muscle fibrosis. Further diseases associated with TGFbeta signaling include cancer, such as colon, gastric, and pancreatic cancer, as well as glioma and NSCLC. In addition, the disclosure provides methods for targeting cancer by modulating TGFbeta signaling in tumour angiogenesis. Other diseases or conditions include those related to tissue scarring. Other diseases include pulmonary diseases such as COPD (Chronic obstructive pulmonary disease). An anti-TGFbetaRII immunoglobulin single variable domain, polypeptide or ligand or fusion protein or composition in accordance with the disclosure may be used in wound healing and/or to prevent or improve the formation of scars. In one aspect, the disclosure provides the anti-TGFbetaRII single variable domain, ligand or antagonist, composition or fusion protein for intradermal delivery. In one aspect, the disclosure provides the anti-TGFbetaRII single variable domain, ligand or antagonist or fusion protein for delivery to the skin of a patient. In one aspect, the disclosure provides the use of the anti-TGFbetaRII single variable domain, ligand or antagonist or fusion protein in the manufacture of a medicament for intradermal delivery. In one aspect, the disclosure provides the use of the anti-TGFbetaRII single variable domain or antagonist or fusion protein in accordance with the disclosure in the manufacture of a medicament for delivery to the skin of a patient.

In one embodiment, the variable domain is substantially monomeric. In a particular embodiment the variable domain is 65%-98% monomeric in solution as determined by SEC-MALS. In another embodiment the variable domain is 65%-100%, 70%-100%, 75%-100%, 80%-100%, 85%-100%, 90%-100%, 95%-100% monomeric in solution as determined by SEC-MALS.

In another embodiment, the variable domain, ligand, fusion protein or polypeptide as disclosed herein, particularly when in a pharmaceutical composition, does not contain any one or combination or all of the following post-translational modifications: deamidation, oxidation or glycosylation. In a particular embodiment the variable domain, ligand, fusion protein or polypeptide according to the disclosure does not deamidate.

Suitably, the composition is for therapy or prophylaxis of a TGFbeta-mediated condition in a human.

Accordingly, in one embodiment, there is provided an anti-TGFbetaRII dAb for treating fibrosis of the skin, in particular keloid disease or Dupuytren's Contracture. Suitably, the anti-TGFbetaRII dAb is provided as a substantially monomeric dAb for intradermal delivery, preferably lacking any tag (i.e., untagged) such as a myc or another purification tag.

In one aspect, the composition is a pharmaceutical composition and further comprises a pharmaceutically acceptable carrier, excipient or diluent.

In another aspect, there is provided a method of treating and/or preventing an TGFbeta-mediated condition in a human patient, the method comprising administering a composition comprising an anti-TGFbetaRII immunoglobulin single variable domain, polypeptide or ligand in accordance with the disclosure the to the patient.

In a further aspect, the disclosure provides an intradermal delivery device containing a composition in accordance with the disclosure. Suitably, such a device is a microneedle or collection of microneedles.

An a further aspect, there is provided a kit comprising an anti-TGFbetaRII single variable domain or polypeptide as disclosed herein and a device, such as an intradermal delivery device, for applying said single variable domain or polypeptide to the skin.

DETAILED DESCRIPTION

Within this specification, the disclosure has been described, with reference to embodiments, in a way which enables a clear and concise specification to be written. It is intended and should be appreciated that embodiments may be variously combined or separated without parting from the disclosure.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook, et al., Molecular Cloning: A Laboratory Manual, 2d ed. (1989) Cold Spring Harbor Laboratory Press, Cold Spring Harbor, N.Y. and Ausubel, et al., Short Protocols in Molecular Biology (1999) 4th Ed, John Wiley & Sons, Inc., which are incorporated herein by reference) and chemical methods.

Immunoglobulin: As used herein, "immunoglobulin" refers to a family of polypeptides which retain the immunoglobulin fold characteristic of antibody molecules, which contain two β sheets and, usually, a conserved disulphide bond.

Domain: As used herein "domain" refers to a folded protein structure which retains its tertiary structure independently of the rest of the protein. Generally, domains are responsible for discrete functional properties of proteins and in many cases may be added, removed or transferred to other proteins without loss of function of the remainder of the protein and/or of the domain. By single antibody variable domain or immunoglobulin single variable domain is meant a folded polypeptide domain comprising sequences characteristic of antibody variable domains. It therefore includes complete antibody variable domains and modified variable domains, for example in which one or more loops have been replaced by sequences which are not characteristic of antibody variable domains, or antibody variable domains which have been truncated or comprise N- or C-terminal extensions, as well as folded fragments of variable domains which retain at least in part the binding activity and specificity of the full-length domain.

Immunoglobulin single variable domain: The phrase "immunoglobulin single variable domain" refers to an antibody variable domain ($V_H$, $V_{HH}$, $V_L$) or binding domain that specifically binds an antigen or epitope independently of different or other V regions or domains i.e. is monovalent. An immunoglobulin single variable domain can be present in a format (e.g., homo- or hetero-multimer) with other variable regions or variable domains where the other regions or domains are not required for antigen binding by the single immunoglobulin variable domain (i.e., where the immunoglobulin single variable domain binds antigen independently of the additional variable domains). A "domain antibody" or "dAb" is an "immunoglobulin single variable domain" as the term is used herein. A "single antibody variable domain" or an "antibody single variable domain" is the same as an "immunoglobulin single variable domain" as the term is used herein. An immunoglobulin single variable domain is in one embodiment a human antibody variable domain, but also includes single antibody variable domains from other species such as rodent (for example, as disclosed in WO 00/29004, the contents of which are incorporated herein by reference in their entirety), nurse shark and Camelid VHH dAbs. Camelid VHH are immunoglobulin single variable domain polypeptides that are derived from species including camel, llama, alpaca, dromedary, and guanaco, which produce heavy chain antibodies naturally devoid of light chains. The VHH may be humanized.

In all aspects of the disclosure, the immunoglobulin single variable domain is independently selected from antibody heavy chain and light chain single variable domains, e.g. $V_H$, $V_L$ and $V_{HH}$.

As used herein an "antibody" refers to IgG, IgM, IgA, IgD or IgE or a fragment (such as a Fab, F(ab')$_2$, Fv, disulphide linked Fv, scFv, closed conformation multispecific antibody, disulphide-linked scFv, diabody) whether derived from any species naturally producing an antibody, or created by recombinant DNA technology; whether isolated from, for example, serum, B-cells, hybridomas, transfectomas, yeast or bacteria.

Antibody format: In one embodiment, the immunoglobulin single variable domain, polypeptide or ligand in accordance with the disclosure can be provided in any antibody format. As used herein, "antibody format" refers to any suitable polypeptide structure in which one or more antibody variable domains can be incorporated so as to confer binding specificity for antigen on the structure. A variety of suitable antibody formats are known in the art, such as, chimeric antibodies, humanized antibodies, human antibodies, single chain antibodies, bispecific antibodies, antibody heavy chains, antibody light chains, homodimers and heterodimers of antibody heavy chains and/or light chains, antigen-binding fragments of any of the foregoing (e.g., a Fv fragment (e.g., single chain Fv (scFv), a disulfide bonded Fv), a Fab fragment, a Fab' fragment, a F(ab')$_2$ fragment), a single antibody variable domain (e.g., a dAb, $V_H$, $V_{HH}$, $V_L$, and modified versions of any of the foregoing (e.g., modified by the covalent attachment of polyethylene glycol or other suitable polymer or a humanized $V_{HH}$). In one embodiment, alternative antibody formats include alternative scaffolds in which the CDRs of any molecules in accordance with the disclosure can be grafted onto a suitable protein scaffold or skeleton, such as an affibody, a SpA scaffold, an LDL receptor class A domain, an avimer (see, e.g., U.S. Patent Application Publication Nos. 2005/0053973, 2005/0089932, 2005/0164301) or an EGF domain. Further, the ligand can be bivalent (heterobivalent) or multivalent (heteromultivalent) as described herein. In other embodiments, a "Universal framework" may be used wherein "Universal framework" refers to a single antibody framework sequence corresponding to the regions of an antibody conserved in sequence as defined by Kabat ("Sequences of Proteins of Immunological Interest", US Department of Health and Human Services) or corresponding to the human germline immunoglobulin repertoire or structure as defined by Chothia and Lesk, (1987) J. Mol. Biol. 196:910-917. The disclosure provides for the use of a single framework, or a set of such frameworks, which has been found to permit the derivation of virtually any binding specificity through variation in the hypervariable regions alone.

In embodiments of the disclosure described throughout this disclosure, instead of the use of an anti-TGFbetaRII "dAb" in a peptide or ligand of the disclosure, it is contemplated that one of ordinary skill in the art can use a polypeptide or domain that comprises one or more or all 3 of the CDRs of a dAb of the disclosure that binds TGFbetaRII (e.g., CDRs grafted onto a suitable protein scaffold or skeleton, e.g. an affibody, an SpA scaffold, an LDL receptor class A domain or an EGF domain). The disclosure as a whole is to be construed accordingly to provide disclosure of polypeptides using such domains in place of a dAb. In this respect, see WO2008096158, the disclosure of which is incorporated by reference.

In one embodiment, the anti-TGFbetaRII immunoglobulin single variable domain is any suitable immunoglobulin variable domain, and optionally is a human variable domain or a variable domain that comprises or is derived from a human framework region (e.g., DP47 or DPK9 framework regions).

Antigen: As described herein an "antigen" is a molecule that is bound by a binding domain according to the present disclosure. Typically, antigens are bound by antibody ligands and are capable of raising an antibody response in vivo. It may be, for example, a polypeptide, protein, nucleic acid or other molecule.

Epitope: An "epitope" is a unit of structure conventionally bound by an immunoglobulin $V_H/V_L$ pair. Epitopes define the minimum binding site for an antibody, and thus represent the target of specificity of an antibody. In the case of a single domain antibody, an epitope represents the unit of structure bound by a variable domain in isolation.

Binding: Typically, specific binding is indicated by a dissociation constant (Kd) of 50 nanomolar or less, optionally 250 picomolar or less. Specific binding of an antigen-binding protein to an antigen or epitope can be determined by a suitable assay, including, for example, Scatchard analysis and/or competitive binding assays, such as radioimmunoassays (RIA), enzyme immunoassays such as ELISA and sandwich competition assays, and the different variants thereof.

Binding affinity: Binding affinity is optionally determined using surface plasmon resonance (SPR) and BIACORE™ (Karlsson et al., 1991), using a BIACORE™ system (Uppsala, Sweden). The BIACORE™ system uses surface plasmon resonance (SPR, Welford K. 1991, Opt. Quant. Elect. 23:1; Morton and Myszka, 1998, Methods in Enzymology 295: 268) to monitor biomolecular interactions in real time, and uses surface plasmon resonance which can detect changes in the resonance angle of light at the surface of a thin gold film on a glass support as a result of changes in the refractive index of the surface up to 300 nm away. BIACORE™ analysis conveniently generates association rate constants, dissociation rate constants, equilibrium dissociation constants, and affinity constants. Binding affinity is obtained by assessing the association and dissociation rate constants using a BIACORE™ surface plasmon resonance system (BIACORE™, Inc.). A biosensor chip is activated for covalent coupling of the target according to the manufacturer's (BIACORE™) instructions. The target is then diluted and injected over the chip to obtain a signal in response units of immobilized material. Since the signal in resonance units (RU) is proportional to the mass of immobilized material, this represents a range of immobilized target densities on the matrix. Dissociation data are fit to a one-site model to obtain $k_{off}$+/−s.d. (standard deviation of measurements). Pseudo-first order rate constant (Kd's) are calculated for each association curve, and plotted as a function of protein concentration to obtain $k_{on}$+/−s.e. (standard error of fit). Equilibrium dissociation constants for binding, Kd's, are calculated from SPR measurements as $k_{off}/k_{on}$.

Another aspect of the disclosure provides an anti-TGFbetaRII immunoglobulin single variable domain that specifically binds to human TGFbetaRII. In one embodiment, the variable domain binds human TGFbetaRII with an equilibrium dissociation constant (KD) of about 50 nM, 40 nM, 30 nM, 20 nM, 10 nM or less, optionally about 9, 8, 7, 6 or 5 nM or less, optionally about 4 nM or less, about 3 nM or less or about 2 nM or less or about 1 nM or less, optionally about 500 pM or less. Suitably, where the variable domain has an equilibrium dissociation constant in the range of about 50 nM to 500 pM, it is particularly suitable for local administration to a tissue of interest such as the lung. In this embodiment, a high concentration of such a "moderate affinity" binder can be provided as an effective therapeutic. In another embodiment, the variable domain binds human TGFbetaRII with an equilibrium dissociation constant (KD) of about 500 pM or less, optionally about 450 pM, 400 pM, 350 pM, 300 pM, 250 pM, 200 pM, 150 pM, 100 pM, 50 pM or less, optionally about 40 pM, 30 pM, 20 pM, 10 pM or less. Suitably, where the variable domain has a dissociation constant in the range of about 500 pM to 10 pM, it is particularly suitable for systemic administration such that the amount in any one tissue of interest is sufficient to provide an effective therapy. In this embodiment, a low concentration of such a "high affinity" binder can be provided as an effective therapeutic.

In one embodiment, single variable domains of the present disclosure show cross-reactivity between human TGFbetaRII and TGFbetaRII from another species, such as mouse TGFbetaRII. In this embodiment, the variable domains specifically bind human and mouse TGFbetaRII. This is particularly useful, since drug development typically requires testing of lead drug candidates in mouse systems before the drug is tested in humans. The provision of a drug that can bind human and mouse species allows one to test results in these system and make side-by-side comparisons of data using the same drug. This avoids the complication of needing to find a drug that works against a mouse TGFbetaRII and a separate drug that works against human TGFbetaRII, and also avoids the need to compare results in humans and mice using non-identical drugs. Cross reactivity between other species used in disease models such as dog or monkey such as cynomolgus monkey is also envisaged.

Optionally, the binding affinity of the immunoglobulin single variable domain for at least mouse TGFbetaRII and the binding affinity for human TGFbetaRII differ by no more than a factor of 10, 50 or 100.

CDRs: The immunoglobulin single variable domains (dAbs) described herein contain complementarity determining regions (CDR1, CDR2 and CDR3). The locations of CDRs and frame work (FR) regions and a numbering system have been defined by Kabat et al. (Kabat, E. A. et al., Sequences of Proteins of Immunological Interest, Fifth Edition, U.S. Department of Health and Human Services, U.S. Government Printing Office (1991)). The amino acid sequences of the CDRs (CDR1, CDR2, CDR3) of the $V_H$ (CDRH1 etc.) and $V_L$ (CDRL1 etc.) (Vκ) dAbs disclosed herein will be readily apparent to the person of skill in the art based on the well known Kabat amino acid numbering system and definition of the CDRs. According to the Kabat numbering system, the most commonly used method based on sequence variability, heavy chain CDR-H3 have varying lengths, insertions are numbered between residue H100 and H101 with letters up to K (i.e. H100, H100A . . . H100K, H101). CDRs can alternatively be determined using the system of Chothia (based on location of the structural loop regions) (Chothia et al., (1989) Conformations of immunoglobulin hypervariable regions; Nature 342, p877-883), according to AbM (compromise between Kabat and Chothia) or according to the Contact method (based on crystal structures and prediction of contact residues with antigen) as follows. See http://www.bioinf.org.uk/abs/for suitable methods for determining CDRs.

Once each residue has been numbered, one can then apply the following CDR definitions:

| Kabat: |
|---|
| CDR H1: 31-35/35A/35B |
| CDR H2: 50-65 |
| CDR H3: 95-102 |
| CDR L1: 24-34 |

-continued

CDR L2: 50-56
CDR L3: 89-97

Chothia:

CDR H1: 26-32
CDR H2: 52-56
CDR H3: 95-102
CDR L1: 24-34
CDR L2: 50-56
CDR L3: 89-97

AbM:

| (using Kabat numbering): | (using Chothia numbering): |
|---|---|
| CDR H1: 26-35/35A/35B | 26-35 |
| CDR H2: 50-58 | — |
| CDR H3: 95-102 | — |
| CDR L1: 24-34 | — |
| CDR L2: 50-56 | — |
| CDR L3: 89-97 | — |

Contact:

| (using Kabat numbering): | (using Chothia numbering): |
|---|---|
| CDR H1: 30-35/35A/35B | 30-35 |
| CDR H2: 47-58 | — |
| CDR H3: 93-101 | — |
| CDR L1: 30-36 | — |
| CDR L2: 46-55 | — |
| CDR L3: 89-96 | — |

("—" means the same numbering as Kabat)

Accordingly, a person skilled in the art is able to deduce from a given single variable domain sequence, e.g. one having a sequence as set out in any one of SEQ ID NO:1-38, 204, 206, 208, 214, 234, 236, 238, 240, 263, 265, 267, 269, 271, 273, 275, 277, 279, 281, 283, 285 and 287 which CDR sequences are contained within them using the various methods outlined herein. For example, for a given single variable domain sequence e.g. SEQ ID NO:1 a skilled person is able to determine the CDR1, CDR2 and CDR3 sequences contained therein using any one or a combination of the CDR definition methods mentioned above. When using the Kabat CDR definition, the skilled person is able to determine that CDR1, CDR2 and CDR 3 sequences are those set forth in SEQ ID NO:77, 113 and 149 respectively. Suitably, CDR sequences are determined using the method of Kabat described herein. In one embodiment, the CDR sequences of each sequence are those set out in tables 1, 2, 9 and 13. In an embodiment a CDR1 sequence is a CDR1 sequence selected from SEQ ID NO:77-112, 241, 244, 247, and 250. In an embodiment a CDR2 sequence is a CDR2 sequence selected from SEQ ID NO:113-148, 242, 245, 248, and 251. In an embodiment a CDR3 sequence is a CDR3 sequence selected from SEQ ID NO:149-184, 243, 246, 249, and 252.

A CDR variant or variant binding unit includes an amino acid sequence modified by at least one amino acid, wherein said modification can be chemical or a partial alteration of the amino acid sequence (for example by no more than 10 amino acids), which modification permits the variant to retain the biological characteristics of the unmodified sequence. For example, the variant is a functional variant which specifically binds to TGFbetaRII. A partial alteration of the CDR amino acid sequence may be by deletion or substitution of one to several amino acids, or by addition or insertion of one to several amino acids, or by a combination thereof (for example by no more than 10 amino acids). The CDR variant or binding unit variant may contain 1, 2, 3, 4, 5 or 6 amino acid substitutions, additions or deletions, in any combination, in the amino acid sequence. The CDR variant or binding unit variant may contain 1, 2 or 3 amino acid substitutions, insertions or deletions, in any combination, in the amino acid sequence. The substitutions in amino acid residues may be conservative substitutions, for example, substituting one hydrophobic amino acid for an alternative hydrophobic amino acid. For example leucine may be substituted with valine, or isoleucine.

TGFbetaRII: As used herein "TGFbetaRII" (transforming growth factor beta type II receptor; TGFβRII) refers to naturally occurring or endogenous mammalian TGFbetaRII proteins and to proteins having an amino acid sequence which is the same as that of a naturally occurring or endogenous corresponding mammalian TGFbetaRII protein (e.g., recombinant proteins, synthetic proteins (i.e., produced using the methods of synthetic organic chemistry)). Accordingly, as defined herein, the term includes mature TGFbetaRII protein, polymorphic or allelic variants, and other isoforms of TGFbetaRII and modified or unmodified forms of the foregoing (e.g., lipidated, glycosylated). Naturally occurring or endogenous TGFbetaRII includes wild type proteins such as mature TGFbetaRII, polymorphic or allelic variants and other isoforms and mutant forms which occur naturally in mammals (e.g., humans, non-human primates). Such proteins can be recovered or isolated from a source which naturally expresses TGFbetaRII, for example. These proteins and proteins having the same amino acid sequence as a naturally occurring or endogenous corresponding TGFbetaRII, are referred to by the name of the corresponding mammal. For example, where the corresponding mammal is a human, the protein is designated as a human TGFbetaRII. Human TGFbetaRII is described, for example, by Lin, et al., Cell 1992, Vol. 68(4), p. 775-785 and GenBank Accession No. M85079.

Human TGFbetaRII is a transmembrane receptor consisting of 567 amino acids with an extracellular domain of approximately 159 amino acids, a transmembrane domain and a cytoplasmic domain which comprises a protein kinase domain for signal transduction.

As used herein "TGFbetaRII" also includes a portion or fragment of TGFbetaRII. In one embodiment, such a portion or fragment includes the extracellular domain of TGFbetaRII or a portion thereof.

By "anti-TGFbetaRII" with reference to an immunoglobulin single variable domain, polypeptide, ligand, fusion protein or so forth is meant a moiety which recognises and binds TGFbetaRII. In one embodiment an "anti-TGFbetaRII" specifically recognises and/or specifically binds to the protein TGFbetaRII, and, suitably, human TGFbetaRII. In another embodiment, the anti-TGFbetaRII immunoglobulin single variable domain in accordance with the disclosure also binds to mouse TGFbetaRII (GenBank accession number NM_029575; described, for example in Massague et al., Cell 69 (7), 1067-1070 (1992)).

"TGFbeta" includes isoforms such as TGFbeta1, TGFbeta2 and TGFbeta3.

TGFbeta binds TGFbetaRII and, in a complex with TGFbetaRI initiates a signaling pathway. Accordingly, TGFbeta activity and inhibition or neutralization of TGFbeta activity can be determined through any assay which measures an output of TGFbeta signaling. TGFbeta signaling is reviewed, for example in Itoh, et al., Eur. J. Biochem 2000, Vol. 267, p. 6954; Dennler, et al., Journal of Leucocyte Biol. 2002, 71(5), p. 731-40. Thus, TGFbeta activity can be tested in a number of different assays familiar to the person skilled in the art. "Inhibition" or "Neutralization" means that a biological activity of TGFbeta is reduced either totally or partially in the presence of the immunoglobulin single variable domain of the present disclosure in comparison to the activity of TGF-beta in the absence of such immunoglobulin single variable domain.

In one embodiment, an inhibition or neutralisation of TGF-beta activity is tested in an IL-11 release assay. In this embodiment, the ability of the immunoglobulin single variable domain in accordance with the disclosure is tested for its ability to inhibit human TGFbeta1 (TGFbeta1; TGF-β1) stimulated IL-11 release from cells such as A549 cells. TGF-beta1 (TGF-β1) binds directly to TGFbetaRII (TGF-βRII) and induces the assembly of the TGFbetaRI/RII (TGF-βRI/II) complex. TGFbetaRI (TGF-βRI) is phosphorylated and is able to signal through several pathways including the Smad 4 pathway. Activation of the Smad 4 pathway results in the release of IL-11. The IL-11 is secreted into the cell supernatant and is then measured by colourmetric ELISA. Suitable IL-11 release assays are described herein, such as the Human IL-11 Quantikine ELISA assay kit supplied by R & D systems (ref. D1100).

In another embodiment, TGFbeta activity is tested in an assay for the ability of the immunoglobulin single variable domain in accordance with the disclosure to inhibit TGFbeta-induced expression of CAGA-luciferase in MC3T3-E1 cells in a MC3T3-E1 luciferase assay. Three copies of a TGFbeta-responsive sequence motif, termed a CAGA box are present in the human PAI-1 promoter and specifically binds Smad3 and 4 proteins. Cloning multiple copies of the CAGA box into a luciferase reporter construct confers TGFbeta responsiveness to cells transfected with the reporter system. One suitable assay is described herein and uses MC3T3-E1 cells (mouse osteoblasts) stably transfected with a $[CAGA]_{12}$-luciferase reporter construct (Dennler, et al., (1998) EMBO J. 17, 3091-3100).

Other suitable assays include a human SBE beta-lactamase cell assay (INVITROGEN®, cell sensor assay). Examples of suitable assays are described herein.

Suitably, the immunoglobulin single variable domain, polypeptide, ligand or fusion protein in accordance with the disclosure does not, itself activate TGFbetaRII receptor signalling. Accordingly, in one embodiment, the immunoglobulin single variable domain, polypeptide, ligand or fusion protein in accordance with the disclosure is devoid of agonist activity at 10 μM. Agonist activity can be determined by testing a compound of interest in a TGFbetaRII assay as described herein in the absence of TGFbeta. Where TGFbeta is absent, agonist activity of a compound of interest would be detected by detecting TGFbetaRII signalling.

Homology: Sequences similar or homologous (e.g., at least about 70% sequence identity) to the sequences disclosed herein are also part of the disclosure. In some embodiments, the sequence identity at the amino acid level can be about 75%, 80%, 85%, 90%, 91%, 92%, 93%, 94%, 95%, 96%, 97%, 98%, 99% or higher. At the nucleic acid level, the sequence identity can be about 60%, 65%, 70%, 75%, 80%, 85%, 90%, 91%, 92%, 93%, 94%, 95%, 96%, 97%, 98%, 99% or higher. Alternatively, substantial identity exists when the nucleic acid segments will hybridize under selective hybridization conditions (e.g., very high stringency hybridization conditions), to the complement of the strand. The nucleic acids may be present in whole cells, in a cell lysate, or in a partially purified or substantially pure form.

As used herein, the terms "low stringency," "medium stringency," "high stringency," or "very high stringency" conditions describe conditions for nucleic acid hybridization and washing. Guidance for performing hybridization reactions can be found in Current Protocols in Molecular Biology, John Wiley & Sons, N.Y. (1989), 6.3.1-6.3.6, which is incorporated herein by reference in its entirety. Aqueous and non-aqueous methods are described in that reference and either can be used. Specific hybridization conditions referred to herein are as follows: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and optionally (4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

Calculations of "homology" or "sequence identity" or "similarity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least about 30%, optionally at least about 40%, optionally at least about 50%, optionally at least about 60%, and optionally at least about 70%, 80%, 85% 90%, 91%, 92%, 93%, 94%, 95%, 96%, 97%, 98%, 99% or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "homology" is equivalent to amino acid or nucleic acid "identity"). The percent identity between the two sequences is a function of the number of identical positions shared by the sequences, taking into account the number of gaps, and the length of each gap, which need to be introduced for optimal alignment of the two sequences.

Amino acid and nucleotide sequence alignments and homology, similarity or identity, as defined herein are optionally prepared and determined using the algorithm BLAST 2 Sequences, using default parameters (Tatusova, T. A. et al., FEMS Microbiol Lett, 174:187-188 (1999)). Alternatively, the BLAST algorithm (version 2.0) is employed for sequence alignment, with parameters set to default values. BLAST (Basic Local Alignment Search Tool) is the heuristic search algorithm employed by the programs blastp, blastn, blastx, tblastn, and tblastx; these programs ascribe significance to their findings using the statistical methods of Karlin and Altschul, 1990, Proc. Natl. Acad. Sci. USA 87(6):2264-8.

Ligand: As used herein, the term "ligand" refers to a compound that comprises at least one peptide, polypeptide or protein moiety that has a binding site with binding specificity for TGFbetaRII. A ligand can also be referred to as a "binding moiety".

The ligands or binding moieties according to the disclosure optionally comprise immunoglobulin variable domains which have different binding specificities, and do not contain variable domain pairs which together form a binding site for target compound (i.e., do not comprise an immunoglobulin heavy chain variable domain and an immunoglobulin light chain variable domain that together form a binding site for TGFbetaRII). Optionally, each domain which has a binding site that has binding specificity for a target is an immunoglobulin single variable domain (e.g., immunoglobulin single heavy chain variable domain (e.g., $V_H$, $V_{HH}$), immunoglobulin single light chain variable domain (e.g., $V_L$)) that has binding specificity for a desired target (e.g., TGFbetaRII).

Thus, "ligands" include polypeptides that comprise two or more immunoglobulin single variable domains wherein each immunoglobulin single variable domain binds to a different target. Ligands also include polypeptides that comprise at least two immunoglobulin single variable domains or the CDR sequences of the single variable domains that bind different targets in a suitable format, such as an antibody format (e.g., IgG-like format, scFv, Fab, Fab', F(ab')$_2$) or a suitable protein scaffold or skeleton, such as an affibody, a SpA scaffold, an LDL receptor class A domain, an EGF domain, avimer and dual- and multi-specific ligands as described herein.

The polypeptide domain which has a binding site that has binding specificity for a target (e.g., TGFbetaRII) can also be a protein domain comprising a binding site for a desired target, e.g., a protein domain is selected from an affibody, a SpA domain, an LDL receptor class A domain, an avimer (see, e.g., U.S. Patent Application Publication Nos. 2005/0053973, 2005/0089932, 2005/0164301). If desired, a "ligand" can further comprise one or more additional moieties that can each independently be a peptide, polypeptide or protein moiety or a non-peptidic moiety (e.g., a polyalkylene glycol, a lipid, a carbohydrate). For example, the ligand can further comprise a half-life extending moiety as described herein (e.g., a polyalkylene glycol moiety, a moiety comprising albumin, an albumin fragment or albumin variant, a moiety comprising transferrin, a transferrin fragment or transferrin variant, a moiety that binds albumin, a moiety that binds neonatal Fc receptor).

Competes: As referred to herein, the term "competes" means that the binding of a first target (e.g., TGFbetaRII) to its cognate target binding domain (e.g., immunoglobulin single variable domain) is inhibited in the presence of a second binding domain (e.g., immunoglobulin single variable domain) that is specific for said cognate target. For example, binding may be inhibited sterically, for example by physical blocking of a binding domain or by alteration of the structure or environment of a binding domain such that its affinity or avidity for a target is reduced. See WO2006038027 for details of how to perform competition ELISA and competition BIA-CORE™ experiments to determine competition between first and second binding domains, the details of which are incorporated herein by reference to provide explicit disclosure for use in the present disclosure. The disclosure includes antigen binding proteins, specifically single variable domains, polypeptides, ligands and fusion proteins, that compete with any one of single variable domains of SEQ ID NO:1-38. In a particular embodiment there is provided a TGFbetaRII binding protein which competes with any one of single variable domains of SEQ ID NO:1-38 and also has a KD of 50 nM or less to TGFbetaRII. In a particular embodiment the KD is between 10 pM and 50 nM. In a particular embodiment, the KD is between 10 pM and 10 nM. In a particular embodiment, the KD is between 100 pM and 10 nM. In a particular embodiment the KD is approximately 100 pM.

TGFbeta signaling: Suitably, the single variable domain, polypeptide or ligand of the disclosure can neutralize TGFbeta signaling through TGFbetaRII. By "neutralizing", it is meant that the normal signaling effect of TGFbeta is blocked such that the presence of TGFbeta has a neutral effect on TGFbetaRII signaling. Suitable methods for measuring a neutralizing effect include assays for TGFbeta signaling as described herein. In one embodiment, neutralization is observed as a % inhibition of TFGbeta activity in a TGFbeta signaling assay. In one embodiment, the single variable domain or polypeptide binds to the extracellular domain of TGFbetaRII thereby inhibiting/blocking the binding of TGFbeta to the extracellular domain of TGFbetaRII. Suitably, the single variable domain or polypeptide is useful where there is an excess of bioavailable TGFbeta and the single variable domain or polypeptide serves to inhibit the signaling activity of the bioavailable TGFbeta through inhibiting binding or TGFbeta to its cognate receptor TGFbetaRII.

As used herein, the term "antagonist of TGFbetaRII" or "anti-TGFbetaRII antagonist" or the like refers to an agent (e.g., a molecule, a compound) which binds TGFbetaRII and can inhibit a (i.e., one or more) function of TGFbetaRII. For example, an antagonist of TGFbetaRII can inhibit the binding of TGFbeta to TGFbetaRII and/or inhibit signal transduction mediated through TGFbetaRII. Accordingly, TGFbeta-mediated processes and cellular responses can be inhibited with an antagonist of TGFbetaRII.

In one embodiment, the ligand (e.g., immunoglobulin single variable domain) that binds TGFbetaRII inhibits binding of TGFbeta to a TGFbetaRII receptor with an inhibitory concentration 50 (IC50) that is ≤about 10 µM, ≤about 1 µM, ≤about 100 nM, ≤about 50 nM, ≤about 10 nM, ≤about 5 nM, ≤about 1 nM, ≤about 500 pM, ≤about 300 pM, ≤about 100 pM, or ≤about 10 pM. In a particular embodiment, an anti-TGFbetaRII immunoglobulin single variable domain of the disclosure has an IC50 of 15 µM or less. The IC50 is optionally determined using an in vitro TGFbeta receptor binding assay, or cell assay, such as the assay described herein.

It is also contemplated that the ligand (e.g., immunoglobulin single variable domain) optionally inhibit TGFbetaRII induced functions in a suitable in vitro assay with a neutralizing dose 50 (ND50) that is ≤about 10 µM, ≤about 1 µM, ≤about 100 nM, ≤about 50 nM, ≤about 10 nM, ≤about 5 nM, ≤about 1 nM, ≤about 500 pM, ≤about 300 pM, ≤about 100 pM, ≤about 10 pM, ≤about 1 pM about 500 fM, ≤about 300 fM, ≤about 100 fM, ≤about 10 fM. In a particular embodiment, an anti-TGFbetaRII immunoglobulin single variable domain of the disclosure achieves greater than 40% neutralisation of TGF-β.

"dual-specific ligand": In one embodiment, the immunoglobulin single variable domain, polypeptide or ligand in accordance with the disclosure can be part of a "dual-specific ligand" which refers to a ligand comprising a first antigen or epitope binding site (e.g., first immunoglobulin single variable domain) and a second antigen or epitope binding site (e.g., second immunoglobulin single variable domain), wherein the binding sites or variable domains are capable of binding to two antigens (e.g., different antigens or two copies of the same antigen) or two epitopes on the same antigen which are not normally bound by a monospecific immunoglobulin. For example, the two epitopes may be on the same antigen, but are not the same epitope or sufficiently adjacent to be bound by a monospecific ligand. In one embodiment, dual-specific ligands according to the disclosure are composed of binding sites or variable domains which have different specificities, and do not contain mutually complementary variable domain pairs (i.e. $V_H/V_L$ pairs) which have the same specificity (i.e., do not form a unitary binding site).

In one embodiment, a "dual-specific ligand" may bind to TGFbetaRII and to another target molecule. For example, another target molecule may be a tissue-specific target molecule such that the dual-specific ligand of the disclosure enables an anti-TGFbetaRII polypeptide or immunoglobulin single variable domain in accordance with the disclosure to be targeted to a tissue of interest. Such tissues include lung, liver and so forth.

Multispecific dAb multimers are also provided. This includes a dAb multimer comprising an anti-TGFbetaRII immunoglobulin single variable domain according to any aspect of the disclosure and one or more single variable domains each of which binds to a different target (e.g. a target other than TGFbetaRII). In an embodiment a bispecific dAb multimer is provided e.g. a dab multimer comprising one or more anti-TGFbetaRII immunoglobulin single variable domains according to any aspect of the disclosure and one or more dabs which bind to a second, different target. In an embodiment a trispecific dAb multimer is provided.

The ligands of the disclosure (e.g., polypeptides, dAbs and antagonists) can be formatted as a fusion protein that contains a first immunoglobulin single variable domain that is fused directly to a second immunoglobulin single variable domain. If desired such a format can further comprise a half-life extending moiety. For example, the ligand can comprise a first immunoglobulin single variable domain that is fused directly to a second immunoglobulin single variable domain that is fused directly to an immunoglobulin single variable domain that binds serum albumin.

Generally, the orientation of the polypeptide domains that have a binding site with binding specificity for a target, and whether the ligand comprises a linker, is a matter of design choice. However, some orientations, with or without linkers, may provide better binding characteristics than other orientations. All orientations (e.g., dAb1-linker-dAb2; dAb2-linker-dAb1) are encompassed by the disclosure are ligands that contain an orientation that provides desired binding characteristics can be easily identified by screening.

Polypeptides and dAbs according to the disclosure, including dAb monomers, dimers and trimers, can be linked to an antibody Fc region, comprising one or both of $C_H2$ and $C_H3$ domains, and optionally a hinge region. For example, vectors encoding ligands linked as a single nucleotide sequence to an Fc region may be used to prepare such polypeptides. In an embodiment there is provided a dAb-Fc fusion.

The disclosure moreover provides dimers, trimers and polymers of the aforementioned dAb monomers.

Target: As used herein, the phrase "target" refers to a biological molecule (e.g., peptide, polypeptide, protein, lipid, carbohydrate) to which a polypeptide domain which has a binding site can bind. The target can be, for example, an intracellular target (e.g., an intracellular protein target), a soluble target (e.g., a secreted), or a cell surface target (e.g., a membrane protein, a receptor protein). In one embodiment, the target is TGFbetaRII. In another embodiment, the target is TGFbetaRII extracellular domain.

Complementary: As used herein "complementary" refers to when two immunoglobulin domains belong to families of structures which form cognate pairs or groups or are derived from such families and retain this feature. For example, a $V_H$ domain and a $V_L$ domain of an antibody are complementary; two $V_H$ domains are not complementary, and two $V_L$ domains are not complementary. Complementary domains may be found in other members of the immunoglobulin superfamily, such as the Vα and Vβ (or γ and δ) domains of the T-cell receptor. Domains which are artificial, such as domains based on protein scaffolds which do not bind epitopes unless engineered to do so, are non-complementary. Likewise, two domains based on (for example) an immunoglobulin domain and a fibronectin domain are not complementary.

"Affinity" and "avidity" are terms of art that describe the strength of a binding interaction. With respect to the ligands of the disclosure, avidity refers to the overall strength of binding between the targets (e.g., first target and second target) on the cell and the ligand. Avidity is more than the sum of the individual affinities for the individual targets.

Nucleic acid molecules, vectors and host cells: The disclosure also provides isolated and/or recombinant nucleic acid molecules encoding ligands (single variable domains, fusion proteins, polypeptides, dual-specific ligands and multispecific ligands) as described herein.

Nucleic acids referred to herein as "isolated" are nucleic acids which have been separated away from the nucleic acids of the genomic DNA or cellular RNA of their source of origin (e.g., as it exists in cells or in a mixture of nucleic acids such as a library), and include nucleic acids obtained by methods described herein or other suitable methods, including essentially pure nucleic acids, nucleic acids produced by chemical synthesis, by combinations of biological and chemical methods, and recombinant nucleic acids which are isolated (see e.g., Daugherty, B. L. et al., Nucleic Acids Res., 19(9): 2471 2476 (1991); Lewis, A. P. and J. S. Crowe, Gene, 101: 297-302 (1991)).

Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes.

In certain embodiments, the isolated and/or recombinant nucleic acid comprises a nucleotide sequence encoding an immunoglobulin single variable domain, polypeptide or ligand, as described herein, wherein said ligand comprises an amino acid sequence that has at least about 80%, at least about 85%, at least about 90%, at least about 91%, at least about 92%, at least about 93%, at least about 94%, at least about 95%, at least about 96%, at least about 97%, at least about 98%, or at least about 99% amino acid sequence identity with the amino acid sequence of a dAb that binds TGFbetaRII disclosed herein, e.g. amino acid sequences set out in any of SEQ ID NOS: 1-38. Nucleotide sequence identity can be determined over the whole length of the nucleotide sequence that encodes the selected anti-TGFbetaRII dAb. In an embodiment the nucleic acid sequence comprises or consists of a nucleic acid sequence at least 80% identical to of any one of SEQ ID NO:39-66. In an embodiment the nucleic acid sequence comprises or consists of a nucleic acid sequence of any one of SEQ ID NO:39-76.

Embodiments of the disclosure also provide codon optimized nucleotide sequences encoding polypeptides and variable domains as disclosed herein e.g. optimised for expression in bacterial, mammalian or yeast cells.

The disclosure also provides a vector comprising a recombinant nucleic acid molecule of the disclosure. In certain embodiments, the vector is an expression vector comprising one or more expression control elements or sequences that are operably linked to the recombinant nucleic acid of the disclosure. The disclosure also provides a recombinant host cell comprising a recombinant nucleic acid molecule or vector of the disclosure. Suitable vectors (e.g., plasmids, phagemids), expression control elements, host cells and methods for producing recombinant host cells of the disclosure are well-known in the art, and examples are further described herein.

Suitable expression vectors can contain a number of components, for example, an origin of replication, a selectable marker gene, one or more expression control elements, such as a transcription control element (e.g., promoter, enhancer, terminator) and/or one or more translation signals, a signal sequence or leader sequence, and the like. Expression control elements and a signal sequence, if present, can be provided by the vector or other source. For example, the transcriptional and/or translational control sequences of a cloned nucleic acid encoding an antibody chain can be used to direct expression.

A promoter can be provided for expression in a desired host cell. Promoters can be constitutive or inducible. For example, a promoter can be operably linked to a nucleic acid encoding an antibody, antibody chain or portion thereof, such that it directs transcription of the nucleic acid. A variety of suitable promoters for prokaryotic (e.g., lac, tac, T3, T7 promoters for E. coli) and eukaryotic (e.g., Simian Virus 40 early or late promoter, Rous sarcoma virus long terminal repeat promoter, cytomegalovirus promoter, adenovirus late promoter) hosts are available.

In addition, expression vectors typically comprise a selectable marker for selection of host cells carrying the vector, and, in the case of a replicable expression vector, an origin of replication. Genes encoding products which confer antibiotic or drug resistance are common selectable markers and may be used in prokaryotic (e.g., lactamase gene (ampicillin resistance), Tet gene for tetracycline resistance) and eukaryotic cells (e.g., neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated. Suitable expression vectors for expression in mammalian cells and prokaryotic cells (E. coli), insect cells (Drosophila Schnieder S2 cells, Sf9) and yeast (P. methanolica, P. pastoris, S. cerevisiae) are well-known in the art.

Suitable host cells can be prokaryotic, including bacterial cells such as E. coli, B. subtilis and/or other suitable bacteria; eukaryotic cells, such as fungal or yeast cells (e.g., Pichia pastoris, Aspergillus sp., Saccharomyces cerevisiae, Schizosaccharomyces pombe, Neurospora crassa), or other lower eukaryotic cells, and cells of higher eukaryotes such as those from insects (e.g., Drosophila Schnieder S2 cells, Sf9 insect cells (WO 94/26087 (O'Connor)), mammals (e.g., COS cells, such as COS-1 (ATCC Accession No. CRL-1650) and COS-7 (ATCC Accession No. CRL-1651), CHO (e.g., ATCC Accession No. CRL-9096, CHO DG44 (Urlaub, G. and Chasin, L A., Proc. Natl. Acad. Sci. USA, 77(7):4216-4220 (1980))), 293 (ATCC Accession No. CRL-1573), HeLa (ATCC Accession No. CCL-2), CV1 (ATCC Accession No. CCL-70), WOP (Dailey, L., et al., J. Virol., 54:739-749 (1985), 3T3, 293T (Pear, W. S., et al., Proc. Natl. Acad. Sci. U.S.A., 90:8392-8396 (1993)) NS0 cells, SP2/0, HuT 78 cells and the like, or plants (e.g., tobacco). (See, for example, Ausubel, F. M. et al., eds. Current Protocols in Molecular Biology, Greene Publishing Associates and John Wiley & Sons Inc. (1993). In some embodiments, the host cell is an isolated host cell and is not part of a multicellular organism (e.g., plant or animal). In certain embodiments, the host cell is a non-human host cell. The disclosure also provides a method for producing a ligand (e.g., dual-specific ligand, multispecific ligand) of the disclosure, comprising maintaining a recombinant host cell comprising a recombinant nucleic acid of the disclosure under conditions suitable for expression of the recombinant nucleic acid, whereby the recombinant nucleic acid is expressed and a ligand is produced. In some embodiments, the method further comprises isolating the ligand.

Reference is made to WO200708515, page 161, line 24 to page 189, line 10 for details of disclosure that is applicable to embodiments of the present disclosure. This disclosure is hereby incorporated herein by reference as though it appears explicitly in the text of the present disclosure and relates to the embodiments of the present disclosure, and to provide explicit support for disclosure to incorporated into claims below. This includes disclosure presented in WO200708515, page 161, line 24 to page 189, line 10 providing details of the "Preparation of Immunoglobulin Based Ligands", "Library vector systems", "Library Construction", "Combining Single Variable Domains", "Characterisation of Ligands", "Structure of Ligands", "Skeletons", "Protein Scaffolds", "Scaffolds for Use in Constructing Ligands", "Diversification of the Canonical Sequence" and "Therapeutic and diagnostic compositions and uses", as well as definitions of "operably linked", "naive", "prevention", "suppression", "treatment", "allergic disease", "Th2-mediated disease", "therapeutically-effective dose" and "effective".

The phrase, "half-life" refers to the time taken for the serum concentration of the immunoglobulin single variable domain, polypeptide or ligand to reduce by 50%, in vivo, for example due to degradation of the ligand and/or clearance or sequestration of the ligand by natural mechanisms. The ligands of the disclosure can be stabilized in vivo and their half-life increased by binding to molecules which resist degradation and/or clearance or sequestration. Typically, such molecules are naturally occurring proteins which themselves have a long half-life in vivo. The half-life of a ligand is increased if its functional activity persists, in vivo, for a longer period than a similar ligand which is not specific for the half-life increasing molecule. Thus a ligand specific for HSA and a target molecules is compared with the same ligand wherein the specificity to HSA is not present, that is does not bind HSA but binds another molecule. Typically, the half-life is increased by 10%, 20%, 30%, 40%, 50% or more. Increases in the range of 2×, 3×, 4×, 5×, 10×, 20×, 30×, 40×, 50× or more of the half-life are possible. Alternatively, or in addition, increases in the range of up to 30×, 40×, 50×, 60×, 70×, 80×, 90×, 100×, 150× of the half life are possible.

Formats: Increased half-life can be useful in in vivo applications of immunoglobulins, especially antibodies and most especially antibody fragments of small size. Such fragments (Fvs, disulphide bonded Fvs, Fabs, scFvs, dAbs) are generally rapidly cleared from the body. dAbs, polypeptides or ligands in accordance with the disclosure can be adapted to provide increased half-life in vivo and consequently longer persistence times in the body of the functional activity of the ligand.

Methods for pharmacokinetic analysis and determination of ligand half-life will be familiar to those skilled in the art. Details may be found in Kenneth, A et al: Chemical Stability of Pharmaceuticals: A Handbook for Pharmacists and in Peters et al, Pharmacokinetic analysis: A Practical Approach (1996). Reference is also made to "Pharmacokinetics", M Gibaldi & D Perron, published by Marcel Dekker, 2nd Rev. ex edition (1982), which describes pharmacokinetic parameters such as t alpha and t beta half lives and area under the curve (AUC).

Half lives (t½ alpha and t½ beta) and AUC can be determined from a curve of serum concentration of ligand against time. The WINNONLIN™ analysis package (available from Pharsight Corp., Mountain View, Calif. 94040, USA) can be used, for example, to model the curve. In a first phase (the alpha phase) the ligand is undergoing mainly distribution in the patient, with some elimination. A second phase (beta phase) is the terminal phase when the ligand has been distributed and the serum concentration is decreasing as the ligand is cleared from the patient. The t alpha half life is the half life of the first phase and the t beta half life is the half life of the second phase. Thus, in one embodiment, the present disclosure provides a ligand or a composition comprising a ligand according to the disclosure having a tα halflife in the range of 15 minutes or more. In one embodiment, the lower end of the range is 30 minutes, 45 minutes, 1 hour, 2 hours, 3 hours, 4 hours, 5 hours, 6 hours, 7 hours, 10 hours, 11 hours or 12 hours. In addition, or alternatively, a ligand or composition according to the disclosure will have a tα half life in the range of up to and including 12 hours. In one embodiment, the upper end of the range is 11, 10, 9, 8, 7, 6 or 5 hours. An example of a suitable range is 1 to 6 hours, 2 to 5 hours or 3 to 4 hours.

In one embodiment, the present disclosure provides a ligand (polypeptide, dAb or antagonist) or a composition comprising a ligand according to the disclosure having a tβ halflife in the range of about 2.5 hours or more. In one embodiment, the lower end of the range is about 3 hours, about 4 hours, about 5 hours, about 6 hours, about 7 hours, about 10 hours, about 11 hours, or about 12 hours. In addition, or alternatively, a ligand or composition according to the disclosure has a tβ halflife in the range of up to and including 21 days. In one embodiment, the upper end of the range is about 12 hours, about 24 hours, about 2 days, about 3 days, about 5 days, about 10 days, about 15 days or about 20 days. In one embodiment a ligand or composition according to the disclosure will have a tβ half life in the range about 12 to about 60 hours. In a further embodiment, it will be in the range about 12 to about 48 hours. In a further embodiment still, it will be in the range about 12 to about 26 hours.

In addition, or alternatively to the above criteria, the present disclosure provides a ligand or a composition comprising a ligand according to the disclosure having an AUC value (area under the curve) in the range of about 1 mg·min/ml or more. In one embodiment, the lower end of the range is about 5, about 10, about 15, about 20, about 30, about 100, about 200 or about 300 mg·min/ml. In addition, or alternatively, a ligand or composition according to the disclosure has an AUC in the range of up to about 600 mg·min/ml. In one embodiment, the upper end of the range is about 500, about 400, about 300, about 200, about 150, about 100, about 75 or about 50 mg·min/ml. In one embodiment a ligand according to the disclosure will have a AUC in the range selected from the group consisting of the following: about 15 to about 150 mg·min/ml, about 15 to about 100 mg·min/ml, about 15 to about 75 mg·min/ml, and about 15 to about 50 mg·min/ml.

Polypeptides and dAbs of the disclosure and antagonists comprising these can be formatted to have a larger hydrodynamic size, for example, by attachment of a PEG group, serum albumin, transferrin, transferrin receptor or at least the transferrin-binding portion thereof, an antibody Fc region, or by conjugation to an antibody domain. For example, polypeptides dAbs and antagonists formatted as a larger antigen-binding fragment of an antibody or as an antibody (e.g., formatted as a Fab, Fab', F(ab)$_2$, F(ab')$_2$, IgG, scFv).

As used herein, "hydrodynamic size" refers to the apparent size of a molecule (e.g., a protein molecule, ligand) based on the diffusion of the molecule through an aqueous solution. The diffusion or motion of a protein through solution can be processed to derive an apparent size of the protein, where the size is given by the "Stokes radius" or "hydrodynamic radius" of the protein particle. The "hydrodynamic size" of a protein depends on both mass and shape (conformation), such that two proteins having the same molecular mass may have differing hydrodynamic sizes based on the overall conformation of the protein.

Hydrodynamic size of the ligands (e.g., dAb monomers and multimers) of the disclosure may be determined using methods which are well known in the art. For example, gel filtration chromatography may be used to determine the hydrodynamic size of a ligand. Suitable gel filtration matrices for determining the hydrodynamic sizes of ligands, such as cross-linked agarose matrices, are well known and readily available.

The size of a ligand format (e.g., the size of a PEG moiety attached to a dAb monomer), can be varied depending on the desired application. For example, where ligand is intended to leave the circulation and enter into peripheral tissues, it is desirable to keep the hydrodynamic size of the ligand low to facilitate extravazation from the blood stream. Alternatively, where it is desired to have the ligand remain in the systemic circulation for a longer period of time the size of the ligand can be increased, for example by formatting as an Ig like protein.

Half-life extension by targeting an antigen or epitope that increases half-live in vivo: The hydrodynamic size of a ligand and its serum half-life can also be increased by conjugating or associating an TGFbetaRII binding polypeptide, dAb or ligand of the disclosure to a binding domain (e.g., antibody or antibody fragment) that binds an antigen or epitope that increases half-live in vivo, as described herein. For example, the TGFbetaRII binding agent (e.g., polypeptide) can be conjugated or linked to an anti-serum albumin or anti-neonatal Fc receptor antibody or antibody fragment, e.g. an anti-SA or anti-neonatal Fc receptor dAb, Fab, Fab' or scFv, or to an anti-SA affibody or anti-neonatal Fc receptor Affibody or an anti-SA avimer, or an anti-SA binding domain which comprises a scaffold selected from, but not limited to, the group consisting of CTLA-4, lipocallin, SpA, an affibody, an avimer, GroEI and fibronectin (see WO2008096158 for disclosure of these binding domains, which domains and their sequences are incorporated herein by reference and form part of the disclosure of the present text). Conjugating refers to a composition comprising polypeptide, dAb or antagonist of the disclosure that is bonded (covalently or noncovalently) to a binding domain such as a binding domain that binds serum albumin.

Typically, a polypeptide that enhances serum half-life in vivo is a polypeptide which occurs naturally in vivo and which resists degradation or removal by endogenous mechanisms which remove unwanted material from the organism (e.g., human). For example, a polypeptide that enhances serum half-life in vivo can be selected from proteins from the extracellular matrix, proteins found in blood, proteins found at the blood brain barrier or in neural tissue, proteins localized to the kidney, liver, lung, heart, skin or bone, stress proteins, disease-specific proteins, or proteins involved in Fc transport. Suitable polypeptides are described, for example, in WO2008/096158.

Such an approach can also be used for targeted delivery of a single variable domain, polypeptide or ligand in accordance with the disclosure to a tissue of interest. In one embodiment targeted delivery of a high affinity single variable domain in accordance with the disclosure is provided.

dAbs that Bind Serum Albumin: The disclosure in one embodiment provides a polypeptide or antagonist (e.g., dual specific ligand comprising an anti-TGFbetaRII dAb (a first dAb)) that binds to TGFbetaRII and a second dAb that binds serum albumin (SA), the second dAb binding SA. Details of dual specific ligands are found in WO03002609, WO04003019, WO2008096158 and WO04058821.

In particular embodiments of the ligands and antagonists, the dAb binds human serum albumin and competes for binding to albumin with a dAb selected from the group consisting of any of the dAb sequences disclosed in WO2004003019 (which sequences and their nucleic acid counterpart are incorporated herein by reference and form part of the disclosure of the present text), any of the dAb sequences disclosed in WO2007080392 (which sequences and their nucleic acid counterpart are incorporated herein by reference and form part of the disclosure of the present text), any of the dAb sequences disclosed in WO2008096158 (which sequences and their nucleic acid counterpart are incorporated herein by reference and form part of the disclosure of the present text).

In certain embodiments, the dAb binds human serum albumin and comprises an amino acid sequence that has at least about 80%, or at least about 85%, or at least about 90%, or at least about 95%, or at least about 96%, or at least about 97%, or at least about 98%, or at least about 99% amino acid sequence identity with the amino acid sequence of a dAb described in any of WO2004003019, WO2007080392 or WO2008096158. For example, the dAb that binds human serum albumin can comprise an amino acid sequence that has at least about 90%, or at least about 95%, or at least about 96%, or at least about 97%, or at least about 98%, or at least about 99% amino acid sequence identity with the amino acid sequence of any of these dAbs. In certain embodiments, the dAb binds human serum albumin and comprises an amino acid sequence that has at least about 80%, or at least about 85%, or at least about 90%, or at least about 95%, or at least about 96%, or at least about 97%, or at least about 98%, or at least about 99% amino acid sequence identity with the amino acid sequence of the amino acid sequence of any of these dAbs.

In more particular embodiments, the dAb is a Vκ dAb that binds human serum albumin. In more particular embodiments, the dAb is a $V_H$ dAb that binds human serum albumin.

Suitable Camelid $V_{HH}$ that bind serum albumin include those disclosed in WO2004041862 (Ablynx N.V.) and in WO2007080392 (which $V_{HH}$ sequences and their nucleic acid counterpart are incorporated herein by reference and form part of the disclosure of the present text). In certain embodiments, the Camelid $V_{HH}$ binds human serum albumin and comprises an amino acid sequence that has at least about 80%, or at least about 85%, or at least about 90%, or at least about 95%, or at least about 96%, or at least about 97%, or at least about 98%, or at least about 99% amino acid sequence identity with those sequences disclosed in WO2007080392 or any one of SEQ ID NOS:518-534, these sequence numbers corresponding to those cited in WO2007080392 or WO 2004041862.

In an alternative embodiment, the antagonist or ligand comprises a binding moiety specific for TGFbetaRII (e.g., human TGFbetaRII), wherein the moiety comprises non-immunoglobulin sequences as described in WO2008096158, the disclosure of these binding moieties, their methods of production and selection (e.g., from diverse libraries) and their sequences are incorporated herein by reference as part of the disclosure of the present text).

Conjugation to a half-life extending moiety (e.g., albumin): In one embodiment, a (one or more) half-life extending moiety (e.g., albumin, transferrin and fragments and analogues thereof) is conjugated or associated with the TGFbetaRII-binding polypeptide, dAb or antagonist of the disclosure. Examples of suitable albumin, albumin fragments or albumin variants for use in a TGFbetaRII-binding format are described in WO2005077042, which disclosure is incorporated herein by reference and forms part of the disclosure of the present text.

Further examples of suitable albumin, fragments and analogs for use in a TGFbetaRII-binding format are described in WO 03076567, which disclosure is incorporated herein by reference and which forms part of the disclosure of the present text.

Where a (one or more) half-life extending moiety (e.g., albumin, transferrin and fragments and analogues thereof) is used to format the TGFbetaRII-binding polypeptides, dAbs and antagonists of the disclosure, it can be conjugated using any suitable method, such as, by direct fusion to the TGFbetaRII-binding moiety (e.g., anti-TGFbetaRII dAb), for example by using a single nucleotide construct that encodes a fusion protein, wherein the fusion protein is encoded as a single polypeptide chain with the half-life extending moiety located N- or C-terminally to the TGFbetaRII binding moiety. Alternatively, conjugation can be achieved by using a peptide linker between moieties, e.g., a peptide linker as described in WO03076567 or WO2004003019 (these linker disclosures being incorporated by reference in the present disclosure to provide examples for use in the present disclosure).

Conjugation to PEG: In other embodiments, the half-life extending moiety is a polyethylene glycol moiety. In one embodiment, the antagonist comprises (optionally consists of) a single variable domain of the disclosure linked to a polyethylene glycol moiety (optionally, wherein said moiety has a size of about 20 to about 50 kDa, optionally about 40 kDa linear or branched PEG). Reference is made to WO04081026 for more detail on PEGylation of dAbs and binding moieties. In one embodiment, the antagonist consists of a dAb monomer linked to a PEG, wherein the dAb monomer is a single variable domain according to the disclosure.

In another embodiment, a single variable domain, ligand or polypeptide in accordance with the disclosure may be linked to a toxin moiety or toxin.

Protease resistance: Single variable domains, polypeptides or ligands in accordance with the disclosure can be modified to improve their resistance to protease degradation. As used herein, a peptide or polypeptide (e.g. a domain antibody (dAb)) that is "resistant to protease degradation" is not substantially degraded by a protease when incubated with the protease under conditions suitable for protease activity. A polypeptide (e.g., a dAb) is not substantially degraded when no more than about 25%, no more than about 20%, no more than about 15%, no more than about 14%, no more than about 13%, no more than about 12%, no more than about 11%, no more than about 10%, no more than about 9%, no more than about 8%, no more than about 7%, no more than about 6%, no more than about 5%, no more than about 4%, no more than about 3%, no more that about 2%, no more than about 1%, or substantially none of the protein is degraded by protease after incubation with the protease for about one hour at a temperature suitable for protease activity. For example at 37 or 50 degrees C. Protein degradation can be assessed using any suitable method, for example, by SDS-PAGE or by functional assay (e.g., ligand binding) as described herein.

Methods for generating dAbs with enhanced protease resistance are disclosed, for example, in WO2008149143. In one embodiment, the single variable domain, polypeptide or ligand in accordance with the disclosure is resistant to degradation by leucozyme and/or trypsin. Polypeptides, immunoglobulin single variable domains and ligands of the disclosure may be resistant to one or more of the following: serine protease, cysteine protease, aspartate proteases, thiol proteases, matrix metalloprotease, carboxypeptidase (e.g., carboxypeptidase A, carboxypeptidase B), trypsin, chymotrypsin, pepsin, papain, elastase, leukozyme, pancreatin, thrombin, plasmin, cathepsins (e.g., cathepsin G), proteinase (e.g., proteinase 1, proteinase 2, proteinase 3), thermolysin, chymosin, enteropeptidase, caspase (e.g., caspase 1, caspase 2, caspase 4, caspase 5, caspase 9, caspase 12, caspase 13), calpain, ficain, clostripain, actimidain, bromelain, and separase. In particular embodiments, the protease is trypsin, elastase or leucozyme. The protease can also be provided by a biological extract, biological homogenate or biological preparation. Polypeptides, immunoglobulin single variable domains and ligands as disclosed herein may be selected in the presence of lung proteases, such that said polypeptides, immunoglobulin single variable domains and ligands are resistant to said lung proteases. In one embodiment, the protease is a protease found in sputum, mucus (e.g., gastric mucus, nasal mucus, bronchial mucus), bronchoalveolar lavage, lung homogenate, lung extract, pancreatic extract, gastric fluid, saliva. In one embodiment, the protease is one found in the eye and/or tears. Examples of such proteases found in the eye include caspases, calpains, matrix metalloproteases, disintegrin, metalloproteinases (e.g. ADAMs—a disintegrin and metalloproteinase) and ADAM with thrombospondin motifs, the proteosomes, tissue plasminogen activator, secretases, cathepsin B and D, cystatin C, serine protease PRSS1, ubiquitin proteosome pathway (UPP). In one embodiment, the protease is a non bacterial protease. In an embodiment, the protease is an animal, e.g., mammalian, e.g., human, protease. In an embodiment, the protease is a GI tract protease or a pulmonary tissue protease, e.g., a GI tract protease or a pulmonary tissue protease found in humans. Such protease listed here can also be used in the methods described, for example, in WO2008149143, involving exposure of a repertoire of library to a protease.

Stability: In one aspect of the disclosure, the polypeptides, single variable domains, dAbs, ligands, compositions or formulations of the disclosure are substantially stable after incubation (at a concentration of polypeptide or variable domain of 1 mg/ml) at 37 to 50° C. for 14 days in Britton Robinson or PBS buffer. In one embodiment, at least 65, 70, 75, 80, 85, 86, 87, 88, 89, 90, 91, 92, 93, 94, 95, 96, 97, 98, 99% of the polypeptide, antagonist or variable domain etc. remains unaggregated after such incubation at 37 degrees C. In one embodiment, at least 65, 70, 75, 80, 85, 86, 87, 88, 89, 90, 91, 92, 93, 94, 95, 96, 97, 98, 99% of the polypeptide or variable domain remains monomeric after such incubation at 37 degrees C.

In one embodiment, at least 5, 10, 15, 20, 25, 30, 35, 40, 45, 50, 55, 60, 65, 70, 75, 80, 85, 86, 87, 88, 89, 90, 91, 92, 93, 94, 95, 96, 97, 98, 99% of the polypeptide, antagonist or variable domain remains unaggregated after such incubation at 50 degrees C. In one embodiment, at least 5, 10, 15, 20, 25, 30, 35, 40, 45, 50, 55, 60, 65, 70, 75, 80, 85, 86, 87, 88, 89, 90, 91, 92, 93, 94, 95, 96, 97, 98, 99% of the polypeptide or variable domain remains monomeric after such incubation at 50 degrees C. In one embodiment, no aggregation of the polypeptides, variable domains, antagonists is seen after any one of such incubations. In one embodiment, the pI of the polypeptide or variable domain remains unchanged or substantially unchanged after incubation at 37 degrees C. at a concentration of polypeptide or variable domain of 1 mg/ml in Britton-Robinson buffer. In one aspect of the disclosure, the polypeptides, variable domains, antagonists, compositions or formulations of the disclosure are substantially stable after incubation (at a concentration of polypeptide or variable domain of 100 mg/ml) at 4° C. for 7 days in Britton Robinson buffer or PBS at a pH of 7 to 7.5 (e.g., at pH7 or pH7.5). In one embodiment, at least 95, 95.5, 96, 96.5, 97, 97.5, 98, 98.5, 99 or 99.5% of the polypeptide, antagonist or variable domain remains unaggregated after such incubation. In one embodiment, at least 95, 95.5, 96, 96.5, 97, 97.5, 98, 98.5, 99 or 99.5% of the polypeptide or variable domain remains monomeric after such incubation. In one embodiment, no aggregation of the polypeptides, variable domains, antagonists is seen after any one of such incubations.

In one aspect of the disclosure, the polypeptides, variable domains, antagonists, compositions or formulations of the disclosure are substantially stable after nebulisation (e.g. at a concentration of polypeptide or variable domain of 40 mg/ml) e.g., at room temperature, 20 degrees C. or 37° C., for 1 hour, e.g. jet nebuliser, e.g. in a Pari LC+ cup. In one embodiment, at least 65, 70, 75, 80, 85, 86, 87, 88, 89, 90, 91, 92, 93, 94, 95, 95.5, 96, 96.5, 97, 97.5, 98, 98.5, 99 or 99.5% of the polypeptide, antagonist or variable domain remains unaggregated after such nebulisation. In one embodiment, at least 65, 70, 75, 80, 85, 86, 87, 88, 89, 90, 91, 92, 93, 94, 95, 95.5, 96, 96.5, 97, 97.5, 98, 98.5, 99 or 99.5% of the polypeptide or variable domain remains monomeric after such nebulisation. In one embodiment, no aggregation of the polypeptides, variable domains, antagonists is seen after any one of such nebulisation.

Monomeric form: In one embodiment, the dAb of the present disclosure is identified to be preferentially monomeric. Suitably, the disclosure provides a (substantially) pure monomer. In one embodiment, the dAb is at least 65%, 70%, 75%, 80%, 85%, 90%, 95%, 98%, 99% pure or 100% pure monomer. To determine whether dAbs are monomeric or form higher order oligomers in solution, they can be analysed by SEC-MALLS. SEC MALLS (size exclusion chromatography with multi-angle-LASER-light-scattering) is a non-invasive technique for the characterizing of macromolecules in solution, that is familiar to any skilled in the art. Briefly, proteins (at concentration of 1 mg/mL in buffer Dulbecco's PBS) are separated according to their hydrodynamic properties by size exclusion chromatography (column: TSK3000; S200). Following separation, the propensity of the protein to scatter light is measured using a multi-angle-LASER-light-scattering (MALLS) detector. The intensity of the scattered light while protein passes through the detector is measured as a function of angle. This measurement taken together with the protein concentration determined using the refractive index (RI) detector allows calculation of the molar mass using appropriate equations (integral part of the analysis software Astra v.5.3.4.12).

Therapeutic use: The disclosure provides a method for treating, suppressing or preventing diseases associated with TGFbeta signaling. In one embodiment, such disease may be caused or contributed to by dysregulated TGFbeta signaling, by overexpression of TGFbeta or by high levels of bioavailable TGFbeta. Diseases associated with TGFbeta signaling include diseases relating to fibroses of various tissues, such as pulmonary fibrosis including idiopathic pulmonary fibrosis (IPF) and other interstitial lung disease such as acute respiratory distress syndrome (ARDS), fibrosis of the liver including cirrhosis and chronic hepatitis, rheumatoid arthritis, ocular disorders, vascular conditions such as restenosis, fibrosis of the skin including keloid of skin and scarring following wound healing and Dupuytren's Contracture, and kidney such as nephritis, kidney fibrosis and nephrosclerosis or a vascular condition such as restenosis. Other diseases associated with TGFbeta signaling include vascular diseases such as hypertension, pre-eclampsia, hereditary haemorrhagic telangtiectasia type I (HHT1), HHT2, pulmonary arterial hypertension, aortic aneurysms, Marfan syndrome, familial aneurysm disorder, Loeys-Dietz syndrome, arterial tortuosity syndrome (ATS). Other diseases associated with TGFbeta signaling include diseases of the musculoskeletal system such as Duchenne's muscular dystrophy and muscle fibrosis. Further diseases associated with TGFbeta signaling include cancer such as colon, gastric and pancreatic cancer as well as glioma and NSCLC. In addition, the disclosure provides methods for targeting cancer by, for example, modulating TGFbeta signaling in the tumour angiogenesis or through treatment of the cancer stroma. Other diseases or conditions include those related to tissue scarring. Other diseases include pulmonary diseases such as COPD (Chronic obstructive pulmonary disease), liver diseases such as liver failure (e.g. viral hepatitis, alcohol, obesity, autoimmune, metabolic, obstructive), kidney diseases including renal failure (e.g. diabetes, hypertension), hypertrophic cardiomyopathy, transplant rejection (lung/liver/kidney) and hypertrophic and keloid scarring.

"Fibrosis" is the result of excess deposition of extracellular matrix components such as collagen causing overgrowth, scarring and/or hardening of tissues.

"Skin Fibrosis": cutaneous fibrosis covers a variety of human disorders with differing aetiology, but with a common dysregulation of connective tissue metabolism, particularly of dermal fibroblasts. Specific examples of cutaneous fibrosis include keloid disease, hypertrophic scars (HS) and scleroderma. Keloid disease and hypertrophic scars, although not subgroups of the same condition are both resultant from scarring following wound healing, with Keloids spreading beyond the original wound site whilst hypertrophic scar is constrained within the margins of the original wound. Scleroderma, however is used to describe fibrosis of the skin in systemic sclerosis which is a systemic condition resulting in fibrosis of multiple organs. In an embodiment, the variable domain, ligand, fusion protein or polypeptide as disclosed herein is used to prevent or treat keloid disease, hypertrophic scars or scleroderma.

"Keloids" are fibrous overgrowths at sites of cutaneous injury that form as a result of an abnormal wound-healing process in genetically susceptible individuals and, unlike normal scars, do not regress. Predominantly observed in patients with darkly pigmented skin, "Keloid disease" is a benign dermal fibroproliferative tumor unique to humans that never becomes malignant.

"Dupuytren's contracture" is a localized formation of scar tissue beneath the skin of the palm of the hand. The scarring accumulates in a tissue (fascia) that normally covers the tendons that pull the fingers to grip. As Dupuytren contracture progresses, more of the fascia becomes thickened and shortened, resulting in flexion contracture of the hand where the fingers bend towards the palm and cannot be fully extended (straightened), resulting in extreme cases to loss of use of the hand.

Scarring occurs following, surgery, injury or trauma to tissues or organs within the body. They are a consequence of repair mechanisms that generate extracellular matrix to replace missing normal tissue. The skin represents the most frequently injured tissue resulting in dermal scarring, which can result in adverse consequences including: loss of function; contracture; and, poor aesthetics which may have cause psychological effects to the sufferer. Scars can be defined 'a macroscopic disturbance of the normal structure and function of the skin architecture, resulting from the end product of wound healing' (Fergusson et al., 1996). Currently no therapies exist to prevent or improve scarring effectively.

The role of TGFbeta in pulmonary fibrosis has been observed (Wynn et al., J. Pathology 2008, 214, p. 199-210; Sime et al. J. Clinical Immunology 1997, Vol. 100, p. 768-776). A shift to increased production of Th2 cytokines and decreased production of Th1 cytokines is observed as a result of unknown lung injury. Overexpression of TGFbeta stimulates angiogenesis, fibroblast activation, deposition of ECM, and fibrogenesis. Animal models (e.g. TGFbeta overexpression, SMAD3 KO, inhibition of TGFbetaR signaling) show that TGFbeta is a key mediator for the development of pulmonary fibrosis.

"Idiopathic pulmonary fibrosis (IPF)" is a chronic and progressive disease resulting in abnormal and excessive deposition of fibrotic tissue in the pulmonary interstitium without a known cause. There is an incidence of approximately 10-20 cases per 100,000 in U.S per year. The prevalence increases sharply with age, reaching 175 cases per 100,000 over the age of 75 with onset usually occurring between 50 and 70 yrs. The five year survival rate is 20% with a mean survival of 2.8 years. Symptoms include a dry cough and progressive breathlessness, abnormal chest x-ray or HRCT and reduced lung volumes. Current treatments include corticosteroids (Prednisone), immunosuppressives (cyclophosphamide) or transplantation although none of the currently available therapies have a proven efficacy. In one embodiment, the single variable domain or polypeptide of the present disclosure provides a treatment for IPF.

Suitably, a successful treatment for Idiopathic pulmonary fibrosis (IPF) will show any one of a decrease in lung fibroblast proliferation, an increase in lung fibroblast apoptosis, a decrease in excessive extracellular matrix synthesis and deposition, an increase in extracellular matrix breakdown and remodelling or will show some protection against ongoing tissue injury and restoration of normal histopathology.

Suitably, a successful treatment would decelerate disease progression.

The efficacy of a treatment for IPF can be demonstrated in the bleomycin induced pulmonary fibrosis model. In one embodiment, the immunoglobulin single variable domain of the present disclosure cross reacts with mouse TGFbetaRII such that its efficacy can be tested in the mouse model.

TGFbeta is an important cell signaling molecule in the modulation of cell behaviour in ocular tissues. Overactivation of TGFbeta is implicated in the pathogenesis of fibrotic diseases in eye tissue which can be wound healing-related and lead to impaired vision and ocular tissue homeostasis (reviewed, for example, by Saika, Laboratory Investigation (2006), 86, 106-115).

Accordingly, in one embodiment, diseases associated with TGFbeta signaling include ocular disorders such as fibrotic diseases of the eye tissue. Fibrotic disease of the eye may occur in the cornea, conjunctiva, lens or retina. Ocular disorders include proliferative vitreoretinopathy (PVR), a disorder of post-retinal detachment and retinal fibrosis, diabetic retinopathy, glaucoma, such as open-angle glaucoma, angle-closure, congenital and pseudo-exfoliation syndrome, wound healing reactions in the lens, such as post chemical or thermal burn, or Stevens-Johnson's syndrome, and post-cataract surgery complications. TGFbeta also has a role in cataract development (Wormstone et al. Exp Eye Res; 83 1238-1245, 2006). A number of ocular disorders occur as a result of fibrosis post surgery. In addition, over activity of TGFbeta2 (transforming growth factor β2) is believed to cause scarring in and around the eye after glaucoma filtration surgery. TGFbeta2 is the predominant isoform involved in pathological scarring of ocular tissues including the cornea, retina, conjunctiva and trabelular meshwork. Scarring or fibrosis of the trabelular meshwork can lead to occlusion of the normal aqueous outflow pathway leading to raised intraocular pressure and risk of glaucoma development. TGFbeta 2 has been shown to be a pathological agent in pre-clinical models of glaucoma disease. TGFbeta2 levels are elevated in patients with glaucoma, in vitro treatment of huTM cells with TGF-beta-2 leads to phenotypic changes and upregulation of ECM modulating proteins (MMP-2, PAI-I) (Lutjen-Drecol (2005), Experimental Eye Research, Vol. 81, Issue 1, pages 1-4; Liton (2005), Biochemical and Biophysical Research Communications Vol. 337, issue 4, p. 1229-1236; Fuchshofer et al (2003), Experimental Eye Research, Vol. 77, issue 6, p. 757-765; Association for Research in Vision and Ophthalmology (ARVO) conference poster #1631 2009). Moreover, overexpression of TGFbeta in the eye leads to glaucoma-like pathology in mice (ARVO conference poster #5108 2009) and delivery of TGFbeta-2 using AAV has been shown to inhibit retinal ganglion cell loss in a rat model of glaucoma (ARVO conference poster #5510 2009). More recently, oxidative stress induction in cultured human optic nerve head astrocytes has been shown to increase TFGbeta2 secretion (Yu et al (2009) Invest. Ophthalmol. Vis. Sci. 50: 1707-1717). This all indicates that reduction of TGFbeta 2 levels might minimize the characteristic optic nerve head changes seen in glaucoma. However, TGFbeta is also known to have an immunosuppressive role and so in some aspects can be protective so a reduction in elevated levels of TGFbeta2 rather than a complete knock down may be preferred in treatment of chronic ocular conditions such as glaucoma. Accordingly, diseases which can be treated using the dAbs and compositions etc. in accordance with the disclosure include scarring post glaucoma filtration surgery.

Accordingly, in one aspect there is provided a method for treating, suppressing or preventing a disease associated with TGFbeta signaling and, in particular, dysregulated TGFbeta signaling, comprising administering to a mammal in need thereof a therapeutically-effective dose or amount of a polypeptide, fusion protein, single variable domain, antagonist or composition according to the disclosure.

In another aspect, the disclosure provides an immunoglobulin single variable domain, polypeptide, ligand or fusion protein in accordance with the disclosure for use as a medicament. Suitable a medicament may comprise an immunoglobulin single variable domain etc. in accordance with the disclosure formatted as described herein.

Suitably, the medicament is a pharmaceutical composition. In a further aspect of the disclosure, there is provided a composition (e.g., pharmaceutical composition) comprising a polypeptide, single variable domain, ligand, composition or antagonist according to the disclosure and a physiologically or pharmaceutically acceptable carrier, diluent or excipient. In one embodiment, the composition comprises a vehicle for delivery. In particular embodiments, the polypeptide, fusion protein, single variable domain, antagonist or composition is administered via pulmonary delivery, such as by inhalation (e.g., intrabronchial, intranasal or oral inhalation, intranasal such as by drops) or by systemic delivery (e.g., parenteral, intravenous, intramuscular, intraperitoneal, intraarterial, intrathecal, intraarticular, subcutaneous, vaginal or rectal administration). In another embodiment, the polypeptide, single variable domain, ligand or fusion protein or compositions in accordance with the disclosure is administered to the eye e.g. by topical administration, as eye drops, particulate polymer system, gel or implant, or by intraocular injection e.g. into the vitreous humour. Delivery can be targeted to particular regions of the eye such as the surface of the eye, or the tear ducts or lacrimal glands or to the anterior or posterior chambers of the eye such as the vitreous humour). It can also be useful if the immunoglobulin single variable domain, composition etc. is delivered to the eye along with an ocular penetration enhancer e.g. sodium caprate or with a viscosity enhancer e.g. Hydroxypropylmethylcellulose (HPMC). In further embodiments, the polypeptide, fusion protein, single variable domain, antagonist or composition is administered to the skin; by topical delivery to the surface of the skin and/or delivery to a region(s) within the skin e.g. intradermal delivery.

Although the most accessible organ of the body for delivery, the skin's outermost barrier, the stratum corneum (SC), acts as a rate limiting barrier for drug delivery. Traditionally, intradermal injection has been required to circumvent the SC allowing delivery of drug to site of action in deeper skin layers. Delivery however, maybe achieved through other transdermal delivery approaches. Formulation methodologies maybe utilised for delivery, including: chemical enhancers to alter the lipid structure of the SC; peptide facilitators enabling transfollicular transport; and encapsidation in particles including, liposome's, niosomes, ethosomes and transfersomes, which are believed to aid local fluidisation of the lipids and formation of depots for prolonged effect. Iontophoresis, involving the application of a small electrical potential across the skin, has been used for localised drug delivery. Iontophoresis allows for both the delivery of charged and neutral molecules by electromigration and electroosmosis respectively. Microneedles, can be employed to create micron-sized channels in the skin to overcome the SC, allowing proteins to pass through these channels to the lower epidermis. Microneedles can be broadly classified into solid and hollow microneedles. Solid microneedles, maybe used to disrupt the SC, prior to drug administration, coated to allow delivery as drug dissolves from the needles, or soluble allowing drug release as the needles dissolve in situ. Hollow microneedles allow for infusion of a liquid formulation of drug substance. Electroporation, unlike iontophoresis requires higher voltages >50V, to alter skin permeability in order to enhance drug penetration. Thermal and radiofrequency ablation methodologies allow for disruption of the SC through localised heating and ablation of the SC. In heat ablation this results following application of high temperature for short periods of time, whereas radiofrequency ablation involves use of radiofrquencies, to vibrate microelectrodes on the skin, resulting in localised heating. Disruption of the SC can also be achieved through Laser abrasion, application of low frequency ultrasound waves (sonophoresis) and jet injectors utilising high velocities to propel drug through the SC.

Moreover, the present disclosure provides a method for the treatment of disease using a polypeptide, single variable domain, composition, ligand or antagonist according to the present disclosure. In one embodiment the disease is a tissue fibrosis such as keloid disease or Dupuytren's Contracture.

In an aspect of the disclosure, the polypeptide, single variable domain, ligand, composition or antagonist is provided for therapy and/or prophylaxis of a disease or condition associated with TGFbeta signaling in a human. In another aspect, there is provided the use of the polypeptide, single variable domain, composition or antagonist, in the manufacture of a medicament for therapy or prophylaxis of a disease or condition associated with TGFbeta signaling in a human. In another aspect, there is provided a method of treating and/or preventing a disease or condition associated with TGFbeta signaling in a human patient, the method comprising administering the polypeptide, single variable domain, composition or antagonist to the patient. The disclosure also relates to therapeutic methods that comprise administering a therapeutically effective amount of a ligand of the disclosure (e.g., antagonist, or single variable domain) to a subject in need thereof.

In other embodiments, the disclosure relates to a method for treating idiopathic pulmonary fibrosis comprising administering to a subject in need thereof a therapeutically effective amount of a ligand of the disclosure (e.g., antagonist, or single variable domain).

The disclosure also relates to a drug delivery device comprising the composition (e.g., pharmaceutical composition) of the disclosure. In some embodiments, the drug delivery device comprises a plurality of therapeutically effective doses of ligand.

In other embodiments, the drug delivery device is selected from the group consisting of parenteral delivery device, intravenous delivery device, intramuscular delivery device, intraperitoneal delivery device, transdermal or intradermal delivery device, pulmonary delivery device, intraarterial delivery device, intrathecal delivery device, intraarticular delivery device, subcutaneous delivery device, intranasal delivery device, ocular delivery device, vaginal delivery device, rectal delivery device, syringe, a transdermal delivery device, an intradermal delivery device, a capsule, a tablet, a nebulizer, an inhaler, an atomizer, an aerosolizer, a mister, a dry powder inhaler, a metered dose inhaler, a metered dose sprayer, a metered dose mister, a metered dose atomizer, and a catheter. In an embodiment the drug delivery device is a transdermal or intradermal delivery device.

Suitably, the disclosure provides a pulmonary delivery device containing a polypeptide, single variable domain, composition or antagonist according to the disclosure. The device can be an inhaler or an intranasal administration device. Suitably, the pulmonary delivery device enables delivery of a therapeutically effective dose of a ligand etc. in accordance with the disclosure.

In another embodiment, the disclosure provides an ocular delivery device containing a polypeptide, single variable domain, composition or antagonist according to the disclosure. Suitably, the ocular delivery device enables delivery of a therapeutically effective dose of a ligand etc. in accordance with the disclosure.

As used herein, the term "dose" refers to the quantity of ligand administered to a subject all at one time (unit dose), or in two or more administrations over a defined time interval. For example, dose can refer to the quantity of ligand (e.g., ligand comprising an immunoglobulin single variable domain that binds TGFbetaRII) administered to a subject over the course of one day (24 hours) (daily dose), two days, one week, two weeks, three weeks or one or more months (e.g., by a single administration, or by two or more administrations). The interval between doses can be any desired amount of time. In a particular embodiment, the single variable domain or polypeptide of the invention is administered into the skin by injection, in particular by intradermal delivery, weekly or fortnightly or every 7-10 days, for example every 7, 8, 9 or 10 days.

In one embodiment, the single variable domain of the disclosure is provided as a dAb monomer, optionally unformatted (e.g., not PEGylated or half-life extended) or linked to a PEG, optionally as a dry powder formulation, optionally for delivery to a patient by inhalation (e.g., pulmonary delivery), optionally for treating and/or preventing a lung condition (e.g., Idiopathic pulmonary fibrosis).

The ligands of the disclosure provide several advantages. For example, as described herein, the ligand can be tailored to have a desired in vivo serum half-life. Domain antibodies are much smaller than conventional antibodies, and can be administered to achieve better tissue penetration than conventional antibodies. Thus, dAbs and ligands that comprise a dAb provide advantages over conventional antibodies when administered to treat disease, such as TGFbeta-signaling-mediated disease. In particular, pulmonary delivery of a dAb of the present disclosure to treat idiopathic pulmonary fibrosis enables specific local delivery of an inhibitor of TGFbeta signaling. Advantageously, an unformatted dAb monomer which specifically binds to and inhibits TGFbetaRII is small enough to be absorbed into the lung through pulmonary delivery.

The examples of WO2007085815 are incorporated herein by reference to provide details of relevant assays, formatting and experiments that can be equally applied to ligands of the present disclosure.

All publications, including but not limited to patents and patent applications, cited in this specification are herein incorporated by reference as though fully set forth.

The disclosure is further described, for the purposes of illustration only, in the following examples.

EXAMPLES

Example 1

Selection of dAbs which Bind TGFbetaRII

Selection of dAbs which Bind Mouse TGFbetaRII
Naïve Selections: 4G and 6G naïve phage libraries, phage libraries displaying antibody single variable domains expressed from the GAS1 leader sequence (see WO2005093074) for 4G and additionally with heat/cool pre-selection for 6G (see WO04101790), were used. The DOM23 leads were isolated by panning pools of VH and VK libraries (identified as 4G H11-19 and 6G VH2-4 (VH dAbs) and 4G κ1, 4G κ2 and 6G κ (Vκ dAbs) against the recombinant mouse and human TGF-β RII/Fc chimera protein. These chimeric proteins were made by expression of a DNA sequence encoding the amino acids residues 24 to 159 of the extracellular domain of human TGF-β Receptor Type II (Lin, et al, 1992, *Cell* 68:775-785) fused to the Fc region of human IgG1 in a human embryonic kidney cell line, HEK-F.

The recombinant mouse and human TGF-β RII/Fc chimera proteins were biotinylated using EZ-LINK™ Sulfo-NHS-LC-Biotin reagent (Pierce, Rockford, USA) (Henderikx, et al., 2002, Selection of antibodies against biotinylated antigens. Antibody Phage Display: Methods and protocols, Ed. O'Brien and Atkin, Humana Press). The phage libraries were pooled into six groups; 4G κ1 and κ2, 6G κ, 4G H11-13, 4G H14-16, 4G H17-19 and 6G VH2-4. $1 \times 10^{11}$ phage per library were pooled.

The phage were blocked in 2% MARVEL™ milk powder in phosphate buffered saline (MPBS) with the addition of 10 uM Human IgG Fc fragment (Native IgG Fc fragment derived from human myeloma plasma IgG, Calbiochem, California, US, cat. no. 401104) for one hour. 200 nM biotinylated mouse TGF-β RII/Fc was incubated with the blocked phage and Fc fragment mixture for 1 hour at room temperature and then captured on streptavidin DYNAbeads™ (Dynal, UK) for five minutes. The beads were washed seven times with 1 ml phosphate buffered saline/0.1% TWEEN™ (PBST), followed by a wash with 1 ml phosphate buffered saline (PBS). The biotinylated mouse TGF-β RII/Fc-bound phage were eluted in 500 ul 1 mg/ml trypsin in PBS for 10 minutes and then used to infect 1.75 ml of log-phase *Escherichia coli* TG1 for 30 minutes. Cells were plated on 2×TYE (Trypton Yeast Extract) agar plates supplemented with 15 ug/ml tetracycline. For subsequent rounds of selections, cells were scraped from the plates and used to inoculate 50 ml 2×TY (Trypton Yeast)+15 ug/ml tetracycline cultures that were grown overnight at 37° C. for phage amplification.

Amplified phage was recovered by centrifugation of the overnight culture for 10 minutes at 4566 g. 40 ml of supernatant containing the amplified phage was added to 10 ml of PEG/NaCl (20% v/w PEG 8000+2.5M NaCl) and incubated on ice for 45 to 60 minutes. The samples were centrifuged for 30 minutes at 4566 g to pellet the precipitated phage. The supernatant was discarded and the phage pellet was resuspended in 2 ml 15% v/v glycerol/PBS. The phage sample was transferred to 2 ml Eppendorf tubes and centrifuged for 10 minutes at g to remove any remaining bacterial cell debris. The phage was used as input phage for the second round of selection. The second round of selection was performed as described for the first round, except approximately $1 \times 10^{10}$ phage were added, and either 200 nM human TGF-β RII/Fc or 20 nM mouse TGF-β RII/Fc was used in the selections.

Second round outputs were cloned from the fd-phage vector, pDOM4 into pDOM10. Vector pDOM4, is a derivative of the fd phage vector in which the gene III signal peptide sequence is replaced with the yeast glycolipid anchored surface protein (GAS) signal peptide. It also contains a c-myc tag between the leader sequence and gene III, which puts the gene III back in frame. This leader sequence functions well both in phage display vectors but also in other prokaryotic expression vectors and can be universally used. pDOM10 is a plasmid vector designed for soluble expression of dAbs. It is based on pUC119 vector, with expression under the control of the LacZ promoter. Expression of dAbs into the supernatant was ensured by fusion of the dAb gene to the universal GAS leader signal peptide (see WO2005093074) at the N-terminal end. In addition, a FLAG-tag was appended at the C-terminal end of the dAbs.

Subcloning of the dAb genes was performed by isolating pDOM4 DNA from the cells infected by the selected dAb-displaying fd-phage using a QIAPREP™ Spin MINIPREP™ kit in accordance with the manufacturer's instructions (cat. no. 27104, Qiagen). The DNA was amplified by PCR using biotinylated oligonucleotides DOM57 (5' TTGCAG-GCGTGGCAACAGCG-3' (SEQ ID NO:197) and DOME (5'-CACGACGTTGTAAAACGACGGCC-3' (SEQ ID NO:198)), digested with SalI and NotI restriction endonucleases and ligated with pDOM10 digested with SalI and NotI. The ligation products were transformed by electroporation into $E\ coli$ HB2151 cells and plated on TYE plates (Trypton Yeast Extract) supplemented with 100 μg/ml of carbenicillin (TYE-carb). Individual clones were picked and expressed in overnight express auto-induction medium (high-level protein expression system, Novagen), supplemented with 100 μg/ml carbenicillin. in 96-well plates, grown with shaking at either 30° C. or 37° C. These expression plates were then centrifuged at 1800 g for 10 minutes. dAb clones that bound mouse and/or human TGF-β RII/Fc were identified by an ELISA and BIACORE™ (GE HEALTHCARE™) screen or by MSD (Meso Scale Discovery) binding assay screen. For the ELISA, 96-well Maxisorp™ immuno plates (Nunc, Denmark) were coated with either human or mouse TGF-β RII/Fc overnight at 4° C. The wells were washed three times with PBST and then blocked with 1% TWEEN™ in PBS (1% TPBS) for 1 hour at room temperature. The block was removed and a 1:1 mixture of 1% TPBS and dAb supernatant was added for 1 hour at room temperature. The plate was washed three times with PBST and the detection antibody (Monoclonal anti-FLAG M2-peroxidase antibody, Sigma-Aldrich, UK) was added and incubated for 1 hour at room temperature. The plates were developed using a colourimetric substrate (SUREBLUE™ 1-component TMB Microwell Peroxidase solution, KPL, Maryland, USA) and the optical density (OD) measured at 450 nM, the $OD_{450}$ being proportional to the amount of bound detection antibody. For BIACORE™, supernatants were diluted 1:1 in HBS-EP buffer and screened on BIACORE™ for binding to biotinylated human and mouse TGF-β RII/Fc (SA chip coated with 1500 Ru biotinylated hRII-Fc and 1550 Ru biotinylated mRII-Fc in accordance with the manufacturer's recommendations) (BIACORE™, GE HEALTHCARE™). Samples were run on BIACORE™ at a flow rate of 50 μl/min.

Naïve Human Selections and Screening

Selection of dAbs which Bind Human TGFbetaRII

Naïve selections were performed as described for mouse TGFbRII but using 150 and 15 nM biotinylated human TGF-bRII/Fc at round one and two, respectively. A third round was performed using the same method as for round two, but with 1.5 nM biotinylated human TGFbRII/Fc.

The third round outputs were cloned from the fd-phage vector, pDOM4 into pDOM10. Subcloning of the dAb genes was performed by isolating pDOM4 DNA from the cells infected by the selected dAb-displaying fd-phage using a QIAPREP™ Spin MIDIPREP™ kit in accordance with the manufacturer's instructions (cat. no. 27104, Qiagen). The plasmid DNA was digested with SalI and NotI restriction endonucleases and the dAb gene insert ligated with pDOM10 digested with SalI, NotI and PstI restriction endonucleases. The ligation products were transformed by electroporation into $E.\ coli$ HB2151 cells and plated on TYE plates (Trypton Yeast Extract) supplemented with 100 μg/ml of carbenicillin (TYE-carb). Individual clones were picked and expressed in 96-well plates at 250 rpm, 30° C. 72 hours, in 1 ml/well overnight express auto-induction medium (Novagen) supplemented with 100 μg/ml carbenicillin. These plates were then centrifuged at 1800 g for 10 minutes. The soluble dAb supernatants were screened for antigen binding in the TGFbRII MSD binding assay combined with the fluorescent polarization concentration determination assay. The number of human TGFbRII binders was high and there were too many clones to take forward for further characterization. Therefore, a subset of clones was sequenced and those with unique sequences were further characterized.

TGFβRII MSD Binding Assay

This assay was used to determine the binding activity of anti-TGFbRII dAbs. TGFbRII-Fc antigen was coated onto a MSD plate, which was subsequently blocked to prevent non-specific binding. Serially diluted supernatants containing soluble FLAG-tagged dAb were added. After incubation, the plate was washed and only dAbs that bound specifically to TGFBRII-Fc remained bound to the plate. Bound dAbs were detected with a ruthenylated anti-FLAG tagged antibody and MSD read buffer. If the concentration of the dAbs in the supernatant dilutions was determined using the Fluorescent Polarisation Concentration Determination assay, then concentration binding curves were plotted.

0.5 ul per well of either 60 μg/ml human TGFbRII-Fc, 60 μg/ml mouse TGFbRII-Fc or 60 ug/ml human IgG1 Fc (R&D systems, catalogue number 110-HG) was spotted onto 384 well MSD high bind plates (Meso Scale Discovery). The plates were air-dried at room temperature for a minimum of four hours and no longer than overnight. The plates were blocked with 50 ul per well of 5% MARVEL™ in Tris buffered saline (TBS)+0.1% TWEEN™ 20 for either 1 hour at room temperature or overnight at 4° C. The blocking reagent was removed from the wells by flicking the plates. A 1:3 dilution series of the dAb supernatants was prepared in 2×TY medium. The dAbs were expressed in the pDOM10 expression vector so were the dAb protein was expressed as a FLAG fusion protein. The blocking reagent was removed and 10 ul per well of the diluted dAb supernatants were transferred to the blocked MSD plates. The dAbs supernatants were screened as either 4 point curves or as 11 point curves. In addition to the diluted dAb supernatants, two controls were included in each plate, one low control (normalised to 0% binding), with no TGFbRII binding specificity and a high control (normalised to 100% binding) with high TGFbRII binding specificity, data not shown.

The plates were incubated with the dAb supernatants and the control samples for one hour at room temperature and then washed three times with 50 ul per well of TBS+0.1% TWEEN™. 15 ul/well of ruthenylated anti-FLAG antibody was added to the plates and incubated for one hour at room temperature. The anti-FLAG antibody (anti-FLAG M2 monoclonal antibody, Sigma, UK, catalogue number F3165) was conjugated to ruthenium II tris-bipyridine N-hydroxy succinimide following the manufacturer's instructions (Meso Scale Discovery, catalogue number R91BN-1). The ruthenylated anti-FLAG antibody was added to all wells except to the mouse anti-human IgG1 Fc antibody control wells. Instead, 15 ul/well of anti-Mouse MSD tag (Meso Scale Discovery, catalogue number R31AC-1) were added. The anti-Mouse MSD tag was diluted in 2% MARVEL™ in TBS+0.1% TWEEN™ 20 to a final concentration of 750 ng/ml. The plates were incubated at room temperature for one hour and washed three times with 50 ul per well of TBS+0.1% TWEEN™. 35 ul 1×MSD read buffer (Meso Scale Discovery) was added to each well and the plates were read on a MSD Sector 6000 reader (Meso Scale Discovery).

Data were analysed using XC50 Activity Base. All data was normalised to the mean of the high and low control wells on each plate, with the low control normalised to 0% binding and the high control normalised to 100% binding. A four parameter curve fit was applied to the normalised data and concentration binding curves using dAb concentrations calculated using the Fluorescent Polarisation Concentration Determination of dAbs in supernatants assay, were plotted.

The four parameter fit used was as follows:

$$y = \frac{(a-d)}{1+\left(\frac{x}{c}\right)^b} + d,$$

where a is the minimum, b is the Hill slope, c is the XC50 and d is the maximum.

Fluorescence Polarisation Concentration Determination of dAbs in Supernatants Assay This assay allows the concentration of soluble FLAG-tagged dAbs expressed in supernatants to be determined. A fluorescently labelled-FLAG peptide was mixed with an anti-FLAG antibody. The fluorescent molecules were excited with polarised light at a wavelength of 531 nM and the emitted polarised light was read at a wavelength of 595 nM. The addition of a FLAG-tagged dAb resulted in the displacement of the fluorescent peptide from the anti-FLAG antibody which in turn resulted in reduced polarisation of the emission signal. A standard curve of known concentrations of purified FLAG-tagged VH dummy dAb was prepared and was used to back calculate the concentration of the soluble dAbs in the supernatants. The concentration data was combined with binding activity data, allowing concentration binding curves to be plotted for dAb supernatants.

The dAb supernatants were serially diluted 1:2 in 2×TY medium (1:2, 1:4, 1:8 and 1:16), followed by a 1:10 dilution in phosphate buffered saline (PBS). The diluted supernatants were transferred to a black 384 well plate. A standard curve was set up by serially diluting purified VH Dummy dAb 1:1.7 in 10% v/v 2×TY medium in PBS. The highest dAb concentration was 10 uM and there were 16 dilutions in total. 5 ul of each dilution was transferred to the 384 well plate. A mixture of 5 nM FLAG peptide labelled at the c-terminus with Cy3b, 100 mM anti-FLAG M2 monoclonal antibody (Sigma, catalogue number F3165), 0.4 mg/ml bovine serum albumin (BSA) in 2 mM CHAPs buffer was prepared. 5 ul of the mixture was transferred to the wells containing the diluted dAbs (both supernatants and standard curve wells). The plate was centrifuged at 1000 rpm (216 g) for 1 minute and then incubated in the dark at room temperature for 15 minutes. The plates were read on an ENVISION™ reader (Perkin Elmer) fitted with the following filters;

Excitation filter: BODIPY TMR FP 531
Emission filter 1: BODIPY TMR FP P pol 595
Emission filter 2: BODIPY TMR FP P pol 595
Mirror: BODIPY TMR FP Dual Enh The standard curve was plotted and used to back calculate the concentrations of the soluble dAbs in the supernatants.

Mouse and human TGF-β RII/Fc-binding dAbs identified in the ELISA, BIACORE™ and MSD binding assays were expressed in overnight express autoinduction medium (ONEX™, Novagen) at either 30° C. for 48 to 72 hours. The cultures were centrifuged (4,600 rpm for 30 minutes) and the supernatants were incubated with STREAMLINE™-protein A beads (Amersham Biosciences, GE HEALTHCARE™, UK. Binding capacity: 5 mg of dAb per ml of beads), either overnight at 4° C. or at room temperature for at least one hour. The beads were packed into a chromatography column and washed with either 1× or 2×PBS, followed by 10 or 100 mM Tris-HCl pH 7.4 (Sigma, UK). Bound dAbs were eluted with 0.1 M glycine-HCl pH 2.0 and neutralized with 1M Tris pH 8.0. The OD at 280 nm of the dAbs was measured and protein concentrations were determined using extinction coefficients calculated from the amino acid compositions of the dAbs.

The amino acid and nucleic acid sequences of the anti-human and anti-murine TGFRII dAb naive leads are given below.

```
Dom23h 802 amino acid sequence
                                                         (SEQ ID NO: 1)
EVQLLESGGGLVQPGGSLRLSCAASGFTFSEGTMWWVRQAPGKGLEWVSAILAAGSNTYYADSVKGRFTISRD

NSKNTLYLQMNSLRAEDTAVYYCAKKRQERDGFDYWGQGTLVTVSS

Dom23h 802 nucleic acid sequence
                                                         (SEQ ID NO: 39)
GAGGTGCAGCTGTTGGAGTCTGGGGGAGGCTTGGTACAGCCTGGGGGGTCCCTGCGTCTCTCCTGTGCAGC

CTCCGGATTCACCTTTAGTGAGGGGACGATGTGGTGGGTCCGCCAGGCTCCAGGGAAGGGTCTAGAGTGGG
```

-continued

TCTCAGCTATTTTGGCTGCTGGTTCTAATACATACTACGCAGACTCCGTGAAGGGCCGGTTCACCATCTCCC

GCGACAATTCCAAGAACACGCTGTATCTGCAAATGAACAGCCTGCGTGCCGAGGACACCGCGGTATATTACT

GTGCGAAAAAGAGGCAGGAGCGGGATGGGTTTGACTACTGGGGTCAGGGAACCCTGGTCACCGTCTCGAGC

Dom23h 803 amino acid sequence (SEQ ID NO: 2)

EVQLLESGGGLVQPGGSLRLSCAASGFTFSAGRMWWVRQAPGKGLEWVSAINRDGTRTYYADSVKGRFTISRD

NSKNTLYLQMNSLRAEDTAVYYCAKHDDGHGNFDYWGQGTLVTVSS

Dom23h 803 nucleic acid sequence (SEQ ID NO: 40)

GAGGTGCAGCTGTTGGAGTCTGGGGGAGGCTTGGTACAGCCTGGGGGGTCCCTGCGTCTCTCCTGTGCAGC

CTCCGGATTCACCTTTAGTGCTGGGCGGATGTGGTGGGTCCGCCAGGCTCCAGGGAAGGGTCTAGAGTGGG

TCTCAGCGATTAATCGGGATGGTACTAGGACATACTACGCAGACTCCGTGAAGGGCCGGTTCACCATCTCCC

GTGACAATTCCAAGAACACGCTGTATCTGCAAATGAACAGCCTGCGTGCCGAGGACACCGCGGTATATTACT

GTGCGAAACATGATGATGGTCATGGTAAGACTACTGGGGTCAGGGAACCCTGGTCACCGTCTCGAGC

DOM23h-813 amino acid sequence (SEQ ID NO: 3)

EVQLLESGGGLVQPGGSLRLSCAASGSTFTDDRMWWVRQAPGKGLEWVSAIQPDGHTTYYADSVKGRFTISR

DNSKNTLYLQMNSLRAEDTAVYYCAEQDVKGSSSFDYWGQGTLVTVSS

DOM23h-813 nucleic acid sequence (SEQ ID NO: 41)

GAGGTGCAGCTGTTGGAGTCTGGGGGAGGCTTGGTACAGCCTGGGGGGTCCCTGCGTCTCTCCTGTGCAGC

CTCCGGATCCACCTTTACGGATGATAGGATGTGGTGGGTCCGCCAGGCTCCAGGGAAGGGTCTAGAGTGGG

TCTCAGCTATTCAGCCTGATGGTCATACGACATACTACGCAGACTCCGTGAAGGGCCGGTTCACCATCTCCC

GCGACAATTCCAAGAACACGCTGTATCTGCAAATGAACAGCCTGCGTGCCGAGGACACCGCGGTATATTACT

GTGCGGAACAGGATGTTAAGGGGTCGTCTTCGTTTGACTACTGGGGTCAGGGAACCCTGGTCACCGTCTCG

AGC

DOM23h-815 amino acid sequence (SEQ ID NO: 4)

EVQLLESGGGLVQPGGSLRLSCAASGFTFAEDRMWWVRQAPGKGLEWVSAIDPQGQHTYYADSVKGRFTISRD

NSKNTLYLQMNSLRAEDTAVYYCAKQSTGSATSDYWGQGTLVTVSS

DOM23h-815 nucleic acid sequence (SEQ ID NO: 42)

GAGGTGCAGCTGTTGGAGTCTGGGGGAGGCTTGGTACAGCCTGGGGGGTCCCTGCGTCTCTCCTGTGCAGC

CTCCGGATTCACCTTTGCGGAGGATCGGATGTGGTGGGTCCGCCAGGCTCCAGGGAAGGGTCTAGAGTGGG

TCTCAGCTATTGATCCTCAGGGTCAGCATACATACTACGCAGACTCCGTGAAGGGCCGGTTCACCATCTCCC

GCGACAATTCCAAGAACACGCTGTATCTGCAAATGAACAGCCTGCGTGCCGAGGACACCGCGGTATATTACT

GTGCGAAACAGTCTACTGGGTCTGCTACGTCTGACTACTGGGGTCAGGGAACCCTGGTCACCGTCTCGAGC

DOM23h-828 amino acid sequence (SEQ ID NO: 5)

EVQLLESGGGLVQPGGSLRLSCAASGFTFMSYRMWWVRQAPGKGLEWVSAISPSGSDTYYADSVKGRFTISRD

NSKNTLYLQMNSLRAEDTAVYYCAKQVVEYSRTHKGVFDYWGQGTLVTVSS

DOM23h-828 nucleic acid sequence (SEQ ID NO: 43)

GAGGTGCAGCTGTTGGAGTCTGGGGGAGGCTTGGTACAGCCTGGGGGGTCCCTGCGTCTCTCCTGTGCAGC

CTCCGGATTCACCTTTATGAGTTATAGGATGTGGTGGGTCCGCCAGGCTCCAGGGAAGGGTCTAGAGTGGG

TCTCAGCTATTTCTCCGAGTGGTAGTGATACATACTACGCAGACTCCGTGAAGGGCCGGTTCACCATCTCCC

GCGACAATTCCAAGAACACGCTGTATCTGCAAATGAACAGCCTGCGTGCCGAGGACACCGCGGTATATTACT

GTGCGAAACAGGTGGTGGAGTATTCGCGTACTCATAAGGGTGTGTTTGACTACTGGGGTCAGGGAACCCTG

GTCACCGTCTCGAGC

-continued

DOM23h-830 amino acid sequence
(SEQ ID NO: 6)
EVQLLESGGGLVQPGGFLRLSCAASGFTFEGYRMWWVRQAPGKGLEWVSAIDSLGDRTYYADSVKGRFTISRD
NSKNTLYLQMNSLRAEDTAVYYCAKQGLTHQSPSTFDYWGQGTLVTVSS DOM23h-830 nucleic acid sequence
(SEQ ID NO: 44)
GAGGTGCAGCTGTTGGAGTCTGGGGGAGGCTTGGTACAGCCTGGGGGGTTCCTGCGTCTCTCCTGTGCAGC
CTCCGGATTCACCTTTGAGGGGTATAGGATGTGGTGGGTCCGCCAGGCTCCAGGGAAGGGTCTAGAGTGGG
TCTCAGCTATTGATTCTCTGGGTGATCGTACATACTACGCAGACTCCGTGAAGGGCCGGTTCACCATCTCCC
GCGACAATTCCAAGAACACGCTGTATCTGCAAATGAACAGTCTGCGTGCCGAGGACACCGCGGTATATTACT
GTGCGAAACAGGGGCTTACGCATCAGTCTCCGAGTACGACTACTGGGGTCAGGGAACCCTGGTCACCG
TCTCGAGC DOM23h-831 amino acid sequence
(SEQ ID NO: 7)
EVQLLESGGGLVQPGGSLRLSCAASGFTFEAYKMTWVRQAPGKGLEWVSYITPSGGQTYYADSVKGRFTISRDN
SKNTLYLQMNSLRAEDTAVYYCAKYGSSFDYWGQGTLVTVSS DOM23h-831 nucleic acid sequence
(SEQ ID NO: 45)
GAGGTGCAGCTGTTGGAGTCTGGGGGAGGCTTGGTACAGCCTGGAGGGTCCCTGCGTCTCTCCTGTGCAGC
CTCCGGATTCACCTTTGAGGCGTATAAGATGACGTGGGTCCGCCAGGCTCCAGGGAAGGGTCTGGAGTGGG
TCTCATATATTACGCCGTCTGGTGGTCAGACATACTACGCAGACTCCGTGAAGGGCCGGTTCACCATCTCCC
GCGACAATTCCAAGAACACGCTGTATCTGCAAATGAACAGCCTGCGTGCCGAGGACACCGCGGTATATTACT
GTGCGAAATATGGTTCGAGGACTACTGGGGTCAGGGAACCCTGGTCACCGTCTCGAGC DOM23h-840 amino acid sequence
(SEQ ID NO: 8)
EVQLLESGGGLVQPGGSLRLSCAASGFTFGDRMWWVRQAPGKGLEWVSAIEGAGSDTYYADSVKGRFTISRD
NSKNTLYLQMNSLRAEDTAVYYCAKQASRNSPFDYWGQGTLVTVSS DOM23h-840 nucleic acid sequence
(SEQ ID NO: 46)
GAGGTGCAGCTGTTGGAGTCTGGGGGAGGCTTGGTACAGCCTGGGGGGTCCCTGCGTCTCTCCTGTGCAGC
CTCCGGATTCACCTTTGGGGATGGTCGTATGTGGTGGGTCCGCCAGGCTCCAGGGAAGGGTCTAGAGTGGG
TCTCAGCTATTGAGGGGGCGGGTTCGGATACATACTACGCAGACTCCGTGAAGGGCCGGTTCACCATCTCCC
GCGACAATTCCAAGAACACGCTGTATCTGCAAATGAACAGCCTGCGTGCCGAGGACACCGCGGTATATTACT
GTGCGAAACAGGCGTCGCGGAATTCGCCGTTTGACTACTGGGGTCAGGGGACCCTGGTCACCGTCTCGAGC DOM23h-842 amino acid sequence
(SEQ ID NO: 9)
EVQLLESGGGLVQPGGSLRLSCAASGFTFDDSEMAWARQAPGKGLEWVSLIRRNGNATYYADSVKGRFTISRD
NSKNTLYLQMNSLRAEDTAVYYCAKVTKDRSVLFDYWGQGTLVTVSS DOM23h-842 nucleic acid sequence
(SEQ ID NO: 47)
GAGGTGCAGCTGTTGGAGTCTGGGGGAGGCTTGGTACAGCCTGGGGGGTCCCTGCGTCTCTCCTGTGCAGC
CTCCGGATTCACCTTTGATGATAGTGAGATGGCGTGGGCCCGCCAGGCTCCAGGGAAGGGTCTAGAGTGGG
TCTCACTTATTCGGCGTAATGGTAATGCTACATACTACGCAGACTCCGTGAAGGGCCGGTTCACCATCTCCC
GCGACAATTCCAAGAACACGCTGTATCTGCAAATGAACAGCCTGCGTGCCGAGGACACCGCGGTATATTACT
GTGCGAAAGTTACGAAGGATCGTTCTGTGCTTTTTGACTACTGGGGTCAGGGAACCCTGGTCACCGTCTCGA
GC DOM23h-843 amino acid sequence
(SEQ ID NO: 10)
EVQLLESGGGLVQPGGSLRLSCAASGFTFDQDRMWWVRQAPGKGLEWVSAIESGGHRTYYADSVKGRFTISRD
NSKNTLYLQMNSLRAEDTAVYYCAKQNESGRSGFDYWGQGTLVTVSS DOM23h-843 nucleic acid sequence
(SEQ ID NO: 48)
GAGGTGCAGCTGTTGGAGTCTGGGGGAGGCTTGGTACAGCCTGGGGGGTCCCTGCGTCTCTCCTGTGCAGC

CTCCGGATTCACCTTTGATCAGGATCGGATGTGGTGGGTCCGCCAGGCTCCAGGGAAGGGTCTAGAGTGGG

TCTCAGCTATTGAGAGTGGTGGTCATAGGACATACTACGCAGACTCCGTGAAGGGCCGGTTCACCATCTCCC

GCGACAATTCCAAGAACACGCTGTATCTGCAAATGAACAGCCTGCGTGCCGAGGACACCGCGGTATATTACT

GTGCGAAACAGAATGAGTCGGGGCGTTCGGGGACTACTGGGGTCAGGGAACCCTGGTCACCGTCTCG

AGC

DOM23h-850 amino acid sequence
(SEQ ID NO: 11)
EVQLLESGGGLVQPGGSLRLSCAASGFTFDAARMWWARQAPGKGLEWVSAIADIGNTTYYADSVKGRFTISRD

NSKNTLYLQMNSLRAEDTAVYYCAKQSGSEDHFDYWGQGTLVTVSS

DOM23h-850 nucleic acid sequence
(SEQ ID NO: 49)
GAGGTGCAGCTGTTGGAGTCTGGGGGAGGCTTGGTACAGCCTGGGGGGTCCCTGCGTCTCTCCTGTGCAGC

CTCCGGATTCACCTTTGATGCGGCTAGGATGTGGTGGGCCCGCCAGGCTCCAGGGAAGGGTCTAGAGTGGG

TCTCAGCGATTGCGGATATTGGTAATACTACATACTACGCAGACTCCGTGAAGGGCCGGTTCACCATCTCCC

GCGACAATTCCAAGAACACGCTGTATCTGCAAATGAACAGCCTGCGTGCCGAGGACACCGCGGTATATTACT

GTGCGAAACAGTCTGGTTCGGAGGATCAGACTACTGGGGTCAGGGAACCCTGGTCACCGTCTCGAGC

DOM23h-854 amino acid sequence
(SEQ ID NO: 12)
EVQLLESGGGLVQPGGSLRLSCAASGFTFAQDRMWWVRQAPGKGLEWVSAISGSGGSTYYADSVKGRFTISRD

NSKNTLYLQMNSLRAEDTAVYYCAKQDLHGTSSLFDYWGQGTLVTVSS

DOM23h-854 nucleic acid sequence
(SEQ ID NO: 50)
GAGGTGCAGCTGTTGGAGTCCGGGGGAGGCTTGGTACAGCCTGGGGGGTCCCTGCGTCTCTCCTGTGCAGC

CTCCGGATTCACCTTTGCTCAGGATCGGATGTGGTGGGTCCGCCAGGCTCCAGGGAAGGGTCTAGAGTGGG

TCTCAGCTATTAGTGGTAGTGGTGGTAGCACATACTACGCAGACTCCGTGAAGGGCCGGTTCACCATCTCCC

GCGACAATTCCAAGAACACGCTGTATCTGCAAATGAACAGCCTGCGTGCCGAGGACACCGCGGTATATTACT

GTGCGAAACAGGATTTGCATGGTACTAGTTCTTTGTTTGACTACTGGGGTCAGGGAACCCTGGTCACCGTCT

CGAGC

DOM23h-855 amino acid sequence
(SEQ ID NO: 13)
EVQLLESGGGLVQPGGSLRLSCAASGFTFENTSMGWVRQAPGKGLEWVSRIDPKGSHTYYADSVKGRFTISRD

NSKNTLYLQMNSLRAEDTAVYYCAKQRELGKSHFDYWGQGTLVTVSS

DOM23h-855 nucleic acid sequence
(SEQ ID NO: 51)
GAGGTGCAGCTGTTGGAGTCTGGGGGAGGCTTGGTACAGCCTGGGGGGTCCCTGCGTCTCTCCTGTGCAGC

CTCCGGATTCACCTTTGAGAATACGAGTATGGGTTGGGTCCGCCAGGCTCCAGGGAAGGGTCTAGAGTGGG

TCTCACGTATTGATCCTAAGGGTAGTCATACATACTACGCAGACTCCGTGAAGGGCCGGTTCACCATCTCCC

GCGACAATTCCAAGAATACGCTGTATCTGCAAATGAACAGCCTGCGTGCCGAGGACACCGCGGTATATTACT

GTGCGAAACAGCGTGAGTTGGGTAAGTCGCAGACTACTGGGGTCAGGGAACCCTGGTCACCGTCTCG

AGC

DOM23h-865 amino acid sequence
(SEQ ID NO: 14)
EVQLLESGGGLVQPGGSLRLSCAASGFTFRSYEMTWVRQAPGKGLEWVSKIDPSGRFTYYADSVKGRFTISRDN

SKNTLYLQMNSLRAEDTAVYYCAKGRTDLQLFDYWGQGTLVTVSS

DOM23h-865 nucleic acid sequence
(SEQ ID NO: 52)
GAGGTGCAGCTGTTGGAGTCTGGGGGAGGCTTGGTACAGCCTGGGGGGTCCCTGCGTCTCTCCTGTGCAGC

CTCCGGATTCACCTTTCGTAGTTATGAGATGACTTGGGTCCGCCAGGCTCCAGGGAAGGGTCTAGAGTGGGT

CTCAAAGATTGATCCTTCGGGTCGIIIIACATACTACGCAGACTCCGTGAAGGGCCGGTTCACCATCTCCCG

CGACAATTCCAAGAACACGCTGTATCTGCAAATGAACAGCCTGCGTGCCGAGGATACCGCGGTATATTACTG

TGCGAAAGGTCGGACGGATCTTCAGCTTTTTGACTACTGGGGTCAGGGAACCCTGGTCACCGTCTCGAGC

DOM23h-866 amino acid sequence
(SEQ ID NO: 15)
EVQLLESGGGLVQPGGSLRLSCAASGFTFSNYWMRWARQAPGKGLEWVSYITPKGDHTYYADSVKGRFTISRD

NSKNTLYLQMNSLRAEDTAVYYCAESLHNERVKHFDYWGQGTLVTVSS

DOM23h-866 nucleic acid sequence
(SEQ ID NO: 53)
GAGGTGCAGCTGTTGGAGTCTGGGGGAGGCTTGGTACAGCCTGGGGGGTCCCTGCGTCTCTCCTGTGCAGC

CTCCGGATTCACCIIIICGAATTATTGGATGCGGTGGGCCCGCCAGGCTCCAGGGAAGGGTCTAGAGTGGG

TCTCATATATTACTCCTAAGGGTGATCATACATACTACGCAGACTCCGTGAAGGGCCGGTTCACCATCTCCCG

CGACAATTCCAAGAACACGCTGTATCTGCAAATGAACAGCCTGCGTGCCGAGGACACCGCGGTATATTACTG

TGCGAATCGCTTCATAATGAGCGTGTTAAGCA GACTACTGGGGTCAGGGAACCCTGGTCACCGTCTC

GAGC

DOM23h-874 amino acid sequence
(SEQ ID NO: 16)
EVQLLESGGGLVQPGGSLRLSCAASGFTFTSYRMWWVRQAPGKGLEWVSVIDSTGSATYYADSVKGRFTISRD

NSKNTLYLQMNSLRAEDTAVYYCAKQQAGSAMGEFDYWGQGTLVTVSS

DOM23h-874 nucleic acid sequence
(SEQ ID NO: 54)
GAGGTGCAGCTGTTGGAGTCTGGGGGAGGCTTGGTACAGCCTGGGGGGTCCCTGCGTCTCTCCTGTGCAGC

CTCCGGATTCACCTTTACTAGTTATCGTATGTGGTGGGTCCGCCAGGCTCCAGGGAAGGGTCTAGAGTGGGT

CTCAGTTATTGATTCTACTGGTTCGGCTACATACTACGCAGACTCCGTGAAGGGCCGGTTCACCATCTCCCG

CGACAATTCCAAGAACACGCTGTATCTGCAAATGAACAGCCTGCGTGCCGAGGATACCGCGGTATATTACTG

TGCGAAACAGCAGGCTGGGAGTGCGATGGGGGAGTTTGACTACTGGGGTCAGGGAACCCTGGTCACCGTCT

CGAGC

DOM23h-883 amino acid sequence
(SEQ ID NO: 17)
EVQLLESGGGLVQPGGSLRLSCAASGFTFVNYRMWWVRQAPGKGLEWVSAISGSGDKTYYADSVKGRFTISRD

NSKNTLYLQMNSLRAEDTAVYYCAKHGLSFDYWGQGTLVTVSS

DOM23h-883 nucleic acid sequence
(SEQ ID NO: 55)
GAGGTGCAGCTGTTGGAGTCTGGGGGAGGCTTGGTACAGCCTGGGGGGTCCCTGCGTCTCTCCTGTGCAGC

CTCCGGATTCACCTTTGTTAATTATCGTATGTGGTGGGTCCGCCAGGCTCCAGGGAAGGGTCTAGAGTGGGT

CTCAGCTATTAGTGGTAGTGGTGATAAGACATACTACGCAGACTCCGTGAAGGGCCGGTTCACCATCTCCCG

CGACAATTCCAAGAACACGCTGTATCTGCAAATGAACAGCCTGCGTGCCGAGGACACCGCGGTATATTACTG

TGCGAAACATGGGCTGTCGTTTGACTACTGGGGTCAGGGAACCCTGGTCACCGTCTCGAGC

DOM23h-903 amino acid sequence
(SEQ ID NO: 18)
EVQLLESGGGLVQPGGSLRLSCAASGFTFNDMRMWWVRQAPGKGLEWVSVINADGNRTYYADSVKGRFTISR

DNSKNTLYLQMNSLRAEDTAVYYCAKDGLPFDYWGQGTLVTVSS

DOM23h-903 nucleic acid sequence
(SEQ ID NO: 56)
GAGGTGCAGCTGTTGGAGTCTGGGGGAGGCTTGGTACAGCCTGGGGGGTCCCTGCGTCTCTCCTGTGCAGC

CTCCGGATTCACCTTTAATGATATGAGGATGTGGTGGGTCCGCCAGGCTCCAGGGAAGGGTCTAGAGTGGG

TCTCAGTGATTAATGCTGATGGTAATAGGACATACTACGCAGACTCCGTGAAGGGCCGGTTCACCATCTCCC

GCGACAATTCCAAGAACACGCTGTATCTGCAAATGAACAGCCTGCGTGCCGAGGATACCGCGGTATATTACT

GTGCGAAAGATGGGCTGCCGACTACTGGGGTCAGGGAACCCTGGTCACCGTCTCGAGC

DOM23m-4 amino acid sequence
(SEQ ID NO: 19)
EVQLLESGGGLVQPGGSLRLSCAASGFTFTTYGMGWVRQAPGKGLEWVSWIEKTGNKMADSVKGRFTISRD

NSKNTLYLQMNSLRAEDTAVYYCAKAGRHIKVRSRDFDYWGQGTLVTVSS

DOM23m-4 nucleic acid sequence
(SEQ ID NO: 57)
GAGGTGCAGCTGTTGGAGTCTGGGGGAGGCTTGGTACAGCCTGGGGGGTCCCTGCGTCTCTCCTGTGCAGC

CTCCGGATTCACCTTTACGACTTATGGTATGGGTTGGGTCCGCCAGGCTCCAGGGAAGGGTCTAGAGTGGG

TCTCATGGATTGAGAAGACGGGTAATAAGACATACTACGCAGACTCCGTGAAGGGCCGGTTCACCATCTCCC

GCGACAATTCCAAGAACACGCTGTATCTGCAAATGAACAGCCTGCGTGCCGAGGACACCGCGGTATATTACT

GTGCGAAAGCGGGGAGGCATATTAAGGTGCGTTCGAGGGAGACTACTGGGGTCAGGGAACCCTGGTC

ACCGTCTCGAGC

DOM23m-29 amino acid sequence
(SEQ ID NO: 20)
EVQLLESGGGLVQPGGSLRLSCAASGFTFKRYSMGWVRQAPGKGLEWVSVINDLGSLTYYADSVKGRFTISRDN

SKNTLYLQMNSLRAEDTAVYYCAKGNISMVRPGSWFDYWGQGTLVTVSS

DOM23m-29 nucleic acid sequence
(SEQ ID NO: 58)
GAGGTGCAGCTGTTGGAGTCTGGGGGAGGCTTGGTACAGCCTGGGGGGTCCCTGCGTCTCTCCTGTGCAGC

CTCCGGATTCACCTTTAAGAGGTATTCTATGGGTTGGGTCCGCCAGGCTCCAGGGAAGGGTCTAGAGTGGG

TCTCAGTTATTAATGATCTGGGTAGTTTGACATACTACGCAGACTCCGTGAAGGGCCGGTTCACCATCTCCC

GCGACAATTCCAAGAACACGCTGTATCTGCAAATGAACAGCCTGCGTGCCGAGGACACCGCGGTATATTACT

GTGCGAAAGGGAATATTAGTATGGTGAGGCCGGGGAGTTGGTTTGACTACTGGGGTCAGGGAACCCTGGTC

ACCGTCTCGAGC

DOM23m-32 amino acid sequence
(SEQ ID NO: 21)
EVQLLESGGGLVQPGGSLRLSCAASGFTFFEYPMGWVRQAPGKGLEWVSISGDGQRTYYADSVKGRFTISRD

NSKNTLYLQMNSLRAEDTAVYYCAKSHTGTVRHLETFDYWGQGTLVTVSS

DOM23m-32 nucleic acid sequence
(SEQ ID NO: 59)
GAGGTGCAGCTGTTGGAGTCTGGGGGAGGCTTGGTACAGCCTGGGGGGTCCCTGCGTCTCTCCTGTGCAGC

CTCCGGATTCACCTTTTTTGAGTATCCTATGGGTTGGGTCCGCCAGGCTCCAGGGAAGGGTCTAGAGTGGGT

CTCAGTTATTAGTGGGGATGGTCAGCGGACATACTACGCAGACTCCGTGAAGGGCCGGTTCACCATCTCCCG

CGACAATTCCAAGAACACGCTGTATCTGCAAATGAACAGCCTGCGTGCCGAGGACACCGCGGTATATTACTG

TGCGAAAAGTCATACGGGGACTGTGAGGCATCTGGAGACGTTTGACTACTGGGGTCAGGGAACCCTGGTCA

CCGTCTCGAGC

DOM23m-62 amino acid sequence
(SEQ ID NO: 22)
EVQLLESGGGLVQPGGSLRLSCAASGFTFGQESMYWVRQAPGKGLEWVSAISGSGGSTYYADSVKGRFTISRD

NSKNTLYLQMNSLRAEDTAVYYCAKSGTRIKQGFDYWGQGTLVTVSS

-continued

DOM23m-62 nucleic acid sequence
(SEQ ID NO: 60)
GAGGTGCAGCTGTTGGAGTCTGGGGGAGGCTTGGTACAGCCTGGGGGGTCCCTGCGTCTCTCCTGTGCAGC
CTCCGGATTCACCTTTGGTCAGGAGAGTATGTATTGGGTCCGCCAGGCTCCAGGGAAGGGTCTAGAGTGGG
TCTCAGCTATTAGTGGTAGTGGTGGTAGCACATACTACGCAGACTCCGTGAAGGGCCGGTTCACCATCTCCC
GCGACAATTCCAAGAACACGCTGTATCTGCAAATGAACAGCCTGCGTGCCGAGGACACCGCGGTATATTACT
GTGCGAAAAGTGGTACGCGGATTAAGCAGGGGACTACTGGGGTCAGGGAACCCTGGTCACCGTCTCG
AGC DOM23m-71 amino acid sequence
(SEQ ID NO: 23)
EVQLLESGGGLVQPGGSLRLSCAASGFTFMDYRMYWVRQAPGKGLEWVSGIDPTGLRTYYADSVKGRFTISRD
NSKNTLYLQMNSLRAEDTAVYYCAKIKWGEMGSYKTFDYWGQGTLVTVSS DOM23m-71 nucleic acid sequence
(SEQ ID NO: 61)
GAGGTGCAGCTGTTGGAGTCTGGGGGAGGCTTGGTACAGCCTGGGGGGTCCCTGCGTCTCTCCTGTGCAGC
CTCCGGATTCACCTTTATGGATTATAGGATGTATTGGGTCCGCCAGGCTCCAGGGAAGGGTCTAGAGTGGGT
CTCAGGGATTGATCCTACTGGTTTGCGGACATACTACGCAGACTCCGTGAAGGGCCGGTTCACCATCTCCCG
CGACAATTCCAAGAACACGCTGTATCTGCAAATGAACAGCCTGCGTGCCGAGGACACCGCGGTATATTACTG
TGCGAAAATTAAGTGGGGGGAGATGGGGAGTTATAAGACGACTACTGGGGTCAGGGAACCCTGGTCA
CCGTCTCGAGC DOM23m-72 amino acid sequence
(SEQ ID NO: 24)
EVQLLESGGGLVQPGGSLRLSCAASGFTFMDYDMSWVRQAPGKGLEWVSMIREDGGKTYYADSVKGRFTISRD
NSKNTLYLQMNSLRAEDTAVYYCAKARVPYRRGHRDNFDYWGQGTLVTVSS DOM23m-72 nucleic acid sequence
(SEQ ID NO: 62)
GAGGTGCAGCTGTTGGAGTCTGGGGGAGGCTTGGTACAGCCTGGGGGGTCCCTGCGTCTCTCCTGTGCAGC
CTCCGGATTCACCTTTATGGATTATGATATGAGTTGGGTCCGCCAGGCTCCAGGGAAGGGTCTAGAGTGGGT
CTCAATGATTCGTGAGGATGGTGGTAAGACATACTACGCAGACTCCGTGAAGGGCCGGTTCACCATCTCCCG
CGACAATTCCAAGAACACGCTGTATCTGCAAATGAACAGCCTGCGTGCCGAGGACACCGCGGTATATTACTG
TGCGAAAGCGAGGGTGCCTTATCGGCGTGGGCATAGGGATAAGACTACTGGGGTCAGGGAACCCTGG
TCACCGTCTCGAGC DOM23m-81 amino acid sequence
(SEQ ID NO: 25)
EVQLLESGGGLVQPGGSLRLSCAASGFTFEPVIMGWVRQAPGKGLEWVSAIEARGGGTYYADSVKGRFTISRDN
SKNTLYLQMNSLRAEDTAVYYCAKPGRHLSQDFDYWGQGTLVTVSS DOM23m-81 nucleic acid sequence
(SEQ ID NO: 63)
GAGGTGCAGCTGTTGGAGTCTGGGGGAGGCTTGGTACAGCCTGGGGGGTCCCTGCGTCTCTCCTGTGCAGC
TTCCGGATTCACCTTTGAGCCGGTTATTATGGGTGGGTCCGCCAGGCTCCAGGGAAGGGTCTAGAGTGGG
TCTCAGCTATTGAGGCGCGGGGTGGGGGACATACTACGCAGACTCCGTGAAGGGCCGGTTCACCATCTCC
CGCGACAATTCCAAGAACACGCTGTATCTGCAAATGAACAGCCTGCGTGCCGAGGACACCGCGGTATATTAC
TGTGCGAAACCTGGGCGGCATCTTAGTCAGGAGACTACTGGGGTCAGGGAACCCTGGTCACCGTCTCG
AGC DOM23m-99 amino acid sequence
(SEQ ID NO: 26)
EVQLLESGGGLVQPGGSLRLSCAASGFTFDRYRMMWVRQAPGKGLEWVSTIDPAGMLTY
YADSVKGRFTISRDNSKNTLYLQMNSLRAEDTAVYYCAKRLASRSHFDYWGQGTLVTVSS DOM23m-99 nucleic acid sequence
(SEQ ID NO: 64)
GAGGTGCAGCTGTTGGAGTCTGGGGGAGGCTTGGTACAGCCTGGGGGGTCCCTGCGTCTCTCCTGTGCAGC

CTCCGGATTCACCTTTGATCGGTATCGTATGATGTGGGTCCGCCAGGCTCCAGGGAAGGGTCTAGAGTGGG

TCTCAACGATTGATCCTGCTGGTATGCTTACATACTACGCAGACTCCGTGAAGGGCCGGTTCACCATCTCCC

GCGACAATTCCAAGAACACGCTGTATCTGCAAATGAACAGCCTGCGTGCCGAGGACACCGCGGTATATTACT

GTGCGAAAAGGCTGGCTTCGCGGAGTCAGACTACTGGGGTCAGGGAACCCTGGTCACCGTCTCGAGC

DOM23m-101 amino acid sequence
(SEQ ID NO: 27)
EVQLLESGGGLVQPGGSLRLSCAASGFTFSEYDMAWVRQAPGKGLEWVSRIRSDGVRTYYADSVKGRFTISRD

NSKNTLYLQMNSLRAEDTAVYYCAKDRAKNGWFDYWGQGTLVTVSS

DOM23m-101 nucleic acid sequence
(SEQ ID NO: 65)
GAGGTGCAGCTGTTGGAGTCTGGGGGAGGCTTGGTACAGCCTGGGGGGTCCCTGCGTCTCTCCTGTGCAGC

CTCCGGATTCACCIIIICTGAGTATGATATGGCTTGGGTCCGCCAGGCTCCAGGGAAGGGTCTTGAGTGGGT

CTCACGGATTCGTTCTGATGGTGTTAGGACATACTACGCAGACTCCGTGAAGGGCCGGTTCACCATCTCCCG

CGACAATTCCAAGAACACGCTGTATCTGCAAATGAACAGCCTGCGTGCCGAGGACACCGCGGTATATTACTG

TGCGAAAGATCGTGCTAAGAATGGTTGGTTTGACTACTGGGGTCAGGGAACCCTGGTCACCGTCTCGAGC

DOM23h-352 amino acid sequence
(SEQ ID NO: 28)
EVQLLESGGGLVQPGGSLRLSCAASGFTFDKYKMAWVRQAPGKGLEWVSLIFPNGVPTYYANSVKGRFTISRDN

SKNTLYLQMNSLRAEDTAVYYCAKYSGQGRDFDYWGQGTLVTVSS

DOM23h-352 nucleic acid sequence
(SEQ ID NO: 66)
GAGGTGCAGCTGTTGGAGTCTGGGGGAGGCTTGGTACAGCCTGGGGGGTCCCTGCGTCTCTCCTGTGCAGC

CTCCGGATTCACCTTTGATAAGTATAAGATGGCTTGGGTCCGCCAGGCTCCAGGGAAGGGTCTGGAGTGGG

TCTCACTTATTTTTCCGAATGGTGTTCCTACATACTACGCAAACTCCGTGAAGGGCCGGTTCACCATCTCCCG

CGACAATTCCAAGAACACGCTGTATCTGCAAATGAACAGCCTGCGTGCCGAGGACACCGCGGTATATTACTG

TGCGAAATATAGTGGTCAGGGCGGGAGACTACTGGGGTCAGGGAACCCTGGTCACCGTCTCGAGC

40

The CDRs as defined by Kabat of these anti-human and anti-murine TGFRII dAb naive leads are shown in Tables 1 and 2, below, respectively.

TABLE 1

CDR Sequences of anti-human TGFβRII dAbs

| Clone | CDR1 | CDR2 | CDR3 |
|---|---|---|---|
| DOM23h-802 | SEGTMW (SEQ ID NO: 77) | AILAAGSNTYYADSVKG (SEQ ID NO: 113) | KRQERDGFDY (SEQ ID NO: 149) |
| DOM23h-803 | SAGRMW (SEQ ID NO: 78) | AINRDGTRTYYADSVKG (SEQ ID NO: 114) | HDDGHGNFDY (SEQ ID NO: 150) |
| DOM23h-813 | TDDRMW (SEQ ID NO: 79) | AIQPDGHTTYYADSVKG (SEQ ID NO: 115) | EQDVKGSSSFDY (SEQ ID NO: 151) |
| DOM23h-815 | AEDRMW (SEQ ID NO: 80) | AIDPQGQHTYYADSVKG (SEQ ID NO: 116) | QSTGSATSDY (SEQ ID NO: 152) |
| DOM23h-828 | MSYRMW (SEQ ID NO: 81) | AISPSGSDTYYADSVKG (SEQ ID NO: 117) | QVVEYSRTHKGVFDY (SEQ ID NO: 153) |
| DOM23h-830 | EGYRMW (SEQ ID NO: 82) | AIDSLGDRTYYADSVKG (SEQ ID NO: 118) | QGLTHQSPSTFDY (SEQ ID NO: 154) |
| DOM23h-831 | EAYKMT (SEQ ID NO: 83) | YITPSGGQTYYADSVKG (SEQ ID NO: 119) | YGSSFDY (SEQ ID NO: 155) |

TABLE 1-continued

CDR Sequences of anti-human TGFβRII dAbs

| Clone | CDR1 | CDR2 | CDR3 |
|---|---|---|---|
| DOM23h-840 | GDGRMW (SEQ ID NO: 84) | AIEGAGSDTYYADSVKG (SEQ ID NO: 120) | QASRNSPFDY (SEQ ID NO: 156) |
| DOM23h-842 | DDSEMA (SEQ ID NO: 85) | LIRRNGNATYYADSVKG (SEQ ID NO: 121) | VTKDRSVLFDY (SEQ ID NO: 157) |
| DOM23h-843 | DQDRMW (SEQ ID NO: 86) | AIESGGHRTYYADSVKG (SEQ ID NO: 122) | QNESGRSGFDY (SEQ ID NO: 158) |
| DOM23h-850 | DAARMW (SEQ ID NO: 87) | AIADIGNTTYYADSVKG (SEQ ID NO: 123) | QSGSEDHFDY (SEQ ID NO: 159) |
| DOM23h-854 | AQDRMW (SEQ ID NO: 88) | AISGSGGSTYYADSVKG (SEQ ID NO: 124) | QDLHGTSSLFDY (SEQ ID NO: 160) |
| DOM23h-855 | ENTSMG (SEQ ID NO: 89) | RIDPKGSHTYYADSVKG (SEQ ID NO: 125) | QRELGKSHFDY (SEQ ID NO: 161) |
| DOM23h-865 | RSYEMT (SEQ ID NO: 90) | KIDPSGRFTYYADSVKG (SEQ ID NO: 126) | GRTDLQLFDY (SEQ ID NO: 162) |
| DOM23h-866 | SNYWMR (SEQ ID NO: 91) | YITPKGDHTYYADSVKG (SEQ ID NO: 127) | SLHNERVKHFDY (SEQ ID NO: 163) |
| DOM23h-874 | TSYRMW (SEQ ID NO: 92) | VIDSTGSATYYADSVKG (SEQ ID NO: 128) | QQAGSAMGEFDY (SEQ ID NO: 164) |
| DOM23h-883 | VNYRMW (SEQ ID NO: 93) | AISGSGDKTYYADSVKG (SEQ ID NO: 129) | HGLSFDY (SEQ ID NO: 165) |
| DOM23h-903 | NDMRMW (SEQ ID NO: 94) | VINADGNRTYYADSVKG (SEQ ID NO: 130) | DGLPFDY (SEQ ID NO: 166) |

TABLE 2

CDR Sequences of anti-murine TGFβRII dAbs

| Clone | CDR1 | CDR2 | CDR3 |
|---|---|---|---|
| DOM23m-4 | TTYGMG (SEQ ID NO: 95) | WIEKTGNKTYYADSVKG (SEQ ID NO: 131) | AGRHIKVRSRDFDY (SEQ ID NO: 167) |
| DOM23m-29 | KRYSMG (SEQ ID NO: 96) | VINDLGSLTYYADSVKG (SEQ ID NO: 132) | GNISMVRPGSWFDY (SEQ ID NO: 168) |
| DOM23m-32 | FEYPMG (SEQ ID NO: 97) | VISGDGQRTYYADSVKG (SEQ ID NO: 133) | SHTGTVRHLETFDY (SEQ ID NO: 169) |
| DOM23m-62 | GQESMY (SEQ ID NO: 98) | AISGSGGSTYYADSVKGR (SEQ ID NO: 134) | SGTRIKQGFDY (SEQ ID NO: 170) |
| DOM23m-71 | MDYRMY (SEQ ID NO: 99) | GIDPTGLRTYYADSVKG (SEQ ID NO: 135) | IKWGEMGSYKTFDY (SEQ ID NO: 171) |
| DOM23m-72 | MDYDMS (SEQ ID NO: 100) | MIREDGGKTYYADSVKGR (SEQ ID NO: 136) | ARVPYRRGHRDNFDY (SEQ ID NO: 172) |
| DOM23m-81 | EPVIMG (SEQ ID NO: 101) | AIEARGGGTYYADSVKG (SEQ ID NO: 137) | PGRHLSQDFDY (SEQ ID NO: 173) |
| DOM23m-99 | DRYRMM (SEQ ID NO: 102) | TIDPAGMLTYYADSVKG (SEQ ID NO: 138) | RLASRSHFDY (SEQ ID NO: 174) |
| DOM23m-101 | SEYDMA (SEQ ID NO: 103) | RIRSDGVRTYYADSVKG (SEQ ID NO: 139) | DRAKNGWFDY (SEQ ID NO: 175) |
| DOM23h-352 | DKYKMA (SEQ ID NO: 104) | LIFPNGVPTYYANSVKG (SEQ ID NO: 140) | YSGQGRDFDY (SEQ ID NO: 176) |

Example 2

DSC (Differential Scanning Calorimetry)—Naive Clones dAbs thermal stability was determined using Differential Scanning calorimetry (DSC). dAbs were dialysed overnight into PBS to a final concentration of 1 mg/ml. The dialysis buffer was used as a reference for all samples. DSC measurements were performed using the GE HEALTHCARE™-MICROCAL™VP-DSC capillary cell microcalorimeter, at a heating rate of 180° C./hour. A typical scan range was from 20-90° C. for both the reference buffer and the protein sample. A rescan was performed each time in order to assess the extent of protein refolding under these experimental conditions. After each protein sample scan, the capillary cell was cleaned with a solution of 5% DECON™ (Fisher-Scientific) in water followed by a PBS scan. Resulting data traces were analyzed using Origin 7.0 software. The DSC trace obtained from the reference buffer scan was subtracted from that of the protein sample scan. The precise molar concentration of the protein sample was entered into the data analysis routine to yield values for melting temperature (Tm), enthalpy (ΔH) and Van't Hoff enthalpy (ΔHv) values. Data were fitted to a non-2-state model (N2M). The best fit was obtained with either 1 or 2 transition events. The Tm values obtained for the dAbs described in this patent range from 52.1° C. to 73.3° C. Tm values and percentage of refolding are shown in Table 3.

TABLE 3

| | DSC Apparent Tm ° C. | | | |
|---|---|---|---|---|
| | 1-transition N2M | 2-transition N2M | | |
| dAb Name | Tm | Tm1 | Tm2 | % refolding |
| DOM23h-802 | — | 56.28 | 57.54 | 0 |
| DOM23h-803 | — | 61.19 | 64.59 | 23 |
| DOM23h-813 | 52.11 | — | — | 100 |
| DOM23h-815 | 65.13 | — | — | 93 |
| DOM23h-828 | — | 60.86 | 59.40 | 0 |
| DOM23h-830 | — | 57.01 | 58.15 | 0 |
| DOM23h-831 | — | 55.29 | 57.19 | 0 |
| DOM23h-840 | 63.70 | — | — | 100 |
| DOM23h-842 | 63.08 | — | — | 27 |
| DOM23h-843 | 60.15 | — | — | 60 |
| DOM23h-850 | 58.27 | — | — | 60 |
| DOM23h-854 | — | 55.31 | 58.20 | 30 |
| DOM23h-855 | 70.32 | — | — | 88 |
| DOM23h-865 | 63.02 | — | — | 0 |
| DOM23h-866 | — | 52.88 | 55.77 | 18 |
| DOM23h-874 | — | 58.83 | 60.15 | 0 |
| DOM23h-883 | — | 66.78 | 59.14 | 0 |
| DOM23h-903 | — | 59.11 | 61.98 | 24 |
| DOM23m-4 | — | 57.1 | 61.3 | 0 |
| DOM23m-29 | 68 | — | — | 0 |
| DOM23m-32 | — | 70.4 | 73.3 | 25 |
| DOM23m-62 | — | — | — | — |
| DOM23m-71 | 63 | — | — | 0 |
| DOM23m-72 | — | — | — | — |
| DOM23m-81 | — | — | — | — |
| DOM23m-99 | — | 58.5 | 59 | 0 |
| DOM23m-101 | 64 | — | — | 30 |
| DOM23m-352 | 66 | — | — | 50 |

All molecules maintain tertiary structure up to at least 52° C. upon heating.

Example 3

SEC-MALS (Size Exclusion Chromatography with Multi-Angle-LASER-Light Scattering)—Naive Clones To determine whether dAbs are monomeric or form higher order oligomers in solution, they were analyzed by SEC-MALLS (Size Exclusion Chromatography with Multi-Angle-LASER-Light-Scattering). Agilent 1100 series HPLC system with an autosampler and a UV detector (controlled by Empower software) was connected to Wyatt Mini Dawn Treos (Laser Light Scattering (LS) detector) and Wyatt Optilab rEX DRI (Differential Refractive Index (RI) detector). The detectors were connected in the following order -UV-LS-RI. Both RI and LS instruments operate at a wavelength of 658 nm; the UV signal was monitored at 280 nm and 220 nm. Domain antibodies (100 microliters injection at a concentration of 1 mg/mL in PBS) were separated according to their hydrodynamic properties by size exclusion chromatography using a GE HEALTHCARE™ 10/300 Superdex 75 column. The mobile phase was PBS plus 10% ethanol. The intensity of the scattered light while protein passed through the detector was measured as a function of angle. This measurement taken together with the protein concentration determined using the RI detector allowed calculation of the molar mass using appropriate equations (integral part of the analysis software Astra v.5.3.4.14). All the dAbs described herein have a monomeric content ranging from 65% to 98%. Data is shown in Table 4.

TABLE 4

| dAb name | Monomer by SEC-MALLS (%) |
|---|---|
| DOM23h-802 | 92.5 |
| DOM23h-803 | 96.4 |
| DOM23h-813 | 96.6 |
| DOM23h-815 | 98 |
| DOM23h-828 | 80 |
| DOM23h-830 | 65 |
| DOM23h-831 | 72 |
| DOM23h-840 | 91 |
| DOM23h-842 | 91.6 |
| DOM23h-843 | 90.2 |
| DOM23h-850 | 97.7 |
| DOM23h-854 | 83.4 |
| DOM23h-855 | 96.3 |
| DOM23h-865 | 83 |
| DOM23h-866 | 92.4 |
| DOM23h-874 | 92.6 |
| DOM23h-883 | 93.5 |
| DOM23h-903 | 96.5 |
| DOM23m-4* | 93 |
| DOM23m-29* | 95 |
| DOM23m-32* | 92 |
| DOM23m-62 | Not determined |
| DOM23m-71* | 88 |
| DOM23m-72 | Not determined |
| DOM23m-81 | Not determined |
| DOM23m-99 | 79 |
| DOM23m-101 | 77.4 |
| DOM23m-352 | 93 |

*These dAbs were run using the same SEC-MALLS set up as described above except that the HPLC used was a Shimadzu LC-20AD Prominence system. These dAbs were also run on a Superdex75 column but the mobile phase buffer was PBS.

The molecules listed in the tables 3 and 4 were chosen on the basis of Solution State (propensity for monomer) content and Thermal stability. All molecules show a ≥65% propensity for monomerisation and maintain tertiary structure up to at least 52° C. upon heating.

Example 4

Assays for TGFbetaRII Inhibition (Naive Clones)

MC3T3-E1 Luciferase Assay—Method m1:

The MC3T3-E1 luciferase assay measures the ability of dAbs to inhibit TGFβ-induced expression of CAGA-luciferase in MC3T3-E1 cells. Three copies of a TGFβ-responsive sequence motif, termed a CAGA box are present in the human PAI-1 promoter and specifically bind Smad3 and 4 proteins. Cloning multiple copies of the CAGA box into a luciferase reporter construct confers TGFβ responsiveness to cells transfected with the reporter system. This assay uses MC3T3-E1 cells (mouse osteoblasts) stably transfected with a $[CAGA]_{12}$-luciferase reporter construct (Dennler, et al. (1998) EMBO J. 17, 3091-3100).

Soluble dAbs were tested for their ability to block TGF-β1 signaling via the Smad3/4 pathway.

The protocol used to generate the data which appears as method m1 in table 5, is as follows. Briefly, $2.5 \times 10^4$ MC3T3-E1 cells per well in assay medium (RPMI medium (Gibco, Invitrogen Ltd, Paisley, UK), 10% heat inactivated foetal calf serum, and 1% penicillin/streptomycin) were added to a tissue culture 96 well plate (Nunc), followed by the dAb and TGF-β1 (final concentration 1 ng/ml) and incubated for six hours at 37° C., 5% $CO_2$. dAbs were dialysed into PBS prior to being tested in the assay. BRIGHTGLOW™ luciferase reagent (Promega, UK) was added to the wells and incubated at room temperature for two minutes to allow the cells to lyse, and the resulting luminescence measured on a luminometer.

The assay was performed multiple times to obtain an average and range of maximum % inhibitions values which are summarised in Table 5. This method has been modified and is described Below.

Modified MC3T3-E1 Luciferase Assay—Method m2.

MC3T3-E1 cells were added to 96 well plates (Nunc 13610) at $1.25 \times 10^4$ per well in "plating medium" (MEM-Alpha+Ribonucleosides, +Deoxyribonucleosides (Invitrogen 22571), 5% Charcoal stripped FCS (Perbio Sciences UK Ltd; SH30068.03), 1/100 Sodium Pyruvate (Invitrogen11360), 250 μg/ml of Geneticin 50 mg/ml (Invitrogen, 10131027), and incubated overnight at 37° C., 5% $CO_2$. The media from the cells was replaced with "assay media" (DMEM (Invitrogen 31966021,) 25 mM Hepes (Invitrogen)), and purified dAbs in PBS at 4× final assay concentration were titrated in "assay media" and added to the cell plates, followed by TGF-β1 (R&D, 240B) at 4× the EC80. The plates were incubated for six hours at 37° C., 5% $CO_2$. STEADYLITE™ luciferase reagent (PerkinElmer 6016987) was added to the wells and incubated at room temperature for 30 minutes, and the resulting luminescence measured on a the ENVISION™ plate reader.

Each dAb was titrated in duplicate in an assay and a maximum % inhibition determined (n=2). The assay was performed multiple times to obtain an average and range of maximum % inhibitions values which are summarised in Table 5. The assay QC parameters were met; in-house small molecule showing an IC50 range from 100 to 900 nM for the mouse assays. Also, the robust Z factors were greater than 0.4 and the TGF-β EC80 was within 6 fold of the concentration added to the assay.

A549 IL-11 Release Assay—h1

The A549 Interleukin-11 (IL-11) release assay measures the ability of dAbs to inhibit human TGF-β1 stimulated IL-11 release from A549 cells. TGF-β1 binds directly to TGF-βRII and induces the assembly of the TGF-βRI/II complex. TGF-βRI is phosphorylated and is able to signal through several pathways including the Smad4 pathway. Activation of the Smad4 pathway results in the release of IL-11. The IL-11 is secreted into the cell supernatant and is then measured by colourmetric ELISA.

Soluble dAbs were tested for their ability to block TGF-β1 signalling via the Smad4 pathway. Briefly, $1 \times 10^5$ A549 cells per well in "assay medium" (DMEM high glucose medium (Gibco™, Invitrogen Ltd, Paisley, UK), 10% heat inactivated foetal calf serum (PAA, Austria), 10 mM HEPES (Sigma, UK) and 1% penicillin/streptomycin (PAA, Austria)) were added to a tissue culture 96 well plate (Nunc), followed by the dAb and TGF-β1 (final concentration 3 ng/ml) (R&D Systems, Abingdon, UK) and incubated overnight at 37° C., 5% $CO_2$. dAbs were dialysed into PBS prior to being assayed. The concentration of IL-11 released into the supernatant was measured using a Human IL-11 DUOSET™ (R&D systems, Abingdon, UK), in accordance with the manufacturer's instructions.

The A549 IL-11 release assay is referred to in tables 5 and 6 as assay method h1. The assay was performed multiple times to obtain an average and range of maximum % inhibitions values which are summarised in Table 5. The assay QC parameters were met; in-house small molecule showing an IC50 range from 50 to 500 nM for the human assays.

SBE-bla HEK 293T Cell Sensor Assay—h2:

Members of the Smad family of signal transduction molecules are components of an intracellular pathway that transmits TGF-β signals from the cell surface to nucleus. TGF-β1 binds directly to TGF-βRII and induces the assembly of the TGF-βRI/II complex. Smad2 and Smad3 are then phosphorylated by TGF-βRI, and subsequently form a heteromeric complex with the co-smad family member Smad4. These complexes are translocated to the nucleus where they bind DNA and regulate gene transcription.

Cell Sensor SBE-bla HEK 293T cells contain a beta-lactamase reporter gene under control of the Smad binding element (SBE) which was stably integrated into HEK 293T cells (Invitrogen, UK). The cells are responsive to TGF-βI and can be used to detect agonists/antagonists of the Smad2/3 signaling pathway.

Soluble dAbs were tested for their ability to block TGF-β1 signaling via this pathway following the method below, which was based on an optimised method from Invitrogen, UK, (cell line K1108).

The assay was performed direct from frozen cells which had been grown for at least 4 passages in growth media (DMEM high glucose, Invitrogen 21068028, 10% Dialysed U.S. FBS. Invitrogen 26400-044, 0.1 mM (1/100) Non essential amino acids. Invitrogen 11140-050, 25 mM (1/40) HEPES buffer. Sigma H0887, 1 mM (1/100) Sodium pyruvate. Invitrogen 11360-070, 1% GLUTAMAX™. (200 mM Invitrogen 35050038), 5 μg/ml of Blasticidin. Invitrogen R21001) and frozen in house (at $4 \times 10^7$/ml). The cells were plated at 20,000 cells per well in cell culture plates (Costar 3712) in plating media (as above with 1% FCS and no blasticidin). After incubating the cells overnight, the purified dAbs were diluted in "assay media" (DMEM (Invitrogen 31966021,) 25 mM Hepes (Invitrogen) and added to the cells at 4× final assay concentration. After a 1 hour incubation at 37° C., TGF-β (R&D Systems; 240B) was added at 4×EC80 and incubated for a further 5 hours. The LIVEBLAZER™ substrate (Invitrogen K1030), was made up according to the manufacturer's instructions and added at 8× the volume. The plates were incubated in the dark at room temperature for 16 hours and read on the ENVISION™ plate reader according to the Invitrogen protocol.

The SBE-bla HEK CELLSENSOR™ assay is referred to in tables 5 and 6 as method h2. Each dAb was titrated in duplicate in an assay and an IC50 determined and maximum % inhibition determined (n=2). Due to the difficulty of obtaining full curves in the mouse assay, only % inhibitions are quoted in table 5. The assay was performed multiple times to obtain an average and a range of values which are summarised in Tables 5 and 6. The arithmetric mean IC50 was calculated using pIC50's (−log of IC50), and the range calculated adding and subtracting the log standard deviation from mean pIC50, and then transforming back to IC50. The assay QC parameters were met; in-house small molecule showing an IC50 range from 50 to 500 nM for the human assays. Also, the robust Z factors were greater than 0.4 and the TGF-β EC80 was within 6 fold of the concentration added to the assay The results are shown in Tables 5 and 6.

TABLE 5

Cell Functional assay data for mouse specific clones plus VH Dummy dAb.

| | Mouse 3T3 cell assay | | | | Human IL-11 release (h1) or SBE-bla HEK CELLSENSOR ™ assay (h2) | | | | |
|---|---|---|---|---|---|---|---|---|---|
| | Assay | max % inhibition | | | Assay | max % inhibition | | | |
| | Method | Average | SD | range | n | Method | Average | SD | range | n |
| DOM23m-04 | m1 | 73.3 | 8.4 | 68.8-83 | 3 | h1 | 70.7 | 6.4 | 67-78 | 3 |
| DOM23m-04 | | | | | | h2 | 69.0 | | | 1 |
| DOM23m-29 | m1 | 54.2 | 5.2 | 50.5-57.9 | 2 | | | | | |
| DOM23m-32 | m1 | 39.7 | 4.0 | 36.9-42.5 | 2 | | | | | |
| DOM23m-62 | m1 | 78.6 | | | 1 | h1 | 79.0 | | | 1 |
| DOM23m-71 | m1 | 44.9 | 9.3 | 38.3-51.4 | 2 | h1 | −2.0 | | | 1 |
| DOM23m-72 | m1 | 17.5 | 24.7 | 0-34.9 | 2 | h1 | 1.7 | | | 1 |
| DOM23m-81 | m2 | 30.3 | 11.5 | 21-47 | 4 | | | | | |
| DOM23m-99 | m2 | 46.5 | 28.0 | 26.7-93.5 | 6 | | | | | |
| DOM23m-101 | m2 | 48.0 | 19 | 22.0-74.1 | 12 | h2 | 59.8 | 27.0 | 17-81 | 5 |
| DOM23h-352 | m2 | 48.0 | 23.9 | 16.8-78.9 | 16 | h2 | 46.7 | 36.5 | 5.7-86 | 5 |
| VHDUM-2 | m2 | 21.4 | 13.2 | 21-33.9 | 15 | h2 | 46.0 | 29.6 | 17-84 | 6 |
| VHDUM-2 | m1 | 22.5 | 0 | 22.5 | 2 | | | | | |

TABLE 6

Cell Functional data for human specific clones plus VH Dummy dAb.

| | | IC50 nM | | |
|---|---|---|---|---|
| Assay method | dAb | Mean | IC50 range (+/− log SD) | n |
| h2 | DOM23h-802 | >11062 | 6592-18562 | 6 |
| h2 | DOM23h-803 | >11619 | 5890-22922 | 6 |
| h2 | DOM23h-813 | >9328 | 4301-20230 | 6 |
| h2 | DOM23h-815 | 7122 | 3026-16764 | 4 |
| h2 | DOM23h-828 | 9899.07 | 4441-22065 | 4 |
| h2 | DOM23h 830 | 6299 | 5442-7291 | 4 |
| h2 | DOM23h-831 | >3126 | 534-18291 | 8 |
| h2 | DOM23h 840 | 2915 | 650-13081 | 7 |
| h2 | DOM23h 842 | 2042 | 2223-18704 | 4 |
| h2 | DOM23h-843 | >9007 | 3396-23894 | 8 |
| h2 | DOM23h-850 | 5350 | 2358-12137 | 6 |
| h2 | DOM23h-854 | >9551 | 3085-29569 | 8 |
| h2 | DOM23h-855 | >4467 | 1088-18339 | 8 |
| h2 | DOM23h 865 | 5559 | 1070-28893 | 4 |
| h2 | DOM23h 866 | >1762 | 195-15900 | 6 |
| h2 | DOM23h 874 | >925 | 89-9591 | 6 |
| h2 | DOM23h 883 | 10123 | 60-17344 | 6 |
| h2 | DOM23h 903 | 1048 | 492-223 | 5 |
| h2 | VHDummy-2 | >25119 | 25000-50000 | 12 |

The mouse clones were selected on the basis that they showed greater than 40% neutralisation of TGF-β in several assays. The only exception to this was DOM23m-72. The clones also showed good neutralisation curves (data not shown). The human clones were selected on the basis that the average IC50's were less than 15 μM.

Example 5

Error Prone Affinity Maturation of Naive Clones (from Example 1)

Error-prone mutagenesis was performed to improve the affinity of the dAbs identified as active with suitable biophysical characteristics (described above).

Phage Library Construction: Error prone libraries of DOM23h-843, DOM23h-850, DOM23h-854, DOM23h-855, DOM23h-865, DOM23h-866, DOM23h-874, DOM23h-883, DOM23h-439 and DOM23h-903, were made using GENEMORPH™ II Random Mutagenesis kit (Stratagene, Cat No 200550). The target dAb genes were amplified by PCR using Taq DNA polymerase and oligonucleotides DOM008 (5'-AGCGGATAACAATTTCACACAGGA-3' (SEQ ID NO:185)) and DOM009 (5'-CGCCAGGGTTTTC-CCAGTCACGAC-3' (SEQ ID NO:186)), followed by re-amplification of the diluted PCR product with oligonucleotides DOM172 (5' TTGCAGGCGTGGCAACAGCG-3' (SEQ ID NO:187)) and DOM173 (5f-CACGACGTTG-TAAAACGACGGCC-3' (SEQ ID NO:188)), and MUTAZYME™ II DNA polymerase, according to manufacturer's instructions. This PCR product was further amplified using Taq DNA polymerase and oligonucleotides DOM172 and DOM173, to increase the DNA product yield. The PCR product was digested with Sal I and Not I restriction endonucleases. Undigested product and digested ends were removed from the digested product using streptavidin beads (Dynal Biotech, UK). For the anti-human error prone selections digested product was ligated into pDOM4 phage vector digested with Sal I and Not I restriction endonucleases and used to transform E. coli TB1 cells. The transformed cells were plated on 2×TY agar supplemented with 15 μg/ml tetracycline, yielding library sizes of >1×10⁷ transformants.

Human TGFbetaRII specific dAb Error-prone selections: Three rounds of selection were performed with the DOM23h-843, DOM23h-850, DOM23h-854, DOM23h-855, DOM23h-865, DOM23h-866, DOM23h-874, DOM23h-883, DOM23h-903, and DOM23h-439 libraries. Round one was performed using 1 nM biotinylated human TGFbetaRII/Fc (N13241-57). Two different methods were followed for rounds two and three, method 1 using the dimeric TGFbetaRII/Fc form of the antigen and method two using the soluble, monomeric form of TGFbetaRII. Method 1: Round two was performed with 1 nM biotinylated human TGFbetaRII/Fc with 1 uM non-biotinylated human TGFbetaRII/Fc competitor. Round three was performed with 100 pM biotinylated human TGFbetaRII/Fc with 1 uM non-biotinylated human TGFbetaRII/Fc (N12717-4). Method 2: Round two was performed with 1 nM biotinylated human TGFbetaRII with 1 uM non-biotinylated human TGFbetaRII competitor. Round three was performed with 100 pM biotinylated human TGFbetaRII with 1 uM non-biotinylated human TGFbetaRII competitor.

Second and third round selection outputs were subcloned into the pDOM13 vector, as described above. Individual clones were picked and expressed in 96 well plates at 850 rpm, 37° C. for 24 hours, 90% humidity in 0.5 ml/well overnight express auto-induction medium supplemented with 100 µg/ml carbenicillin. Plates were then centrifuged at 1800 g for 10 minutes. Supernatants were diluted either 1/5 or 1/2 in HBS-EP buffer and screened on BIACORE™ for binding to biotinylated human TGF-β RII/Fc (SA chip coated with 1000 Ru biotinylated hRII-Fc in accordance with the manufacturer's recommendations) (BIACORE™, GE HEALTHCARE™). Samples were run on BIACORE™ at a flow rate of 50 µl/min. Clones that bound with a high number of resonance units (RUs) or with an improved off-rate compared to the parent clone were expressed in 50 ml overnight express autoinduction medium at 30° C. for 48 to 72 hours and centrifuged at 4,600 rpm for 30 minutes. The supernatants were incubated overnight at 4° C. with Streamline-protein A beads. The beads were then packed into drip columns, washed with 5 column volumes of 2×PBS, followed by one bed volume of 10 mM Tris-HCl pH 7.4 and bound dAbs were eluted in 0.1 M glycine-HCl, pH 2.0 and neutralised with 1 M Tris-HCl, pH 8.0. The OD at 280 nm of the dAbs was measured and protein concentrations were determined using extinction coefficients calculated from the amino acid compositions of the dAbs.

In vitro analysis of off rate improved error prone selections: Purified dAbs were subjected to the same tests as those from the naive selections, namely, Biacore, SBE-bla HEK 293T Cell Sensor assay (h2), DSC, and SEC-MALS. Examples of clones improved over parent are shown in table 6A. IC50 values are a mean of 'n' number of experiments.

TABLE 6A

| DOM23h | On-rate ka1 (1/Ms) | Off-rate kd1 (1/s) | Affinity KD | ka Fold improvement | kd Fold improvement | KD Fold improvement | Mean IC50 (nM)* |
|---|---|---|---|---|---|---|---|
| 439 | 2.08E+06 | 5.02E−02 | 2.42E−08 | | | | 3570 (3) |
| 439-20 | 4.43E+06 | 3.54E−03 | 7.99E−10 | 2.1 | 14.2 | 30.3 | 48 (10) |
| 843 | 9.05E+05 | 3.43E−01 | 3.78E−07 | | | | 1947 (3) |
| 843-13 | 5.11E+06 | 2.11E−02 | 4.13E−09 | 5.6 | 16.2 | 91.7 | 540 (4) |
| 855 | 3.35E+05 | 3.15E−01 | 9.41E−07 | | | | >25000 (3) |
| 855-21 | 1.86E+06 | 3.36E−02 | 1.80E−08 | 5.6 | 9.4 | 52.3 | 18580 (6) |

*number of experiments for calculation of mean IC50s provided in parenthesis

Affinity Matured Sequences

```
DOM23h-855-21 nucleic acid sequence
                                              (SEQ ID NO: 203)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGAATACGAGTATGGGTTGGGTCCGCCAGGCT

CCAGGGAAGGGTCTAGAGTGGGTCTCACGTATTGATCCTAAGGGTAGTCATACATACTAC

ACAGACTCCGTGAAGGGCCGGTTCACCATCTCCCGCGACAATTCCAAGAATACGCTGTAT

CTGCAAATGAACAGCCTGCGTGCCGAGGACACCGCGGTATATTACTGTGCGAAACAGCGT

GAGTTGGGTAAGTCGTAGACTACTGGGGTCAGGGAACCCTGGTCACCGTCTCGAGC

DOM23h-855-21 amino acid sequence
                                              (SEQ ID NO: 204)
EVQLLESGGGLVQPGGSLRLSCAASGFTFENTSMGWVRQAPGKGLEWVSRIDPKGSHTYY

TDSVKGRFTISRDNSKNTLYLQMNSLRAEDTAVYYCAKQRELGKSYFDYWGQGTLVTVSS

DOM23h-843-13 nucleic acid sequence
                                              (SEQ ID NO: 205)
GAGGTGCAGCTGTTGGAGTCTGGGGGAGGCCTGGTACAGCCTGGGGGGTCCCTGCGTCTC

TCCTGTGCAGCCTCCGGATTCACCTTTGATCAGGATCGGATGTGGTGGGTCCGCCAGGCC

CCAGGGAAGGGTCTAGAGTGGGTCTCAGCTATTGAGAGTGGTGGTCATAGGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAATCAGAAT

AAGTCGGGCGTTCGGGGACTACTGGGGTCAGGGAACCCTGGTCACCGTCTCGAGC
```

-continued

DOM23h-843-13 amino acid sequence
(SEQ ID NO: 206)
EVQLLESGGGLVQPGGSLRLSCAASGFTFDQDRMWWVRQAPGKGLEWVSAIESGGHRTY
YADSVKGRFTISRDNSKNTLYLQMNSLRAEDTAVYYCANQNKSGRSGFDYWGQGTLVTVSS DOM23h-439-20 nucleic acid sequence
(SEQ ID NO: 207)
GAGGTGCAGCTGTTGGAGTCTGGGGGAGGCTTGGTACAGCCTGGGGGGTCCCTGCGTCTCTCCTGTGCAGC
CTCCGGATTCACCTTTGGGACGGAGCAGATGTGGTGGGTCCGCCAGGCTCCAGGGAAGGGTCTAGAGTTTG
TCTCACGTATTGATTCGCCTGGTGGGAGGACATACTACGCAGACTCCGTGAAGGGCCGGTTCACCATCTCCC
GCGACAATTCCAAGAACACGCTGTATCTGCAAATGAACAGCCTGCGTGCCGAGGACACCGCGGTATATTACT
GTGCGAAACGGCATGCGGCTGGGGTTTCGGGTACTTATTTTGACTACTGGGGTCAGGGAACCCTGGTCACC
GTCTCGAGC DOM23h-439-20 amino acid sequence
(SEQ ID NO: 208)
EVQLLESGGGLVQPGGSLRLSCAASGFTFGTEQMWWVRQAPGKGLEFVSRIDSPGGRTYYADSVKGRFTISRD
NSKNTLYLQMNSLRAEDTAVYYCAKRHAAGVSGTYFDYWGQGTLVTVSS Example 6

Affinity Maturation of DOM23h-271-7 Lineage

DOM23h-271 amino acid sequence
(SEQ ID NO: 199)
EVQLLESGGGLVQPGGSLRLSCAASGFTFTEYRMWWVRQAPGKGLEWVSAIEPIGNRTYYADSVKGRFTISRDN
SKNTLYLQMNSLRAEDTAVYYCAKQIPGRKWTANSRFDYWGQGTLVTVSS DOM23h-271 nucleic acid sequence
(SEQ ID NO: 200)
GAGGTGCAGCTGTTGGAGTCTGGGGGAGGCTTGGTACAGCCTGGGGGGTCCCTGCGTCTCTCCTGTGCAGC
CTCCGGATTCACCTTTACGGAGTATAGGATGTGGTGGGTCCGCCAGGCTCCGGGGAAGGGTCTCGAGTGGG
TCTCAGCGATTGAGCCGATTGGTAATCGTACATACTACGCAGACTCCGTGAAGGGCCGGTTCACCATCTCCC
GCGACAATTCCAAGAACACGCTGTATCTGCAAATGAACAGCCTGCGTGCCGAGGATACCGCGGTATATTACT
GTGCGAAACAGATTCCGGGGCGTAAGTGGACTGCTAATTCGCGGTTTGACTACTGGGGTCAGGGAACCCTG
GTCACCGTCTCGAGC DOM23h-271-7 amino acid sequence
(SEQ ID NO: 201)
EVQLLESGGGLVQPGGSLRLSCAASGFTFTEYRMWWVRQAPGKGLEWVSAIEPIGNRTYYADSVKGRFTISRDN
SKNTLYLQMNSLRAEDTAVYYCAKQIPGRKWTANSRFDYWGQGTLVTVSS DOM23h-271-7 nucleic acid sequence
(SEQ ID NO: 202)
GAGGTGCAGCTGTTGGAGTCTGGGGGAGGCTTGGTACAGCCTGGGGGGTCCCTGCGTCTCTCCTGTGCAGC
CTCCGGATTCACCTTTACGGAGTATAGGATGTGGTGGGTCCGCCAGGCTCCGGGGAAGGGTCTCGAGTGGG
TCTCAGCGATTGAGCCGATTGGTAATCGTACATACTACGCAGACTCCGTGAAGGGCCGGTTCACCATCTCCC
GCGACAATTCCAAGAACACGCTGTATCTGCAAATGAACAGCCTGCGTGCCGAGGATACCGCGGTATATTACT
GTGCGAAACAGATTCCGGGGCGTAAGTGGACTGCTAATTCGCGGTTTGACTACTGGGGTCAGGGAACCCTG
GTCACCGTCTCGAGC Domain antibody DOM23h-271(SEQ ID No:199) had been isolated from the phage libraries in a previous selection campaign and variant DOM23h-271-7 (SEQ ID NO:201) was isolated following error prone affinity maturation, both as described in WO 2011/012609DOM23h-271-7 (SEQ ID NO:201) was selected for further affinity maturation based on its binding kinetics, sequence and biophysical behaviour. Affinity maturation was performed using degenerative mutagenesis to re-diversify the CDRs, and improved leads were identified using DNA display or phage display. Two types of libraries were constructed to re-diversify the CDRs, and these are referred to as triplet and doped libraries. To make the triplet libraries oligonucleotide primers were designed to cover each CDR, and within each primer the codons for three amino acids were replaced with NNS codons, so that three positions were diversified. Multiple oligonucleotides were used to cover all targeted amino acids within each CDR: 2 for CDR1, 3 for CDR2 and 6 for CDR3. Complementary oligonucleotide primers were used to amplify a sequence fragment containing each mutated CDR, and also an overlapping sequence fragment covering the rest of the dAb coding sequence. These fragments were mixed and assembled by splice extension overlap PCR to produce the full length dAb coding sequence. This product was PCR amplified using primers DOM172 (SEQ ID NO:187) and DOM173 (SEQ ID NO:188), digested with SalI and NotI, and ligated into similarly cut pDOM4 (described above) for phage selections, or pIE2A2 (described in WO2006018650) for DNA Display selections. The doped libraries were constructed using a similar method, essentially as described in WO2006018650. A single degenerate oligonucleotide primer was used to cover all mutations within each CDR. Within each primer the amino acids to be diversified were specified using degenerate codons to specify multiple amino acids. Five amino acids were diversified in CDR1, 7 in CDR2, and 13 in CDR3. In the primers the following degenerate coding is used: 'a'=91% A+3% T+3% G+3% C; 'g'=91% G+3% T+3% C+3% A; 'c'=91% C+3% T+3% G+3% A; 't'=91% T+3% A+3% G+3% C; 'S'=50% G and 50% C. Capital letters indicate 100% of the specified nucleotide. The primers used were:

pIE2A2 vector using flanking primers. The product was purified from an eGel (Invitrogen) and diluted to 1.7 or 0.85 nM in 1 mg/ml BSA. For selection of improved binders the doped and Triplet libraries were processed separately under slightly different conditions. The Triplet CDR libraries were combined to give pooled CDR 1, 2 or 3 libraries. Ten rounds of selection were used for each type of library. For both methods, after 2 selection cycles, the diversified CDR's were amplified and recombined by splice overlap extension PCR to produce a 4th library with mutations in all 3 CDRs.

For the doped libraries $5 \times 10^8$ copies of DNA were mixed with 50 ul of EXPRESSWAY™ In vitro translation mix (Invitrogen). Each reaction contained 10.0 µl SLYD™ extract; 10.0 µl 2.5× reaction buffer; 12.5 µl 2× feed buffer; 1.0 µl Methionine (75 mM); 1.26 µl Amino Acid mix (50 mM); 15 µl $H_2O$; 0.5 µl T7 Polymerase; 0.25 µl anti-HA mAb 3F10 (Roche, cat. 1 867 423); and 1.5 µl Glutathione (100 mM) (Sigma). This was added to 800 µl of hydrophobic phase (4.5% SPAN™-80, (Fluka)+0.5% Triton X-100 (Sigma) in Light white mineral oil (Sigma)) in a 4 ml glass vial (CHROMACOL™ 4SV P837) and stirred at 2000 rpm for 4-5 minutes. The tubes were sealed and incubated for 3 hours at 30° C. All subsequent steps were done at room temperature. To extract the DNA-protein complexes 200 µl of C+ buffer (10 mM Tris, 0.1 M KCl, 0.05% TWEEN™-20, 5 mM $MgCl_2$, 1% BSA, pH 7.4) and 500 µl of Hexane was added to the vial, mixed and transferred to a microtube and centrifuged at 13000 g for 1 minute. The organic phase was removed and the aqueous phase re-extracted with 800 µl of Hexane 3-5 more times until the interface was almost clear. For the first 5 rounds of selections the biotinylated TGFbRII-FC was pre-bound to Streptavidin DYNAbeads™ (Invitrogen) and added to the extracted complexes to give an antigen concentration equivalent to 40, 40, 10, 5 and 5 nM antigen (rounds 1, 2, 3, 4 and 5 respectively). T1 beads were used for selections 1-3, and C1 for selections 4 and 5. After 30 minutes incubation the beads were washed 3-5 times with C+ buffer. The DNA complexes remaining bound to the beads were then recovered by PCR with flanking primers. Selection rounds 6-10 were referred to as 'soluble' selections, where the Biotinylated TGFbRII-FC was added directly to the complexes after

```
271-7R1deg CDR1
                                                                  (SEQ ID NO: 189)
(GCAGCCTCCGGATTCACCTTTacSgaStatagSATGtgSTGGGTCCGCCAGGCTCCGGGG);

271-7R2deg CDR2
                                                                  (SEQ ID NO: 190)
(GGGTCTCGAGTGGGTCTCAgcSATTgaSccSatSggSaaScgSACATACTACGCAGACTCCGTG);

271-7R3deg CDR3:
                                                                  (SEQ ID NO: 191)
(GCGGTATATTACTGTGCGAAAcaSatSccSggScgSaaStgSacSgcSaaStcScgSttSGACTACTGGGGTCAGGG).
```

The degenerate library primers were used in the same way as the triplet primers. Each diversified CDR was amplified separately and then combined with a parental sequence fragment using splice extension overlap. The fragments were subcloned to pDOM4 and pIE2A2 using SalI and NotI.

DNA Display

Selections were performed using in vitro compartmentalisation in emulsions and DNA display using the scArc DNA binding protein essentially as described in WO2006018650. Briefly, TGFbRII-FC antigen was biotinylated using a 5:1 molar ratio of Biotin and the EZ-LINK™ Sulpho-NHS-LC-Biotin kit (Thermo #21327). A DNA fragment containing the Arc operator sequences and expression cassette containing the diversified dAb library was PCR amplified from the extraction to give a concentration of 5, 5, 4, 5 and 5 nM (rounds 6, 7, 8, 9 and 10 respectively), and incubated for 30 minutes to allow binding to be established. Non-biotinylated TGFbRII-FC was then added as a competitor to 74, 750, 400, 250 and 250 nM (rounds 6, 7, 8, 9 and 10 respectively), and incubated for 15, 15, 30, 30 and 30 minutes (rounds 6, 7, 8, 9 and 10 respectively). In rounds 9 and 10 a double stranded oligonucleotide containing the ARC operator sequence was included at 50 nM in the C+ buffer used in the hexane extractions to reduce cross-reactions between any non-complexed DNA and excess protein released from the emulsions. After the competition period 10 µl of C1 Streptavidin DYNAbeads™ were added. After 10 minutes the beads were washed 5 times with Buffer C+ and the bound complexes recovered by PCR with flanking primers as previously described. The PCR product was purified on an eGel and used for the next selection cycle. Following the 10th selection the recovered product was cut with SalI and NotI enzymes, and cloned into similarly cut pDOM13 for expression.

The triplet libraries were selected using a similar method, except that 1×10$^9$ DNA copies were used in the first round selection, and 5×10$^8$ thereafter. Also, the incubation time for protein expression in the emulsion was reduced to 2 hours. Soluble Biotinylated TGFbRII FC was used in all ten selection rounds at 25, 10, 5, 5, 5, 5, 2.5, 2.5, 2.5, 2.5, 2.5, 2.5 nM respectively. The Biotinylated target was incubated with the extracted complexes for 30 minutes. In selection rounds 5-10 the non-biotinylated TGFbRII-FC competitor was added to a final concentration of 250 nM for 15, 30, 60, 60, 75, and 90 minutes respectively before addition of C1 streptavidin DYNAbeads™. In round 5 competition was at room temperature, but from round 6 the competition temperature was increased to 30° C. The Arc Operator decoy oligo was included in selection rounds 1-4 to reduce cross complexing of defective DNA.

Following selections the dAb encoding inserts were excised from the DNA display expression cassettes using SalI and NotI, and cloned into the pDOM13 bacterial expression vector. The dAbs were sequenced and expressed in TB ONEX™ medium and supernatants were screened by BIACORE™ to identify clones with improved off-rates when compared to parent. Clones with improved off-rates were expressed and purified, and were assessed for affinity by BIACORE™ and potency in the cell sensor assay. Clones giving poor kinetic profiles, containing unfavourable sequence motifs, or giving very low yields were not pursued. Three were selected to be of further interest. Clones DOM23h-271-21 (SEQ ID NO:29) and DOM23h-271-22 (SEQ ID NO:30) were isolated from doped library selections. Clone DOM23h-271-27 (SEQ ID NO:31) was isolated from a triplet library selection. The affinity of the selected clones for human TGFbRII-FC is shown in table 7.

TABLE 7

|  | Ka(M$^{-1}$·s$^{-1}$) | Kd (s$^{-1}$) | KD (nM) |
|---|---|---|---|
| DOM23h-271-7* | 5.37E+6 | 5.10E-2 | 9.49 |
| DOM23h-271-21 | 3.21E+6 | 4.72E-4 | 0.147 |

TABLE 7-continued

|  | Ka(M$^{-1}$·s$^{-1}$) | Kd (s$^{-1}$) | KD (nM) |
|---|---|---|---|
| DOM23h-271-22 | 3.22E+6 | 9.19E-4 | 0.286 |
| DOM23h-271-27 | 2.17E+6 | 1.26E-3 | 0.578 |

*N.B. values in the above table are for ranking purposes only since the fitting for DOM23h-271-7 to the 1:1 model was poor, although the affinity matured samples fitted well to this model.

Phage Display:

Triplet or doped libraries in separate CDR1, CDR2 and CDR3 pools were subjected to rounds of phage selection as described above against either biotinylated human TGF-β RII/Fc antigen over 4 rounds in concentrations of 10 nM, 1 nM, 100 pM and 20 pM respectively, or two rounds of selection using 20 pM followed by 2 pM antigen. Inserts from phage selections were cloned into the pDOM10 expression vector and supernatants with off rates improved over parent were selected for further study. Domain antibodies were expressed and purified their affinity and bioactivity against human TGF-β RII/Fc antigen tested on the BIACORE™ T100 and in the Cell sensor assay described above (data not shown). The affinity of the selected clones for human TGF-bRII-FC is shown in table 8.

TABLE 8

| Sample | Ka (M-1·s-1) | Kd (s-1) | KD (M) |
|---|---|---|---|
| 271-101 | 3.73E+06 | 0.02014 | 5.40E-09 |
| 271-102 | 9.35E+06 | 0.01531 | 1.64E-09 |
| 271-105a* | 3.29E+06 | 0.00747 | 2.27E-09 |
| 271-105b* | 3.07E+06 | 0.007977 | 2.60E-09 |
| 271-106a* | 7.39E+06 | 0.02333 | 3.16E-09 |
| 271-106b* | 6.77E+06 | 0.01947 | 2.88E-09 |
| 271-114 | 1.04E+07 | 0.07084 | 6.80E-09 |
| 271-7a* | 3.04E+06 | 0.04193 | 1.38E-08 |
| 271-7b* | 2.42E+06 | 0.04448 | 1.84E-08 |

*The designation "a" and "b" refer to separate supernatants resulting from different colonies of the numbered clones.

The sequence of the selected clones with improved activity was determined and the full sequences and CDR sequences are shown below.

```
DOM23h-271-21 amino acid sequence
                                                (SEQ ID NO: 29)
EVQLLESGGGLVQPGGSLRLSCAASGFTFTEYRMWWVRQAPGKGLEWVSAIEPIGNRTYYADSVKGRFTISRDN

SKNTLYLQMNSLRAEDTAVYYCAKQMPGRKWTAKFRWDYWGQGTLVIVSS

DOM23h-271-21 nucleic acid sequence
                                                (SEQ ID NO: 67)
GAGGTGCAGCTGTTGGAGTCTGGGGGAGGCTTGGTACAGCCTGGGGGGTCCCTGCGTCTCTCCTGTGCAGC

CTCCGGATTCACCTTTACCGAGTATAGGATGTGGTGGGTCCGCCAGGCTCCGGGGAAGGGTCTCGAGTGGG

TCTCAGCGATTGAGCCGATTGGTAATCGTACATACTACGCAGACTCCGTGAAGGGCCGGTTCACCATCTCCC

GCGACAATTCCAAGAACACGCTGTATCTGCAAATGAACAGCCTGCGTGCCGAGGATACCGCGGTATATTACT

GTGCGAAACAGATGCCGGGCCGGAAGTGGACGGCCAAGTTCCGCTGGGACTACTGGGGTCAGGGAACCCTG

GTCATCGTCTCGAGC

DOM23h-271-22 amino acid sequence
                                                (SEQ ID NO: 30)
EVQLLESGGGLVQPGGSLRLSCAASGFTFTEYRMWWVRQAPGKGLEWVSAIEPIGNRTYYADSVKGRFTISRDN

SKNTLYLQMNSLRAEDTAVYYCAKQMPGQKWMAKSRFDYWGQGTLVTVSS
```

DOM23h-271-22 nucleic acid sequence
(SEQ ID NO: 68)
GAGGTGCAGCTGTTGGAGTCTGGGGGAGGCTTGGTACAGCCTGGGGGGTCCCTGCGTCTCTCCTGTGCAGC

CTCCGGATTCACCTTTACGGAGTATAGGATGTGGTGGGTCCGCCAGGCTCCGGGGAAGGGTCTCGAGTGGG

TCTCAGCGATTGAGCCGATTGGTAATCGTACATACTACGCAGACTCCGTGAAGGGCCGGTTCACCATCTCCC

GCGACAATTCCAAGAACACGCTGTATCTGCAAATGAACAGCCTGCGTGCCGAGGATACCGCGGTATATTACT

GTGCGAAACAGATGCCCGGCCAGAAGTGGATGGCCAAGTCCCGCTTCGACTACTGGGGTCAGGGAACCCTG

GTCACCGTCTCGAGC

DOM23h-271-27 amino acid sequence
(SEQ ID NO: 31)
EVQLLESGGGLVQPGGSLRLSCAASGFTFTEYRMWWVRQAPGKGLEWVSAIEPIGQKMADSVKGRFTISRD

NSKNTLYLQMNSLRAEDTAVYYCAKQIPGRKWTANSRFDYWGQGTLVIVSS

DOM23h-271-27 nucleic acid sequence
(SEQ ID NO: 69)
GAGGTGCAGCTGTTGGAGTCTGGGGGAGGCTTGGTACAGCCTGGGGGGTCCCTGCGTCTCTCCTGTGCAGC

CTCCGGATTCACCTTTACGGAGTATAGGATGTGGTGGGTCCGCCAGGCTCCAGGGAAGGGTCTCGAGTGGG

TCTCAGCGATTGAGCCGATTGGTCAGAAGACATACTACGCAGACTCCGTGAAGGGCCGGTTCACCATCTCCC

GCGACAATTCCAAGAACACGCTGTATCTGCAAATGAACAGCCTGCGTGCCGAGGATACCGCGGTATATTACT

GTGCGAAACAGATTCCGGGGCGTAAGTGGACTGCTAATTCGCGGTTTGACTACTGGGGTCAGGGAACCCTG

GTCATCGTCTCGAGC

DOM23h-271-101 amino acid sequence
(SEQ ID NO: 32)
EVQLLESGGGLVQPGGSLRLSCAASGFTFTEYRMWWVRQAPGKGLEWVSAIEPIGNRTYYADSVKGRFTISRDN

SKNTLYLQMNSLRAEDTAVYYCAKQIPGRKWTANGRKDYWGQGTLVTVSS

DOM23h-271-101 nucleic acid sequence
(SEQ ID NO: 70)
GAGGTGCAGCTGTTGGAGTCTGGGGGAGGCTTGGTACAGCCTGGGGGGTCCCTGCGTCTCTCCTGTGCAGC

CTCCGGATTCACCTTTACGGAGTATAGGATGTGGTGGGTCCGCCAGGCTCCGGGGAAGGGTCTCGAGTGGG

TCTCAGCGATTGAGCCGATTGGTAATCGTACATACTACGCAGACTCCGTGAAGGGCCGGTTCACCATCTCCC

GCGACAATTCCAAGAACACGCTGTATCTGCAAATGAACAGCCTGCGTGCCGAGGATACCGCGGTATATTACT

GTGCGAAACAGATTCCGGGGCGTAAGTGGACTGCTAATGGTCGTAAGGACTACTGGGGTCAGGGAACCCTG

GTCACCGTCTCGAGC

DOM23h-271-102 amino acid sequence
(SEQ ID NO: 33)
EVQLLESGGGLVQPGGSLRLSCAASGSTFTEYRMWWVRQAPGKGLEWVSAIEPIGHRTYYADSVKGRFTISRD

NSKNTLYLQMNSLRAEDTAVYYCAKQIPGRKWTANSRFDYWGQGTLVTVSS

DOM23h-271-102 nucleic acid sequence
(SEQ ID NO: 71)
GAGGTGCAGCTGTTGGAGTCTGGGGGAGGCTTGGTACAGCCTGGGGGGTCCCTGCGTCTCTCCTGTGCAGC

CTCCGGATCCACCTTTACGGAGTATAGGATGTGGTGGGTCCGCCAGGCTCCGGGGAAGGGTCTCGAGTGGG

TCTCAGCGATTGAGCCGATTGGTCATAGGACATACTACGCAGACTCCGTGAAGGGCCGGTTCACCATCTCCC

GCGACAATTCCAAGAACACGCTGTATCTGCAAATGAACAGCCTGCGTGCCGAGGATACCGCGGTATATTACT

GTGCGAAACAGATTCCGGGGCGTAAGTGGACTGCTAATTCGCGGTTTGACTACTGGGGTCAGGGAACCCTG

GTCACCGTCTCGAGC

DOM23h-271-105 amino acid sequence
(SEQ ID NO: 34)
EVQLLESGGGLVQPGGSLRLSCAASGFTFTEYRMWWVRQAPGKGLEWVSAIEPIGNRTY

YADSVKGRFTISRDNSKNTLYLQMNSLRAEDTAVYYCAKQIPGQRWTGNSRFDYWGQGTL

-continued

VTVSS

DOM23h-271-105 nucleic acid sequence
(SEQ ID NO: 72)
GAGGTGCAGCTGTTGGAGTCTGGGGGAGGCTTGGTACAGCCTGGGGGGTCCCTGCGTCTCTCCTGTGCAGC

CTCCGGATTCACCTTTACGGAGTATAGGATGTGGTGGGTCCGCCAGGCTCCGGGGAAGGGTCTCGAGTGGG

TCTCAGCGATTGAGCCGATTGGTAATCGTACATACTACGCAGACTCCGTGAAGGGCCGGTTCACCATCTCCC

GCGACAATTCCAAGAACACGCTGTATCTGCAAATGAACAGCCTGCGTGCCGAGGATACCGCGGTATATTACT

GTGCGAAACAGATTCCGGGGCAGCGGTGGACTGGTAATTCGCGGTTTGACTACTGGGGTCAGGGAACCCTG

GTCACCGTCTCGAGC

DOM23h-271-106 amino acid sequence
(SEQ ID NO: 35)
EVQLLESGGGLVQPGGSLRLSCAASGFTFTEYRMWWVRQAPGKGLEWVSAIEPIGNRTYYADSVKGRFTISRDN

SKNTLYLQMNSLRAEDTAVYYCAKQFPGRKWTANSRSDYWGQGTLVTVSS

DOM23h-271-106 nucleic acid sequence
(SEQ ID NO: 73)
GAGGTGCAGCTGTTGGAGTCTGGGGGAGGCTTGGTACAGCCTGGGGGGTCCCTGCGTCTCTCCTGTGCAGC

CTCCGGATTCACCTTTACGGAGTATAGGATGTGGTGGGTCCGCCAGGCTCCGGGGAAGGGTCTCGAGTGGG

TCTCAGCGATTGAGCCGATTGGTAATCGTACATACTACGCAGACTCCGTGAAGGGCCGGTTCACCATCTCCC

GCGACAATTCCAAGAACACGCTGTATCTGCAAATGAACAGCCTGCGTGCCGAGGATACCGCGGTATATTACT

GTGCGAAACAGTTTCCGGGGCGTAAGTGGACTGCTAATTCGCGGTCTGACTACTGGGGTCAGGGAACCCTG

GTCACCGTCTCGAGC

DOM23h-271-114 amino acid sequence
(SEQ ID NO: 36)
EVQLLESGGGLVQPGGSLRLSCAASGFTFTEYRMWWVRQAPGKGLEWVSAIEPIGNRTYYADSVKGRFTISRDN

SKNTLYLQMNSLRAEDTAVYYCAKQIPGRKGTANSRFDYWGQGTLVTVSS

DOM23h-271-114 nucleic acid sequence
(SEQ ID NO: 74)
GAGGTGCAGCTGTTGGAGTCTGGGGGAGGCTTGGTACAGCCTGGGGGGTCCCTGCGTCTCTCCTGTGCAGC

CTCCGGATTCACCTTTACGGAGTATAGGATGTGGTGGGTCCGCCAGGCTCCGGGGAAGGGTCTCGAGTGGG

TCTCAGCGATTGAGCCGATTGGTAATCGTACATACTACGCAGACTCCGTGAAGGGCCGGTTCACCATCTCCC

GCGACAATTCCAAGAACACGCTGTATCTGCAAATGAACAGCCTGCGTGCCGAGGATACCGCGGTATATTACT

GTGCGAAACAGATTCCGGGGCGTAAGGGAACTGCTAATTCGCGGTTTGACTACTGGGGTCAGGGAACCCTG

GTCACCGTCTCGAGC

TABLE 9

CDR sequences of 271 affinity matured clones with improved activity

| | CDR1 (Kabat 26-35) | CDR2 (Kabat 50-65) | CDR3 (Kabat 95-102) |
|---|---|---|---|
| DOM23h-271-21 | GFTFTEYRMW (SEQ ID NO: 105) | AIEPIGNRTYYADSVKG (SEQ ID NO: 141) | QMPGRKWTAKFRWDY (SEQ ID NO: 177) |
| DOM23h-271-22 | GFTFTEYRMW (SEQ ID NO: 106) | AIEPIGNRTYYADSVKG (SEQ ID NO: 142) | QMPGQKWMAKSRFDY (SEQ ID NO: 178) |
| DOM23h-271-27 | GFTFTEYRMW (SEQ ID NO: 107) | AIEPIGQKTYYADSVKG (SEQ ID NO: 143) | QIPGRKWTANSRFDY (SEQ ID NO: 179) |
| DOM23h-271-101 | GFTFTEYRMW (SEQ ID NO: 108) | AIEPIGNRTYYADSVKG (SEQ ID NO: 144) | QIPGRKWTANGRKDY (SEQ ID NO: 180) |
| DOM23h-271-102 | GSTFTEYRMW (SEQ ID NO: 109) | AIEPIGHRTYYADSVKG (SEQ ID NO: 145) | QIPGRKWTANSRFDY (SEQ ID NO: 181) |
| DOM23h-271-105 | GFTFTEYRMW (SEQ ID NO: 110) | AIEPIGNRTYYADSVKG (SEQ ID NO: 146) | QIPGQRWTGNSRFDY (SEQ ID NO: 182) |

TABLE 9-continued

CDR sequences of 271 affinity matured clones with improved activity

| | CDR1 (Kabat 26-35) | CDR2 (Kabat 50-65) | CDR3 (Kabat 95-102) |
|---|---|---|---|
| DOM23h-271-106 | GFTFTEYRMW (SEQ ID NO: 111) | AIEPIGNRTYYADSVKG (SEQ ID NO: 147) | QFPGRKWTANSRSDY (SEQ ID NO: 183) |
| DOM23h-271-114 | GFTFTEYRMW (SEQ ID NO: 112) | AIEPIGNRTYYADSVKG (SEQ ID NO: 148) | QIPGRKGTANSRFDY (SEQ ID NO: 184) |

N.B CDR2 and CDR3 are as defined by Kabat.
CDR1 is defined by a combination of the Kabat and Chothia methods.

Generic Method for Binding Kinetics—T100

BIACORE™ analysis was carried out using a capture surface on a CM4 chip. Anti-human IgG was used as the capturing agent and coupled to a CM4 biosensor chip by primary amine coupling. The Antigen molecule fused to the human Fc was captured on this immobilised surface to a level from 250 to 300 resonance units and defined concentrations of Domain antibodies diluted in running buffer were passed over this captured surface. An injection of buffer over the captured antigen surface was used for double referencing. The captured surface was regenerated, after each domain antibody injection using 3M magnesium chloride solution; the regeneration removed the captured antigen but did not significantly affect the ability of the surface to capture antigen in a subsequent cycle. All runs were carried out at 25° C. using HBS-EP buffer as running buffer. Data were generated using the BIACORE™ T100 and fitted to the 1:1 binding model inherent to the software. When non-specific binding was seen at the top concentration, the binding curve at this concentration was removed from the analysis set.

Further Diversification of CDR3

The DOM23h-271-7 derivatives with the highest affinity contained methionines in position 96 and 100B. These positions, along with positions 99, 100D, 100E and 100G were diversified using NNK mutagenesis to determine whether substitutions could be made. The NNK library was constructed as described above using primer PEP-26-F to introduce diversity at the selected positions in DOM23h-271-22 or DOM23h-271-102 background. DOM23h-271-102 contains mutations at position 27 and 55 that confer improved affinity over DOM23h-271-7.

DNA display libraries were constructed and selected on biotinylated hTGFbRII-FC as described above using concentrations of 5 nM; 0.5 nM; 0.1 nM; 0.1 nM; 0.1 nM; and 0.1 nM in successive rounds. In selection rounds 4-6 the non-biotinylated TGFbRII-FC competitor was added to a final concentration of 100 nM for 60, 90, and 90 minutes respectively before addition of C1 streptavidin DYNAbeads™. Following selection the dAb inserts were PCR amplified using primers PelB NcoVh and PEP011, cut with NcoI and EcoRI, and cloned into the bacterial expression vector pC10.

PelB NcoVh
(SEQ ID NO: 210)
GCCCAGCCGGCCATGGCGGAGGTGCAGCTGTTGGAGTCTGGG

PEP011
(SEQ ID NO: 211)
GAATTCGCGGCCGCCTATTAGCTCGAGACGGTGACCAGGG

The cloned products were expressed and screened by Biacore. Clones with off-rates similar or better than DOM23h-271-22 were sequenced, purified, and assessed for affinity by BIACORE™ and potency in the cell sensor assay. Clones giving poor kinetic profiles, containing unfavourable sequence motifs, or giving very low yields were not pursued. DOM23h-271-50 was selected for further affinity maturation.

PEP-26-F
(SEQ ID NO: 209)
GCGGTATATTACTGTGCGAAACAGNNSCCCGGCNNSAAGTGGNNSGCCNNSNNSCGCNNSGACTACTGGGGTCAGGGAACC

DOM-271-50 nucleic acid sequence
(SEQ ID NO: 212)
GAGGTGCAGCTGTTGGAGTCTGGGGGAGGCTTGGTACAGCCTGGGGGGTCCCTGCGTCTCTCCTGTGCAGC

CTCCGGATCCACCTTTACGGAGTATAGGATGTGGTGGGTCCGCCAGGCTCCGGGGAAGGGTCTCGAGTGGG

TCTCAGCGATTGAGCCGATTGGTCATAGGACATACTACGCAGACTCCGTGAAGGGCCGGTTCACCATCTCCC

GCGACAATTCCAAGAACACGCTGTATCTGCAAATGAACAGCCTGCGTGCCGAGGATACCGCGGTATATTACT

GTGCGAAACAGGCGCCCGGCGAGAAGTGGCTCGCCCGGGGCCGCTTGGACTACTGGGGTCAGGGAACCCTG

GTCACCGTCTCGAGC

DOM-271-50 amino acid sequence
(SEQ ID NO: 213 and duplicate entry SEQ ID NO: 214)
EVQLLESGGGLVQPGGSLRLSCAASGSTFTEYRMWWVRQAPGKGLEWVSAIEPIGHRTYYADSVKGRFTISRD

NSKNTLYLQMNSLRAEDTAVYYCAKQAPGEKWLARGRLDYWGQGTLVTVSS

Example 7

Introduction of Mutations into TGFbRII dAb Sequences (DOM23h-271 Lineage) at Positions 61 and 64

The D61N and K64R double mutations have previously been introduced into various TGFRβII dAb lineages and have been shown to improve potency (WO2011/012609). These mutations were introduced into TGFbRII dAb DOM23h-271 lineages to see if a similar improvement in potency could be achieved. Alternative mutations at this position were explored to determine whether further enhancements in potency could be achieved.

Mutations were introduced into the DOM23h-271 (SEQ ID NO:199) backbone by overlap extension using the polymerase chain reaction (PCR) (Ho, et al., Gene 1989 77(1)); complementary oligonucleotide primers were used to generate two DNA fragments having overlapping or complementary ends. These fragments were combined in a subsequent assembly PCR in which the overlapping ends anneal, allowing the 3' overlap of each strand to serve as a primer for the 3' extension of the complementary strand and the resulting fusion product to be amplified further by PCR. Specific alterations in the nucleotide sequence were introduced by incorporating nucleotide changes into the overlapping oligonucleotide primers. The target dAb gene fragments were amplified by two separate PCRs using SUPERTAQ™ polymerase (HT Biotechnology). DOM23h-271 was selected as it has a low affinity for TGFbRII so that improvements in affinity were clearly measurable using BIACORE™. The mutations at positions 61 and 64 were encoded using a degenerate oligonucleotide to mutate both positions in combination, with the intension of using affinity selection to enrich for mutants with improved binding affinity. As the NR mutation is known to dominate this mutation was avoided in the library by employing a restricted codon, NNG, at position 61. This codon encodes 13 amino acids but does not include the amino acids F, Y, C, H, I, N or D. Free Cys was not favoured within a dAb, and asparagine was also not wanted at this position, so only 5 desirable amino acids combinations were excluded. At position 64 an NNK codon was used to provide the full range of possible amino acids.

The oligonucleotide pairs used to introduce the mutations were PE008 (flanks the 5' start of the dAb gene: 5'-TTGCAG-GCGTGGCAACAGCGTCGACAGAGGTG-CAGCTGTTGGAG-3') (SEQ ID NO:192) with 271-6164 R (5'-GCGTAGTATGTACGATTACCAATCGG-3') (SEQ ID NO:193) and mutated 271-6164 deg-F (mutated residues underlined: 5f-GGTAATCGTACATACTACGCA<u>NNG</u>TCCGTG<u>NNK</u>GGCCGGTTCACCATCTCCCGC-3') (SEQ ID NO: 194) with AS1309 (flanks the 3' end of the dAb gene: 5'-TGTGTGTGTGTGGCGGCCGCGCTC-GAGACGGTGACCAGGGTTCCCTGACCCCA-3') (SEQ ID NO:195). The two PCR fragments were recombined in an assembly PCR using SUPERTAQ™ DNA polymerase without the addition of primers. The fusion product was then amplified by the addition of flanking primers PE008 and AS1309 to the PCR reaction. The mutated dAb was digested with Sal I and Not I restriction endonucleases, ligated into similarly cut pDOM13 expression vector and transformed into E. Coli HB2151 cells. The D61N, K64R mutation was also introduced into DOM23h-271 in the same way, but substituting primer 271-6164 NR—F (5'-GGTAATCGTACAT-ACTACGCAAACTCCGTGCGCGGCCGGT-TCACCATCTCCCGC-3') (SEQ ID NO:196) for 271-6164 deg-F. The mutated dAbs were identified by sequencing. 129 clones with novel combinations of mutations at position 61 and 64 were identified, though 11 carried additional mutations from PCR errors. These are shown in table 11. N.B. Clones with enhanced affinity are underlined. Clones with additional mutations are indicated by asterisks To determine the effect of the mutations the selected clones were expressed in TB ONEX™ in 96 well plates for 72 hours at 30° C. or 24 hours at 37° C. The supernatants were clarified by centrifugation and filtered through a 0.22 µm filter before off-rate evaluation by BIACORE™

BIACORE™ A100 analysis was carried out using a capture surface on a CM5 chip. Anti-human IgG was used as the capturing agent and coupled to a CM5 biosensor chip by primary amine coupling. The Antigen molecule fused to the human Fc was captured on this immobilised surface to a level from 200 to 300 resonance units and supernatants or purified domain antibodies were passed over this captured surface. An injection of media or buffer over the captured antigen surface was used for double referencing. On each flow cell, a protein A spot allowed to confirm the presence of domain antibody on each sample injected. The surfaces were regenerated, after each domain antibody injection using 3M magnesium chloride solution; the regeneration removed the captured antigen but did not significantly affect the ability of the surface to capture antigen in a subsequent cycle. All runs were carried out at 25° C. using HBS-EP buffer as running buffer. Data were generated using the BIACORE™ A100 and analyzed using its inherent software. Kinetics from purified samples were fitted to the 1:1 binding model while supernatant off-rates were analyzed using the 1:1 dissociation model and/or using the binding level and the stability level of each sample in comparison to the parent molecule.

Of clones tested 46 were identified with improved off-rate by comparison to the parent DOM23h-271 dAb, as indicated in table 11. Mutations D61R and D61K were found to enhance binding independent of mutations at position 64. A number of combinations appeared better than the original D61N, K64R mutations, and these included RE, RM, RF and RY.

A selection of mutants with improved off-rate were purified and subjected to full BIACORE™ A100 kinetic analysis to determine their affinity (Table 10). The thermal stability of the mutants was also determined by generation of melting profiles in the presence of SYPRO™ Orange (Invitrogen). Briefly, the purified dAbs were diluted to 50 and 100 ug/ml in a 1:500 dilution of SYPRO™ Orange in PBS, and subjected to a 30-90° C. melt curve in a Mini OPTICON™ PCR machine (BioRad). The Tm of the major positive transition was determined at each concentration and used to calculate an estimated Tm value at 1 mg/ml as an indication of the melting temperature for comparison (Table 10).

The mutations D61R, K64D and D61R, K64F were selected as they had a good improvement in affinity for a reduced impact in Tm. These mutations were transferred to an affinity matured DOM23h-271 derivative DOM23h-271-22 (SEQ ID NO:30) to make dAbs DOM23h-271-39 (SEQ ID NO:37) and DOM23h-271-40 (SEQ ID NO:38). These mutations were found to give an enhancement in affinity by BIACORE™ including cross reactivity with murine TGFbRII FC, and enhanced potency by cell sensor assay. However the mutations were also found to reduce the Tm as measured by DSC, and increase aggregation of the dabs in PBS, as measured by SEC MALLS. These assays were carried out as described above, except that the buffer for SEC MALLS was 0.4M Nacl, 0.1M Sodium Phosphate and 10% isopropanol pH7. These results are summarized in table 12 (mean values are given for the human cell sensor assay and the mouse 3T3 luciferase assay).

Sequences of dabs referred to in this example are given below:

DOM23h-271-39 amino acid sequence
(SEQ ID NO: 37)
EVQLLESGGGLVQPGGSLRLSCAASGFT-
FTEYRMWWVRQAPGKGLEWVSAIEPIGNRTYYARSVDGRFTISRD

NSKNTLYLQMNSLRAEDTAVYYCAKQMPGQKWMAKSRFDYWGQGTLVTVSS

DOM23h-271-39 nucleic acid sequence
(SEQ ID NO: 75)
GAGGTGCAGCTGTTGGAGTCTGGGGGAG-
GCTTGGTACAGCCTGGGGGGTCCCTGCGTCTCTCCTGTGCAGCCTCC

GGATTCACCTTTACGGAGTATAGGAT-
GTGGTGGGTCCGCCAGGCTCCGGGGAAGGGTCTCGAGTGGGTCTCAGCG

ATTGAGCCGATTGGTAATCGTACATAC-
TACGCACGCTCCGTGGACGGCCGGTTCACCATCTCCCGCGACAATTCCA

AGAACACGCTGTATCTGCAAATGAA-
CAGCCTGCGTGCCGAGGATACCGCGGTATATTACTGTGCGAAACAGATGCC

CGGCCAGAAGTGGATGGCCAAGTC-
CCGCTTCGACTACTGGGGTCAGGGAACCCTGGTCACCGTCTCGAGC

DOM23h-271-40 amino acid sequence
(SEQ ID NO: 38)
EVQLLESGGGLVQPGGSLRLSCAASGFT-
FTEYRMWWVRQAPGKGLEWVSAIEPIGNRTYYARSVFGRFTISRDN

SKNTLYLQMNSLRAEDTAVYYCAKQMPGQKWMAKSRFDYWGQGTLVIVSS

DOM23h-271-40 nucleic acid sequence
(SEQ ID NO: 76)
GAGGTGCAGCTGTTGGAGTCTGGGGGAG-
GCTTGGTACAGCCTGGGGGGTCCCTGCGTCTCTCCTGTGCAGCCTCC

GGATTCACCTTTACGGAGTATAGGAT-
GTGGTGGGTCCGCCAGGCTCCGGGGAAGGGTCTCGAGTGGGTCTCAGCG

ATTGAGCCGATTGGTAATCGTACATAC-
TACGCACGCTCCGTGTTCGGCCGGTTCACCATCTCCCGCGACAATTCCA

AGAACACGCTGTATCTGCAAATGAA-
CAGCCTGCGTGCCGAGGATACCGCGGTATATTACTGTGCGAAACAGATGCC

CGGCCAGAAGTGGATGGCCAAGTC-
CCGCTTCGACTACTGGGGTCAGGGAACCCTGGTCACCGTCTCGAGC

TABLE 10

| Description | Mutation | Est. Tm 1 mg/ml | KD (nM) |
|---|---|---|---|
| 1A2 | RA | 53.08 | 2.24 |
| 1D9 | RD | 52.35 | 1.17 |
| 3F11 | RE | 53.08 | 3.27 |
| 1G11 | RM | 51.81 | 0.97 |
| 3C9 | RF | 54.08 | 1.39 |
| 1E6 | RY | 49.62 | 1.17 |
| 1B11 | RV | 53.41 | 1.88 |
| 3D9 | KG | 48.69 | 4.34 |
| 1D5 | KF | 48.09 | 3.69 |
| 3D4 | KT | 54.74 | 4.26 |
| 1H11 | LW | 53.68 | 4.17 |
| 1B2 | VW | 52.68 | 1.79 |
| 2C12 | NR | 51.49 | 3.34 |
| 271 | DK | 58.21 | N/D |

N.B. the mutation corresponds to 'XY' wherein X is position 61 and Y is position 64

TABLE 11

Mutations inserted into DOM23h-271 at positions 61 and 64.

| 61\64 | A | R | N | D | C | Q | E | G | H | I | L | K | M |
|---|---|---|---|---|---|---|---|---|---|---|---|---|---|
| A |  | 1D6* |  |  |  |  |  |  |  |  | 1C10 | 3B11 |  |
| R | 1A2 | 1A3 | 3F4 | 1D9 | 2C4 | 1A8 | 3F11 | 3G8 |  | 1A4 |  | 3C2 | 1G11 |
| N |  | 2C12 |  |  |  |  |  |  |  |  |  |  |  |
| D |  |  |  |  |  |  |  |  |  |  | 3H6 (wt) |  |  |
| C |  |  |  |  |  |  |  |  |  |  |  |  |  |
| Q | 1B6* | 1E8 |  |  |  |  |  | 1B10 |  | 1H12 | 1D11 |  |  |
| E |  | 2A3 |  |  | 1F12 |  |  | 2G4 |  |  | 3H7 |  |  |
| G | 1D1 | 1B5 |  |  |  | 3B12 |  | 1E5 |  |  | 3G11 | 3D12 |  |
| H |  |  |  |  |  |  |  |  |  |  |  |  |  |
| I |  |  |  |  |  |  |  |  |  |  |  |  |  |
| L | 1D2 | 3E11 | 2A9 |  |  | 1B4 | 1H3 | 1A9 |  | 1F1 | 1G9 | 1H10 | 1C9 |
| K |  | 2E5 |  |  |  | — | 2B4 | 3D9 |  |  |  | 3E12 |  |
| M |  |  |  |  |  |  | 1G6 | 2D3* |  |  | 1E7 | 2E6 | 3C12 |
| F |  |  |  |  |  |  |  |  |  |  |  |  |  |
| P |  |  | 2A8 |  |  |  | 1A5 | 2C11 |  |  |  |  |  |
| S |  | 3C3 |  | 3E7 |  |  |  | 3E5 |  |  | 1H4 | 2B10 | 1C11 |
| T |  | 1E3 | 1D10* |  |  | 2C1 |  | 1C1 |  | 2A5 | 3G9 |  |  |
| W | 2F10 | 1E12 |  |  |  | 2C2 |  | 2A2 |  |  | 2A6 |  | 1D4 |
| Y |  |  |  |  |  |  |  |  |  |  |  |  |  |
| V |  | 1C12 |  |  | 2B9 | 1H6 | 1D3* | 3C1 |  | 2G2 | 2F7 | 1F7 |  |

| 61\64 | F | P | S | T | W | Y | V |
|---|---|---|---|---|---|---|---|
| A |  | 3C10* | 3B10 | 1A12 |  |  | 3G3* |
| R |  | 3C9* | 2F5 | 1H1 | 1H2 | 1E6 | 1B11 |

TABLE 11-continued

Mutations inserted into DOM23h-271 at positions 61 and 64.

| | | | | | | |
|---|---|---|---|---|---|---|
| N | | | | | | |
| D | | | | | | |
| C | | | | | | |
| Q | | | | 1C8 | <u>3F7</u> | 2C10 |
| E | | 1F10 | 2B11 | 3D6 | | |
| G | | | 2B6 | 2G5 | 2D5 | |
| H | | | | | | |
| I | | | | | | |
| L | 2C9 | 1H5 | 1G2 | 1E4 | 1H11 | |
| K | <u>1D5</u> | <u>1G7</u> | <u>2E9</u>* | <u>3D4</u> | <u>1B1</u> | 1F2 |
| M | 2F6 | <u>3H1</u> | 3B5* | 1A6 | 1E11 | 3B8* |
| F | | | | | | |
| P | 3H2 | | 1G5 | | 3G12 | |
| S | 1B7 | 2C8 | 3B1 | | <u>3D5</u> | |
| T | 2H10 | | | 2A4 | <u>3D11</u> | |
| W | | | 3B2 | 2B1 | | |
| Y | | | | | | |
| V | | <u>2H4</u> | 3C7 | <u>1B2</u> | | <u>2G6</u> |

Clones with improved off-rate are underlined.
Clones with additional mutations are indicated by asterisks

TABLE 12

| | Mutation | Human Cell sensor IC50 (nM) | Mouse 3T3 Luciferase assay IC50 (nM) | Human TGFbRII KD (pM) | Cyno TGFbRII KD (pM) | Mouse TGRbRII KD (pM) | Tm (DSC) | Aggregation (SEC-MALS) |
|---|---|---|---|---|---|---|---|---|
| DOM23h-271-22 | — | 39.01 | >17780 | 202.00 | 225.00 | — | 60 | 91.8% Monomer 8.2% Dimer |
| DOM23h-271-39 | RD | 1.17 | 11120 | 14.90 | 24.00 | 1780.00 | 57.5 | 51.6% M/D Eq 38.5% D/T Eq + aggregates |
| DOM23h-271-40 | RF | 0.53 | 1200 | 9.99 | 11.25 | 548.50 | 55.6 | 91.6% M/D Eq 8.4% Trimer/oligomer |

Example 8

Affinity Maturation by CDR Diversification of Lineages DOM23h-439-20, DOM23h-843-13, DOM23h-855-21 and DOM23h-271-50

Domain antibodies DOM23h-855-21(SEQ ID NO:204) and DOM23h-843-13 (SEQ ID NO:206) were isolated from the error prone affinity maturation carried out on naive clones DOM23h-855 (SEQ ID NO:13) and DOM23h-843 (SEQ ID NO:10) respectively, as detailed in example 5. Domain antibody DOM23h-439 was isolated from phage libraries in a previous selection campaign described in WO 2011/012609 and variant DOM23h-439-20 (SEQ ID NO:208) was subsequently isolated by error prone affinity maturation as detailed in example 5. Domain antibody DOM23h-271-50 (SEQ ID NO:214) was generated by CDR3 re-diversification of CDR-directed affinity matured variant DOM23h-271-22 (SEQ ID NO:30) as detailed in Example 6. DOM23h-855-21, DOM23h-843-13, DOM23h-439-20 and DOM23h-271-50 were all selected for further affinity maturation based on their binding kinetics, potency in the SBE-bla HEK 293T cell sensor assay, sequence and biophysical behaviour. Affinity maturation was performed using degenerative mutagenesis to re-diversify the CDRs, and improved leads were identified using phage display. Diversity was introduced into the CDRs by construction of either doped or NNK libraries.

DOM23h-271-50 was affinity matured using NNK libraries (saturation mutagenesis), oligonucleotide primers were designed to cover each CDR and within each primer the codons for 5 amino acids were replaced with NNK codons so that 5 positions are diversified simultaneously. Single or multiple oligonucleotides were used to cover all targeted amino acids within each CDR; 1 for CDR1, 2 for CDR2 and 3 for CDR3. CDR-directed affinity maturation was achieved using polymerase chain reaction (PCR); Complementary oligonucleotide primers were used to amplify a sequence fragment containing each mutated CDR, and also an overlapping sequence fragment covering the rest of the dAb coding sequence. These fragments were mixed and assembled by splice extension overlap PCR to produce the full length dAb coding sequence. This product was PCR amplified using primers PeIB NcoVh (SEQ ID NO:210) and PEP044 (5'-GGAACCCTGGTCACCGTCTCGAGCGCG-GCCGCATAATAAGAATTCA-3' SEQ ID NO:215), digested with NcoI and NotI, and ligated into NotI and NcoI digested pDOM4-gene3-pelB hybrid vector. pDOM4-gene3-pelB hybrid vector is a modified version of the pDOM4 vector described above but has been modified to replace the GAS leader sequence with the pelB (pectate lyase B) signal peptide.

The domain antibodies DOM23h-855-21, DOM23h-843-13 and DOM23h-439-20 were affinity matured using doped libraries. The doped libraries were constructed essentially as described above and in WO2006018650. A single degenerate oligonucleotide primer was used to cover all mutations within each CDR. Within each primer the amino acids to be diversified were specified using degenerate codons to encode multiple amino acids. The following degenerate coding was used: 'a'=85% A+5% T+5% G+5% C; 'g'=85% G+5% T+5% C+5% A; 'c'=85% C+5% T+5% G+5% A; 't'=85% T+5% A+5% G+5% C.; 'S'=50% G and 50% C. Capital letters indicate 100% of the specified nucleotide. For the DOM23h-439-20 doped library five amino acids were diversified in CDR1, 6 in CDR2 and 11 in CDR3 to include the phenyalanine at position 100. For the DOM23h-855-21 doped library five amino acids were diversified in CDR1, 7 in CDR2 and 8 in CDR3. For the DOM23h-843-13 doped library five amino acids were diversified in CDR1, 6 in CDR2 and 8 in CDR3, position 94 before the CDR3 was also diversified by introducing the codon VRK. For each of the dAbs, 4 doped libraries were constructed, one to diversify CDR1, one to diversify CDR2, one to diversify CDR3 and a fourth where all CDRs were diversified. The degenerate library primers were used in the same way as the triplet primers. Each diversified CDR was amplified separately and then combined with a parental sequence fragment using splice extension overlap, the full length product was amplified using primers PelB NcoVh (SEQ ID NO:210) and DOM173 (SEQ ID NO:188). The fragments were subcloned to pDOM4-gene3-pelB hybrid vector using NcoI and NotI.

Degenerate Primer Sequences:

```
23h-439-20 CDRH1
                                                            (SEQ ID NO: 216)
5'-GCAGCCTCCGGATTCACCTTTggSacSgagcagATGtggTGGGTCCGCCAGGCTCCAGGG-3'

23h-439-20 CDRH2
                                                            (SEQ ID NO: 217)
5'-AAGGGTCTAGAGTTTGTCTCAcgSATTgattcSccSGGTggScgSACATACTACGCAGACTCCGTG-3'

23h-439-20 CDRH3
                                                            (SEQ ID NO: 218)
5'-GCGGTATATTACTGTGCGAAAcgScatgcSgcSggSgtStcSggSacStaYtttGACTACTGGGGTCAGGGAACC-3'

23h-843-13 CDRH1
                                                            (SEQ ID NO: 219)
5'-GCAGCCTCCGGATTCACCTTTgatcaggatcgSATGtggTGGGTCCGCCAGGCCCCAGGG-3'

23h-843-13 CDRH2
                                                            (SEQ ID NO: 220)
5'-AAGGGTCTAGAGTGGGTCTCAgcSATTgagtcSggSGGTcatcgSACATACTACGCAGACTCCGTG-3'

23h-843-13 CDRH3
                                                            (SEQ ID NO: 221)
5'-ACCGCGGTATATTACTGTGCGVRKcagaataagtcSggScgStcSggSTTTGACTACTGGGGTCAGGGA-3'

23h-855-21 CDRH1
                                                            (SEQ ID NO: 222)
5'-GCAGCCTCCGGATTCACCTTTgagaatacStcSATGggSTGGGTCCGCCAGGCTCCAGGG-3'

23h-855-21 CDRH2
                                                            (SEQ ID NO: 223)
5'-AAGGGTCTAGAGTGGGTCTCAcgSATTgatccSaagGGTtcScatACATACTACacSGACTCCGTGAAGGGCCGGT
TCACC-3'

23h-855-21 CDRH3
                                                            (SEQ ID NO: 224)
5'-GCGGTATATTACTGTGCGAAAcagcgSgagctSggSaagtcStaYTTTGACTACTGGGGTCAGGGA-3'

H1-271-43 R
                                                            (SEQ ID NO: 225)
5'-GCAGCCTCCGGATTCACCTTTNNKNNKNNKNNKATGNNKTGGGTCCGCCAGGCTCCGGGGAAGGGTCTC-3'

H2p1-271-43F
                                                            (SEQ ID NO: 226)
5'-CCGCCAGGCTCCGGGGAAGGGTCTCGAGTGGGTCTCANNKATTNNKNNKNNKGGTNNKCGTACATACTACG
CAGACTCCG-3'

H2p2-271-43 F
                                                            (SEQ ID NO: 227)
5'-CCGCCAGGCTCCGGGGAAGGGTCTCGAGTGGGTCTCAGCGATTGAGNNKNNKNNKNNKNNKACATACTACG
CAGACTCCG-3'

H3p1-271-43 F
                                                            (SEQ ID NO: 228)
5'-ACCGCGGTATATTACTGTGCGAAANNKNNKNNKNNKNNKAAGTGGATGGCCGTGGGCCGCTTGGACTACTG
GGGTCAGGG-3'

H3p2-271-43 F
                                                            (SEQ ID NO: 229)
5'-ACCGCGGTATATTACTGTGCGAAACAGAAGCCCNNKNNKNNKNNKNNKGCCGTGGGCCGCTTGGACTACTG
GGGTCAGGG-3'
```

H3p3-271-43 F (SEQ ID NO: 230)

5'-ACCGCGGTATATTACTGTGCGAAACAGAAGCCCGGCCAGAAGTGGNNKNNKNNKNNKNNKTTGGACTACTG
GGGTCAGGG-3'

Phage Display:

NNK or doped libraries in separate CDR1, CDR2, CDR3 and combined CDR1, 2 and 3 pools were subjected to at least 6 rounds of selection against 100 nM, 10 nM, 1 nM, 1 nM, 0.1 nM and 0.1 nM (rounds 1, 2, 3, 4, 5 and 6 respectively) biotinylated monomeric human TGF-β RII antigen as described in example 1 with the following deviation to the block step; the human IgG Fc fragment which was previously added in example 1 was omitted and the block step performed for a minimum of 20 minutes. In rounds 4 and 6 of selection competition was introduced by incubation with 100 nM non-biotinylated antigen for 30 min (rounds 4 and 6) following the incubation step with the labelled antigen. For DOM 23h-439-20 (CDR1, CDR3 and combined pools) and DOM 23h-855-21 (CDR3) a seventh round of selection was carried out against 0.1 nM biotinylated monomeric human TGF-β RII antigen and 100 nM competition for 120 min or 20 pM biotinylated monomeric human TGF-β RII antigen with 100 nM competition for 30 min. Phage were amplified between rounds of selection by centrifugation of an overnight culture of phage infected TG1 cells for 30 minutes at 4000 g. 40 ml of supernatant containing the amplified phage was added to 10 ml of PEG/NaCl (20% v/w PEG 8000+2.5 M NaCl) and incubated on ice for 60 minutes. The samples were centrifuged for 40 minutes at 4000 g to pellet the precipitated phage. The supernatant was discarded and the phage pellet was resuspended in 1 ml 15% v/v glycerol/PBS. The phage sample was transferred to 2 ml Eppendorf tubes and centrifuged for 10 minutes to remove any remaining bacterial cell debris. Diversified domain antibody Vh genes from the phage selections were PCR amplified using primers PEP011VHStopNotIR (5'-CCCTGGTCACCGTCTC-GAGCTAATAGGCGGCCGCGAATTC-3' (SEQ ID NO: 231) and Nco1 VH F (5'-TATCGTCCATGGCGGAGGTG-CAGCTGTTGGAGTCTGG-3' (SEQ ID NO: 232), digested with NcoI and NotI restriction endonucleases and ligated into the pC10 vector also digested with NcoI and NotI. pC10 is a plasmid vector based on pUC119 vector, with expression under the control an enhanced LacZ promoter designed for soluble expression of dAbs. Expression of dAbs into the supernatant is enabled by fusion of the dAb gene to the pelB signal peptide at the N-terminal end. The ligation products were transformed into chemically competent E. coli HB2151 cells and plated on nutrient agar plates supplemented with 100 μg/ml of carbenicillin. Individual clones were picked and expressed in overnight express auto-induction medium (high-level protein expression system, Novagen), supplemented with 100 μg/ml carbenicillin in 96-well plates and grown with shaking at 250 rpm for either 66 hours at 30° C. or 24 hours at 37° C. Expression plates were then centrifuged at 3500 g for 15 minutes and the supernatants filtered using 0.45μ filter plates (Millipore). Supernatants containing the domain antibodies were screened on the BIACORE™ B4000 against human TGF-β RII and human TGF-β RII/Fc to determine the off-rate (Kd) (data not shown). Biotinylated antigens were captured on an SA chip in accordance with the manufacturer's instructions, analysis was carried out at 25° C. using HBS-EP buffer. Samples were run on BIACORE™ at a flow rate of 30 μl/min. Regeneration of the chip was achieved using glycine at low pH. The data (not shown) were analysed for off-rate by fitting the dissociation phase to the 1:1 dissociation model inherent to the software, supernatants were also analyzed for protein A binding to estimate levels of expression. Domain antibodies with off rates improved over parent were selected for further study. Improved clones were expressed in overnight express autoinduction medium (ONEX™, Novagen) supplemented with 100 ug/ml carbenicillin and antifoam (Sigma) at 30° C. for 48 to 72 hours with shaking at 250 rpm. The cultures were centrifuged (4,200 rpm for 40 minutes) and the supernatants were incubated with STREAMLINE™-protein A beads (Amersham Biosciences, GE HEALTHCARE™, UK. Binding capacity: 5 mg of dAb per ml of beads), at 4° C. or at room temperature for at least one hour. The beads were packed into a chromatography column and washed with PBS, followed by 10 mM Tris-HCl pH 7.4 (Sigma, UK). Bound dAbs were eluted with 0.1 M glycine-HCl pH 2.0 and neutralized with 1M Tris-HCL pH 8.0. The OD at 280 nm of the dAbs was measured and protein concentrations were determined using extinction coefficients calculated from the amino acid compositions of the dAbs. Affinity matured domain antibodies were tested on the BIACORE™ T200 (data for two preferred dAbs are shown in Example 9) and in the SBE-bla HEK 293T Cell Sensor assay (data for two preferred dAbs are shown in Example 11) to determine their affinity and potency. Biophysical properties including thermal stability and solution state were determined using Differential Scanning Colourimetry (DSC) and size exclusion chromatography with multi-angle-LASER-light scattering (SEC-MALS) (data for two preferred dAbs are shown in Example 10).

The amino acid and nucleic acid sequences of affinity matured DOM23h-439-20 and DOM23h-271-50 anti-human TGFRII dAbs DOM23h-439-25 nucleic acid sequence (SEQ ID NO: 233)

GAGGTGCAGCTGTTGGAGTCTGGGGGAGGCTTGGTACAGCCTGGGGGGTCCCTGCGTCTCTCCTGTGCAGC

CTCCGGATTCACCTTTGGGACGGAGCAGATGTGGTGGGTCCGCCAGGCTCCAGGGAAGGGTCTAGAGTTTG

TCTCACGTATTGATTCGCCTGGTGGGAGGACATACTACGCAGACTCCGTGAAGGGCCGGTTCACCATCTCCC

```
GCGACAATTCCAAGAACACGCTGTATCTGCAAATGAACAGCCTGCGTGCCGAGGACACCGCGGTATATTACT

GTGCGAAACGGCGACCCACGGGGGTGTCCGGGACGATGACTACTGGGGTCAGGGAACCCTGGTCACC

GTCTCGAGC

DOM23h-439-25 amino acid sequence
                                                               (SEQ ID NO: 234)
EVQLLESGGGLVQPGGSLRLSCAASGFTFGTEQMWWVRQAPGKGLEFVSRIDSPGGRTYYADSVKGRFTISRD

NSKNTLYLQMNSLRAEDTAVYYCAKRRPTGVSGTFYDYWGQGTLVTVSS

DOM23h-271-123 nucleic acid sequence
                                                               (SEQ ID NO: 235)
GAGGTGCAGCTGTTGGAGTCTGGGGGAGGCTTGGTACAGCCTGGGGGGTCCCTGCGTCTCTCCTGTGCAGC

CTCCGGATCCACCTTTACGGAGTATAGGATGTGGTGGGTCCGCCAGGCTCCGGGGAAGGGTCTCGAGTGGG

TCTCAGCGATTGAGCCGATTGGTCATAGGACATACTACGCAGACTCCGTGAAGGGCCGGTTCACCATCTCCC

GCGACAATTCCAAGAACACGCTGTATCTGCAAATGAACAGCCTGCGTGCCGAGGATACCGCGGTATATTACT

GTGCGAAACAGGCGCCCGGCGAGAAGTGGGCGAGGCGGTGGGATTTGGACTACTGGGGTCAGGGAACCCT

GGTCACCGTCTCGAGC

DOM23h-271-123 amino acid sequence
                                                               (SEQ ID NO: 236)
EVQLLESGGGLVQPGGSLRLSCAASGSTFTEYRMWWVRQAPGKGLEWVSAIEPIGHRTYYADSVKGRFTISRD

NSKNTLYLQMNSLRAEDTAVYYCAKQAPGEKWARRWDLDYWGQGTLVTVSS

DOM23h-439-35 nucleic acid sequence
                                                               (SEQ ID NO: 237)
GAGGTGCAGCTGTTGGAGTCTGGGGGAGGCTTGGTACAGCCTGGGGGGTCCCTGCGTCTC

TCCTGTGCAGCCTCCGGATTCACCTTTGGGACCGATCAGATGTGGTGGGTCCGCCAGGCT

CCAGGGAAGGGTCTAGAGTTTGTCTCACGCATTGATTCCCCCGGTGGGCGGACATACTAC

GCAAACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACGGCAG

CCGGCGGGGGTGTCGGGGAAGTACGTTGACTACTGGGGTCAGGGAACCCTGGTCACCGTC

TCGAGC

DOM23h-439-35 amino acid sequence
                                                               (SEQ ID NO: 238)
EVQLLESGGGLVQPGGSLRLSCAASGFTFGTDQMWWVRQAPGKGLEFVSRIDSPGGRTYYANSVKGRFTISRD

NSKNTLYLQMNSLRAEDTAVYYCAKRQPAGVSGKYVDYWGQGTLVTVSS

DOM23h-271-129 nucleic acid sequence
                                                               (SEQ ID NO: 239)
GAGGTGCAGCTGTTGGAGTCTGGGGGAGGCTTGGTACAGCCTGGGGGGTCCCTGCGTCTC

TCCTGTGCAGCCTCCGGATCCACCTTTACGGAGTATAGGATGTGGTGGGTCCGCCAGGCT

CCGGGGAAGGGTCTCGAGTGGGTCTCAGCGATTGAGCCGATTGGTCATAGGACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAACAGGCG

CCCAATCAGAGGTATGTTGCCCGGGGCCGCTTGGACTACTGGGGTCAGGGAACCCTGGTC

ACCGTCTCGAGC

DOM23h-271-129 amino acid sequence
                                                               (SEQ ID NO: 240)
EVQLLESGGGLVQPGGSLRLSCAASGSTFTEYRMWWVRQAPGKGLEWVSAIEPIGHRTYYADSVKGRFTISRD

NSKNTLYLQMNSLRAEDTAVYYCAKQAPNQRYVARGRLDYWGQGTLVIVSS
```

The CDRs as defined by Kabat of these anti-human TGFRII dAb affinity leads are shown in Table 13

TABLE 13

CDR Sequences of affinity matured anti-human TGFβRII dAbs

| | CDR1 (Kabat 26-35) | CDR2 (Kabat 50-65) | CDR3 (Kabat 95-102) |
|---|---|---|---|
| DOM23h-271423 | GSTFTEYRMW (SEQ ID NO: 241) | AIEPIGHRTYYADSVKG (SEQ ID NO: 242) | QAPGEKWARRWDLDY (SEQ ID NO: 243) |
| DOM23h-271429 | GSTFTEYRMW (SEQ ID NO: 244) | AIEPIGHRTYYADSVKG (SEQ ID NO: 245) | QAPNQRYVARGRLDY (SEQ ID NO: 246) |
| DOM23h-439-25 | GFTFGTEQMW (SEQ ID NO: 247) | RIDSPGGRTYYADSVKG (SEQ ID NO: 248) | RRPTGVSGTFYDY (SEQ ID NO: 249) |
| DOM23h-439-35 | GFTFGTDQMW (SEQ ID NO: 250) | RIDSPGGRTYYANSVKG (SEQ ID NO: 251) | RQPAGVSGKYVDY (SEQ ID NO: 252) |

Further Modification of the DOM23h-439-25 and DOM23h-271-123 Nucleotide Sequence The D61N and K64R mutations as described in example 7 were introduced into the DOM23h-439-25, DOM23h-271-123 and DOM23h-271-129 affinity matured dAbs either in combination or separately. Introduction of a V48I mutation in the DOM23h-439-25 and DOM23h-271-123 dAbs was also tested to determine whether it could confer improvements in potency. Spontaneous mutation at kabat position 48 was observed in a number of improved dAbs from the DOM23h-439 lineage following both test maturation and CDR-directed affinity maturation. An Alanine at the C-terminus of the Vh region, immediately after kabat residue 113 was also added to DOM23h-439-25, DOM23h-271-123 and DOM23h-271-129 and all variants of these dAbs with the afore-mentioned mutations. Mutations were introduced into the DOM23h-439-25 (SEQ ID NO: 234), DOM23h-271-123 (SEQ ID NO: 236) and DOM23h-271-129 (SEQ ID NO: 240) backbones by overlap extension using the polymerase chain reaction (PCR) essentially as described in Example 7. Specific mutations in the nucleotide sequence were introduced by incorporating nucleotide changes into the overlapping oligonucleotide primers, the insertion of the Alanine at the end of the Vh region was achieved by using a 3' oligonucleotide designed to incorporate the Alanine residue after kabat position 113.

The following oligonucleotides were used to introduce the mutations (mutated residues underlined):

439 48I SDM F
(SEQ ID NO: 253)
5'-GGGTCTAGAGTTT<u>ATT</u>TCACGTATTGATTCGCC-3'

439 61N SDM F
(SEQ ID NO: 254)
5'-GGGAGGACATACTACGCA<u>AAC</u>TCCGTGAAGGGCCGG-3'

439 64R SDM F
(SEQ ID NO: 255)
5'-CGCAGACTCCGTG<u>CGT</u>GGCCGGTTCACC-3'

439 61N 64R SDM F
(SEQ ID NO: 256)
5'-GGGAGGACATACTACGCA<u>AAC</u>TCCGTGCGTGGCCGGTTCACC-3'

271 61N SDM F
(SEQ ID NO: 257)
5'-GGACATACTACGCA<u>AAC</u>TCCGTGAAGGGCCGG-3'

271 64R SDM F
(SEQ ID NO: 258)
5'-CGCAGACTCCGTG<u>CGT</u>GGCCGGTTCACC-3'

271 61N 64R SDM F
(SEQ ID NO: 259)
5'-GGACATACTACGCA<u>AAC</u>TCCGTG<u>CGT</u>GGCCGGTTCACC-3'

567 +A rev (Flanks the 3' end of the dAb Vh gene)
(SEQ ID NO: 260)
5'-CCCTGGTCACCGTCTCGAGCGCGTAATAAGCGGCCGCAGATTA-3'

21-23 Fwd (Flanks the 5' end of the dAb Vh gene)
(SEQ ID NO: 261)
5'-ATAAGGCCATGGCGGAGGTGCAGCTGTTGGAGTCTG-3'

To determine the effect of the mutations the dAbs were expressed in TB ONEX™ supplemented with 100 ug/ml carbenicillin and antifoam (Sigma) at 30° C. for 72 hours with shaking at 250 rpm. The cultures were centrifuged (4,200 rpm for 40 minutes) and dAbs affinity purified using STREAMLINE™-protein A beads (Amersham Biosciences, GE HEALTHCARE™, UK) as before. Affinity and potency of the domain antibody variants were determined on the BIACORE™ T200 (data for preferred dAbs is shown in Example 9) and in the SBE-bla HEK 293T Cell Sensor assay (data for preferred dAbs is shown in Example 11).

The amino acid and nucleic acid sequences of DOM23h-439-25 (SEQ ID NO: 234) and DOM23h-271-123 (SEQ ID NO: 236) anti-human TGFRII dAbs modified to include the C-terminal Alanine and D61N, K64R or V48I mutations are given below:

DOM23h-439-40 (DOM23h-439-25 + C-terminal Alanine) Nucleic acid sequence
(SEQ ID NO: 262)
GAGGTGCAGCTGTTGGAGTCTGGGGGAGGCTTGGTACAGCCTGGGGGGTCCCTGCGTCTCTCCTGTGCAGC

CTCCGGATTCACCTTTGGGACGGAGCAGATGTGGTGGGTCCGCCAGGCTCCAGGGAAGGGTCTAGAGTTTG

TCTCACGTATTGATTCGCCTGGTGGGAGGACATACTACGCAGACTCCGTGAAGGGCCGGTTCACCATCTCCC

GCGACAATTCCAAGAACACGCTGTATCTGCAAATGAACAGCCTGCGTGCCGAGGACACCGCGGTATATTACT

GTGCGAAACGGCGACCCACGGGGGTGTCCGGGACGATGACTACTGGGGTCAGGGAACCCTGGTCACC

GTCTCGAGCGCG

DOM23h-439-40 (DOM23h-439-25 + C-terminal Alanine) Amino acid sequence
(SEQ ID NO: 263)
EVQLLESGGGLVQPGGSLRLSCAASGFTFGTEQMWWVRQAPGKGLEFVSRIDSPGGRMADSVKGRFTISRD
NSKNTLYLQMNSLRAEDTAVYYCAKRRPTGVSGTFYDYWGQGTLVTVSSA DOM23h-439-41 (DOM23h-439-25 + C-terminal Alanine + 48I) Nucleic acid sequence
(SEQ ID NO: 264)
GAGGTGCAGCTGTTGGAGTCTGGGGGAGGCTTGGTACAGCCTGGGGGGTCCCTGCGTCTCTCCTGTGCAGC

CTCCGGATTCACCTTTGGGACGGAGCAGATGTGGTGGGTCCGCCAGGCTCCAGGGAAGGGTCTAGAGTTTA

TTTCACGTATTGATTCGCCTGGTGGGAGGACATACTACGCAGACTCCGTGAAGGGCCGGTTCACCATCTCCC

GCGACAATTCCAAGAACACGCTGTATCTGCAAATGAACAGCCTGCGTGCCGAGGACACCGCGGTATATTACT

GTGCGAAACGGCGACCCACGGGGGTGTCCGGGACGATGACTACTGGGGTCAGGGAACCCTGGTCACC

GTCTCGAGCGCG

DOM23h-439-41 (DOM23h-439-25 + C-terminal Alanine + 48I) Amino acid sequence
(SEQ ID NO: 265)
EVQLLESGGGLVQPGGSLRLSCAASGFTFGTEQMWWVRQAPGKGLEFISRIDSPGGRTYYADSVKGRFTISRDN
SKNTLYLQMNSLRAEDTAVYYCAKRRPTGVSGTFYDYWGQGTLVTVSSA DOM23h-439-42 (DOM23h-439-25 + C-terminal Alanine + 61N) Nucleic acid sequence
(SEQ ID NO: 266)
GAGGTGCAGCTGTTGGAGTCTGGGGGAGGCTTGGTACAGCCTGGGGGGTCCCTGCGTCTCTCCTGTGCAGC

CTCCGGATTCACCTTTGGGACGGAGCAGATGTGGTGGGTCCGCCAGGCTCCAGGGAAGGGTCTAGAGTTTG

TCTCACGTATTGATTCGCCTGGTGGGAGGACATACTACGCAAACTCCGTGAAGGGCCGGTTCACCATCTCCC

GCGACAATTCCAAGAACACGCTGTATCTGCAAATGAACAGCCTGCGTGCCGAGGACACCGCGGTATATTACT

GTGCGAAACGGCGACCCACGGGGGTGTCCGGGACGATGACTACTGGGGTCAGGGAACCCTGGTCACC

GTCTCGAGCGCG

DOM23h-439-42 (DOM23h-439-25 + C-terminal Alanine + 61N) Amino acid sequence
(SEQ ID NO: 267)
EVQLLESGGGLVQPGGSLRLSCAASGFTFGTEQMWWVRQAPGKGLEFVSRIDSPGGRTYYANSVKGRFTISRD
NSKNTLYLQMNSLRAEDTAVYYCAKRRPTGVSGTFYDYWGQGTLVTVSSA DOM23h-439-43 (DOM23h-439-25 + C-terminal Alanine + 64R) Nucleic acid sequence
(SEQ ID NO: 268)
GAGGTGCAGCTGTTGGAGTCTGGGGGAGGCTTGGTACAGCCTGGGGGGTCCCTGCGTCTCTCCTGTGCAGC

CTCCGGATTCACCTTTGGGACGGAGCAGATGTGGTGGGTCCGCCAGGCTCCAGGGAAGGGTCTAGAGTTTG

TCTCACGTATTGATTCGCCTGGTGGGAGGACATACTACGCAGACTCCGTGCGTGGCCGGTTCACCATCTCCC

GCGACAATTCCAAGAACACGCTGTATCTGCAAATGAACAGCCTGCGTGCCGAGGACACCGCGGTATATTACT

GTGCGAAACGGCGACCCACGGGGGTGTCCGGGACGATGACTACTGGGGTCAGGGAACCCTGGTCACC

GTCTCGAGCGCG

DOM23h-439-43 (DOM23h-439-25 + C-terminal Alanine + 64R) Amino acid sequence
(SEQ ID NO: 269)
EVQLLESGGGLVQPGGSLRLSCAASGFTFGTEQMWWVRQAPGKGLEFVSRIDSPGGRTYYADSVRGRFTISRD
NSKNTLYLQMNSLRAEDTAVYYCAKRRPTGVSGTFYDYWGQGTLVTVSSA DOM23h-439-44 (DOM23h-439-25 + C-terminal Alanine + 61N64R) Nucleic acid sequence
(SEQ ID NO: 270)
GAGGTGCAGCTGTTGGAGTCTGGGGGAGGCTTGGTACAGCCTGGGGGGTCCCTGCGTCTCTCCTGTGCAGC

CTCCGGATTCACCTTTGGGACGGAGCAGATGTGGTGGGTCCGCCAGGCTCCAGGGAAGGGTCTAGAGTTTG

TCTCACGTATTGATTCGCCTGGTGGGAGGACATACTACGCAAACTCCGTGCGTGGCCGGTTCACCATCTCCC

GCGACAATTCCAAGAACACGCTGTATCTGCAAATGAACAGCCTGCGTGCCGAGGACACCGCGGTATATTACT

GTGCGAAACGGCGACCCACGGGGGTGTCCGGGACGATGACTACTGGGGTCAGGGAACCCTGGTCACC

GTCTCGAGCGCG

DOM23h-439-44 (DOM23h-439-25 + C-terminal Alanine + 61N64R) Amino acid sequence
(SEQ ID NO: 271)
EVQLLESGGGLVQPGGSLRLSCAASGFTFGTEQMWWVRQAPGKGLEFVSRIDSPGGRTYYANSVRGRFTISRD
NSKNTLYLQMNSLRAEDTAVYYCAKRRPTGVSGTFYDYWGQGTLVTVSSA DOM23h-271-130 (DOM23h-271-123 + C-terminal Alanine) Nucleic acid sequence
(SEQ ID NO: 272)
GAGGTGCAGCTGTTGGAGTCTGGGGGAGGCTTGGTACAGCCTGGGGGGTCCCTGCGTCTCTCCTGTGCAGC
CTCCGGATCCACCTTTACGGAGTATAGGATGTGGTGGGTCCGCCAGGCTCCGGGGAAGGGTCTCGAGTGGG
TCTCAGCGATTGAGCCGATTGGTCATAGGACATACTACGCAGACTCCGTGAAGGGCCGGTTCACCATCTCCC
GCGACAATTCCAAGAACACGCTGTATCTGCAAATGAACAGCCTGCGTGCCGAGGATACCGCGGTATATTACT
GTGCGAAACAGGCGCCCGGCGAGAAGTGGGCGAGGCGGTGGGATTTGGACTACTGGGGTCAGGGAACCCT
GGTCACCGTCTCGAGCGCG DOM23h-271-130 (DOM23h-271-123 + C-terminal Alanine) Amino acid sequence
(SEQ ID NO: 273)
EVQLLESGGGLVQPGGSLRLSCAASGSTFTEYRMWWVRQAPGKGLEWVSAIEPIGHRTYYADSVKGRFTISRD
NSKNTLYLQMNSLRAEDTAVYYCAKQAPGEKWARRWDLDYWGQGTLVTVSSA DOM23h-271-131 (DOM23h-271-123 + C-terminal Alanine + 61N) Nucleic acid sequence
(SEQ ID NO: 274)
GAGGTGCAGCTGTTGGAGTCTGGGGGAGGCTTGGTACAGCCTGGGGGGTCCCTGCGTCTCTCCTGTGCAGC
CTCCGGATCCACCTTTACGGAGTATAGGATGTGGTGGGTCCGCCAGGCTCCGGGGAAGGGTCTCGAGTGGG
TCTCAGCGATTGAGCCGATTGGTCATAGGACATACTACGCAAACTCCGTGAAGGGCCGGTTCACCATCTCCC
GCGACAATTCCAAGAACACGCTGTATCTGCAAATGAACAGCCTGCGTGCCGAGGATACCGCGGTATATTACT
GTGCGAAACAGGCGCCCGGCGAGAAGTGGGCGAGGCGGTGGGATTTGGACTACTGGGGTCAGGGAACCCT
GGTCACCGTCTCGAGCGCG DOM23h-271-131 (DOM23h-271-123 + C-terminal Alanine + 61N) Amino acid sequence
(SEQ ID NO: 275)
EVQLLESGGGLVQPGGSLRLSCAASGSTFTEYRMWWVRQAPGKGLEWVSAIEPIGHRTYYANSVKGRFTISRD
NSKNTLYLQMNSLRAEDTAVYYCAKQAPGEKWARRWDLDYWGQGTLVTVSSA DOM23h-271-132 (DOM23h-271-123 + C-terminal Alanine + 64R) Nucleic acid sequence
(SEQ ID NO: 276)
GAGGTGCAGCTGTTGGAGTCTGGGGGAGGCTTGGTACAGCCTGGGGGGTCCCTGCGTCTCTCCTGTGCAGC
CTCCGGATCCACCTTTACGGAGTATAGGATGTGGTGGGTCCGCCAGGCTCCGGGGAAGGGTCTCGAGTGGG
TCTCAGCGATTGAGCCGATTGGTCATAGGACATACTACGCAGACTCCGTGCGTGGCCGGTTCACCATCTCCC
GCGACAATTCCAAGAACACGCTGTATCTGCAAATGAACAGCCTGCGTGCCGAGGATACCGCGGTATATTACT
GTGCGAAACAGGCGCCCGGCGAGAAGTGGGCGAGGCGGTGGGATTTGGACTACTGGGGTCAGGGAACCCT
GGTCACCGTCTCGAGCGCG DOM23h-271-132 (DOM23h-271-123 + C-terminal Alanine + 64R) Amino acid sequence
(SEQ ID NO: 277)
EVQLLESGGGLVQPGGSLRLSCAASGSTFTEYRMWWVRQAPGKGLEWVSAIEPIGHRTYYADSVRGRFTISRD
NSKNTLYLQMNSLRAEDTAVYYCAKQAPGEKWARRWDLDYWGQGTLVTVSSA DOM23h-271-133 (DOM23h-271-123 + C-terminal Alanine + 61N64R) Nucleic acid sequence
(SEQ ID NO: 278)
GAGGTGCAGCTGTTGGAGTCTGGGGGAGGCTTGGTACAGCCTGGGGGGTCCCTGCGTCTCTCCTGTGCAGC
CTCCGGATCCACCTTTACGGAGTATAGGATGTGGTGGGTCCGCCAGGCTCCGGGGAAGGGTCTCGAGTGGG
TCTCAGCGATTGAGCCGATTGGTCATAGGACATACTACGCAAACTCCGTGCGTGGCCGGTTCACCATCTCCC
GCGACAATTCCAAGAACACGCTGTATCTGCAAATGAACAGCCTGCGTGCCGAGGATACCGCGGTATATTACT
GTGCGAAACAGGCGCCCGGCGAGAAGTGGGCGAGGCGGTGGGATTTGGACTACTGGGGTCAGGGAACCCT
GGTCACCGTCTCGAGCGCG DOM23h-271-133 (DOM23h-271-123 + C-terminal Alanine + 61N64R) Amino acid sequence
(SEQ ID NO: 279)
EVQLLESGGGLVQPGGSLRLSCAASGSTFTEYRMWWVRQAPGKGLEWVSAIEPIGHRTYYANSVRGRFTISRD
NSKNTLYLQMNSLRAEDTAVYYCAKQAPGEKWARRWDLDYWGQGTLVTVSSA DOM23h-271-134 (DOM23h-271-123 + C-terminal Alanine + 48I) Nucleic acid sequence
(SEQ ID NO: 280)
GAGGTGCAGCTGTTGGAGTCTGGGGGAGGCTTGGTACAGCCTGGGGGGTCCCTGCGTCTCTCCTGTGCAGC

CTCCGGATCCACCTTTACGGAGTATAGGATGTGGTGGGTCCGCCAGGCTCCGGGGAAGGGTCTCGAGTGGA

TTTCAGCGATTGAGCCGATTGGTCATAGGACATACTACGCAGACTCCGTGAAGGGCCGGTTCACCATCTCCC

GCGACAATTCCAAGAACACGCTGTATCTGCAAATGAACAGCCTGCGTGCCGAGGATACCGCGGTATATTACT

GTGCGAAACAGGCGCCCGGCGAGAAGTGGGCGAGGCGGTGGGATTTGGACTACTGGGGTCAGGGAACCCT

GGTCACCGTCTCGAGCGCG

DOM23h-271-134 (DOM23h-271-123 + C-terminal Alanine + 48I) Amino acid sequence
(SEQ ID NO: 281)
EVQLLESGGGLVQPGGSLRLSCAASGSTFTEYRMWWVRQAPGKGLEWISAIEPIGHRTYYADSVKGRFTISRDN
SKNTLYLQMNSLRAEDTAVYYCAKQAPGEKWARRWDLDYWGQGTLVTVSSA DOM23h-271-135 (DOM23h-271-129 + C-terminal Alanine) Nucleic acid sequence
(SEQ ID NO: 282)
GAGGTGCAGCTGTTGGAGTCTGGGGGAGGCTTGGTACAGCCTGGGGGGTCCCTGCGTCTCTCCTGTGCAGC

CTCCGGATCCACCTTTACGGAGTATAGGATGTGGTGGGTCCGCCAGGCTCCGGGGAAGGGTCTCGAGTGGG

TCTCAGCGATTGAGCCGATTGGTCATAGGACATACTACGCAGACTCCGTGAAGGGCCGGTTCACCATCTCCC

GCGACAATTCCAAGAACACGCTGTATCTGCAAATGAACAGCCTGCGTGCCGAGGATACCGCGGTATATTACT

GTGCGAAACAGGCGCCCAATCAGAGGTATGTTGCCCGGGGCCGCTTGGACTACTGGGGTCAGGGAACCCTG

GTCACCGTCTCGAGCGCG

DOM23h-271-135 (DOM23h-271-129 + C-terminal Alanine) Amino acid sequence
(SEQ ID NO: 283)
EVQLLESGGGLVQPGGSLRLSCAASGSTFTEYRMWWVRQAPGKGLEWVSAIEPIGHRTYYADSVKGRFTISRD
NSKNTLYLQMNSLRAEDTAVYYCAKQAPNQRYVARGRLDYWGQGTLVTVSSA DOM23h-271-136 (DOM23h-271-129 + C-terminal Alanine + 61N) Nucleic acid sequence
(SEQ ID NO: 284)
GAGGTGCAGCTGTTGGAGTCTGGGGGAGGCTTGGTACAGCCTGGGGGGTCCCTGCGTCTCTCCTGTGCAGC

CTCCGGATCCACCTTTACGGAGTATAGGATGTGGTGGGTCCGCCAGGCTCCGGGGAAGGGTCTCGAGTGGG

TCTCAGCGATTGAGCCGATTGGTCATAGGACATACTACGCAAACTCCGTGAAGGGCCGGTTCACCATCTCCC

GCGACAATTCCAAGAACACGCTGTATCTGCAAATGAACAGCCTGCGTGCCGAGGATACCGCGGTATATTACT

GTGCGAAACAGGCGCCCAATCAGAGGTATGTTGCCCGGGGCCGCTTGGACTACTGGGGTCAGGGAACCCTG

GTCACCGTCTCGAGCGCG

DOM23h-271-136 (DOM23h-271-129 + C-terminal Alanine + 61N) Amino acid sequence
(SEQ ID NO: 285)
EVQLLESGGGLVQPGGSLRLSCAASGSTFTEYRMWWVRQAPGKGLEWVSAIEPIGHRTYYANSVKGRFTISRD
NSKNTLYLQMNSLRAEDTAVYYCAKQAPNQRYVARGRLDYWGQGTLVTVSSA DOM23h-271-137 (DOM23h-271-129 + C-terminal Alanine + 61N64R) Nucleic acid sequence
(SEQ ID NO: 286)
GAGGTGCAGCTGTTGGAGTCTGGGGGAGGCTTGGTACAGCCTGGGGGGTCCCTGCGTCTCTCCTGTGCAGC

CTCCGGATCCACCTTTACGGAGTATAGGATGTGGTGGGTCCGCCAGGCTCCGGGGAAGGGTCTCGAGTGGG

TCTCAGCGATTGAGCCGATTGGTCATAGGACATACTACGCAAACTCCGTGCGTGGCCGGTTCACCATCTCCC

GCGACAATTCCAAGAACACGCTGTATCTGCAAATGAACAGCCTGCGTGCCGAGGATACCGCGGTATATTACT

GTGCGAAACAGGCGCCCAATCAGAGGTATGTTGCCCGGGGCCGCTTGGACTACTGGGGTCAGGGAACCCTG

GTCACCGTCTCGAGCGCG

-continued

DOM23h-271-137 (DOM23h-271-129 + C-terminal Alanine + 61N64R) Amino acid sequence
(SEQ ID NO: 287)
EVQLLESGGGLVQPGGSLRLSCAASGSTFTEYRMWWVRQAPGKGLEWVSAIEPIGHRTYYANSVRGRFTISRD

NSKNTLYLQMNSLRAEDTAVYYCAKQAPNQRYVARGRLDYWGQGTLVTVSSA

DOM23h-439-47 (DOM23h-439-42 + 48I) Nucleic acid sequence
(SEQ ID NO: 288)
GAGGTGCAGCTGTTGGAGTCTGGGGGAGGCTTGGTACAGCCTGGGGGGTCCCTGCGTCTCTCCTGTGCAGC

CTCCGGATTCACCTTTGGGACGGAGCAGATGTGGTGGGTCCGCCAGGCTCCAGGGAAGGGTCTAGAGTTTA

TTTCACGTATTGATTCGCCTGGTGGGAGGACATACTACGCAAACTCCGTGAAGGGCCGGTTCACCATCTCC

GCGACAATTCCAAGAACACGCTGTATCTGCAAATGAACAGCCTGCGTGCCGAGGACACCGCGGTATATTACT

GTGCGAAACGGCGACCCACGGGGGTGTCCGGGACGATGACTACTGGGGTCAGGGAACCCTGGTCACC

GTCTCGAGCGCG

DOM23h-439-47 (DOM23h-439-42 + 48I) Amino acid sequence
(SEQ ID NO: 289)
EVQLLESGGGLVQPGGSLRLSCAASGFTFGTEQMWWVRQAPGKGLEFISRIDSPGGRTYYANSVKGRFTISRDN

SKNTLYLQMNSLRAEDTAVYYCAKRRPTGVSGTFYDYWGQGTLVTVSSA

DOM23h-439-48 (DOM23h-439-44 + 48I) Nucleic acid sequence
(SEQ ID NO: 290)
GAGGTGCAGCTGTTGGAGTCTGGGGGAGGCTTGGTACAGCCTGGGGGGTCCCTGCGTCTCTCCTGTGCAGC

CTCCGGATTCACCTTTGGGACGGAGCAGATGTGGTGGGTCCGCCAGGCTCCAGGGAAGGGTCTAGAGTTTA

TTTCACGTATTGATTCGCCTGGTGGGAGGACATACTACGCAAACTCCGTGCGTGGCCGGTTCACCATCTCC

GCGACAATTCCAAGAACACGCTGTATCTGCAAATGAACAGCCTGCGTGCCGAGGACACCGCGGTATATTACT

GTGCGAAACGGCGACCCACGGGGGTGTCCGGGACGATGACTACTGGGGTCAGGGAACCCTGGTCACC

GTCTCGAGCGCG

DOM23h-439-48 (DOM23h-439-44 + 48I) Amino acid sequence
(SEQ ID NO: 291)
EVQLLESGGGLVQPGGSLRLSCAASGFTFGTEQMWWVRQAPGKGLEFISRIDSPGGRTYYANSVRGRFTISRDN

SKNTLYLQMNSLRAEDTAVYYCAKRRPTGVSGTFYDYWGQGTLVTVSSA

Example 9

Biacore Kinetic Analysis of Affinity Matured Domain Antibodies

Anti-human IgG was immobilised on a Biacore CM4 chip by primary amine coupling according to the manufacturer's instructions. Human TGF-β RII/Fc, cynomolgus TGF-β RII/Fc or human Fc fragment were captured on this surface. Domain antibodies were passed over the two captured receptors at 3 concentrations of 100, 10 and 1 nM (DOM23h-439 dAbs) or 100, 25 and 6.25 nM (DOM23h-271 dAbs). Only the 100 nM concentration of each dab was passed over human Fc fragment to confirm specificity of binding to the extracellular TGF-β RII domain. An injection of buffer over the captured antigen surface was used for double referencing. The captured surface was regenerated, after each domain antibody injection using 3M magnesium chloride solution; the regeneration removed the captured antigen but did not significantly affect the ability of the surface to capture antigen in a subsequent cycle. All runs were carried out at 25° C. using HBS-EP buffer as running buffer. Data were generated using the BIACORE™ T200 and fitted to the 1:1 binding model inherent to the software. Table 14 shows the binding kinetics of the dAbs tested. The DOM23h-271 dAbs and the DOM23h-439 lineages were run in separate experiments.

TABLE 14

| | Human TGFBRII | | | Cyno TGFBRII | | |
|---|---|---|---|---|---|---|
| sample | Ka ($M^{-1} \cdot s^{-1}$) | Kd ($s^{-1}$) | KD (M) | Ka ($M^{-1} \cdot s^{-1}$) | Kd ($s^{-1}$) | KD (M) |
| DOM23h-271-123 | 2.89E+06 | 2.93E−04 | 1.02E−10 | 3.08E+06 | 3.20E−04 | 1.04E−10 |
| DOM23h-271-129 | 5.55E+06 | 4.11E−04 | 7.41E−11 | 6.00E+06 | 4.27E−04 | 7.12E−11 |
| DOM23h-271-130 | 2.51E+06 | 3.09E−04 | 1.23E−10 | 2.61E+06 | 3.24E−04 | 1.24E−10 |
| DOM23h-271-131 | 6.26E+06 | 1.36E−04 | 2.17E−11 | 6.81E+06 | 1.44E−04 | 2.12E−11 |
| DOM23h-271-132 | 1.22E+07 | 2.22E−04 | 1.82E−11 | 1.29E+07 | 2.38E−04 | 1.85E−11 |
| DOM23h-271-133 | 8.47E+06 | 7.70E−05 | 9.09E−12 | 8.84E+06 | 8.71E−05 | 9.85E−12 |
| DOM23h-439-25 | 7.77E+06 | 6.34E−04 | 8.17E−11 | 8.99E+06 | 2.73E−03 | 3.04E−10 |
| DOM23h-439-35 | 2.26E+07 | 2.22E−04 | 9.83E−12 | 2.32E+07 | 6.75E−04 | 2.91E−11 |
| DOM23h-439-40 | 1.34E+07 | 1.39E−03 | 1.04E−10 | 9.34E+06 | 3.42E−03 | 3.66E−10 |

TABLE 14-continued

| sample | Human TGFBRII | | | Cyno TGFBRII | | |
|---|---|---|---|---|---|---|
| | Ka ($M^{-1} \cdot s^{-1}$) | Kd ($s^{-1}$) | KD (M) | Ka ($M^{-1} \cdot s^{-1}$) | Kd ($s^{-1}$) | KD (M) |
| DOM23h-439-41 | 1.81E+07 | 1.87E−04 | 1.04E−11 | 1.57E+07 | 5.22E−04 | 3.33E−11 |
| DOM23h-439-42 | 4.09E+07 | 1.31E−04 | 3.20E−12 | 3.72E+07 | 4.10E−04 | 1.10E−11 |
| DOM23h-439-43 | 8.83E+06 | 3.73E−04 | 4.23E−11 | 8.04E+06 | 1.20E−03 | 1.49E−10 |
| DOM23h-439-44 | 2.39E+07 | 6.91E−05 | 2.89E−12 | 2.17E+07 | 1.47E−04 | 6.77E−12 |

Example 10

Biophysical Evaluation of Affinity Matured dAbs

The thermal stability of the dAbs was determined using Differential Scanning calorimeter (DSC). dAbs were dialysed overnight into PBS buffer and adjusted at a final concentration of 1 mg/ml. Dialysis buffer was used as a reference for all samples. DSC was performed using capillary cell microcalorimeter VP-DSC (GE healthcare/Microcal), at a heating rate of 180° C./hour. A typical scan range was from 20-90° C. for both the reference buffer and the protein sample. After each reference buffer and sample pair, the capillary cell was cleaned with a solution of 5% Decon (Fisher-Scientific) in water followed by PBS. Resulting data traces were analyzed using Origin 7.0 software. The DSC trace obtained from the reference buffer was subtracted from the sample trace. The precise molar concentration of the sample was entered into the data analysis routine to yield values for melting temperature (Tm), enthalpy (ΔH) and Vara Hoff enthalpy (ΔHv) values. Data were fitted to a non-2-state model. Best fit and dependencie values were obtained with either 1 or 2 transition events. On-set unfolding temperature was also determined by integrating from zero each sample thermogram. This value was then determined as the temperature at which 4 percentage of the sample was unfolded.

TABLE 14A

| Protein name | Apparent Tm (C.) | On-set temperature (C.) |
|---|---|---|
| DOM23h-439-21 | 60.66 | 52.5 |
| DOM23h-439-25 | 56.34 | 49 |
| DOM23h-439-30 | 57.17 | 50 |
| DOM23h-439-32 | 55.01 | 49 |
| DOM23h-439-33 | 58.93 | 51 |
| DOM23h-439-34 | 56.78 | 50 |
| DOM23h-855-42 | 61.90 | 55 |
| DOM23h-855-43 | 66.81 | 58.6 |
| DOM23h-855-44 | 63.38 | 56 |
| DOM23h-271-123 | 54.82 | 50.6 |
| DOM23h-271-124 | 58.16 | 52 |
| DOM23h-271-125 | 58.26 | 55 |

Analysis of Solution State by Size Exclusion Chromatography with Multi-Angle-LASER-Light Scattering (SEC-MALS)

To determine whether dAbs are monomeric or form higher order oligomers in solution, they were analyzed by SEC-MALLS (Size Exclusion Chromatography with Multi-Angle-LASER-Light-Scattering). Agilent 1100 series HPLC system with an autosampler and a UV detector (controlled by Empower software) was connected to Wyatt Mini Dawn Treos (Laser Light Scattering (LS) detector) and Wyatt Optilab rEX DRI (Differential Refractive Index (RI) detector). The detectors are connected in the following order -UV-LS-RI. Both RI and LS instruments operate at a wavelength of 658 nm; the UV signal is monitored at 280 nm and 220 nm. Domain antibodies (50 microliters injection at a concentration of 1 mg/mL in PBS) were separated according to their hydrodynamic properties by size exclusion chromatography using a TSK2000 column. The mobile phase was 0.2M NaCl, 0.1M NaPO4, 15% n-propanol. The intensity of the scattered light while protein passed through the detector was measured as a function of angle. This measurement taken together with the protein concentration determined using the RI detector allowed calculation of the molar mass using appropriate equations (integral part of the analysis software Astra v.5.3.4.14). The solution state as percentage monomer is shown in Table 15.

TABLE 15

| | Percentage monomer |
|---|---|
| DOM23h-439-21 | 100% |
| DOM23h-439-25 | 100% |
| DOM23h-439-30 | 100% |
| DOM23h-439-32 | 100% |
| DOM23h-439-33 | 98.2% |
| DOM23h-439-34 | 97.7% |
| DOM23h-855-42 | 83.8% |
| DOM23h-855-43 | 83% |
| DOM23h-855-44 | 64.7% |
| DOM23h-271-123 | 100% |
| DOM23h-271-124 | 97.4% |

Example 11

TGFβ-RII Inhibition by Affinity Matured dAbs in the SBE-Bla HEK 293T Cell Sensor Assay The assay was carried out exactly as outlined in example 4, assay h2.

The assay was performed multiple times to obtain an average and a range of values which are summarised in Table 16. The arithmetic mean IC50 was calculated using log IC50s, and the range was calculated by adding and subtracting the log standard deviation from the mean IC50, and then transforming back to IC50. The assay QC parameters were met; the robust Z factors were greater than 0.4 and the TGF-β EC80 was within 6 fold of the concentration added to the assay. The results are shown in Table 16.

TABLE 16

| Cell Functional assay data for human specific clones plus VH Dummy dAb. | | |
|---|---|---|
| | IC50 nM | |
| | Mean | IC50 range (+/− log SD) | n |
| DOM23h-271-123 | 18.3 | 9.8-34.1 | 11 |
| DOM23h-271-129 | 22.7 | 16.6-31.1 | 4 |
| DOM23h-271-130 | 37.0 | 15.1-90.7 | 4 |

TABLE 16-continued

Cell Functional assay data for human specific clones plus VH Dummy dAb.

| | IC50 nM | | |
|---|---|---|---|
| | Mean | IC50 range (+/− log SD) | n |
| DOM23h-271-131 | 6.3 | 4.5-8.9 | 4 |
| DOM23h-271-132 | 21.0 | 16.1-27.5 | 4 |
| DOM23h-271-133 | 2.4 | 1.5-3.8 | 4 |
| DOM23h-439-25 | 4.0 | 1.1-14.7 | 17 |
| DOM23h-439-35 | 0.5 | 0.4-0.7 | 3 |
| DOM23h-439-37 | 0.7 | 0.2-2.2 | 4 |
| DOM23h-439-40 | 14 | 10.8-18.8 | 6 |
| DOM23h-439-41 | 1.7 | 1.3-2.3 | 4 |
| DOM23h-439-42 | 0.7 | 0.2-2.7 | 8 |
| DOM23h-439-43 | 1.0 | 0.7-1.4 | 4 |
| DOM23h-439-44 | 1.3 | 0.5-3.3 | 6 |
| VHDummy2 | >25119 | 25119 | 13 |

Sequence Concordance Table

| SEQ ID NO | DOM number | Description |
|---|---|---|
| 1 | DOM23h-802 | amino acid sequence - naive clone |
| 2 | DOM23h-803 | amino acid sequence - naive clone |
| 3 | DOM23h-813 | amino acid sequence - naive clone |
| 4 | DOM23h-815 | amino acid sequence - naive clone |
| 5 | DOM23h-828 | amino acid sequence - naive clone |
| 6 | DOM23h-830 | amino acid sequence - naive clone |
| 7 | DOM23h-831 | amino acid sequence - naive clone |
| 8 | DOM23h-840 | amino acid sequence - naive clone |
| 9 | DOM23h-842 | amino acid sequence - naive clone |
| 10 | DOM23h-843 | amino acid sequence - naive clone |
| 11 | DOM23h-850 | amino acid sequence - naive clone |
| 12 | DOM23h-854 | amino acid sequence - naive clone |
| 13 | DOM23h-855 | amino acid sequence - naive clone |
| 14 | DOM23h-865 | amino acid sequence - naive clone |
| 15 | DOM23h-866 | amino acid sequence - naive clone |
| 16 | DOM23h-874 | amino acid sequence - naive clone |
| 17 | DOM23h-883 | amino acid sequence - naive clone |
| 18 | DOM23h-903 | amino acid sequence - naive clone |
| 19 | DOM23m-4 | amino acid sequence - naive clone |
| 20 | DOM23m-29 | amino acid sequence - naive clone |
| 21 | DOM23m-32 | amino acid sequence - naive clone |
| 22 | DOM23m-62 | amino acid sequence - naive clone |
| 23 | DOM23m-71 | amino acid sequence - naive clone |
| 24 | DOM23m-72 | amino acid sequence - naive clone |
| 25 | DOM23m-81 | amino acid sequence - naive clone |
| 26 | DOM23m-99 | amino acid sequence - naive clone |
| 27 | DOM23m-101 | amino acid sequence - naive clone |
| 28 | DOM23m-352 | amino acid sequence - naive clone |
| 29 | DOM23h-271-21 | amino acid sequence - affinity matured |
| 30 | DOM23h-271-22 | amino acid sequence - affinity matured |
| 31 | DOM23h-271-27 | amino acid sequence - affinity matured |
| 32 | DOM23h-271-101 | amino acid sequence - affinity matured |
| 33 | DOM23h-271-102 | amino acid sequence - affinity matured |
| 34 | DOM23h-271-105 | amino acid sequence - affinity matured |
| 35 | DOM23h-271-106 | amino acid sequence - affinity matured |
| 36 | DOM23h-271-114 | amino acid sequence - affinity matured |
| 37 | DOM23h-271-39 | amino acid sequence - affinity matured plus D61R K64D mutation |
| 38 | DOM23h-271-40 | amino acid sequence - affinity matured plus D61R K64F mutation |
| 39 | DOM23h-802 | nucleic acid sequence - naive clone |
| 40 | DOM23h-803 | nucleic acid sequence - naive clone |
| 41 | DOM23h-813 | nucleic acid sequence - naive clone |
| 42 | DOM23h-815 | nucleic acid sequence - naive clone |
| 43 | DOM23h-828 | nucleic acid sequence - naive clone |
| 44 | DOM23h-830 | nucleic acid sequence - naive clone |
| 45 | DOM23h-831 | nucleic acid sequence - naive clone |
| 46 | DOM23h-840 | nucleic acid sequence - naive clone |
| 47 | DOM23h-842 | nucleic acid sequence - naive clone |
| 48 | DOM23h-843 | nucleic acid sequence - naive clone |
| 49 | DOM23h-850 | nucleic acid sequence - naive clone |
| 50 | DOM23h-854 | nucleic acid sequence - naive clone |
| 51 | DOM23h-855 | nucleic acid sequence - naive clone |
| 52 | DOM23h-865 | nucleic acid sequence - naive clone |
| 53 | DOM23h-866 | nucleic acid sequence - naive clone |
| 54 | DOM23h-874 | nucleic acid sequence - naive clone |
| 55 | DOM23h-883 | nucleic acid sequence - naive clone |
| 56 | DOM23h-903 | nucleic acid sequence - naive clone |
| 57 | DOM23m-4 | nucleic acid sequence - naive clone |
| 58 | DOM23m-29 | nucleic acid sequence - naive clone |
| 59 | DOM23m-32 | nucleic acid sequence - naive clone |
| 60 | DOM23m-62 | nucleic acid sequence - naive clone |
| 61 | DOM23m-71 | nucleic acid sequence - naive clone |
| 62 | DOM23m-72 | nucleic acid sequence - naive clone |
| 63 | DOM23m-81 | nucleic acid sequence - naive clone |
| 64 | DOM23m-99 | nucleic acid sequence - naive clone |
| 65 | DOM23m-101 | nucleic acid sequence - naive clone |
| 66 | DOM23m-352 | nucleic acid sequence - naive clone |
| 67 | DOM23h-271-21 | nucleic acid sequence - affinity matured |
| 68 | DOM23h-271-22 | nucleic acid sequence - affinity matured |
| 69 | DOM23h-271-27 | nucleic acid sequence - affinity matured |
| 70 | DOM23h-271-101 | nucleic acid sequence - affinity matured |
| 71 | DOM23h-271-102 | nucleic acid sequence - affinity matured |
| 72 | DOM23h-271-105 | nucleic acid sequence - affinity matured |
| 73 | DOM23h-271-106 | nucleic acid sequence - affinity matured |
| 74 | DOM23h-271-114 | nucleic acid sequence - affinity matured |
| 75 | DOM23h-271-39 | nucleic acid sequence - affinity matured plus D61R K64D mutation |
| 76 | DOM23h-271-40 | nucleic acid sequence - affinity matured plus D61R K64F mutation |
| 77 | DOM23h-802 | CDR1 |
| 113 | ... | CDR2 |
| 149 | ... | CDR3 |
| 78 | DOM23h-803 | CDR1 |
| 114 | ... | CDR2 |
| 150 | ... | CDR3 |
| 79 | DOM23h-813 | CDR1 |
| 115 | ... | CDR2 |
| 151 | ... | CDR3 |
| 80 | DOM23h-815 | CDR1 |
| 116 | ... | CDR2 |
| 152 | ... | CDR3 |
| 81 | DOM23h-828 | CDR1 |
| 117 | ... | CDR2 |
| 153 | ... | CDR3 |
| 82 | DOM23h-830 | CDR1 |
| 118 | ... | CDR2 |
| 154 | ... | CDR3 |
| 83 | DOM23h-831 | CDR1 |
| 119 | ... | CDR2 |
| 155 | ... | CDR3 |
| 84 | DOM23h-840 | CDR1 |
| 120 | ... | CDR2 |
| 156 | ... | CDR3 |
| 85 | DOM23h-842 | CDR1 |
| 121 | ... | CDR2 |
| 157 | ... | CDR3 |
| 86 | DOM23h-843 | CDR1 |
| 122 | ... | CDR2 |
| 158 | ... | CDR3 |
| 87 | DOM23h-850 | CDR1 |
| 123 | ... | CDR2 |
| 159 | ... | CDR3 |
| 88 | DOM23h-854 | CDR1 |
| 124 | ... | CDR2 |
| 160 | ... | CDR3 |
| 89 | DOM23h-855 | CDR1 |
| 125 | ... | CDR2 |
| 161 | ... | CDR3 |
| 90 | DOM23h-865 | CDR1 |
| 126 | ... | CDR2 |
| 162 | ... | CDR3 |
| 91 | DOM23h-866 | CDR1 |
| 127 | ... | CDR2 |
| 163 | ... | CDR3 |

-continued

| SEQ ID NO | DOM number | Description |
|---|---|---|
| 92 | DOM23h-874 | CDR1 |
| 128 | ... | CDR2 |
| 164 | ... | CDR3 |
| 93 | DOM23h-883 | CDR1 |
| 129 | ... | CDR2 |
| 165 | ... | CDR3 |
| 94 | DOM23h-903 | CDR1 |
| 130 | ... | CDR2 |
| 166 | ... | CDR3 |
| 95 | DOM23m-4 | CDR1 |
| 131 | ... | CDR2 |
| 167 | ... | CDR3 |
| 96 | DOM23m-29 | CDR1 |
| 132 | ... | CDR2 |
| 168 | ... | CDR3 |
| 97 | DOM23m-32 | CDR1 |
| 133 | ... | CDR2 |
| 169 | ... | CDR3 |
| 98 | DOM23m-62 | CDR1 |
| 134 | ... | CDR2 |
| 170 | ... | CDR3 |
| 99 | DOM23m-71 | CDR1 |
| 135 | ... | CDR2 |
| 171 | ... | CDR3 |
| 100 | DOM23m-72 | CDR1 |
| 136 | ... | CDR2 |
| 172 | ... | CDR3 |
| 101 | DOM23m-81 | CDR1 |
| 137 | ... | CDR2 |
| 173 | ... | CDR3 |
| 102 | DOM23m-99 | CDR1 |
| 138 | ... | CDR2 |
| 174 | ... | CDR3 |
| 103 | DOM23m-101 | CDR1 |
| 139 | ... | CDR2 |
| 175 | ... | CDR3 |
| 104 | DOM23m-352 | CDR1 |
| 140 | ... | CDR2 |
| 176 | ... | CDR3 |
| 105 | DOM23h-271-21 | CDR1 |
| 141 | ... | CDR2 |
| 177 | ... | CDR3 |
| 106 | DOM23h-271-22 | CDR1 |
| 142 | ... | CDR2 |
| 178 | ... | CDR3 |
| 107 | DOM23h-271-27 | CDR1 |
| 143 | ... | CDR2 |
| 179 | ... | CDR3 |
| 108 | DOM23h-271-101 | CDR1 |
| 144 | ... | CDR2 |
| 180 | ... | CDR3 |
| 109 | DOM23h-271-102 | CDR1 |
| 145 | ... | CDR2 |
| 181 | ... | CDR3 |
| 110 | DOM23h-271-105 | CDR1 |
| 146 | ... | CDR2 |
| 182 | ... | CDR3 |
| 111 | DOM23h-271-106 | CDR1 |
| 147 | ... | CDR2 |
| 183 | ... | CDR3 |
| 112 | DOM23h-271-114 | CDR1 |
| 148 | ... | CDR2 |
| 184 | ... | CDR3 |
| 185 | DOM008 | primer |
| 186 | DOM009 | primer |
| 187 | DOM172 | primer |
| 188 | DOM173 | primer |
| 189 | 271-7R1deg CDR1 | primer |
| 190 | 271-7R2deg CDR2 | primer |
| 191 | 271-7R3deg CDR3 | primer |
| 192 | PE008 | primer |
| 193 | 271-6164 R | primer |
| 194 | 271-6164 deg-F | primer |
| 195 | AS1309 | primer |
| 196 | 271-6164 NR-F | primer |

-continued

| SEQ ID NO | DOM number | Description |
|---|---|---|
| 197 | DOM57 | primer |
| 198 | DOM6 | primer |
| 199 | DOM23h-271 | amino acid sequence - naive clone |
| 200 | DOM23h-271 | nucleic acid sequence - naive clone |
| 201 | DOM23h-271-7 | amino acid sequence - naive clone |
| 202 | DOM23h-271-7 | nucleic acid sequence - naive clone |
| 203 | DOM23h-855-21 | nucleic acid sequence - test matured clone |
| 204 | DOM23h-855-21 | amino acid sequence - test matured clone |
| 205 | DOM23h-843-13 | nucleic acid sequence - test matured clone |
| 206 | DOM23h-843-13 | amino acid sequence - test matured clone |
| 207 | DOM23h-439-20 | nucleic acid sequence - test matured clone |
| 208 | DOM23h-439-20 | amino acid sequence - test matured clone |
| 209 | PEP-26-F | Primer |
| 210 | PelB NcoVh | Primer |
| 211 | PEP011 | Primer |
| 212 | DOM-271-50 | nucleic acid sequence - CDR-directed affinity matured clone |
| 213 | DOM-271-50 | amino acid sequence - CDR-directed affinity matured clone |
| 214 | DOM-271-50 | amino acid sequence - CDR-directed affinity matured clone (*duplicate of 213 above*) |
| 215 | PEP044 | Primer |
| 216 | 23h-439-20 CDRH1 | Primer |
| 217 | 23h-439-20 CDRH2 | Primer |
| 218 | 23h-439-20 CDRH3 | Primer |
| 219 | 23h-843-13 CDRH1 | Primer |
| 220 | 23h-843-13 CDRH2 | Primer |
| 221 | 23h-843-13 CDRH3 | Primer |
| 222 | 23h-855-21 CDRH1 | Primer |
| 223 | 23h-855-21 CDRH2 | Primer |
| 224 | 23h-855-21 CDRH3 | Primer |
| 225 | H1-271-43 R | Primer |
| 226 | H2p1-271-43 F | Primer |
| 227 | H2p2-271-43 F | Primer |
| 228 | H3p1-271-43 F | Primer |
| 229 | H3p2-271-43 F | Primer |
| 230 | H3p3-271-43 F | Primer |
| 231 | PEP011VHStopNotIR | Primer |
| 232 | Nco1 VH F | Primer |
| 233 | DOM23h-439-25 | nucleic acid sequence - CDR-directed affinity matured clone |
| 234 | DOM23h-439-25 | amino acid sequence - CDR-directed affinity matured clone |
| 235 | DOM23h-271-123 | nucleic acid sequence - CDR-directed affinity matured clone |
| 236 | DOM23h-271-123 | amino acid sequence - CDR-directed affinity matured clone |
| 237 | DOM23h-439-35 | nucleic acid sequence - CDR-directed affinity matured clone |
| 238 | DOM23h-439-35 | amino acid sequence - CDR-directed affinity matured clone |
| 239 | DOM23h-271-129 | nucleic acid sequence - CDR-directed affinity matured clone |
| 240 | DOM23h-271-129 | amino acid sequence - CDR-directed affinity matured clone |
| 241 | DOM23h-271-123 | CDR1 |
| 242 | DOM23h-271-123 | CDR2 |
| 243 | DOM23h-271-123 | CDR3 |
| 244 | DOM23h-271-129 | CDR1 |
| 245 | DOM23h-271-129 | CDR2 |
| 246 | DOM23h-271-129 | CDR3 |
| 247 | DOM23h-439-25 | CDR1 |
| 248 | DOM23h-439-25 | CDR2 |
| 249 | DOM23h-439-25 | CDR3 |
| 250 | DOM23h-439-35 | CDR1 |
| 251 | DOM23h-439-35 | CDR2 |
| 252 | DOM23h-439-35 | CDR3 |
| 253 | 439 48I SDM F | Primer |

| SEQ ID NO | DOM number | Description |
|---|---|---|
| 254 | 439 61N SDM F | Primer |
| 255 | 439 64R SDM F | Primer |
| 256 | 439 61N 64R SDM F | Primer |
| 257 | 271 61N SDM F | Primer |
| 258 | 271 64R SDM F | Primer |
| 259 | 271 61N 64R SDM F | Primer |
| 260 | 567 +A rev | Primer |
| 261 | 21-23 Fwd | Primer |
| 262 | DOM23h-439-40 | nucleic acid sequence - CDR-directed affinity matured clone |
| 263 | DOM23h-439-40 | amino acid sequence - CDR-directed affinity matured clone |
| 264 | DOM23h-439-41 | nucleic acid sequence - CDR-directed affinity matured clone |
| 265 | DOM23h-439-41 | amino acid sequence - CDR-directed affinity matured clone |
| 266 | DOM23h-439-42 | nucleic acid sequence - CDR-directed affinity matured clone |
| 267 | DOM23h-439-42 | amino acid sequence - CDR-directed affinity matured clone |
| 268 | DOM23h-439-43 | nucleic acid sequence - CDR-directed affinity matured clone |
| 269 | DOM23h-439-43 | amino acid sequence - CDR-directed affinity matured clone |
| 270 | DOM23h-439-44 | nucleic acid sequence - CDR-directed affinity matured clone |
| 271 | DOM23h-439-44 | amino acid sequence - CDR-directed affinity matured clone |
| 272 | DOM23h-271-130 | nucleic acid sequence - CDR-directed affinity matured clone |
| 273 | DOM23h-271-130 | amino acid sequence - CDR-directed affinity matured clone |
| 274 | DOM23h-271-131 | nucleic acid sequence - CDR-directed affinity matured clone |
| 275 | DOM23h-271-131 | amino acid sequence - CDR-directed affinity matured clone |
| 276 | DOM23h-271-132 | nucleic acid sequence - CDR-directed affinity matured clone |
| 277 | DOM23h-271-132 | amino acid sequence - CDR-directed affinity matured clone |
| 278 | DOM23h-271-133 | nucleic acid sequence - CDR-directed affinity matured clone |
| 279 | DOM23h-271-133 | amino acid sequence - CDR-directed affinity matured clone |
| 280 | DOM23h-271-134 | nucleic acid sequence - CDR-directed affinity matured clone |
| 281 | DOM23h-271-134 | amino acid sequence - CDR-directed affinity matured clone |
| 282 | DOM23h-271-135 | nucleic acid sequence - CDR-directed affinity matured clone |
| 283 | DOM23h-271-135 | amino acid sequence - CDR-directed affinity matured clone |
| 284 | DOM23h-271-136 | nucleic acid sequence - CDR-directed affinity matured clone |
| 285 | DOM23h-271-136 | amino acid sequence - CDR-directed affinity matured clone |
| 286 | DOM23h-271-137 | nucleic acid sequence - CDR-directed affinity matured clone |
| 287 | DOM23h-271-137 | amino acid sequence - CDR-directed affinity matured clone |
| 288 | DOM23h-439-47 | nucleic acid sequence - DOM23h-439-42 + 48I |
| 289 | DOM23h-439-47 | amino acid sequence - DOM23h-439-42 + 48I |
| 290 | DOM23h-439-48 | nucleic acid sequence - DOM23h-439-44 + 48I |
| 291 | DOM23h-439-48 | amino acid sequence - DOM23h-439-44 + 48I |

The invention claimed is:

1. An anti-TGFbetaRII immunoglobulin single variable domain comprising the amino acid sequence of SEQ ID NO: 267.

2. An anti-TGFbetaRII immunoglobulin single variable domain as claimed in claim 1, wherein the anti-TGFbetaRII immunoglobulin single variable domain further comprises a C-terminal alanine residue.

3. An anti-TGFbetaRII immunoglobulin single variable domain as claimed in claim 1, wherein said anti-TGFbetaRII immunoglobulin single variable domain binds to human TGFbetaRII.

4. An anti-TGFbeta RII immunoglobulin single variable domain as claimed in claim 3, wherein said anti-TGFbetaRII immunoglobulin single variable domain also binds to mouse TGFbetaRII and/or cyno TGFbetaRII.

5. An immunoglobulin single variable domain as claimed in claim 1, wherein said immunoglobulin single variable domain neutralises TGFbeta activity.

6. An immunoglobulin single variable domain as claimed in claim 1, wherein said immunoglobulin single variable domain inhibits binding of TGFbeta to TGFbetaRII.

7. A pharmaceutical composition comprising an anti-TGFbetaRII immunoglobulin single variable domain comprising an amino acid sequence as set forth in SEQ ID NO: 267 for use in treating tissue fibrosis or for use in wound healing and/or scarring reduction.

8. A pharmaceutical composition comprising an anti-TGFbetaRII immunoglobulin single variable domain comprising an amino acid sequence as set forth in SEQ ID NO: 267 for use in treating keloid disease or Dupuytren's Contracture.

\* \* \* \* \*

```
                        SEQUENCE LISTING

<160> NUMBER OF SEQ ID NOS: 291

<210> SEQ ID NO 1
<211> LENGTH: 119
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 1

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Glu Gly
            20                  25                  30

Thr Met Trp Trp Val Arg Gln Ala Pro Gly Lys Gly Leu Glu Trp Val
        35                  40                  45

Ser Ala Ile Leu Ala Ala Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Lys Arg Gln Glu Arg Asp Gly Phe Asp Tyr Trp Gly Gln Gly
            100                 105                 110

Thr Leu Val Thr Val Ser Ser
        115
```

```
<210> SEQ ID NO 2
<211> LENGTH: 119
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 2

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ala Gly
            20                  25                  30

Arg Met Trp Trp Val Arg Gln Ala Pro Gly Lys Gly Leu Glu Trp Val
        35                  40                  45

Ser Ala Ile Asn Arg Asp Gly Thr Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Asp Asp Gly His Gly Asn Phe Asp Tyr Trp Gly Gln Gly
            100                 105                 110

Thr Leu Val Thr Val Ser Ser
        115

<210> SEQ ID NO 3
<211> LENGTH: 120
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 3

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Ser Thr Phe Thr Asp Asp
            20                  25                  30

Arg Met Trp Trp Val Arg Gln Ala Pro Gly Lys Gly Leu Glu Trp Val
        35                  40                  45

Ser Ala Ile Gln Pro Asp Gly His Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Gln Asp Val Lys Gly Ser Ser Phe Asp Tyr Trp Gly Gln
            100                 105                 110

Gly Thr Leu Val Thr Val Ser Ser
        115                 120

<210> SEQ ID NO 4
<211> LENGTH: 119
<212> TYPE: PRT
<213> ORGANISM: Artificial Sequence
<220> FEATURE:
<223> OTHER INFORMATION: Amino acid sequence identified using molecular
``` biology techniques.

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Glu Asp
            20                  25                  30

Arg Met Trp Trp Val Arg Gln Ala Pro Gly Lys Gly Leu Glu Trp Val
        35                  40                  45

Ser Ala Ile Asp Pro Gln Gly Gln His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Ser Thr Gly Ser Ala Thr Ser Asp Tyr Trp Gly Gln Gly
            100                 105                 110

Thr Leu Val Thr Val Ser Ser
            115

<210> SEQ ID NO 5
<211> LENGTH: 124
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Met Ser Tyr
            20                  25                  30

Arg Met Trp Trp Val Arg Gln Ala Pro Gly Lys Gly Leu Glu Trp Val
        35                  40                  45

Ser Ala Ile Ser Pro Ser Gly Ser Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Val Val Glu Tyr Ser Arg Thr His Lys Val Phe Asp
            100                 105                 110

Tyr Trp Gly Gln Gly Thr Leu Val Thr Val Ser Ser
        115                 120

<210> SEQ ID NO 6
<211> LENGTH: 122
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 6

Glu Val Gln Leu Leu Glu Ser Gly Gly Gly Leu Val Gln Pro Gly Gly
1               5                   10                  15

Phe Leu Arg Leu Ser Cys Ala Ala Ser Gly Phe Thr Phe Glu Gly Tyr
            20                  25                  30

```
Arg Met Trp Trp Val Arg Gln Ala Pro Gly Lys Gly Leu Glu Trp Val
        35                  40                  45

Ser Ala Ile Asp Ser Leu Gly Asp Arg Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gln Gly Leu Thr His Gln Ser Pro Ser Thr Phe Asp Tyr Trp
                100                 105                 110

Gly Gln Gly Thr Leu Val Thr Val Ser Ser
            115                 120
```

<210> SEQ ID NO 7
<211> LENGTH: 116
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 7

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Glu Ala Tyr
                 20                  25                  30

Lys Met Thr Trp Val Arg Gln Ala Pro Gly Lys Gly Leu Glu Trp Val
        35                  40                  45

Ser Tyr Ile Thr Pro Ser Gly Gly Gln Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Tyr Gly Ser Ser Phe Asp Tyr Trp Gly Gln Gly Thr Leu Val
                100                 105                 110

Thr Val Ser Ser
        115
```

<210> SEQ ID NO 8
<211> LENGTH: 119
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 8

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gly Asp Gly
                 20                  25                  30

Arg Met Trp Trp Val Arg Gln Ala Pro Gly Lys Gly Leu Glu Trp Val
        35                  40                  45

Ser Ala Ile Glu Gly Ala Gly Ser Asp Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Val Tyr Tyr Cys
                85                  90                  95

Ala Lys Gln Ala Ser Arg Asn Ser Pro Phe Asp Tyr Trp Gly Gln Gly
               100                 105                 110

Thr Leu Val Thr Val Ser Ser
        115

<210> SEQ ID NO 9
<211> LENGTH: 120
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 9

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Asp Ser
            20                  25                  30

Glu Met Ala Trp Ala Arg Gln Ala Pro Gly Lys Gly Leu Glu Trp Val
        35                  40                  45

Ser Leu Ile Arg Arg Asn Gly Asn Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Thr Lys Asp Arg Ser Val Leu Phe Asp Tyr Trp Gly Gln
               100                 105                 110

Gly Thr Leu Val Thr Val Ser Ser
            115                 120

<210> SEQ ID NO 10
<211> LENGTH: 120
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 10

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Gln Asp
            20                  25                  30

Arg Met Trp Trp Val Arg Gln Ala Pro Gly Lys Gly Leu Glu Trp Val
        35                  40                  45

Ser Ala Ile Glu Ser Gly Gly His Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Asn Glu Ser Gly Arg Ser Gly Phe Asp Tyr Trp Gly Gln
               100                 105                 110

Gly Thr Leu Val Thr Val Ser Ser
            115                 120
```

<210> SEQ ID NO 11
<211> LENGTH: 119
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Ala Ala
            20                  25                  30

Arg Met Trp Trp Ala Arg Gln Ala Pro Gly Lys Gly Leu Glu Trp Val
        35                  40                  45

Ser Ala Ile Ala Asp Ile Gly Asn Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Ser Gly Ser Glu Asp His Phe Asp Tyr Trp Gly Gln Gly
            100                 105                 110

Thr Leu Val Thr Val Ser Ser
        115

<210> SEQ ID NO 12
<211> LENGTH: 121
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Gln Asp
            20                  25                  30

Arg Met Trp Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Asp Leu His Gly Thr Ser Ser Leu Phe Asp Tyr Trp Gly
            100                 105                 110

Gln Gly Thr Leu Val Thr Val Ser Ser
        115                 120

<210> SEQ ID NO 13
<211> LENGTH: 120
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Asn Thr
            20                  25                  30

Ser Met Gly Trp Val Arg Gln Ala Pro Gly Lys Gly Leu Glu Trp Val
        35                  40                  45

Ser Arg Ile Asp Pro Lys Gly Ser His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Arg Glu Leu Gly Lys Ser His Phe Asp Tyr Trp Gly Gln
            100                 105                 110

Gly Thr Leu Val Thr Val Ser Ser
            115                 120

<210> SEQ ID NO 14
<211> LENGTH: 119
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Glu Met Thr Trp Val Arg Gln Ala Pro Gly Lys Gly Leu Glu Trp Val
        35                  40                  45

Ser Lys Ile Asp Pro Ser Gly Arg Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Arg Thr Asp Leu Gln Leu Phe Asp Tyr Trp Gly Gln Gly
            100                 105                 110

Thr Leu Val Thr Val Ser Ser
        115

<210> SEQ ID NO 15
<211> LENGTH: 121
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

```
Trp Met Arg Trp Ala Arg Gln Ala Pro Gly Lys Gly Leu Glu Trp Val
        35                  40                  45

Ser Tyr Ile Thr Pro Lys Gly Asp His Thr Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Ser Leu His Asn Glu Arg Val Lys His Phe Asp Tyr Trp Gly
                100                 105                 110

Gln Gly Thr Leu Val Thr Val Ser Ser
        115                 120

<210> SEQ ID NO 16
<211> LENGTH: 121
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 16

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Thr Ser Tyr
                20                  25                  30

Arg Met Trp Trp Val Arg Gln Ala Pro Gly Lys Gly Leu Glu Trp Val
        35                  40                  45

Ser Val Ile Asp Ser Thr Gly Ser Ala Thr Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Gln Ala Gly Ser Ala Met Gly Glu Phe Asp Tyr Trp Gly
                100                 105                 110

Gln Gly Thr Leu Val Thr Val Ser Ser
        115                 120

<210> SEQ ID NO 17
<211> LENGTH: 116
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 17

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Val Asn Tyr
                20                  25                  30

Arg Met Trp Trp Val Arg Gln Ala Pro Gly Lys Gly Leu Glu Trp Val
        35                  40                  45

Ser Ala Ile Ser Gly Ser Gly Asp Lys Thr Tyr Tyr Ala Asp Ser Val
 50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Lys His Gly Leu Ser Phe Asp Tyr Trp Gly Gln Gly Thr Leu Val
            100                 105                 110

Thr Val Ser Ser
        115

<210> SEQ ID NO 18
<211> LENGTH: 116
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asp Met
            20                  25                  30

Arg Met Trp Trp Val Arg Gln Ala Pro Gly Lys Gly Leu Glu Trp Val
        35                  40                  45

Ser Val Ile Asn Ala Asp Gly Asn Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Leu Pro Phe Asp Tyr Trp Gly Gln Gly Thr Leu Val
            100                 105                 110

Thr Val Ser Ser
        115

<210> SEQ ID NO 19
<211> LENGTH: 123
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Thr Tyr
            20                  25                  30

Gly Met Gly Trp Val Arg Gln Ala Pro Gly Lys Gly Leu Glu Trp Val
        35                  40                  45

Ser Trp Ile Glu Lys Thr Gly Asn Lys Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Gly Arg His Ile Lys Val Arg Ser Arg Asp Phe Asp Tyr
            100                 105                 110

Trp Gly Gln Gly Thr Leu Val Thr Val Ser Ser
        115                 120

<210> SEQ ID NO 20
<211> LENGTH: 123
<212> TYPE: PRT
<213> ORGANISM: Artificial Sequence
<220> FEATURE:
<223> OTHER INFORMATION: Amino acid sequence identified using molecular
     biology techniques.

<400> SEQUENCE: 20

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Lys Arg Tyr
            20                  25                  30

Ser Met Gly Trp Val Arg Gln Ala Pro Gly Lys Gly Leu Glu Trp Val
        35                  40                  45

Ser Val Ile Asn Asp Leu Gly Ser Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asn Ile Ser Met Val Arg Pro Gly Ser Trp Phe Asp Tyr
            100                 105                 110

Trp Gly Gln Gly Thr Leu Val Thr Val Ser Ser
            115                 120
```

<210> SEQ ID NO 21
<211> LENGTH: 123
<212> TYPE: PRT
<213> ORGANISM: Artificial Sequence
<220> FEATURE:
<223> OTHER INFORMATION: Amino acid sequence identified using molecular
     biology techniques.

<400> SEQUENCE: 21

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Phe Glu Tyr
            20                  25                  30

Pro Met Gly Trp Val Arg Gln Ala Pro Gly Lys Gly Leu Glu Trp Val
        35                  40                  45

Ser Val Ile Ser Gly Asp Gly Gln Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser His Thr Gly Thr Val Arg His Leu Glu Thr Phe Asp Tyr
            100                 105                 110

Trp Gly Gln Gly Thr Leu Val Thr Val Ser Ser
            115                 120
```

<210> SEQ ID NO 22
<211> LENGTH: 120
<212> TYPE: PRT
<213> ORGANISM: Artificial Sequence
<220> FEATURE:
<223> OTHER INFORMATION: Amino acid sequence identified using molecular
     biology techniques.

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Gln Glu
            20                  25                  30

Ser Met Tyr Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Gly Thr Arg Ile Lys Gln Gly Phe Asp Tyr Trp Gly Gln
            100                 105                 110

Gly Thr Leu Val Thr Val Ser Ser
        115                 120

<210> SEQ ID NO 23
<211> LENGTH: 123
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Met Asp Tyr
            20                  25                  30

Arg Met Tyr Trp Val Arg Gln Ala Pro Gly Lys Gly Leu Glu Trp Val
        35                  40                  45

Ser Gly Ile Asp Pro Thr Gly Leu Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Lys Trp Gly Glu Met Gly Ser Tyr Lys Thr Phe Asp Tyr
            100                 105                 110

Trp Gly Gln Gly Thr Leu Val Thr Val Ser Ser
        115                 120

<210> SEQ ID NO 24
<211> LENGTH: 124
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Met Asp Tyr
            20                  25                  30

Asp Met Ser Trp Val Arg Gln Ala Pro Gly Lys Gly Leu Glu Trp Val

```
                35                  40                  45
Ser Met Ile Arg Glu Asp Gly Lys Thr Tyr Tyr Ala Asp Ser Val
        50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Ala Arg Val Pro Tyr Arg Arg Gly His Arg Asp Asn Phe Asp
                100                 105                 110
Tyr Trp Gly Gln Gly Thr Leu Val Thr Val Ser Ser
        115                 120

<210> SEQ ID NO 25
<211> LENGTH: 120
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 25

Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Glu Pro Val
                20                  25                  30
Ile Met Gly Trp Val Arg Gln Ala Pro Gly Lys Gly Leu Glu Trp Val
        35                  40                  45
Ser Ala Ile Glu Ala Arg Gly Gly Thr Tyr Tyr Ala Asp Ser Val
        50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Pro Gly Arg His Leu Ser Gln Asp Phe Asp Tyr Trp Gly Gln
                100                 105                 110
Gly Thr Leu Val Thr Val Ser Ser
        115                 120

<210> SEQ ID NO 26
<211> LENGTH: 119
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 26

Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Asp Arg Tyr
                20                  25                  30
Arg Met Met Trp Val Arg Gln Ala Pro Gly Lys Gly Leu Glu Trp Val
        35                  40                  45
Ser Thr Ile Asp Pro Ala Gly Met Leu Thr Tyr Tyr Ala Asp Ser Val
        50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
```

```
                    85                  90                  95

Ala Lys Arg Leu Ala Ser Arg Ser His Phe Asp Tyr Trp Gly Gln Gly
            100                 105                 110

Thr Leu Val Thr Val Ser Ser
        115

<210> SEQ ID NO 27
<211> LENGTH: 119
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 27

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Glu Tyr
            20                  25                  30

Asp Met Ala Trp Val Arg Gln Ala Pro Gly Lys Gly Leu Glu Trp Val
        35                  40                  45

Ser Arg Ile Arg Ser Asp Gly Val Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Ala Lys Asn Gly Trp Phe Asp Tyr Trp Gly Gln Gly
            100                 105                 110

Thr Leu Val Thr Val Ser Ser
        115

<210> SEQ ID NO 28
<211> LENGTH: 119
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 28

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Lys Tyr
            20                  25                  30

Lys Met Ala Trp Val Arg Gln Ala Pro Gly Lys Gly Leu Glu Trp Val
        35                  40                  45

Ser Leu Ile Phe Pro Asn Gly Val Pro Thr Tyr Tyr Ala Asn Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Ser Gly Gln Gly Arg Asp Phe Asp Tyr Trp Gly Gln Gly
            100                 105                 110

Thr Leu Val Thr Val Ser Ser
        115
```

<210> SEQ ID NO 29
<211> LENGTH: 124
<212> TYPE: PRT
<213> ORGANISM: Artificial Sequence
<220> FEATURE:
<223> OTHER INFORMATION: Amino acid sequence identified using molecular biology techniques.

<400> SEQUENCE: 29

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Thr Glu Tyr
            20                  25                  30

Arg Met Trp Trp Val Arg Gln Ala Pro Gly Lys Gly Leu Glu Trp Val
        35                  40                  45

Ser Ala Ile Glu Pro Ile Gly Asn Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Met Pro Gly Arg Lys Trp Thr Ala Lys Phe Arg Trp Asp
            100                 105                 110

Tyr Trp Gly Gln Gly Thr Leu Val Ile Val Ser Ser
        115                 120
```

<210> SEQ ID NO 30
<211> LENGTH: 124
<212> TYPE: PRT
<213> ORGANISM: Artificial Sequence
<220> FEATURE:
<223> OTHER INFORMATION: Amino acid sequence identified using molecular biology techniques.

<400> SEQUENCE: 30

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Thr Glu Tyr
            20                  25                  30

Arg Met Trp Trp Val Arg Gln Ala Pro Gly Lys Gly Leu Glu Trp Val
        35                  40                  45

Ser Ala Ile Glu Pro Ile Gly Asn Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Met Pro Gly Gln Lys Trp Met Ala Lys Ser Arg Phe Asp
            100                 105                 110

Tyr Trp Gly Gln Gly Thr Leu Val Thr Val Ser Ser
        115                 120
```

<210> SEQ ID NO 31
<211> LENGTH: 124
<212> TYPE: PRT
<213> ORGANISM: Artificial Sequence
<220> FEATURE:
<223> OTHER INFORMATION: Amino acid sequence identified using molecular biology techniques.

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Glu Tyr
            20                  25                  30

Arg Met Trp Trp Val Arg Gln Ala Pro Gly Lys Gly Leu Glu Trp Val
        35                  40                  45

Ser Ala Ile Glu Pro Ile Gly Gln Lys Thr Tyr Tyr Ala Asp Ser Val
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Lys Gln Ile Pro Gly Arg Lys Trp Thr Ala Asn Ser Arg Phe Asp
            100                 105                 110

Tyr Trp Gly Gln Gly Thr Leu Val Ile Val Ser Ser
        115                 120

<210> SEQ ID NO 32
<211> LENGTH: 124
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Glu Tyr
            20                  25                  30

Arg Met Trp Trp Val Arg Gln Ala Pro Gly Lys Gly Leu Glu Trp Val
        35                  40                  45

Ser Ala Ile Glu Pro Ile Gly Asn Arg Thr Tyr Tyr Ala Asp Ser Val
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Lys Gln Ile Pro Gly Arg Lys Trp Thr Ala Asn Gly Arg Lys Asp
            100                 105                 110

Tyr Trp Gly Gln Gly Thr Leu Val Thr Val Ser Ser
        115                 120

<210> SEQ ID NO 33
<211> LENGTH: 124
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Thr Glu Tyr
            20                  25                  30

Arg Met Trp Trp Val Arg Gln Ala Pro Gly Lys Gly Leu Glu Trp Val
        35                  40                  45

Ser Ala Ile Glu Pro Ile Gly His Arg Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gln Ile Pro Gly Arg Lys Trp Thr Ala Asn Ser Arg Phe Asp
            100                 105                 110

Tyr Trp Gly Gln Gly Thr Leu Val Thr Val Ser Ser
            115                 120

<210> SEQ ID NO 34
<211> LENGTH: 124
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 34

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Thr Glu Tyr
             20                  25                  30

Arg Met Trp Trp Val Arg Gln Ala Pro Gly Lys Gly Leu Glu Trp Val
         35                  40                  45

Ser Ala Ile Glu Pro Ile Gly Asn Arg Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gln Ile Pro Gly Gln Arg Trp Thr Gly Asn Ser Arg Phe Asp
            100                 105                 110

Tyr Trp Gly Gln Gly Thr Leu Val Thr Val Ser Ser
            115                 120

<210> SEQ ID NO 35
<211> LENGTH: 124
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 35

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Thr Glu Tyr
             20                  25                  30

Arg Met Trp Trp Val Arg Gln Ala Pro Gly Lys Gly Leu Glu Trp Val
         35                  40                  45

Ser Ala Ile Glu Pro Ile Gly Asn Arg Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

```
Ala Lys Gln Phe Pro Gly Arg Lys Trp Thr Ala Asn Ser Arg Ser Asp
            100                 105                 110

Tyr Trp Gly Gln Gly Thr Leu Val Thr Val Ser Ser
        115                 120

<210> SEQ ID NO 36
<211> LENGTH: 124
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Glu Tyr
            20                  25                  30

Arg Met Trp Trp Val Arg Gln Ala Pro Gly Lys Gly Leu Glu Trp Val
        35                  40                  45

Ser Ala Ile Glu Pro Ile Gly Asn Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Ile Pro Gly Arg Lys Gly Thr Ala Asn Ser Arg Phe Asp
            100                 105                 110

Tyr Trp Gly Gln Gly Thr Leu Val Thr Val Ser Ser
        115                 120

<210> SEQ ID NO 37
<211> LENGTH: 124
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Glu Tyr
            20                  25                  30

Arg Met Trp Trp Val Arg Gln Ala Pro Gly Lys Gly Leu Glu Trp Val
        35                  40                  45

Ser Ala Ile Glu Pro Ile Gly Asn Arg Thr Tyr Tyr Ala Arg Ser Val
    50                  55                  60

Asp Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Met Pro Gly Gln Lys Trp Met Ala Lys Ser Arg Phe Asp
            100                 105                 110

Tyr Trp Gly Gln Gly Thr Leu Val Thr Val Ser Ser
        115                 120

<210> SEQ ID NO 38
```

<211> LENGTH: 124
<212> TYPE: PRT
<213> ORGANISM: Artificial Sequence
<220> FEATURE:
<223> OTHER INFORMATION: Amino acid sequence identified using molecular biology techniques.

<400> SEQUENCE: 38

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Thr Glu Tyr
            20                  25                  30

Arg Met Trp Trp Val Arg Gln Ala Pro Gly Lys Gly Leu Glu Trp Val
        35                  40                  45

Ser Ala Ile Glu Pro Ile Gly Asn Arg Thr Tyr Tyr Ala Arg Ser Val
    50                  55                  60

Phe Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Met Pro Gly Gln Lys Trp Met Ala Lys Ser Arg Phe Asp
            100                 105                 110

Tyr Trp Gly Gln Gly Thr Leu Val Thr Val Ser Ser
        115                 120
```

<210> SEQ ID NO 39
<211> LENGTH: 357
<212> TYPE: DNA
<213> ORGANISM: Artificial Sequence
<220> FEATURE:
<223> OTHER INFORMATION: Nucleic acid sequence identified using molecular biology techniques.

<400> SEQUENCE: 39

```
gaggtgcagc tgttggagtc tgggggaggc ttggtacagc ctggggggtc cctgcgtctc    60
tcctgtgcag cctccggatt cacctttagt gaggggacga tgtggtgggt ccgccaggct   120
ccagggaagg gtctagagtg gtctcagct attttggctg ctggttctaa tacatactac   180
gcagactccg tgaagggccg gttcaccatc tcccgcgaca attccaagaa cacgctgtat   240
ctgcaaatga acagcctgcg tgccgaggac accgcggtat attactgtgc gaaaagagg   300 caggagcggg atgggtttga ctactggggt cagggaaccc tggtcaccgt ctcgagc     357
```

<210> SEQ ID NO 40
<211> LENGTH: 357
<212> TYPE: DNA
<213> ORGANISM: Artificial Sequence
<220> FEATURE:
<223> OTHER INFORMATION: Nucleic acid sequence identified using molecular biology techniques.

<400> SEQUENCE: 40

```
gaggtgcagc tgttggagtc tgggggaggc ttggtacagc ctggggggtc cctgcgtctc    60
tcctgtgcag cctccggatt cacctttagt gctgggcgga tgtggtgggt ccgccaggct   120
ccagggaagg gtctagagtg gtctcagcg attaatcggg atggtactag acatactac   180 gcagactccg tgaagggccg gttcaccatc tcccgtgaca attccaagaa cacgctgtat   240
ctgcaaatga acagcctgcg tgccgaggac accgcggtat attactgtgc gaaacatgat   300
gatggtcatg gtaattttga ctactggggt cagggaaccc tggtcaccgt ctcgagc     357
```

<210> SEQ ID NO 41
<211> LENGTH: 360
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 41

| gaggtgcagc tgttggagtc tgggggaggc ttggtacagc ctgggggtc cctgcgtctc | 60 |
| tcctgtgcag cctccggatc cacctttacg gatgataggg tgtggtgggt ccgccaggct | 120 |
| ccagggaagg gtctagagtg ggtctcagct attcagcctg atggtcatac gacatactac | 180 |
| gcagactccg tgaagggccg gttcaccatc tcccgcgaca attccaagaa cacgctgtat | 240 |
| ctgcaaatga acagcctgcg tgccgaggac accgcggtat attactgtgc ggaacaggat | 300 |
| gttaagggt cgtcttcgtt tgactactgg ggtcagggaa ccctggtcac cgtctcgagc | 360 |

<210> SEQ ID NO 42
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 42

| gaggtgcagc tgttggagtc tgggggaggc ttggtacagc ctgggggtc cctgcgtctc | 60 |
| tcctgtgcag cctccggatt cacctttgcg gaggatcgga tgtggtgggt ccgccaggct | 120 |
| ccagggaagg gtctagagtg ggtctcagct attgatcctc aggtcagca tacatactac | 180 |
| gcagactccg tgaagggccg gttcaccatc tcccgcgaca attccaagaa cacgctgtat | 240 |
| ctgcaaatga acagcctgcg tgccgaggac accgcggtat attactgtgc gaaacagtct | 300 |
| actgggtctg ctacgtctga ctactggggt cagggaaccc tggtcaccgt ctcgagc | 357 |

<210> SEQ ID NO 43
<211> LENGTH: 372
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 43

| gaggtgcagc tgttggagtc tgggggaggc ttggtacagc ctgggggtc cctgcgtctc | 60 |
| tcctgtgcag cctccggatt cacctttatg agttatagga tgtggtgggt ccgccaggct | 120 |
| ccagggaagg gtctagagtg ggtctcagct atttctccga gtggtagtga tacatactac | 180 |
| gcagactccg tgaagggccg gttcaccatc tcccgcgaca attccaagaa cacgctgtat | 240 |
| ctgcaaatga acagcctgcg tgccgaggac accgcggtat attactgtgc gaaacaggtg | 300 |
| gtggagtatt cgcgtactca taagggtgtg tttgactact ggggtcaggg aaccctggtc | 360 |
| accgtctcga gc | 372 |

<210> SEQ ID NO 44
<211> LENGTH: 366
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 44

| | | |
|---|---|---|
| gaggtgcagc tgttggagtc tgggggaggc ttggtacagc ctgggggtt cctgcgtctc | 60 |
| tcctgtgcag cctccggatt cacctttgag ggtatagga tgtggtgggt ccgccaggct | 120 |
| ccagggaagg gtctagagtg gtctcagct attgattctc tgggtgatcg tacatactac | 180 |
| gcagactccg tgaagggccg gttcaccatc tcccgcgaca attccaagaa cacgctgtat | 240 |
| ctgcaaatga acagtctgcg tgccgaggac accgcggtat attactgtgc gaaacagggg | 300 |
| cttacgcatc agtctccgag tactttgac tactggggtc agggaaccct ggtcaccgtc | 360 |
| tcgagc | 366 |

<210> SEQ ID NO 45
<211> LENGTH: 348
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 45

| | | |
|---|---|---|
| gaggtgcagc tgttggagtc tgggggaggc ttggtacagc ctggagggtc cctgcgtctc | 60 |
| tcctgtgcag cctccggatt cacctttgag gcgtataaga tgacgtgggt ccgccaggct | 120 |
| ccagggaagg gtctggagtg gtctcatat attacgccgt ctggtggtca gacatactac | 180 |
| gcagactccg tgaagggccg gttcaccatc tcccgcgaca attccaagaa cacgctgtat | 240 |
| ctgcaaatga acagcctgcg tgccgaggac accgcggtat attactgtgc gaaatatggt | 300 |
| tcgagttttg actactgggg tcagggaacc ctggtcaccg tctcgagc | 348 |

<210> SEQ ID NO 46
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 46

| | | |
|---|---|---|
| gaggtgcagc tgttggagtc tgggggaggc ttggtacagc ctgggggtc cctgcgtctc | 60 |
| tcctgtgcag cctccggatt cacctttggg gatggtcgta tgtggtgggt ccgccaggct | 120 |
| ccagggaagg gtctagagtg gtctcagct attgagggg cgggttcgga tacatactac | 180 |
| gcagactccg tgaagggccg gttcaccatc tcccgcgaca attccaagaa cacgctgtat | 240 |
| ctgcaaatga acagcctgcg tgccgaggac accgcggtat attactgtgc gaaacaggcg | 300 |
| tcgcggaatt cgccgtttga ctactggggt caggggaccc tggtcaccgt ctcgagc | 357 |

<210> SEQ ID NO 47
<211> LENGTH: 360
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 47

| | | |
|---|---|---|
| gaggtgcagc tgttggagtc tgggggaggc ttggtacagc ctgggggtc cctgcgtctc | 60 |
| tcctgtgcag cctccggatt cacctttgat gatagtgaga tggcgtgggc ccgccaggct | 120 |
| ccagggaagg gtctagagtg gtctcactt attcggcgta atggtaatgc tacatactac | 180 |

```
gcagactccg tgaagggccg gttcaccatc tcccgcgaca attccaagaa cacgctgtat      240
ctgcaaatga acagcctgcg tgccgaggac accgcggtat attactgtgc gaaagttacg      300
aaggatcgtt ctgtgctttt tgactactgg ggtcagggaa ccctggtcac cgtctcgagc      360

<210> SEQ ID NO 48
<211> LENGTH: 360
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 48
gaggtgcagc tgttggagtc tgggggaggc ttggtacagc ctgggggtc cctgcgtctc       60 tcctgtgcag cctccggatt caccttttgat caggatcgga tgtggtgggt ccgccaggct     120
ccagggaagg gtctagagtg ggtctcagct attgagagtg gtggtcatag gacatactac     180
gcagactccg tgaagggccg gttcaccatc tcccgcgaca attccaagaa cacgctgtat     240
ctgcaaatga acagcctgcg tgccgaggac accgcggtat attactgtgc gaaacagaat    300
gagtcggggc gttcgggttt tgactactgg ggtcagggaa ccctggtcac cgtctcgagc    360

<210> SEQ ID NO 49
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 49
gaggtgcagc tgttggagtc tgggggaggc ttggtacagc ctgggggtc cctgcgtctc      60 tcctgtgcag cctccggatt caccttttgat gcggctagga tgtggtgggc ccgccaggct   120
ccagggaagg gtctagagtg ggtctcagcg attgcggata ttggtaatac tacatactac    180
gcagactccg tgaagggccg gttcaccatc tcccgcgaca attccaagaa cacgctgtat    240
ctgcaaatga acagcctgcg tgccgaggac accgcggtat attactgtgc gaaacagtct   300
ggttcggagg atcattttga ctactggggt cagggaaccc tggtcaccgt ctcgagc       357

<210> SEQ ID NO 50
<211> LENGTH: 363
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 50
gaggtgcagc tgttggagtc cggggaggc ttggtacagc ctgggggtc cctgcgtctc       60 tcctgtgcag cctccggatt caccttttgct caggatcgga tgtggtgggt ccgccaggct   120
ccagggaagg gtctagagtg ggtctcagct attagtggta gtggtggtag cacatactac    180
gcagactccg tgaagggccg gttcaccatc tcccgcgaca attccaagaa cacgctgtat    240
ctgcaaatga acagcctgcg tgccgaggac accgcggtat attactgtgc gaaacaggat   300
ttgcatggta ctagttcttt gtttgactac tggggtcagg gaaccctggt caccgtctcg   360
agc                                                                  363
```

```
<210> SEQ ID NO 51
<211> LENGTH: 360
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 51
gaggtgcagc tgttggagtc tgggggaggc ttggtacagc ctgggggtc  cctgcgtctc      60 tcctgtgcag cctccggatt cacctttgag aatacgagta tgggttgggt ccgccaggct     120
ccagggaagg gtctagagtg ggtctcacgt attgatccta agggtagtca tacatactac     180
gcagactccg tgaagggccg gttcaccatc tcccgcgaca attccaagaa tacgctgtat     240
ctgcaaatga acagcctgcg tgccgaggac accgcggtat attactgtgc gaaacagcgt     300
gagttgggta agtcgcattt tgactactgg ggtcaggaa  ccctggtcac cgtctcgagc     360

<210> SEQ ID NO 52
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 52
gaggtgcagc tgttggagtc tgggggaggc ttggtacagc ctgggggtc  cctgcgtctc      60 tcctgtgcag cctccggatt cacctttcgt agttatgaga tgacttgggt ccgccaggct     120
ccagggaagg gtctagagtg ggtctcaaag attgatcctt cgggtcgttt tacatactac     180
gcagactccg tgaagggccg gttcaccatc tcccgcgaca attccaagaa cacgctgtat     240
ctgcaaatga acagcctgcg tgccgaggat accgcggtat attactgtgc gaaaggtcgg     300
acggatcttc agcttttga  ctactggggt cagggaaccc tggtcaccgt ctcgagc        357

<210> SEQ ID NO 53
<211> LENGTH: 363
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 53
gaggtgcagc tgttggagtc tgggggaggc ttggtacagc ctgggggtc  cctgcgtctc      60 tcctgtgcag cctccggatt caccttttcg aattattgga tgcggtgggc ccgccaggct     120
ccagggaagg gtctagagtg ggtctcatat attactccta agggtgatca tacatactac     180
gcagactccg tgaagggccg gttcaccatc tcccgcgaca attccaagaa cacgctgtat     240
ctgcaaatga acagcctgcg tgccgaggac accgcggtat attactgtgc ggaatcgctt     300
cataatgagc gtgttaagca ttttgactac tggggtcagg gaaccctggt caccgtctcg     360
agc                                                                   363

<210> SEQ ID NO 54
<211> LENGTH: 363
<212> TYPE: DNA
<213> ORGANISM: Artificial Sequence
<220> FEATURE:
<223> OTHER INFORMATION: Nucleic acid sequence identified using
      molecular biology techniques.
```

<400> SEQUENCE: 54

```
gaggtgcagc tgttggagtc tgggggaggc ttggtacagc ctgggggctc cctgcgtctc    60
tcctgtgcag cctccggatt cacctttact agttatcgta tgtggtgggt ccgccaggct   120
ccagggaagg gtctagagtg gtctcagtt attgattcta ctggttcggc tacatactac   180
gcagactccg tgaagggccg gttcaccatc tcccgcgaca attccaagaa cacgctgtat   240
ctgcaaatga acagcctgcg tgccgaggat accgcggtat attactgtgc gaaacagcag   300
gctgggagtg cgatggggga gtttgactac tggggtcagg gaaccctggt caccgtctcg   360
agc                                                                  363
```

<210> SEQ ID NO 55
<211> LENGTH: 348
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 55

```
gaggtgcagc tgttggagtc tgggggaggc ttggtacagc ctgggggctc cctgcgtctc    60
tcctgtgcag cctccggatt cacctttgtt aattatcgta tgtggtgggt ccgccaggct   120
ccagggaagg gtctagagtg gtctcagct attagtggta gtggtgataa acatactac    180
gcagactccg tgaagggccg gttcaccatc tcccgcgaca attccaagaa cacgctgtat   240
ctgcaaatga acagcctgcg tgccgaggac accgcggtat attactgtgc gaaacatggg   300
ctgtcgtttg actactgggg tcagggaacc ctggtcaccg tctcgagc                348
```

<210> SEQ ID NO 56
<211> LENGTH: 348
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 56

```
gaggtgcagc tgttggagtc tgggggaggc ttggtacagc ctgggggctc cctgcgtctc    60
tcctgtgcag cctccggatt cacctttaat gatatgagga tgtggtgggt ccgccaggct   120
ccagggaagg gtctagagtg gtctcagtg attaatgctg atggtaatag acatactac    180
gcagactccg tgaagggccg gttcaccatc tcccgcgaca attccaagaa cacgctgtat   240
ctgcaaatga acagcctgcg tgccgaggat accgcggtat attactgtgc gaaagatggg   300
ctgccttttg actactgggg tcagggaacc ctggtcaccg tctcgagc                348
```

<210> SEQ ID NO 57
<211> LENGTH: 369
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 57

```
gaggtgcagc tgttggagtc tgggggaggc ttggtacagc ctgggggctc cctgcgtctc    60
tcctgtgcag cctccggatt cacctttacg acttatggta tggttgggt ccgccaggct   120
ccagggaagg gtctagagtg gtctcatgg attgagaaga cgggtaataa gacatactac   180
```

```
gcagactccg tgaagggccg gttcaccatc tcccgcgaca attccaagaa cacgctgtat    240
ctgcaaatga acagcctgcg tgccgaggac accgcggtat attactgtgc gaaagcgggg    300
aggcatatta aggtgcgttc gagggatttt gactactggg gtcagggaac cctggtcacc    360
gtctcgagc                                                           369
```

<210> SEQ ID NO 58
<211> LENGTH: 369
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 58

```
gaggtgcagc tgttggagtc tgggggaggc ttggtacagc ctgggggggtc cctgcgtctc     60 tcctgtgcag cctccggatt cacctttaag aggtattcta tgggttgggt ccgccaggct    120
ccagggaagg gtctagagtg gtctcagtt attaatgatc tgggtagttt gacatactac    180
gcagactccg tgaagggccg gttcaccatc tcccgcgaca attccaagaa cacgctgtat    240
ctgcaaatga acagcctgcg tgccgaggac accgcggtat attactgtgc gaaagggaat    300
attagtatgg tgaggccggg gagttggttt gactactggg gtcagggaac cctggtcacc    360
gtctcgagc                                                           369
```

<210> SEQ ID NO 59
<211> LENGTH: 369
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 59

```
gaggtgcagc tgttggagtc tgggggaggc ttggtacagc ctgggggggtc cctgcgtctc     60 tcctgtgcag cctccggatt cacctttttt gagtatccta tgggttgggt ccgccaggct    120
ccagggaagg gtctagagtg gtctcagtt attagtgggg atggtcagcg gacatactac    180
gcagactccg tgaagggccg gttcaccatc tcccgcgaca attccaagaa cacgctgtat    240
ctgcaaatga acagcctgcg tgccgaggac accgcggtat attactgtgc gaaaagtcat    300
acggggactg tgaggcatct ggagacgttt gactactggg gtcagggaac cctggtcacc    360
gtctcgagc                                                           369
```

<210> SEQ ID NO 60
<211> LENGTH: 360
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 60

```
gaggtgcagc tgttggagtc tgggggaggc ttggtacagc ctgggggggtc cctgcgtctc     60 tcctgtgcag cctccggatt cacctttggt caggagagta tgtattgggt ccgccaggct    120
ccagggaagg gtctagagtg gtctcagct attagtggta gtggtggtag cacatactac    180
gcagactccg tgaagggccg gttcaccatc tcccgcgaca attccaagaa cacgctgtat    240
ctgcaaatga acagcctgcg tgccgaggac accgcggtat attactgtgc gaaaagtggt    300
```
acgcggatta agcagggttt tgactactgg ggtcagggaa ccctggtcac cgtctcgagc   360

<210> SEQ ID NO 61
<211> LENGTH: 369
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 61
gaggtgcagc tgttggagtc tgggggaggc ttggtacagc ctgggggtc cctgcgtctc    60 tcctgtgcag cctccggatt cacctttatg gattatagga tgtattgggt ccgccaggct   120
ccagggaagg gtctagagtg ggtctcaggg attgatccta ctggtttgcg gacatactac   180
gcagactccg tgaagggccg gttcaccatc tcccgcgaca attccaagaa cacgctgtat   240
ctgcaaatga acagcctgcg tgccgaggac accgcggtat attactgtgc gaaaattaag   300
tgggggagag tggggagtta taagactttt gactactggg gtcagggaac cctggtcacc   360
gtctcgagc                                                           369

<210> SEQ ID NO 62
<211> LENGTH: 372
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 62
gaggtgcagc tgttggagtc tgggggaggc ttggtacagc ctgggggtc cctgcgtctc    60 tcctgtgcag cctccggatt cacctttatg gattatgata tgagttgggt ccgccaggct   120
ccagggaagg gtctagagtg ggtctcaatg attcgtgagg atggtggtaa gacatactac   180
gcagactccg tgaagggccg gttcaccatc tcccgcgaca attccaagaa cacgctgtat   240
ctgcaaatga acagcctgcg tgccgaggac accgcggtat attactgtgc gaaagcgagg   300
gtgccttatc ggcgtgggca tagggataat tttgactact ggggtcaggg aaccctggtc   360
accgtctcga gc                                                       372

<210> SEQ ID NO 63
<211> LENGTH: 360
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 63
gaggtgcagc tgttggagtc tgggggaggc ttggtacagc ctgggggtc cctgcgtctc    60 tcctgtgcag cttccggatt cacctttgag ccggttatta tggggtgggt ccgccaggct   120
ccagggaagg gtctagagtg ggtctcagct attgaggcgc ggggtggggg gacatactac   180
gcagactccg tgaagggccg gttcaccatc tcccgcgaca attccaagaa cacgctgtat   240
ctgcaaatga acagcctgcg tgccgaggac accgcggtat attactgtgc gaaacctggg   300
cggcatctta gtcaggattt tgactactgg ggtcagggaa ccctggtcac cgtctcgagc   360

<210> SEQ ID NO 64
<211> LENGTH: 357
<212> TYPE: DNA

```
<213> ORGANISM: Artificial Sequence
<220> FEATURE:
<223> OTHER INFORMATION: Nucleic acid sequence identified using
      molecular biology techniques.

<400> SEQUENCE: 64
gaggtgcagc tgttggagtc tggggagggc ttggtacagc ctgggggtc cctgcgtctc      60 tcctgtgcag cctccggatt cacctttgat cggtatcgta tgatgtgggt ccgccaggct    120
ccagggaagg gtctagagtg ggtctcaacg attgatcctg ctggtatgct tacatactac    180
gcagactccg tgaagggccg gttcaccatc tcccgcgaca attccaagaa cacgctgtat    240
ctgcaaatga acagcctgcg tgccgaggac accgcggtat attactgtgc gaaaaggctg    300
gcttcgcgga gtcattttga ctactggggt cagggaaccc tggtcaccgt ctcgagc       357

<210> SEQ ID NO 65
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 65
gaggtgcagc tgttggagtc tggggagggc ttggtacagc ctgggggtc cctgcgtctc      60 tcctgcgcag cctccggatt cacctttct gagtatgata tggcttgggt ccgccaggct     120
ccagggaagg gtcttgagtg ggtctcacgg attcgttctg atggtgttag gacatactac    180
gcagactccg tgaagggccg gttcaccatc tcccgcgaca attccaagaa cacgctgtat    240
ctgcaaatga acagcctgcg tgccgaggac accgcggtat attactgtgc gaaagatcgt    300
gctaagaatg gttggtttga ctactggggt cagggaaccc tggtcaccgt ctcgagc       357

<210> SEQ ID NO 66
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 66
gaggtgcagc tgttggagtc tggggagggc ttggtacagc ctgggggtc cctgcgtctc      60 tcctgtgcag cctccggatt cacctttgat aagtataaga tggcttgggt ccgccaggct    120
ccagggaagg gtctggagtg ggtctcactt attttccga atggtgttcc tacatactac     180
gcaaactccg tgaagggccg gttcaccatc tcccgcgaca attccaagaa cacgctgtat    240
ctgcaaatga acagcctgcg tgccgaggac accgcggtat attactgtgc gaaatatagt    300 ggtcagggc gggattttga ctactggggt cagggaaccc tggtcaccgt ctcgagc        357

<210> SEQ ID NO 67
<211> LENGTH: 372
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 67
gaggtgcagc tgttggagtc tggggagggc ttggtacagc ctgggggtc cctgcgtctc      60 tcctgtgcag cctccggatt cacctttacc gagtatagga tgtggtgggt ccgccaggct    120
```

```
ccggggaagg gtctcgagtg ggtctcagcg attgagccga ttggtaatcg tacatactac    180
gcagactccg tgaagggccg gttcaccatc tcccgcgaca attccaagaa cacgctgtat    240
ctgcaaatga acagcctgcg tgccgaggat accgcggtat attactgtgc gaaacagatg    300
ccgggccgga agtggacggc caagttccgc tgggactact ggggtcaggg aaccctggtc    360
atcgtctcga gc                                                         372
```

<210> SEQ ID NO 68
<211> LENGTH: 372
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 68

```
gaggtgcagc tgttggagtc tggggggaggc ttggtacagc ctgggggtc cctgcgtctc     60 tcctgtgcag cctccggatt cacctttacg gagtatagga tgtggtgggt ccgccaggct    120
ccggggaagg gtctcgagtg ggtctcagcg attgagccga ttggtaatcg tacatactac    180
gcagactccg tgaagggccg gttcaccatc tcccgcgaca attccaagaa cacgctgtat    240
ctgcaaatga acagcctgcg tgccgaggat accgcggtat attactgtgc gaaacagatg    300
cccggccaga agtggatggc caagtcccgc ttcgactact ggggtcaggg aaccctggtc    360
accgtctcga gc                                                         372
```

<210> SEQ ID NO 69
<211> LENGTH: 372
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 69

```
gaggtgcagc tgttggagtc tggggggaggc ttggtacagc ctgggggtc cctgcgtctc     60 tcctgtgcag cctccggatt cacctttacg gagtatagga tgtggtgggt ccgccaggct    120
ccagggaagg gtctcgagtg ggtctcagcg attgagccga ttggtcagaa gacatactac    180
gcagactccg tgaagggccg gttcaccatc tcccgcgaca attccaagaa cacgctgtat    240
ctgcaaatga acagcctgcg tgccgaggat accgcggtat attactgtgc gaaacagatt    300
ccggggcgta agtggactgc taattcgcgg tttgactact ggggtcaggg aaccctggtc    360
atcgtctcga gc                                                         372
```

<210> SEQ ID NO 70
<211> LENGTH: 372
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 70

```
gaggtgcagc tgttggagtc tggggggaggc ttggtacagc ctgggggtc cctgcgtctc     60 tcctgtgcag cctccggatt cacctttacg gagtatagga tgtggtgggt ccgccaggct    120
ccggggaagg gtctcgagtg ggtctcagcg attgagccga ttggtaatcg tacatactac    180
gcagactccg tgaagggccg gttcaccatc tcccgcgaca attccaagaa cacgctgtat    240
```

```
ctgcaaatga acagcctgcg tgccgaggat accgcggtat attactgtgc gaaacagatt    300
ccggggcgta agtggactgc taatggtcgt aaggactact ggggtcaggg aaccctggtc    360
accgtctcga gc                                                       372
```

<210> SEQ ID NO 71
<211> LENGTH: 372
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 71

```
gaggtgcagc tgttggagtc tggggggaggc ttggtacagc ctgggggggtc cctgcgtctc    60 tcctgtgcag cctccggatc cacctttacg gagtatagga tgtggtgggt ccgccaggct    120
ccggggaagg gtctcgagtg ggtctcagcg attgagccga ttggtcatag gacatactac    180
gcagactccg tgaagggccg gttcaccatc tcccgcgaca attccaagaa cacgctgtat    240
ctgcaaatga acagcctgcg tgccgaggat accgcggtat attactgtgc gaaacagatt    300
ccggggcgta agtggactgc taattcgcgg tttgactact ggggtcaggg aaccctggtc    360
accgtctcga gc                                                       372
```

<210> SEQ ID NO 72
<211> LENGTH: 372
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 72

```
gaggtgcagc tgttggagtc tggggggaggc ttggtacagc ctgggggggtc cctgcgtctc    60 tcctgtgcag cctccggatt cacctttacg gagtatagga tgtggtgggt ccgccaggct    120
ccggggaagg gtctcgagtg ggtctcagcg attgagccga ttggtaatcg tacatactac    180
gcagactccg tgaagggccg gttcaccatc tcccgcgaca attccaagaa cacgctgtat    240
ctgcaaatga acagcctgcg tgccgaggat accgcggtat attactgtgc gaaacagatt    300
ccggggcagc ggtggactgg taattcgcgg tttgactact ggggtcaggg aaccctggtc    360
accgtctcga gc                                                       372
```

<210> SEQ ID NO 73
<211> LENGTH: 372
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 73

```
gaggtgcagc tgttggagtc tggggggaggc ttggtacagc ctgggggggtc cctgcgtctc    60 tcctgtgcag cctccggatt cacctttacg gagtatagga tgtggtgggt ccgccaggct    120
ccggggaagg gtctcgagtg ggtctcagcg attgagccga ttggtaatcg tacatactac    180
gcagactccg tgaagggccg gttcaccatc tcccgcgaca attccaagaa cacgctgtat    240
ctgcaaatga acagcctgcg tgccgaggat accgcggtat attactgtgc gaaacagttt    300
ccggggcgta agtggactgc taattcgcgg tctgactact ggggtcaggg aaccctggtc    360
```

```
accgtctcga gc                                                          372
```

<210> SEQ ID NO 74
<211> LENGTH: 372
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 74

```
gaggtgcagc tgttggagtc tggggggaggc ttggtacagc ctgggggtc cctgcgtctc        60 tcctgtgcag cctccggatt cacctttacg gagtatagga tgtggtgggt ccgccaggct       120
ccggggaagg gtctcgagtg ggtctcagcg attgagccga ttggtaatcg tacatactac       180
gcagactccg tgaagggccg gttcaccatc tcccgcgaca attccaagaa cacgctgtat       240
ctgcaaatga acagcctgcg tgccgaggat accgcggtat attactgtgc gaaacagatt       300
ccggggcgta agggaactgc taattcgcgg tttgactact ggggtcaggg aaccctggtc       360
accgtctcga gc                                                          372
```

<210> SEQ ID NO 75
<211> LENGTH: 372
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 75

```
gaggtgcagc tgttggagtc tggggggaggc ttggtacagc ctgggggtc cctgcgtctc        60 tcctgtgcag cctccggatt cacctttacg gagtatagga tgtggtgggt ccgccaggct       120
ccggggaagg gtctcgagtg ggtctcagcg attgagccga ttggtaatcg tacatactac       180
gcacgctccg tggacggccg gttcaccatc tcccgcgaca attccaagaa cacgctgtat       240
ctgcaaatga acagcctgcg tgccgaggat accgcggtat attactgtgc gaaacagatg       300
cccggccaga agtggatggc caagtcccgc ttcgactact ggggtcaggg aaccctggtc       360
accgtctcga gc                                                          372
```

<210> SEQ ID NO 76
<211> LENGTH: 372
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 76

```
gaggtgcagc tgttggagtc tggggggaggc ttggtacagc ctgggggtc cctgcgtctc        60 tcctgtgcag cctccggatt cacctttacg gagtatagga tgtggtgggt ccgccaggct       120
ccggggaagg gtctcgagtg ggtctcagcg attgagccga ttggtaatcg tacatactac       180
gcacgctccg tgttcggccg gttcaccatc tcccgcgaca attccaagaa cacgctgtat       240
ctgcaaatga acagcctgcg tgccgaggat accgcggtat attactgtgc gaaacagatg       300
cccggccaga agtggatggc caagtcccgc ttcgactact ggggtcaggg aaccctggtc       360
accgtctcga gc                                                          372
```

```
<210> SEQ ID NO 77
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 77

Ser Glu Gly Thr Met Trp
1               5

<210> SEQ ID NO 78
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 78

Ser Ala Gly Arg Met Trp
1               5

<210> SEQ ID NO 79
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 79

Thr Asp Asp Arg Met Trp
1               5

<210> SEQ ID NO 80
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 80

Ala Glu Asp Arg Met Trp
1               5

<210> SEQ ID NO 81
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 81

Met Ser Tyr Arg Met Trp
1               5

<210> SEQ ID NO 82
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 82
```

```
Glu Gly Tyr Arg Met Trp
1               5

<210> SEQ ID NO 83
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 83

Glu Ala Tyr Lys Met Thr
1               5

<210> SEQ ID NO 84
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 84

Gly Asp Gly Arg Met Trp
1               5

<210> SEQ ID NO 85
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 85

Asp Asp Ser Glu Met Ala
1               5

<210> SEQ ID NO 86
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 86

Asp Gln Asp Arg Met Trp
1               5

<210> SEQ ID NO 87
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 87

Asp Ala Ala Arg Met Trp
1               5

<210> SEQ ID NO 88
<211> LENGTH: 6
<212> TYPE: PRT
<213> ORGANISM: Artificial Sequence
```

```
<220> FEATURE:
<223> OTHER INFORMATION: Amino acid sequence identified using molecular
      biology techniques.

<400> SEQUENCE: 88

Ala Gln Asp Arg Met Trp
1               5

<210> SEQ ID NO 89
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 89

Glu Asn Thr Ser Met Gly
1               5

<210> SEQ ID NO 90
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 90

Arg Ser Tyr Glu Met Thr
1               5

<210> SEQ ID NO 91
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 91

Ser Asn Tyr Trp Met Arg
1               5

<210> SEQ ID NO 92
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 92

Thr Ser Tyr Arg Met Trp
1               5

<210> SEQ ID NO 93
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 93

Val Asn Tyr Arg Met Trp
1               5
```

<210> SEQ ID NO 94
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 94

Asn Asp Met Arg Met Trp
1               5

<210> SEQ ID NO 95
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 95

Thr Thr Tyr Gly Met Gly
1               5

<210> SEQ ID NO 96
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 96

Lys Arg Tyr Ser Met Gly
1               5

<210> SEQ ID NO 97
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 97

Phe Glu Tyr Pro Met Gly
1               5

<210> SEQ ID NO 98
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 98

Gly Gln Glu Ser Met Tyr
1               5

<210> SEQ ID NO 99
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

```
<400> SEQUENCE: 99

Met Asp Tyr Arg Met Tyr
1               5

<210> SEQ ID NO 100
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 100

Met Asp Tyr Asp Met Ser
1               5

<210> SEQ ID NO 101
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 101

Glu Pro Val Ile Met Gly
1               5

<210> SEQ ID NO 102
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 102

Asp Arg Tyr Arg Met Met
1               5

<210> SEQ ID NO 103
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 103

Ser Glu Tyr Asp Met Ala
1               5

<210> SEQ ID NO 104
<211> LENGTH: 6
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 104

Asp Lys Tyr Lys Met Ala
1               5

<210> SEQ ID NO 105
<211> LENGTH: 10
<212> TYPE: PRT
```

```
<213> ORGANISM: Artificial Sequence
<220> FEATURE:
<223> OTHER INFORMATION: Amino acid sequence identified using molecular
      biology techniques.

<400> SEQUENCE: 105

Gly Phe Thr Phe Thr Glu Tyr Arg Met Trp
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 106

Gly Phe Thr Phe Thr Glu Tyr Arg Met Trp
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 107

Gly Phe Thr Phe Thr Glu Tyr Arg Met Trp
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 108

Gly Phe Thr Phe Thr Glu Tyr Arg Met Trp
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 109

Gly Ser Thr Phe Thr Glu Tyr Arg Met Trp
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 110

Gly Phe Thr Phe Thr Glu Tyr Arg Met Trp
1               5                   10
```

<210> SEQ ID NO 111
<211> LENGTH: 10
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 111

Gly Phe Thr Phe Thr Glu Tyr Arg Met Trp
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 112

Gly Phe Thr Phe Thr Glu Tyr Arg Met Trp
1               5                   10

<210> SEQ ID NO 113
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 113

Ala Ile Leu Ala Ala Gly Ser Asn Thr Tyr Tyr Ala Asp Ser Val Lys
1               5                   10                  15

Gly

<210> SEQ ID NO 114
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 114

Ala Ile Asn Arg Asp Gly Thr Arg Thr Tyr Tyr Ala Asp Ser Val Lys
1               5                   10                  15

Gly

<210> SEQ ID NO 115
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 115

Ala Ile Gln Pro Asp Gly His Thr Thr Tyr Tyr Ala Asp Ser Val Lys
1               5                   10                  15

Gly

<210> SEQ ID NO 116

```
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 116

Ala Ile Asp Pro Gln Gly Gln His Thr Tyr Tyr Ala Asp Ser Val Lys
1               5                   10                  15
Gly

<210> SEQ ID NO 117
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 117

Ala Ile Ser Pro Ser Gly Ser Asp Thr Tyr Tyr Ala Asp Ser Val Lys
1               5                   10                  15
Gly

<210> SEQ ID NO 118
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 118

Ala Ile Asp Ser Leu Gly Asp Arg Thr Tyr Tyr Ala Asp Ser Val Lys
1               5                   10                  15
Gly

<210> SEQ ID NO 119
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 119

Tyr Ile Thr Pro Ser Gly Gly Gln Thr Tyr Tyr Ala Asp Ser Val Lys
1               5                   10                  15
Gly

<210> SEQ ID NO 120
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 120

Ala Ile Glu Gly Ala Gly Ser Asp Thr Tyr Tyr Ala Asp Ser Val Lys
1               5                   10                  15
Gly
```

```
<210> SEQ ID NO 121
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 121

Leu Ile Arg Arg Asn Gly Asn Ala Thr Tyr Tyr Ala Asp Ser Val Lys
1               5                   10                  15
Gly

<210> SEQ ID NO 122
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 122

Ala Ile Glu Ser Gly Gly His Arg Thr Tyr Tyr Ala Asp Ser Val Lys
1               5                   10                  15
Gly

<210> SEQ ID NO 123
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 123

Ala Ile Ala Asp Ile Gly Asn Thr Thr Tyr Tyr Ala Asp Ser Val Lys
1               5                   10                  15
Gly

<210> SEQ ID NO 124
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 124

Ala Ile Ser Gly Ser Gly Gly Ser Thr Tyr Tyr Ala Asp Ser Val Lys
1               5                   10                  15
Gly

<210> SEQ ID NO 125
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 125

Arg Ile Asp Pro Lys Gly Ser His Thr Tyr Tyr Ala Asp Ser Val Lys
1               5                   10                  15
Gly
```

```
<210> SEQ ID NO 126
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 126

Lys Ile Asp Pro Ser Gly Arg Phe Thr Tyr Tyr Ala Asp Ser Val Lys
 1               5                  10                  15

Gly

<210> SEQ ID NO 127
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 127

Tyr Ile Thr Pro Lys Gly Asp His Thr Tyr Tyr Ala Asp Ser Val Lys
 1               5                  10                  15

Gly

<210> SEQ ID NO 128
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 128

Val Ile Asp Ser Thr Gly Ser Ala Thr Tyr Tyr Ala Asp Ser Val Lys
 1               5                  10                  15

Gly

<210> SEQ ID NO 129
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 129

Ala Ile Ser Gly Ser Gly Asp Lys Thr Tyr Tyr Ala Asp Ser Val Lys
 1               5                  10                  15

Gly

<210> SEQ ID NO 130
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 130

Val Ile Asn Ala Asp Gly Asn Arg Thr Tyr Tyr Ala Asp Ser Val Lys
 1               5                  10                  15

Gly
```

```
<210> SEQ ID NO 131
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 131

Trp Ile Glu Lys Thr Gly Asn Lys Thr Tyr Tyr Ala Asp Ser Val Lys
1               5                   10                  15
Gly

<210> SEQ ID NO 132
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 132

Val Ile Asn Asp Leu Gly Ser Leu Thr Tyr Tyr Ala Asp Ser Val Lys
1               5                   10                  15
Gly

<210> SEQ ID NO 133
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 133

Val Ile Ser Gly Asp Gly Gln Arg Thr Tyr Tyr Ala Asp Ser Val Lys
1               5                   10                  15
Gly

<210> SEQ ID NO 134
<211> LENGTH: 18
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 134

Ala Ile Ser Gly Ser Gly Gly Ser Thr Tyr Tyr Ala Asp Ser Val Lys
1               5                   10                  15
Gly Arg

<210> SEQ ID NO 135
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 135

Gly Ile Asp Pro Thr Gly Leu Arg Thr Tyr Tyr Ala Asp Ser Val Lys
1               5                   10                  15
```

Gly

<210> SEQ ID NO 136
<211> LENGTH: 18
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 136

Met Ile Arg Glu Asp Gly Gly Lys Thr Tyr Tyr Ala Asp Ser Val Lys
1               5                   10                  15

Gly Arg

<210> SEQ ID NO 137
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 137

Ala Ile Glu Ala Arg Gly Gly Gly Thr Tyr Tyr Ala Asp Ser Val Lys
1               5                   10                  15

Gly

<210> SEQ ID NO 138
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 138

Thr Ile Asp Pro Ala Gly Met Leu Thr Tyr Tyr Ala Asp Ser Val Lys
1               5                   10                  15

Gly

<210> SEQ ID NO 139
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 139

Arg Ile Arg Ser Asp Gly Val Arg Thr Tyr Tyr Ala Asp Ser Val Lys
1               5                   10                  15

Gly

<210> SEQ ID NO 140
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 140

Leu Ile Phe Pro Asn Gly Val Pro Thr Tyr Tyr Ala Asn Ser Val Lys
1               5                   10                  15

Gly

```
<210> SEQ ID NO 141
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 141
```

Ala Ile Glu Pro Ile Gly Asn Arg Thr Tyr Tyr Ala Asp Ser Val Lys
 1               5                  10                  15

Gly

```
<210> SEQ ID NO 142
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 142
```

Ala Ile Glu Pro Ile Gly Asn Arg Thr Tyr Tyr Ala Asp Ser Val Lys
 1               5                  10                  15

Gly

```
<210> SEQ ID NO 143
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 143
```

Ala Ile Glu Pro Ile Gly Gln Lys Thr Tyr Tyr Ala Asp Ser Val Lys
 1               5                  10                  15

Gly

```
<210> SEQ ID NO 144
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 144
```

Ala Ile Glu Pro Ile Gly Asn Arg Thr Tyr Tyr Ala Asp Ser Val Lys
 1               5                  10                  15

Gly

```
<210> SEQ ID NO 145
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 145
```

Ala Ile Glu Pro Ile Gly His Arg Thr Tyr Tyr Ala Asp Ser Val Lys

```
                1               5                  10                  15
Gly

<210> SEQ ID NO 146
<211> LENGTH: 18
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 146

Ala Ile Glu Pro Ile Gly Asn Arg Thr Tyr Tyr Ala Asp Ser Ser Val
 1               5                  10                  15

Lys Gly

<210> SEQ ID NO 147
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 147

Ala Ile Glu Pro Ile Gly Asn Arg Thr Tyr Tyr Ala Asp Ser Val Lys
 1               5                  10                  15

Gly

<210> SEQ ID NO 148
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 148

Ala Ile Glu Pro Ile Gly Asn Arg Thr Tyr Tyr Ala Asp Ser Val Lys
 1               5                  10                  15

Gly

<210> SEQ ID NO 149
<211> LENGTH: 10
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 149

Lys Arg Gln Glu Arg Asp Gly Phe Asp Tyr
 1               5                  10

<210> SEQ ID NO 150
<211> LENGTH: 10
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 150

His Asp Asp Gly His Gly Asn Phe Asp Tyr
 1               5                  10
```

<210> SEQ ID NO 151
<211> LENGTH: 12
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 151

Glu Gln Asp Val Lys Gly Ser Ser Ser Phe Asp Tyr
1               5                   10

<210> SEQ ID NO 152
<211> LENGTH: 10
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 152

Gln Ser Thr Gly Ser Ala Thr Ser Asp Tyr
1               5                   10

<210> SEQ ID NO 153
<211> LENGTH: 15
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 153

Gln Val Val Glu Tyr Ser Arg Thr His Lys Gly Val Phe Asp Tyr
1               5                   10                  15

<210> SEQ ID NO 154
<211> LENGTH: 13
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 154

Gln Gly Leu Thr His Gln Ser Pro Ser Thr Phe Asp Tyr
1               5                   10

<210> SEQ ID NO 155
<211> LENGTH: 7
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 155

Tyr Gly Ser Ser Phe Asp Tyr
1               5

<210> SEQ ID NO 156
<211> LENGTH: 10
<212> TYPE: PRT
<213> ORGANISM: Artificial Sequence
<220> FEATURE:
<223> OTHER INFORMATION: Amino acid sequence identified using molecular
      biology techniques.

```
<400> SEQUENCE: 156

Gln Ala Ser Arg Asn Ser Pro Phe Asp Tyr
1               5                   10

<210> SEQ ID NO 157
<211> LENGTH: 11
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 157

Val Thr Lys Asp Arg Ser Val Leu Phe Asp Tyr
1               5                   10

<210> SEQ ID NO 158
<211> LENGTH: 11
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 158

Gln Asn Glu Ser Gly Arg Ser Gly Phe Asp Tyr
1               5                   10

<210> SEQ ID NO 159
<211> LENGTH: 10
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 159

Gln Ser Gly Ser Glu Asp His Phe Asp Tyr
1               5                   10

<210> SEQ ID NO 160
<211> LENGTH: 12
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 160

Gln Asp Leu His Gly Thr Ser Ser Leu Phe Asp Tyr
1               5                   10

<210> SEQ ID NO 161
<211> LENGTH: 11
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 161

Gln Arg Glu Leu Gly Lys Ser His Phe Asp Tyr
1               5                   10

<210> SEQ ID NO 162
<211> LENGTH: 10
```

```
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 162

Gly Arg Thr Asp Leu Gln Leu Phe Asp Tyr
1               5                   10

<210> SEQ ID NO 163
<211> LENGTH: 12
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 163

Ser Leu His Asn Glu Arg Val Lys His Phe Asp Tyr
1               5                   10

<210> SEQ ID NO 164
<211> LENGTH: 12
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 164

Gln Gln Ala Gly Ser Ala Met Gly Glu Phe Asp Tyr
1               5                   10

<210> SEQ ID NO 165
<211> LENGTH: 7
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 165

His Gly Leu Ser Phe Asp Tyr
1               5

<210> SEQ ID NO 166
<211> LENGTH: 7
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 166

Asp Gly Leu Pro Phe Asp Tyr
1               5

<210> SEQ ID NO 167
<211> LENGTH: 14
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 167

Ala Gly Arg His Ile Lys Val Arg Ser Arg Asp Phe Asp Tyr
```

<210> SEQ ID NO 168
<211> LENGTH: 14
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 168

Gly Asn Ile Ser Met Val Arg Pro Gly Ser Trp Phe Asp Tyr
1               5                   10

<210> SEQ ID NO 169
<211> LENGTH: 14
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 169

Ser His Thr Gly Thr Val Arg His Leu Glu Thr Phe Asp Tyr
1               5                   10

<210> SEQ ID NO 170
<211> LENGTH: 11
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 170

Ser Gly Thr Arg Ile Lys Gln Gly Phe Asp Tyr
1               5                   10

<210> SEQ ID NO 171
<211> LENGTH: 14
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 171

Ile Lys Trp Gly Glu Met Gly Ser Tyr Lys Thr Phe Asp Tyr
1               5                   10

<210> SEQ ID NO 172
<211> LENGTH: 15
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 172

Ala Arg Val Pro Tyr Arg Arg Gly His Arg Asp Asn Phe Asp Tyr
1               5                   10                  15

<210> SEQ ID NO 173
<211> LENGTH: 11
<212> TYPE: PRT
<213> ORGANISM: Artificial Sequence
<220> FEATURE:
<223> OTHER INFORMATION: Amino acid sequence identified using molecular biology techniques.

<400> SEQUENCE: 173

Pro Gly Arg His Leu Ser Gln Asp Phe Asp Tyr
1               5                   10

<210> SEQ ID NO 174
<211> LENGTH: 10
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 174

Arg Leu Ala Ser Arg Ser His Phe Asp Tyr
1               5                   10

<210> SEQ ID NO 175
<211> LENGTH: 10
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 175

Asp Arg Ala Lys Asn Gly Trp Phe Asp Tyr
1               5                   10

<210> SEQ ID NO 176
<211> LENGTH: 10
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 176

Tyr Ser Gly Gln Gly Arg Asp Phe Asp Tyr
1               5                   10

<210> SEQ ID NO 177
<211> LENGTH: 15
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 177

Gln Met Pro Gly Arg Lys Trp Thr Ala Lys Phe Arg Trp Asp Tyr
1               5                   10                  15

<210> SEQ ID NO 178
<211> LENGTH: 15
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 178

Gln Met Pro Gly Gln Lys Trp Met Ala Lys Ser Arg Phe Asp Tyr
1               5                   10                  15

<210> SEQ ID NO 179

```
<211> LENGTH: 15
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 179

Gln Ile Pro Gly Arg Lys Trp Thr Ala Asn Ser Arg Phe Asp Tyr
1               5                   10                  15

<210> SEQ ID NO 180
<211> LENGTH: 15
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 180

Gln Ile Pro Gly Arg Lys Trp Thr Ala Asn Gly Arg Lys Asp Tyr
1               5                   10                  15

<210> SEQ ID NO 181
<211> LENGTH: 15
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 181

Gln Ile Pro Gly Arg Lys Trp Thr Ala Asn Ser Arg Phe Asp Tyr
1               5                   10                  15

<210> SEQ ID NO 182
<211> LENGTH: 15
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 182

Gln Ile Pro Gly Gln Arg Trp Thr Gly Asn Ser Arg Phe Asp Tyr
1               5                   10                  15

<210> SEQ ID NO 183
<211> LENGTH: 15
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 183

Gln Phe Pro Gly Arg Lys Trp Thr Ala Asn Ser Arg Ser Asp Tyr
1               5                   10                  15

<210> SEQ ID NO 184
<211> LENGTH: 15
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 184
```

Gln Ile Pro Gly Arg Lys Gly Thr Ala Asn Ser Arg Phe Asp Tyr
1               5                   10                  15

<210> SEQ ID NO 185
<211> LENGTH: 24
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 185
agcggataac aatttcacac agga                                          24

<210> SEQ ID NO 186
<211> LENGTH: 24
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 186
cgccagggtt ttcccagtca cgac                                          24

<210> SEQ ID NO 187
<211> LENGTH: 20
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 187
ttgcaggcgt ggcaacagcg                                               20

<210> SEQ ID NO 188
<211> LENGTH: 23
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 188
cacgacgttg taaaacgacg gcc                                           23

<210> SEQ ID NO 189
<211> LENGTH: 60
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 189
gcagcctccg gattcacctt tacsgastat agsatgtgst gggtccgcca ggctccgggg   60

<210> SEQ ID NO 190
<211> LENGTH: 64
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 190

```
gggtctcgag tgggtctcag csattgascc satsggsaas cgsacatact acgcagactc    60
cgtg                                                                 64
```

<210> SEQ ID NO 191
<211> LENGTH: 77
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 191

```
gcggtatatt actgtgcgaa acasatsccs ggscgsaast gsacsgcsaa stcscgstts    60
gactactggg gtcaggg                                                   77
```

<210> SEQ ID NO 192
<211> LENGTH: 44
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 192

```
ttgcaggcgt ggcaacagcg tcgacagagg tgcagctgtt ggag                     44
```

<210> SEQ ID NO 193
<211> LENGTH: 26
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 193

```
gcgtagtatg tacgattacc aatcgg                                         26
```

<210> SEQ ID NO 194
<211> LENGTH: 54
<212> TYPE: DNA
<213> ORGANISM: Artificial Sequence
<220> FEATURE:
<223> OTHER INFORMATION: Nucleic acid sequence
<220> FEATURE:
<221> NAME/KEY: misc_feature
<222> LOCATION: 22, 23, 31, 32
<223> OTHER INFORMATION: n = A,T,C or G
<220> FEATURE:
<221> NAME/KEY: misc_feature
<222> LOCATION: 22, 23, 31, 32
<223> OTHER INFORMATION: n = A,T,C or G

<400> SEQUENCE: 194

```
ggtaatcgta catactacgc anngtccgtg nnkggccggt tcaccatctc ccgc           54
```

<210> SEQ ID NO 195
<211> LENGTH: 53
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 195

```
tgtgtgtgtg tggcggccgc gctcgagacg gtgaccaggg ttccctgacc cca            53
```

```
<210> SEQ ID NO 196
<211> LENGTH: 54
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 196
ggtaatcgta catactacgc aaactccgtg cgcggccggt tcaccatctc ccgc         54

<210> SEQ ID NO 197
<211> LENGTH: 20
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 197
ttgcaggcgt ggcaacagcg                                               20

<210> SEQ ID NO 198
<211> LENGTH: 23
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 198
cacgacgttg taaaacgacg gcc                                           23

<210> SEQ ID NO 199
<211> LENGTH: 124
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 199

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Thr Glu Tyr
            20                  25                  30

Arg Met Trp Trp Val Arg Gln Ala Pro Gly Lys Gly Leu Glu Trp Val
        35                  40                  45

Ser Ala Ile Glu Pro Ile Gly Asn Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Ile Pro Gly Arg Lys Trp Thr Ala Asn Ser Arg Phe Asp
            100                 105                 110

Tyr Trp Gly Gln Gly Thr Leu Val Thr Val Ser Ser
        115                 120

<210> SEQ ID NO 200
<211> LENGTH: 372
<212> TYPE: DNA
<213> ORGANISM: Artificial Sequence
<220> FEATURE:
```

```
<223> OTHER INFORMATION: Nucleic acid sequence identified using
      molecular biology techniques.

<400> SEQUENCE: 200
gaggtgcagc tgttggagtc tgggggaggc ttggtacagc ctgggggtc cctgcgtctc      60 tcctgtgcag cctccggatt caccttacg gagtatagga tgtggtgggt ccgccaggct     120
ccggggaagg gtctcgagtg ggtctcagcg attgagccga ttggtaatcg tacatactac    180
gcagactccg tgaagggccg gttcaccatc tcccgcgaca attccaagaa cacgctgtat    240
ctgcaaatga acagcctgcg tgccgaggat accgcggtat attactgtgc gaaacagatt    300
ccggggcgta agtggactgc taattcgcgg tttgactact ggggtcaggg aaccctggtc    360
accgtctcga gc                                                        372

<210> SEQ ID NO 201
<211> LENGTH: 124
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 201

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Thr Glu Tyr
            20                  25                  30

Arg Met Trp Trp Val Arg Gln Ala Pro Gly Lys Gly Leu Glu Trp Val
        35                  40                  45

Ser Ala Ile Glu Pro Ile Gly Asn Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Ile Pro Gly Arg Lys Trp Thr Ala Asn Ser Arg Phe Asp
            100                 105                 110

Tyr Trp Gly Gln Gly Thr Leu Val Thr Val Ser Ser
        115                 120

<210> SEQ ID NO 202
<211> LENGTH: 372
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 202
gaggtgcagc tgttggagtc tgggggaggc ttggtacagc ctgggggtc cctgcgtctc      60 tcctgtgcag cctccggatt caccttacg gagtatagga tgtggtgggt ccgccaggct     120
ccggggaagg gtctcgagtg ggtctcagcg attgagccga ttggtaatcg tacatactac    180
gcagactccg tgaagggccg gttcaccatc tcccgcgaca attccaagaa cacgctgtat    240
ctgcaaatga acagcctgcg tgccgaggat accgcggtat attactgtgc gaaacagatt    300
ccggggcgta agtggactgc taattcgcgg tttgactact ggggtcaggg aaccctggtc    360
accgtctcga gc                                                        372
```

<210> SEQ ID NO 203
<211> LENGTH: 360
<212> TYPE: DNA
<213> ORGANISM: Artificial Sequence
<220> FEATURE:
<223> OTHER INFORMATION: Nucleic acid sequence identified using
molecular biology techniques.

<400> SEQUENCE: 203

```
gaggtgcagc tgttggagtc tgggggaggc ttggtacagc ctgggggtc cctgcgtctc      60 tcctgtgcag cctccggatt cacctttgag aatacgagta tgggttgggt ccgccaggct    120
ccagggaagg gtctagagtg gtctcacgt attgatccta agggtagtca tacatactac      180
acagactccg tgaagggccg gttcaccatc tcccgcgaca attccaagaa tacgctgtat    240
ctgcaaatga acagcctgcg tgccgaggac accgcggtat attactgtgc gaaacagcgt    300
gagttgggta agtcgtattt tgactactgg ggtcagggaa ccctggtcac cgtctcgagc    360
```

<210> SEQ ID NO 204
<211> LENGTH: 120
<212> TYPE: PRT
<213> ORGANISM: Artificial Sequence
<220> FEATURE:
<223> OTHER INFORMATION: Amino acid sequence identified using molecular
biology techniques.

<400> SEQUENCE: 204

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Glu Asn Thr
            20                  25                  30

Ser Met Gly Trp Val Arg Gln Ala Pro Gly Lys Gly Leu Glu Trp Val
        35                  40                  45

Ser Arg Ile Asp Pro Lys Gly Ser His Thr Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Arg Glu Leu Gly Lys Ser Tyr Phe Asp Tyr Trp Gly Gln
            100                 105                 110

Gly Thr Leu Val Thr Val Ser Ser
        115                 120
```

<210> SEQ ID NO 205
<211> LENGTH: 360
<212> TYPE: DNA
<213> ORGANISM: Artificial Sequence
<220> FEATURE:
<223> OTHER INFORMATION: Nucleic acid sequence identified using
molecular biology techniques.

<400> SEQUENCE: 205

```
gaggtgcagc tgttggagtc tgggggaggc ctggtacagc ctgggggtc cctgcgtctc      60 tcctgtgcag cctccggatt cacctttgat caggatcgga tgtggtgggt ccgccaggcc    120
ccagggaagg gtctagagtg gtctcagct attgagagtg gtggtcatag gacatactac     180
gcagactccg tgaagggccg gttcaccatc tcccgcgaca attccaagaa cacgctgtat    240
ctgcaaatga acagcctgcg tgccgaggac accgcggtat attactgtgc gaatcagaat    300
```

```
aagtcggggc gttcgggttt tgactactgg ggtcaggaa ccctggtcac cgtctcgagc    360
```

<210> SEQ ID NO 206
<211> LENGTH: 120
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 206

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Gln Asp
            20                  25                  30

Arg Met Trp Trp Val Arg Gln Ala Pro Gly Lys Gly Leu Glu Trp Val
        35                  40                  45

Ser Ala Ile Glu Ser Gly Gly His Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Gln Asn Lys Ser Gly Arg Ser Gly Phe Asp Tyr Trp Gly Gln
            100                 105                 110

Gly Thr Leu Val Thr Val Ser Ser
        115                 120
```

<210> SEQ ID NO 207
<211> LENGTH: 366
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 207

```
gaggtgcagc tgttggagtc tgggggaggc ttggtacagc ctggggggtc cctgcgtctc    60
tcctgtgcag cctccggatt cacctttggg acggagcaga tgtggtgggt ccgccaggct   120
ccagggaagg gtctagagtt tgtctcacgt attgattcgc tggtgggag acatactac    180 gcagactccg tgaagggccg gttcaccatc tcccgcgaca attccaagaa cacgctgtat   240
ctgcaaatga acagcctgcg tgccgaggac accgcggtat attactgtgc gaaacggcat   300
gcggctgggg tttcgggtac ttattttgac tactggggtc agggaaccct ggtcaccgtc   360
tcgagc                                                              366
```

<210> SEQ ID NO 208
<211> LENGTH: 122
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 208

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gly Thr Glu
            20                  25                  30
```

Gln Met Trp Trp Val Arg Gln Ala Pro Gly Lys Gly Leu Glu Phe Val
            35                  40                  45

Ser Arg Ile Asp Ser Pro Gly Gly Arg Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Arg His Ala Ala Gly Val Ser Gly Thr Tyr Phe Asp Tyr Trp
             100                 105                 110

Gly Gln Gly Thr Leu Val Thr Val Ser Ser
         115                 120

<210> SEQ ID NO 209
<211> LENGTH: 81
<212> TYPE: DNA
<213> ORGANISM: Artificial Sequence
<220> FEATURE:
<223> OTHER INFORMATION: Nucleic acid sequence
<220> FEATURE:
<221> NAME/KEY: misc_feature
<222> LOCATION: 25, 26, 34, 35, 43, 44, 49, 50, 52, 53, 58, 59
<223> OTHER INFORMATION: n = A,T,C or G
<220> FEATURE:
<221> NAME/KEY: misc_feature
<222> LOCATION: 25, 26, 34, 35, 43, 44, 49, 50, 52, 53, 58, 59
<223> OTHER INFORMATION: n = A,T,C or G

<400> SEQUENCE: 209
gcggtatatt actgtgcgaa acagnnsccc ggcnnsaagt ggnnsgccnn snnscgcnns      60
gactactggg gtcagggaac c                                               81

<210> SEQ ID NO 210
<211> LENGTH: 42
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 210
gcccagccgg ccatggcgga ggtgcagctg ttggagtctg gg                        42

<210> SEQ ID NO 211
<211> LENGTH: 40
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 211
gaattcgcgg ccgcctatta gctcgagacg gtgaccaggg                           40

<210> SEQ ID NO 212
<211> LENGTH: 372
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 212
gaggtgcagc tgttggagtc tggggggaggc ttggtacagc ctggggggtc cctgcgtctc    60

-continued

| | |
|---|---|
| tcctgtgcag cctccggatc caccttacg gagtatagga tgtggtgggt ccgccaggct | 120 |
| ccggggaagg gtctcgagtg ggtctcagcg attgagccga ttggtcatag gacatactac | 180 |
| gcagactccg tgaagggccg gttcaccatc tcccgcgaca attccaagaa cacgctgtat | 240 |
| ctgcaaatga acagcctgcg tgccgaggat accgcggtat attactgtgc gaaacaggcg | 300 |
| cccggcgaga agtggctcgc ccggggccgc ttggactact ggggtcaggg aaccctggtc | 360 |
| accgtctcga gc | 372 |

<210> SEQ ID NO 213
<211> LENGTH: 124
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 213

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Thr Glu Tyr
            20                  25                  30

Arg Met Trp Trp Val Arg Gln Ala Pro Gly Lys Gly Leu Glu Trp Val
        35                  40                  45

Ser Ala Ile Glu Pro Ile Gly His Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Ala Pro Gly Glu Lys Trp Leu Ala Arg Gly Arg Leu Asp
            100                 105                 110

Tyr Trp Gly Gln Gly Thr Leu Val Thr Val Ser Ser
        115                 120

<210> SEQ ID NO 214
<211> LENGTH: 124
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 214

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Thr Glu Tyr
            20                  25                  30

Arg Met Trp Trp Val Arg Gln Ala Pro Gly Lys Gly Leu Glu Trp Val
        35                  40                  45

Ser Ala Ile Glu Pro Ile Gly His Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Ala Pro Gly Glu Lys Trp Leu Ala Arg Gly Arg Leu Asp
            100                 105                 110

Tyr Trp Gly Gln Gly Thr Leu Val Thr Val Ser Ser
          115                 120

<210> SEQ ID NO 215
<211> LENGTH: 46
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 215
ggaaccctgg tcaccgtctc gagcgcggcc gcataataag aattca                46

<210> SEQ ID NO 216
<211> LENGTH: 60
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 216
gcagcctccg gattcacctt tggsacsgag cagatgtggt gggtccgcca ggctccaggg    60

<210> SEQ ID NO 217
<211> LENGTH: 66
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 217
aagggtctag agtttgtctc acgsattgat tcsccsggtg gscgsacata ctacgcagac    60
tccgtg                                                               66

<210> SEQ ID NO 218
<211> LENGTH: 75
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 218
gcggtatatt actgtgcgaa acgscatgcs gcsggsgtst csggsacsta ytttgactac    60
tggggtcagg gaacc                                                     75

<210> SEQ ID NO 219
<211> LENGTH: 60
<212> TYPE: DNA
<213> ORGANISM: Artificial Sequence
<220> FEATURE:
<223> OTHER INFORMATION: Nucliec acid sequence identified using
      molecular biology techniques.

<400> SEQUENCE: 219
gcagcctccg gattcacctt tgatcaggat cgsatgtggt gggtccgcca ggccccaggg    60

<210> SEQ ID NO 220
<211> LENGTH: 66
<212> TYPE: DNA
<213> ORGANISM: Artificial Sequence
<220> FEATURE:
<223> OTHER INFORMATION: Nucleic acid sequence identified using -continued

<400> SEQUENCE: 220
aagggtctag agtgggtctc agcsattgag tcsggsggtc atcgsacata ctacgcagac    60
tccgtg                                                              66

<210> SEQ ID NO 221
<211> LENGTH: 69
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 221
accgcggtat attactgtgc gvrkcagaat aagtcsggsc gstcsggstt tgactactgg    60
ggtcaggga                                                           69

<210> SEQ ID NO 222
<211> LENGTH: 60
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 222
gcagcctccg gattcacctt tgagaatacs tcsatgggst gggtccgcca ggctccaggg    60

<210> SEQ ID NO 223
<211> LENGTH: 81
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 223
aagggtctag agtgggtctc acgsattgat ccsaagggtt cscatacata ctacacsgac    60
tccgtgaagg gccggttcac c                                             81

<210> SEQ ID NO 224
<211> LENGTH: 66
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 224
gcggtatatt actgtgcgaa acagcgsgag ctsggsaagt cstaytttga ctactgggt    60 caggga                                                              66

<210> SEQ ID NO 225
<211> LENGTH: 69
<212> TYPE: DNA
<213> ORGANISM: Artificial Sequence
<220> FEATURE:
<223> OTHER INFORMATION: Nucleic acid sequence
<220> FEATURE:
<221> NAME/KEY: misc_feature
<222> LOCATION: 22, 23, 25, 26, 28, 29, 31, 32, 37, 38
<223> OTHER INFORMATION: n = A,T,C or G
<220> FEATURE:
<221> NAME/KEY: misc_feature
<222> LOCATION: 22, 23, 25, 26, 28, 29, 31, 32, 37, 38
<223> OTHER INFORMATION: n = A,T,C or G

<400> SEQUENCE: 225
gcagcctccg gattcacctt tnnknnknnk nnkatgnnkt gggtccgcca ggctccgggg    60
aagggtctc                                                           69

<210> SEQ ID NO 226
<211> LENGTH: 80
<212> TYPE: DNA
<213> ORGANISM: Artificial Sequence
<220> FEATURE:
<223> OTHER INFORMATION: Nucleic acid sequence
<220> FEATURE:
<221> NAME/KEY: misc_feature
<222> LOCATION: 38, 39, 44, 45, 47, 48, 50, 51, 56, 57
<223> OTHER INFORMATION: n = A,T,C or G
<220> FEATURE:
<221> NAME/KEY: misc_feature
<222> LOCATION: 38, 39, 44, 45, 47, 48, 50, 51, 56, 57
<223> OTHER INFORMATION: n = A,T,C or G

<400> SEQUENCE: 226
ccgccaggct ccggggaagg gtctcgagtg ggtctcannk attnnknnkn nkggtnnkcg    60
tacatactac gcagactccg                                               80

<210> SEQ ID NO 227
<211> LENGTH: 80
<212> TYPE: DNA
<213> ORGANISM: Artificial Sequence
<220> FEATURE:
<223> OTHER INFORMATION: Nucleic acid sequence
<220> FEATURE:
<221> NAME/KEY: misc_feature
<222> LOCATION: 47, 48, 50, 51, 53, 54, 56, 57, 59, 60
<223> OTHER INFORMATION: n = A,T,C or G
<220> FEATURE:
<221> NAME/KEY: misc_feature
<222> LOCATION: 47, 48, 50, 51, 53, 54, 56, 57, 59, 60
<223> OTHER INFORMATION: n = A,T,C or G

<400> SEQUENCE: 227
ccgccaggct ccggggaagg gtctcgagtg ggtctcagcg attgagnnkn nknnknnknn    60
kacatactac gcagactccg                                               80

<210> SEQ ID NO 228
<211> LENGTH: 80
<212> TYPE: DNA
<213> ORGANISM: Artificial Sequence
<220> FEATURE:
<223> OTHER INFORMATION: Nucleic acid sequence
<220> FEATURE:
<221> NAME/KEY: misc_feature
<222> LOCATION: 25, 26, 28, 29, 31, 32, 34, 35, 37, 38
<223> OTHER INFORMATION: n = A,T,C or G
<220> FEATURE:
<221> NAME/KEY: misc_feature
<222> LOCATION: 25, 26, 28, 29, 31, 32, 34, 35, 37, 38
<223> OTHER INFORMATION: n = A,T,C or G

<400> SEQUENCE: 228
accgcggtat attactgtgc gaaannknnk nnknnknnka agtggatggc cgtgggccgc    60
ttggactact ggggtcaggg                                               80

<210> SEQ ID NO 229
<211> LENGTH: 80
<212> TYPE: DNA

```
<213> ORGANISM: Artificial Sequence
<220> FEATURE:
<223> OTHER INFORMATION: Nucleic acid sequence
<220> FEATURE:
<221> NAME/KEY: misc_feature
<222> LOCATION: 34, 35, 37, 38, 40, 41, 43, 44, 46, 47
<223> OTHER INFORMATION: n = A,T,C or G
<220> FEATURE:
<221> NAME/KEY: misc_feature
<222> LOCATION: 34, 35, 37, 38, 40, 41, 43, 44, 46, 47
<223> OTHER INFORMATION: n = A,T,C or G

<400> SEQUENCE: 229
accgcggtat attactgtgc gaaacagaag cccnnknnkn nknnknnkgc cgtgggccgc    60
ttggactact ggggtcaggg                                                80

<210> SEQ ID NO 230
<211> LENGTH: 80
<212> TYPE: DNA
<213> ORGANISM: Artificial Sequence
<220> FEATURE:
<223> OTHER INFORMATION: Nucleic acid sequence
<220> FEATURE:
<221> NAME/KEY: misc_feature
<222> LOCATION: 46, 47, 49, 50, 52, 53, 55, 56, 58, 59
<223> OTHER INFORMATION: n = A,T,C or G
<220> FEATURE:
<221> NAME/KEY: misc_feature
<222> LOCATION: 46, 47, 49, 50, 52, 53, 55, 56, 58, 59
<223> OTHER INFORMATION: n = A,T,C or G

<400> SEQUENCE: 230
accgcggtat attactgtgc gaaacagaag cccggccaga agtggnnknn knnknnknnk    60
ttggactact ggggtcaggg                                                80

<210> SEQ ID NO 231
<211> LENGTH: 40
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 231
ccctggtcac cgtctcgagc taataggcgg ccgcgaattc                          40

<210> SEQ ID NO 232
<211> LENGTH: 37
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 232
tatcgtccat ggcggaggtg cagctgttgg agtctgg                             37

<210> SEQ ID NO 233
<211> LENGTH: 366
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 233
gaggtgcagc tgttggagtc tgggggaggc ttggtacagc ctggggggtc cctgcgtctc    60
```

| | |
|---|---|
| tcctgtgcag cctccggatt cacctttggg acggagcaga tgtggtgggt ccgccaggct | 120 |
| ccagggaagg gtctagagtt tgtctcacgt attgattcgc ctggtgggag gacatactac | 180 |
| gcagactccg tgaagggccg gttcaccatc tcccgcgaca attccaagaa cacgctgtat | 240 |
| ctgcaaatga acagcctgcg tgccgaggac accgcggtat attactgtgc gaaacggcga | 300 |
| cccacggggg tgtccgggac gttttatgac tactggggtc agggaaccct ggtcaccgtc | 360 |
| tcgagc | 366 |

```
<210> SEQ ID NO 234
<211> LENGTH: 122
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 234

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gly Thr Glu
            20                  25                  30

Gln Met Trp Trp Val Arg Gln Ala Pro Gly Lys Gly Leu Glu Phe Val
        35                  40                  45

Ser Arg Ile Asp Ser Pro Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Arg Pro Thr Gly Val Ser Gly Thr Phe Tyr Asp Tyr Trp
            100                 105                 110

Gly Gln Gly Thr Leu Val Thr Val Ser Ser
        115                 120
```

```
<210> SEQ ID NO 235
<211> LENGTH: 372
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 235
```

| | |
|---|---|
| gaggtgcagc tgttggagtc tgggggaggc ttggtacagc ctgggggggtc cctgcgtctc | 60 |
| tcctgtgcag cctccggatc cacctttacg gagtatagga tgtggtgggt ccgccaggct | 120 |
| ccggggaagg gtctcgagtg ggtctcagcg attgagccga ttggtcatag gacatactac | 180 |
| gcagactccg tgaagggccg gttcaccatc tcccgcgaca attccaagaa cacgctgtat | 240 |
| ctgcaaatga acagcctgcg tgccgaggat accgcggtat attactgtgc gaaacaggcg | 300 |
| cccggcgaga agtgggcgag gcggtgggat ttggactact ggggtcaggg aaccctggtc | 360 |
| accgtctcga gc | 372 |

```
<210> SEQ ID NO 236
<211> LENGTH: 124
<212> TYPE: PRT
<213> ORGANISM: Artificial Sequence
<220> FEATURE:
<223> OTHER INFORMATION: Amino acid sequence identified using molecular
``` biology techniques.

<400> SEQUENCE: 236

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Thr Glu Tyr
            20                  25                  30

Arg Met Trp Trp Val Arg Gln Ala Pro Gly Lys Gly Leu Glu Trp Val
        35                  40                  45

Ser Ala Ile Glu Pro Ile Gly His Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Ala Pro Gly Glu Lys Trp Ala Arg Arg Trp Asp Leu Asp
            100                 105                 110

Tyr Trp Gly Gln Gly Thr Leu Val Thr Val Ser Ser
        115                 120
```

<210> SEQ ID NO 237
<211> LENGTH: 366
<212> TYPE: DNA
<213> ORGANISM: Artificial Sequence
<220> FEATURE:
<223> OTHER INFORMATION: Nucleic acid sequence identified using molecular biology techniques.

<400> SEQUENCE: 237

```
gaggtgcagc tgttggagtc tggggggaggc ttggtacagc ctgggggtc cctgcgtctc      60
tcctgtgcag cctccggatt cacctttggg accgatcaga tgtggtgggt ccgccaggct     120
ccagggaagg gtctagagtt tgtctcacgc attgattccc ccggtgggcg acatatactac    180
gcaaactccg tgaagggccg gttcaccatc tcccgcgaca attccaagaa cacgctgtat    240
ctgcaaatga acagcctgcg tgccgaggac accgcggtat attactgtgc gaaacggcag    300
ccggcggggg tgtcggggaa gtacgttgac tactggggtc agggaaccct ggtcaccgtc    360
tcgagc                                                               366
```

<210> SEQ ID NO 238
<211> LENGTH: 122
<212> TYPE: PRT
<213> ORGANISM: Artificial Sequence
<220> FEATURE:
<223> OTHER INFORMATION: Amino acid sequence identified using molecular biology techniques.

<400> SEQUENCE: 238

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Thr Asp
            20                  25                  30

Gln Met Trp Trp Val Arg Gln Ala Pro Gly Lys Gly Leu Glu Phe Val
        35                  40                  45

Ser Arg Ile Asp Ser Pro Gly Gly Arg Thr Tyr Tyr Ala Asn Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Arg Gln Pro Ala Gly Val Ser Gly Lys Tyr Val Asp Tyr Trp
            100                 105                 110

Gly Gln Gly Thr Leu Val Thr Val Ser Ser
        115                 120

<210> SEQ ID NO 239
<211> LENGTH: 372
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 239
gaggtgcagc tgttggagtc tgggggaggc ttggtacagc ctgggggtc cctgcgtctc      60 tcctgtgcag cctccggatc cacctttacg gagtatagga tgtggtgggt ccgccaggct    120
ccggggaagg gtctcgagtg ggtctcagcg attgagccga ttggtcatag gacatactac    180
gcagactccg tgaagggccg gttcaccatc tcccgcgaca attccaagaa cacgctgtat    240
ctgcaaatga acagcctgcg tgccgaggat accgcggtat attactgtgc gaaacaggcg    300
cccaatcaga ggtatgttgc ccggggccgc ttggactact ggggtcaggg aaccctggtc    360
accgtctcga gc                                                        372

<210> SEQ ID NO 240
<211> LENGTH: 124
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 240

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Ser Thr Phe Thr Glu Tyr
             20                  25                  30

Arg Met Trp Trp Val Arg Gln Ala Pro Gly Lys Gly Leu Glu Trp Val
         35                  40                  45

Ser Ala Ile Glu Pro Ile Gly His Arg Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gln Ala Pro Asn Gln Arg Tyr Val Ala Arg Gly Arg Leu Asp
            100                 105                 110

Tyr Trp Gly Gln Gly Thr Leu Val Thr Val Ser Ser
        115                 120

<210> SEQ ID NO 241
<211> LENGTH: 10
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 241
```

```
Gly Ser Thr Phe Thr Glu Tyr Arg Met Trp
1               5                   10

<210> SEQ ID NO 242
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 242

Ala Ile Glu Pro Ile Gly His Arg Thr Tyr Tyr Ala Asp Ser Val Lys
1               5                   10                  15

Gly

<210> SEQ ID NO 243
<211> LENGTH: 15
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 243

Gln Ala Pro Gly Glu Lys Trp Ala Arg Arg Trp Asp Leu Asp Tyr
1               5                   10                  15

<210> SEQ ID NO 244
<211> LENGTH: 10
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 244

Gly Ser Thr Phe Thr Glu Tyr Arg Met Trp
1               5                   10

<210> SEQ ID NO 245
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 245

Ala Ile Glu Pro Ile Gly His Arg Thr Tyr Tyr Ala Asp Ser Val Lys
1               5                   10                  15

Gly

<210> SEQ ID NO 246
<211> LENGTH: 15
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 246

Gln Ala Pro Asn Gln Arg Tyr Val Ala Arg Gly Arg Leu Asp Tyr
1               5                   10                  15
```

```
<210> SEQ ID NO 247
<211> LENGTH: 10
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 247

Gly Phe Thr Phe Gly Thr Glu Gln Met Trp
1               5                   10

<210> SEQ ID NO 248
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 248

Arg Ile Asp Ser Pro Gly Gly Arg Thr Tyr Tyr Ala Asp Ser Val Lys
1               5                   10                  15

Gly

<210> SEQ ID NO 249
<211> LENGTH: 13
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 249

Arg Arg Pro Thr Gly Val Ser Gly Thr Phe Tyr Asp Tyr
1               5                   10

<210> SEQ ID NO 250
<211> LENGTH: 10
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 250

Gly Phe Thr Phe Gly Thr Asp Gln Met Trp
1               5                   10

<210> SEQ ID NO 251
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 251

Arg Ile Asp Ser Pro Gly Gly Arg Thr Tyr Tyr Ala Asn Ser Val Lys
1               5                   10                  15

Gly

<210> SEQ ID NO 252
<211> LENGTH: 13
<212> TYPE: PRT
<213> ORGANISM: Artificial Sequence
<220> FEATURE:
```

```
<223> OTHER INFORMATION: Amino acid sequence identified using molecular
      biology techniques.

<400> SEQUENCE: 252

Arg Gln Pro Ala Gly Val Ser Gly Lys Tyr Val Asp Tyr
 1               5                  10

<210> SEQ ID NO 253
<211> LENGTH: 33
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 253
gggtctagag tttatttcac gtattgattc gcc                                  33

<210> SEQ ID NO 254
<211> LENGTH: 36
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 254
gggaggacat actacgcaaa ctccgtgaag ggccgg                               36

<210> SEQ ID NO 255
<211> LENGTH: 28
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 255
cgcagactcc gtgcgtggcc ggttcacc                                        28

<210> SEQ ID NO 256
<211> LENGTH: 42
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 256
gggaggacat actacgcaaa ctccgtgcgt ggccggttca cc                        42

<210> SEQ ID NO 257
<211> LENGTH: 32
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 257
ggacatacta cgcaaactcc gtgaagggcc gg                                   32

<210> SEQ ID NO 258
<211> LENGTH: 28
<212> TYPE: DNA
<213> ORGANISM: Artificial Sequence
<220> FEATURE:
```

<223> OTHER INFORMATION: Nucleic acid sequence identified using
molecular biology techniques.

<400> SEQUENCE: 258
cgcagactcc gtgcgtggcc ggttcacc                                          28

<210> SEQ ID NO 259
<211> LENGTH: 38
<212> TYPE: DNA
<213> ORGANISM: Artificial Sequence
<220> FEATURE:
<223> OTHER INFORMATION: Nucleic acid sequence identified using
molecular biology techniques.

<400> SEQUENCE: 259
ggacatacta cgcaaactcc gtgcgtggcc ggttcacc                               38

<210> SEQ ID NO 260
<211> LENGTH: 43
<212> TYPE: DNA
<213> ORGANISM: Artificial Sequence
<220> FEATURE:
<223> OTHER INFORMATION: Nucleic acid sequence identified using
molecular biology techniques.

<400> SEQUENCE: 260
ccctggtcac cgtctcgagc gcgtaataag cggccgcaga tta                         43

<210> SEQ ID NO 261
<211> LENGTH: 36
<212> TYPE: DNA
<213> ORGANISM: Artificial Sequence
<220> FEATURE:
<223> OTHER INFORMATION: Nucleic acid sequence identified using
molecular biology techniques.

<400> SEQUENCE: 261
ataaggccat ggcggaggtg cagctgttgg agtctg                                 36

<210> SEQ ID NO 262
<211> LENGTH: 369
<212> TYPE: DNA
<213> ORGANISM: Artificial Sequence
<220> FEATURE:
<223> OTHER INFORMATION: Nucleic acid sequence identified using
molecular biology techniques.

<400> SEQUENCE: 262
gaggtgcagc tgttggagtc tgggggaggc ttggtacagc ctggggggtc cctgcgtctc       60
tcctgtgcag cctccggatt cacctttggg acggagcaga tgtggtgggt ccgccaggct      120
ccagggaagg gtctagagtt tgtctcacgt attgattcgc ctggtgggag gacatactac      180
gcagactccg tgaagggccg gttcaccatc tcccgcgaca attccaagaa cacgctgtat      240
ctgcaaatga acagcctgcg tgccgaggac accgcggtat attactgtgc gaaacggcga      300
cccacggggg tgtccgggac gttttatgac tactggggtc agggaaccct ggtcaccgtc      360
tcgagcgcg                                                              369

<210> SEQ ID NO 263
<211> LENGTH: 123
<212> TYPE: PRT
<213> ORGANISM: Artificial Sequence
<220> FEATURE:
<223> OTHER INFORMATION: Amino acid sequence identified using molecular
biology techniques.

-continued

<400> SEQUENCE: 263

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Thr Glu
            20                  25                  30

Gln Met Trp Trp Val Arg Gln Ala Pro Gly Lys Gly Leu Glu Phe Val
        35                  40                  45

Ser Arg Ile Asp Ser Pro Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Arg Pro Thr Gly Val Ser Gly Thr Phe Tyr Asp Tyr Trp
            100                 105                 110

Gly Gln Gly Thr Leu Val Thr Val Ser Ser Ala
        115                 120

<210> SEQ ID NO 264
<211> LENGTH: 369
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 264
gaggtgcagc tgttggagtc tgggggaggc ttggtacagc ctggggggtc cctgcgtctc      60
tcctgtgcag cctccggatt cacctttggg acggagcaga tgtggtgggt ccgccaggct     120
ccagggaagg gtctagagtt tatttcacgt attgattcgc ctggtgggag acatactac     180 gcagactccg tgaagggccg gttcaccatc tcccgcgaca attccaagaa cacgctgtat     240
ctgcaaatga acagcctgcg tgccgaggac accgcggtat attactgtgc gaaacggcga     300
cccacggggg tgtccgggac gttttatgac tactggggtc agggaaccct ggtcaccgtc     360
tcgagcgcg                                                             369

<210> SEQ ID NO 265
<211> LENGTH: 123
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 265

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Thr Glu
            20                  25                  30

Gln Met Trp Trp Val Arg Gln Ala Pro Gly Lys Gly Leu Glu Phe Ile
        35                  40                  45

Ser Arg Ile Asp Ser Pro Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                    85                  90                  95
Ala Lys Arg Arg Pro Thr Gly Val Ser Gly Thr Phe Tyr Asp Tyr Trp
                100                 105                 110

Gly Gln Gly Thr Leu Val Thr Val Ser Ser Ala
        115                 120
```

<210> SEQ ID NO 266
<211> LENGTH: 369
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 266

| gaggtgcagc tgttggagtc tgggggaggc ttggtacagc ctgggggggtc cctgcgtctc | 60 |
| tcctgtgcag cctccggatt cacctttggg acggagcaga tgtggtgggt ccgccaggct | 120 |
| ccagggaagg gtctagagtt tgtctcacgt attgattcgc tggtggggag gacatactac | 180 |
| gcaaactccg tgaagggccg gttcaccatc tcccgcgaca attccaagaa cacgctgtat | 240 |
| ctgcaaatga acagcctgcg tgccgaggac accgcggtat attactgtgc gaaacggcga | 300 |
| cccacgggggg tgtccgggac gttttatgac tactgggggtc agggaacccct ggtcaccgtc | 360 |
| tcgagcgcg | 369 |

<210> SEQ ID NO 267
<211> LENGTH: 123
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 267

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gly Thr Glu
                20                  25                  30

Gln Met Trp Trp Val Arg Gln Ala Pro Gly Lys Gly Leu Glu Phe Val
            35                  40                  45

Ser Arg Ile Asp Ser Pro Gly Arg Thr Tyr Tyr Ala Asn Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Arg Arg Pro Thr Gly Val Ser Gly Thr Phe Tyr Asp Tyr Trp
                100                 105                 110

Gly Gln Gly Thr Leu Val Thr Val Ser Ser Ala
        115                 120
```

<210> SEQ ID NO 268
<211> LENGTH: 369
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 268

```
gaggtgcagc tgttggagtc tgggggaggc ttggtacagc ctggggggtc cctgcgtctc        60
tcctgtgcag cctccggatt cacctttggg acggagcaga tgtggtgggt ccgccaggct       120
ccagggaagg gtctagagtt tgtctcacgt attgattcgc ctggtgggag acatactac        180 gcagactccg tgcgtggccg gttcaccatc tcccgcgaca attccaagaa cacgctgtat       240
ctgcaaatga acagcctgcg tgccgaggac accgcggtat attactgtgc gaaacggcga       300
cccacggggg tgtccgggac gttttatgac tactggggtc agggaaccct ggtcaccgtc       360
tcgagcgcg                                                               369
```

<210> SEQ ID NO 269
<211> LENGTH: 123
<212> TYPE: PRT
<213> ORGANISM: Artificial Sequence
<220> FEATURE:
<223> OTHER INFORMATION: Amino acid sequence identified using molecular biology techniques.

<400> SEQUENCE: 269

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gly Thr Glu
            20                  25                  30

Gln Met Trp Trp Val Arg Gln Ala Pro Gly Lys Gly Leu Glu Phe Val
        35                  40                  45

Ser Arg Ile Asp Ser Pro Gly Gly Arg Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Arg Pro Thr Gly Val Ser Gly Thr Phe Tyr Asp Tyr Trp
            100                 105                 110

Gly Gln Gly Thr Leu Val Thr Val Ser Ser Ala
        115                 120
```

<210> SEQ ID NO 270
<211> LENGTH: 369
<212> TYPE: DNA
<213> ORGANISM: Artificial Sequence
<220> FEATURE:
<223> OTHER INFORMATION: Nucleic acid sequence identified using molecular biology techniques.

<400> SEQUENCE: 270

```
gaggtgcagc tgttggagtc tgggggaggc ttggtacagc ctggggggtc cctgcgtctc        60
tcctgtgcag cctccggatt cacctttggg acggagcaga tgtggtgggt ccgccaggct       120
ccagggaagg gtctagagtt tgtctcacgt attgattcgc ctggtgggag acatactac        180 gcaaactccg tgcgtggccg gttcaccatc tcccgcgaca attccaagaa cacgctgtat       240
ctgcaaatga acagcctgcg tgccgaggac accgcggtat attactgtgc gaaacggcga       300
cccacggggg tgtccgggac gttttatgac tactggggtc agggaaccct ggtcaccgtc       360
tcgagcgcg                                                               369
```

<210> SEQ ID NO 271
<211> LENGTH: 123
<212> TYPE: PRT
<213> ORGANISM: Artificial Sequence
<220> FEATURE:
<223> OTHER INFORMATION: Amino acid sequence identified using molecular
    biology techniques.

<400> SEQUENCE: 271

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Thr Glu
            20                  25                  30

Gln Met Trp Trp Val Arg Gln Ala Pro Gly Lys Gly Leu Glu Phe Val
        35                  40                  45

Ser Arg Ile Asp Ser Pro Gly Gly Arg Thr Tyr Tyr Ala Asn Ser Val
50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Arg Pro Thr Gly Val Ser Gly Thr Phe Tyr Asp Tyr Trp
            100                 105                 110

Gly Gln Gly Thr Leu Val Thr Val Ser Ser Ala
        115                 120

<210> SEQ ID NO 272
<211> LENGTH: 375
<212> TYPE: DNA
<213> ORGANISM: Artificial Sequence
<220> FEATURE:
<223> OTHER INFORMATION: Nucleic acid sequence identified using
    molecular biology techniques.

<400> SEQUENCE: 272
gaggtgcagc tgttggagtc tgggggaggc ttggtacagc ctggggggtc cctgcgtctc      60
tcctgtgcag cctccggatc cacctttacg gagtatagga tgtggtgggt ccgccaggct     120
ccggggaagg gtctcgagtg gtctcagcg attgagccga ttggtcatag acatactac       180 gcagactccg tgaagggccg gttcaccatc tcccgcgaca attccaagaa cacgctgtat     240
ctgcaaatga acagcctgcg tgccgaggat accgcggtat attactgtgc gaaacaggcg     300
cccggcgaga gtgggcgagg cggtgggat ttggactact ggggtcaggg aaccctggtc      360
accgtctcga gcgcg                                                      375

<210> SEQ ID NO 273
<211> LENGTH: 125
<212> TYPE: PRT
<213> ORGANISM: Artificial Sequence
<220> FEATURE:
<223> OTHER INFORMATION: Amino acid sequence identified using molecular
    biology techniques.

<400> SEQUENCE: 273

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Thr Glu Tyr
            20                  25                  30

Arg Met Trp Trp Val Arg Gln Ala Pro Gly Lys Gly Leu Glu Trp Val
        35                  40                  45

Ser Ala Ile Glu Pro Ile Gly His Arg Thr Tyr Tyr Ala Asp Ser Val
50                  55                  60

Lys Gly Arg Phe Thr Ile Ser Arg Asp Asn Ser Lys Asn Thr Leu Tyr

```
                65                  70                  75                  80
Leu Gln Met Asn Ser Leu Arg Ala Glu Asp Thr Ala Val Tyr Tyr Cys
                    85                  90                  95

Ala Lys Gln Ala Pro Gly Glu Lys Trp Ala Arg Arg Trp Asp Leu Asp
                100                 105                 110

Tyr Trp Gly Gln Gly Thr Leu Val Thr Val Ser Ser Ala
                115                 120                 125
```

<210> SEQ ID NO 274
<211> LENGTH: 375
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 274

```
gaggtgcagc tgttggagtc tgggggaggc ttggtacagc ctgggggtc cctgcgtctc      60 tcctgtgcag cctccggatc cacctttacg gagtatagga tgtggtgggt ccgccaggct    120
ccggggaagg gtctcgagtg ggtctcagcg attgagccga ttggtcatag acatactac    180 gcaaactccg tgaagggccg gttcaccatc tcccgcgaca attccaagaa cacgctgtat    240
ctgcaaatga acagcctgcg tgccgaggat accgcggtat attactgtgc gaaacaggcg    300
cccggcgaga gtgggcgagg cggtgggat ttggactact ggggtcaggg aaccctggtc    360
accgtctcga gcgcg                                                      375
```

<210> SEQ ID NO 275
<211> LENGTH: 125
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 275

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Ser Thr Phe Thr Glu Tyr
                 20                  25                  30

Arg Met Trp Trp Val Arg Gln Ala Pro Gly Lys Gly Leu Glu Trp Val
             35                  40                  45

Ser Ala Ile Glu Pro Ile Gly His Arg Thr Tyr Tyr Ala Asn Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Lys Gln Ala Pro Gly Glu Lys Trp Ala Arg Arg Trp Asp Leu Asp
                100                 105                 110

Tyr Trp Gly Gln Gly Thr Leu Val Thr Val Ser Ser Ala
                115                 120                 125
```

<210> SEQ ID NO 276
<211> LENGTH: 375
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 276

```
gaggtgcagc tgttggagtc tggggggaggc ttggtacagc ctgggggggtc cctgcgtctc    60
tcctgtgcag cctccggatc caccttttacg gagtatagga tgtggtgggt ccgccaggct   120
ccggggaagg gtctcgagtg gtctcagcg attgagccga ttggtcatag gacatactac    180
gcagactccg tgcgtggccg gttcaccatc tcccgcgaca attccaagaa cacgctgtat   240
ctgcaaatga acagcctgcg tgccgaggat accgcggtat attactgtgc gaaacaggcg   300
cccggcgaga gtgggcgag gcggtgggat ttggactact ggggtcaggg aaccctggtc   360
accgtctcga gcgcg                                                    375
```

<210> SEQ ID NO 277
<211> LENGTH: 125
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 277

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Ser Thr Phe Thr Glu Tyr
            20                  25                  30

Arg Met Trp Trp Val Arg Gln Ala Pro Gly Lys Gly Leu Glu Trp Val
        35                  40                  45

Ser Ala Ile Glu Pro Ile Gly His Arg Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Ala Pro Gly Glu Lys Trp Ala Arg Arg Trp Asp Leu Asp
            100                 105                 110

Tyr Trp Gly Gln Gly Thr Leu Val Thr Val Ser Ser Ala
        115                 120                 125
```

<210> SEQ ID NO 278
<211> LENGTH: 375
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 278

```
gaggtgcagc tgttggagtc tggggggaggc ttggtacagc ctgggggggtc cctgcgtctc    60
tcctgtgcag cctccggatc caccttttacg gagtatagga tgtggtgggt ccgccaggct   120
ccggggaagg gtctcgagtg gtctcagcg attgagccga ttggtcatag gacatactac    180
gcaaactccg tgcgtggccg gttcaccatc tcccgcgaca attccaagaa cacgctgtat   240
ctgcaaatga acagcctgcg tgccgaggat accgcggtat attactgtgc gaaacaggcg   300
cccggcgaga gtgggcgag gcggtgggat ttggactact ggggtcaggg aaccctggtc   360
accgtctcga gcgcg                                                    375
```

<210> SEQ ID NO 279

<211> LENGTH: 125
<212> TYPE: PRT
<213> ORGANISM: Artificial Sequence
<220> FEATURE:
<223> OTHER INFORMATION: Amino acid sequence identified using molecular biology techniques.

<400> SEQUENCE: 279

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Thr Glu Tyr
            20                  25                  30

Arg Met Trp Trp Val Arg Gln Ala Pro Gly Lys Gly Leu Glu Trp Val
        35                  40                  45

Ser Ala Ile Glu Pro Ile Gly His Arg Thr Tyr Tyr Ala Asn Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Ala Pro Gly Glu Lys Trp Ala Arg Arg Trp Asp Leu Asp
            100                 105                 110

Tyr Trp Gly Gln Gly Thr Leu Val Thr Val Ser Ser Ala
        115                 120                 125
```

<210> SEQ ID NO 280
<211> LENGTH: 375
<212> TYPE: DNA
<213> ORGANISM: Artificial Sequence
<220> FEATURE:
<223> OTHER INFORMATION: Nucleic acid sequence identified using molecular biology techniques.

<400> SEQUENCE: 280

```
gaggtgcagc tgttggagtc tgggggaggc ttggtacagc ctggggggtc cctgcgtctc      60
tcctgtgcag cctccggatc cacctttacg gagtatagga tgtggtgggt ccgccaggct     120
ccggggaagg gtctcgagtg gatttcagcg attgagccga ttggtcatag gacatactac     180
gcagactccg tgaagggccg gttcaccatc tcccgcgaca attccaagaa cacgctgtat     240
ctgcaaatga acagcctgcg tgccgaggat accgcggtat attactgtgc gaaacaggcg     300
cccggcgaga gtgggcgag gcggtgggat ttggactact ggggtcaggg aaccctggtc     360
accgtctcga gcgcg                                                      375
```

<210> SEQ ID NO 281
<211> LENGTH: 125
<212> TYPE: PRT
<213> ORGANISM: Artificial Sequence
<220> FEATURE:
<223> OTHER INFORMATION: Amino acid sequence identified using molecular biology techniques.

<400> SEQUENCE: 281

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Thr Glu Tyr
            20                  25                  30

Arg Met Trp Trp Val Arg Gln Ala Pro Gly Lys Gly Leu Glu Trp Ile
        35                  40                  45

Ser Ala Ile Glu Pro Ile Gly His Arg Thr Tyr Tyr Ala Asp Ser Val
```

```
                    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Lys Gln Ala Pro Gly Glu Lys Trp Ala Arg Arg Trp Asp Leu Asp
                100                 105                 110

Tyr Trp Gly Gln Gly Thr Leu Val Thr Val Ser Ser Ala
            115                 120                 125

<210> SEQ ID NO 282
<211> LENGTH: 375
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 282
gaggtgcagc tgttggagtc tgggggaggc ttggtacagc ctggggggtc cctgcgtctc      60
tcctgtgcag cctccggatc cacctttacg gagtatagga tgtggtgggt ccgccaggct     120
ccggggaagg gtctcgagtg ggtctcagcg attgagccga ttggtcatag acatactac     180 gcagactccg tgaagggccg gttcaccatc tcccgcgaca attccaagaa cacgctgtat     240
ctgcaaatga acagcctgcg tgccgaggat accgcggtat attactgtgc gaaacaggcg     300
cccaatcaga ggtatgttgc ccggggccgc ttggactact ggggtcaggg aaccctggtc     360
accgtctcga gcgcg                                                       375

<210> SEQ ID NO 283
<211> LENGTH: 125
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 283

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Ser Thr Phe Thr Glu Tyr
                20                  25                  30

Arg Met Trp Trp Val Arg Gln Ala Pro Gly Lys Gly Leu Glu Trp Val
            35                  40                  45

Ser Ala Ile Glu Pro Ile Gly His Arg Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Lys Gln Ala Pro Asn Gln Arg Tyr Val Ala Arg Gly Arg Leu Asp
                100                 105                 110

Tyr Trp Gly Gln Gly Thr Leu Val Thr Val Ser Ser Ala
            115                 120                 125

<210> SEQ ID NO 284
<211> LENGTH: 375
<212> TYPE: DNA
<213> ORGANISM: Artificial Sequence
```

<220> FEATURE:
<223> OTHER INFORMATION: Nucleic acid sequence identified using
      molecular biology techniques.

<400> SEQUENCE: 284
gaggtgcagc tgttggagtc tgggggaggc ttggtacagc ctgggggtc cctgcgtctc      60 tcctgtgcag cctccggatc cacctttacg gagtatagga tgtggtgggt ccgccaggct    120
ccggggaagg gtctcgagtg ggtctcagcg attgagccga ttggtcatag gacatactac    180
gcaaactccg tgaagggccg gttcaccatc tcccgcgaca attccaagaa cacgctgtat    240
ctgcaaatga acagcctgcg tgccgaggat accgcggtat attactgtgc gaaacaggcg    300
cccaatcaga ggtatgttgc ccggggccgc ttggactact ggggtcaggg aaccctggtc    360
accgtctcga gcgcg                                                     375

<210> SEQ ID NO 285
<211> LENGTH: 125
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 285

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Ser Thr Phe Thr Glu Tyr
            20                  25                  30

Arg Met Trp Trp Val Arg Gln Ala Pro Gly Lys Gly Leu Glu Trp Val
        35                  40                  45

Ser Ala Ile Glu Pro Ile Gly His Arg Thr Tyr Tyr Ala Asn Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Ala Pro Asn Gln Arg Tyr Val Ala Arg Gly Arg Leu Asp
            100                 105                 110

Tyr Trp Gly Gln Gly Thr Leu Val Thr Val Ser Ser Ala
        115                 120                 125

<210> SEQ ID NO 286
<211> LENGTH: 375
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 286
gaggtgcagc tgttggagtc tgggggaggc ttggtacagc ctgggggtc cctgcgtctc      60 tcctgtgcag cctccggatc cacctttacg gagtatagga tgtggtgggt ccgccaggct    120
ccggggaagg gtctcgagtg ggtctcagcg attgagccga ttggtcatag gacatactac    180
gcaaactccg tgcgtggccg gttcaccatc tcccgcgaca attccaagaa cacgctgtat    240
ctgcaaatga acagcctgcg tgccgaggat accgcggtat attactgtgc gaaacaggcg    300
cccaatcaga ggtatgttgc ccggggccgc ttggactact ggggtcaggg aaccctggtc    360
accgtctcga gcgcg                                                     375

<210> SEQ ID NO 287
<211> LENGTH: 125
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 287

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Ser Thr Phe Thr Glu Tyr
            20                  25                  30

Arg Met Trp Trp Val Arg Gln Ala Pro Gly Lys Gly Leu Glu Trp Val
        35                  40                  45

Ser Ala Ile Glu Pro Ile Gly His Arg Thr Tyr Tyr Ala Asn Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Ala Pro Asn Gln Arg Tyr Val Ala Arg Gly Arg Leu Asp
            100                 105                 110

Tyr Trp Gly Gln Gly Thr Leu Val Thr Val Ser Ser Ala
        115                 120                 125

<210> SEQ ID NO 288
<211> LENGTH: 369
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 288
gaggtgcagc tgttggagtc tgggggaggc ttggtacagc ctggggggtc cctgcgtctc      60
tcctgtgcag cctccggatt cacctttggg acggagcaga tgtggtgggt ccgccaggct     120
ccagggaagg gtctagagtt tatttcacgt attgattcgc ctggtgggag acatactac     180 gcaaactccg tgaagggccg gttcaccatc tcccgcgaca attccaagaa cacgctgtat    240
ctgcaaatga acagcctgcg tgccgaggac accgcggtat attactgtgc gaaacggcga    300
cccacggggg tgtccgggac gttttatgac tactggggtc agggaaccct ggtcaccgtc    360
tcgagcgcg                                                            369

<210> SEQ ID NO 289
<211> LENGTH: 123
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 289

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gly Thr Glu
            20                  25                  30

Gln Met Trp Trp Val Arg Gln Ala Pro Gly Lys Gly Leu Glu Phe Ile

```
                  35                  40                  45
Ser Arg Ile Asp Ser Pro Gly Gly Arg Thr Tyr Tyr Ala Asn Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Arg Arg Pro Thr Gly Val Ser Gly Thr Phe Tyr Asp Tyr Trp
            100                 105                 110

Gly Gln Gly Thr Leu Val Thr Val Ser Ser Ala
            115                 120
```

<210> SEQ ID NO 290
<211> LENGTH: 369
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 290

```
gaggtgcagc tgttggagtc tgggggaggc ttggtacagc ctggggggtc cctgcgtctc    60
tcctgtgcag cctccggatt cacctttggg acggagcaga tgtggtgggt ccgccaggct   120
ccagggaagg gtctagagtt tatttcacgt attgattcgc ctggtgggag acatactac    180 gcaaactccg tgcgtggccg gttcaccatc tcccgcgaca attccaagaa cacgctgtat   240
ctgcaaatga acagcctgcg tgccgaggac accgcggtat attactgtgc gaaacggcga   300
cccacggggg tgtccggac gttttatgac tactggggtc agggaaccct ggtcaccgtc   360
tcgagcgcg                                                            369
```

<210> SEQ ID NO 291
<211> LENGTH: 123
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 291

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Gly Thr Glu
             20                  25                  30

Gln Met Trp Trp Val Arg Gln Ala Pro Gly Lys Gly Leu Glu Phe Ile
         35                  40                  45

Ser Arg Ile Asp Ser Pro Gly Gly Arg Thr Tyr Tyr Ala Asn Ser Val
 50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Arg Arg Pro Thr Gly Val Ser Gly Thr Phe Tyr Asp Tyr Trp
            100                 105                 110

Gly Gln Gly Thr Leu Val Thr Val Ser Ser Ala
            115                 120
```